US008044090B2

(12) United States Patent
Chen et al.

(10) Patent No.: US 8,044,090 B2
(45) Date of Patent: *Oct. 25, 2011

(54) N-(2-ARYLETHYL)BENZYLAMINES AS ANTAGONISTS OF THE 5-HT6 RECEPTOR

(75) Inventors: Zhaogen Chen, Noblesville, IN (US); Michael Philip Cohen, Indianapolis, IN (US); Matthew Joseph Fisher, Mooresville, IN (US); Bruno Giethlen, Altorf (FR); James Ronald Gillig, Indianapolis, IN (US); Jefferson Ray McCowan, Indianapolis, IN (US); Shawn Christopher Miller, Morgantown, IN (US); John Mehnert Schaus, Zionsville, IN (US)

(73) Assignee: Eli Lilly, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/504,242

(22) Filed: Jul. 16, 2009

(65) Prior Publication Data
US 2009/0306110 A1 Dec. 10, 2009

Related U.S. Application Data

(63) Continuation of application No. 11/608,922, filed on Dec. 11, 2006, now abandoned, which is a continuation of application No. 10/472,741, filed as application No. PCT/US02/05115 on Mar. 15, 2002, now Pat. No. 7,157,488.

(60) Provisional application No. 60/279,928, filed on Mar. 29, 2001, provisional application No. 60/329,449, filed on Oct. 15, 2001.

(51) Int. Cl.
A61K 31/4045 (2006.01)
A61K 31/137 (2006.01)
C07D 209/14 (2006.01)
(52) U.S. Cl. ......................... 514/418; 514/654; 548/503
(58) Field of Classification Search .................. 514/418, 514/654; 548/503
See application file for complete search history.

(56) References Cited

U.S. PATENT DOCUMENTS

| | | | |
|---|---|---|---|
| 3,597,149 A | 8/1971 | Masuda et al. | |
| 5,070,096 A | 12/1991 | Mohrs et al. | |
| 5,093,340 A | 3/1992 | Mohrs et al. | |
| 5,202,336 A | 4/1993 | Mohrs et al. | |
| 6,187,805 B1 | 2/2001 | McAllister et al. | |
| 6,750,348 B1 | 6/2004 | Bridger et al. | |
| 7,157,488 B2 * | 1/2007 | Chen et al. | 514/418 |
| 2007/0099909 A1 | 5/2007 | Chen | |

FOREIGN PATENT DOCUMENTS

| | | |
|---|---|---|
| CZ | 105267 | 10/1962 |
| CZ | 105995 | 12/1962 |
| FR | 2181559 | 7/1973 |
| GB | 2 085 006 | 4/1982 |
| JP | 63-93765 A | 4/1988 |
| WO | WO 93/11761 | 6/1993 |
| WO | WO 95/06638 | 3/1995 |
| WO | WO 95/30655 | 11/1995 |
| WO | WO 99/16746 | 4/1999 |
| WO | WO 00/34242 | 6/2000 |
| WO | WO-0042045 A2 | 7/2000 |

OTHER PUBLICATIONS

ACS Chemcats 2000:1020106, Order No. STOCK1S-08349, CAS Registry No. 302795-49-9.
Bos et al., "5-HT6 receptor antagonists: lead optimization and biological evaluation of N-aryl and N-heteroaryl 4-amino-benzene sulfonamides," Eur J. Med. Chem., vol. 36, pp. 165-178 (2001).
Bourson et al, "Determination of the Role of the 5-ht6 Receptor in the Rat Brain: A Study using Antisense Oligonucleotides," J. of Pharm. and Experimental Therapeutics, vol. 274, No. 1, pp. 173-180 (1995).
Meneses, Alfredo, "Effects of the 5-HT6 receptor antagonist Ro 04-6790 on learning consolidation," Behavioral Brain Research, vol. 118, pp. 107-110 (2001).
Rogers et al., "5-HT6 receptor antagonists enhance retention of a water maze task in the rat," PsvchopharmacoloEy, vol. 158, pp. 114-119 (2001).
Glennon, et al. "Influence of Amine Substituents on 5-HT2A versus 5-HT2C—Binding of Phenylakllyl- and Indolylalkylamines" J. Med. Chem., 1994, 37, 1929-1935.
Glennon, et al., 5-HT6 Serotonin Receptor Binding of Indolealkylamines: A Preliminary Structure-Affinity Investigation. Med. Chem. Res., 1999, 9, 108-117.
Ide et al. "Pharmacologically Active Compounds from Alkoxy-B-phenylethylamines" Journal of the American Chemical Society 1937, 726-731.
Tsai et al. "N1-(Benzenesulfonyl)tryptamines as Novel 5-HT6 Antagonists" Bioorganic & Medicinal Chemistry Letters 2000, 2295-2299.
Bromidge et al. "Phenyl Benzenesulfonamides are Novel and Selective 5-HT6 Antagonists: Identification of..." Bioorganic & Medicinal Chemistry Letters 2001, 55-58.

(Continued)

Primary Examiner — Joseph Kosack
(74) Attorney, Agent, or Firm — Kitae Lim; Stephen G. Kalinchak

(57) ABSTRACT

The present invention provides compounds of formula (I), which are antagonists of the 5-HT$_6$ receptor.

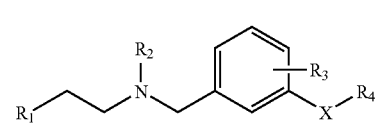

(I)

10 Claims, No Drawings

OTHER PUBLICATIONS

Isaac et al. "6-Bicyclopiperazinyl-1-arylsulfonylindoles and 6-Bicyclopiperidinyl-1-arylsulfonylindoles Derivatives as Novel, Potent, and Selective 5-HT6 Receptor Antagonists" Bioorganic & Medicinal Chemistry Letters 2000, 1719-1721.

Database Crossfire Beilstein Online! Beilstein Institut zur Forderung der Chemischen Wissenschaften, Frankfurt am Main, DE; (3-ethoxy-benzyl)-(3-ethoxy-phenethyl)-amine), Database accession No. 3365863: XP002209140, 1992.

Database Crossfire Beilstein Online! Beilstein Institut zur Forderung der Chemischen Wissenschaften, Frankfurt am Main, DE; (3-ethoxy-benzyl)-(4-ethoxy-phenethyl)-amine), IDE, BUCK: Database accession No. 3365864; XP002209139, 1992.

Database Crossfire Beilstein Online! Beilstein Institut zur Forderung der Chemischen Wissenschaften, Frankfurt am Main, DE; (3-ethoxy-benzyl)-(2-ethoxy-henethyl)-amine), IDE, BUCK: Database accession No. 3380345; XP002209141, 1992.

Barton, et al., "886. Phenol Oxidation and Biosynthesis. Part VI. The Biogenesis of Amaryllidaceae Alkaloids," Barton, Kirby, Taylor and Thomas, pp. 4545-4558 (1963).

Vinogradova, et al., "Synthesis Based on b-Phenylethylamines. IV. Synthesis and Antiarrhythmic Activity of Substituted Phenylalkylamines and N-Benzyltetrahydroisoquinolines," vol. 29, No. 3, pp. 259-414 (1993).

Vinogradova, et al., "Syntheses Based on b-Ethylamines. VIII. Synthesis of Substituted 2-Benzyltetrahydroisoquinolines and Their Influence on Bile Secretion," vol. 30, No. 3, pp. 368-370 (1994).

* cited by examiner

N-(2-ARYLETHYL)BENZYLAMINES AS ANTAGONISTS OF THE 5-HT6 RECEPTOR

CROSS-REFERENCE TO RELATED APPLICATIONS

The present application is a continuation of application U.S. Ser. No. 11/608,922, filed Dec. 11, 2006 now abandoned, which is a continuation of application U.S. Ser. No. 10/472,741, filed Feb. 27, 2004, now U.S. Pat. No. 7,157,488, issued Jan. 2, 2007, which is a 35 U.S.C. 371 National Stage Entry under PCT/US02/05115, filed Mar. 15, 2002, which claims the benefit of U.S. Provisional Application Ser. No. 60/279,928, filed Mar. 29, 2001 and U.S. Provisional Application Ser. No. 60/329,449, filed Oct. 15, 2001.

The present invention relates to the field of pharmaceutical and organic chemistry and is concerned with compounds which are antagonists of the 5-HT$_6$ receptor.

The 5-HT$_6$ receptor is a member of the G-protein coupled receptor superfamily of serotonin receptors, and, like the 5-HT$_4$ and 5-HT$_7$ receptors, it is positively coupled to adenylate cyclase.[1] The rat 5-HT$_6$ receptor was first cloned in 1993[2,3] and the cloning of the human homologue, to which it shares a 89% sequence identity, was reported in 1996.[4] The localization of 5-HT$_6$ receptors in rat brain has been studied using mRNA quantification by Northern analysis and RT-PCR, immunohistochemistry, and autoradiography.[2, 3, 5, 6, 7, 8] These methods have consistently found high levels of the receptor in olfactory tubercle, hippocampus, striatum, nucleus accumbens, and cortical regions. 5-HT$_6$ receptors are either absent or present in very low levels in peripheral tissues.[2, 3]

To date, there are no known high affinity, selective agonists at the 5-HT$_6$ receptor. Serotonin itself has only moderate affinity for the 5-HT$_6$ receptor (Ki=65 nM) and the most selective agonist reported to date, N,N-dimethyl-2-ethyl-5-methoxytryptamine, has Ki=81 nM and only 3.5-fold selectivity versus the 5-HT$_{2A}$ receptor.[9]

Much of the recent interest in the 5-HT$_6$ receptor is due to the observation that several psychotropic agents are high affinity antagonists at the human 5-HT$_6$ receptor.[4, 10] These compounds include amitriptyline (Ki=65 nM) and the atypical antipsychotics clozapine (Ki=9.5 nM), olanzapine (Ki=10 nM), and quetiapine (33 nM). None of these compounds, however, are selective. The first selective 5-HT$_6$ receptor antagonists reported are Ro 04-6790 and Ro 63-0563. Their usefulness is limited by their moderate affinity (Ki=50 nM and 12 nM, respectively) and poor pharmacokinetics.[11] A series of 5-HT$_6$ receptor antagonists, culminating in SB-271,046, has been reported.[12] This compound has high affinity (Ki=1.2 nM) and selectivity (>200-fold versus >55 receptors, enzymes and ion channels) and is 80% bioavailable. A selective radioligand [$^{125}$I]-SB-258,585 has been used for radioligand binding and autoradiographic studies.[13, 14] These compounds are useful tools for preclinical studies on the 5-HT$_6$ receptor.

The rationale for the use of selective 5-HT$_6$ receptor antagonists to treat cognitive dysfunction is based on three lines of reasoning: the ability of selective 5-HT$_6$ receptor antagonists to modulate cholinergic and glutamatergic neuronal function, clinical studies of the atypical antipsychotics clozapine and olanzapine on cognitive function, the activity of selective 5-HT$_6$ receptor antagonists in animal models of cognitive function.

Selective 5-HT$_6$ receptor antagonists modulate cholinergic and glutamatergic neuronal function. Cholinergic and glutamatergic neuronal systems play important roles in cognitive function. Cholinergic neuronal pathways are known to be important to memory formation and consolidation. Centrally acting anticholinergic agents impair cognitive function in animal and clinical studies and loss of cholinergic neurons is one of the hallmarks of Alzheimer's disease. Conversely, stimulation of cholinergic function has been known to improve cognitive performance and the only two agents currently approved for the treatment of cognitive deficit in Alzheimer's disease, tacrine and donepezil, are both acetylcholinesterase inhibitors. The glutamatergic system in the prefrontal cortex is also known to be involved in cognitive function.[26, 27]

Blocking 5-HT$_6$ receptor function has been shown to elicit procholinergic effects in vivo. Administration (icv) to rats of antisense oligonucleotides targeting the 5-HT$_6$ receptor sequence induced yawning and stretching behavior that was blocked by the cholinergic antagonist atropine.[15] The selective 5-HT$_6$ receptor antagonist Ro 04-6790 induced stretching behavior in a dose-dependent manner. This behavior was blocked by the centrally acting anticholinergic agents scopolamine and atropine but not by methyl-scopolamine at doses known to be peripherally selective.[16] Ro 04-6790 was also shown to block the rotational behavior induced by scopolamine administration to rats with unilateral nigrostriatal 6-OH-DA lesions. It did not block rotational behavior induced by L-DOPA or amphetamine.[17] Ro 04-6790 reversed scopolamine induced performance deficits in the object recognition test, a model of cognitive function. Another selective 5-1-HT$_6$ receptor antagonist, SB-271046, potentiated the yawning behavior induced by the cholinesterase inhibitor physostigmine.[18] These studies suggest that 5-HT$_6$ receptor blockade facilitates cholinergic transmission. In in vivo microdialysis studies, SD-271,046 (10 mg/kg, sc) increases glutamate release in the prefrontal cortex through a neuronal mechanism.[25]

Clinical studies of the atypical antipsychotics clozapine and olanzapine on cognitive function. The atypical antipsychotics clozapine and olanzapine are both high affinity, albeit nonselective, 5-HT$_6$ receptor antagonists.[4] On the other hand, risperidone and the typical antipsychotic haloperidol do not have significant affinity for the 5-HT$_6$ receptor. Clinical differences seen with these sets of drugs may be attributable to 5-HT$_6$ receptor blockade. Goldberg et al. reported no beneficial cognitive effect of clozapine treatment in a small (N=15) trial in treatment resistant schizophrenics.[19] In contrast, Meltzer et al.[20] in a larger study of treatment-resistant schizophrenics (N=36), observed improvements in several domains of neuropsychological function at six weeks and six months following initiation of clozapine treatment. In non-treatment resistant schizophrenics, clozapine was more effective than placebo in improving cognitive function by several measures.[21] This effect was seen at six months and persisted throughout the 12 month study. The effect of olanzapine, risperidone, and haloperidol on cognitive function has been compared in a multicenter, double blind study in schizophrenics.[22] The olanzapine group showed a statistically significant improvement in cognitive function over either haloperidol or risperidone treatment. This effect was apparent after 6 weeks treatment and continued throughout the 54 weeks of the study. Animal studies suggest that these effects could be mediated through the release of acetylcholine in the prefrontal cortex.[23]

Activity of selective 5-HT$_6$ receptor antagonists in animal models of cognitive function. With the recent development of the selective 5-HT$_6$ receptor antagonists Ro-04,6790 and SB-271,046, there have been several reports on the activity of these compounds in models of cognitive function. The selective 5-HT$_6$ receptor antagonist SB-271,046 improved performance in the Morris water maze.[24] These results are consistent with the finding that chronic icv administration of antisense oligonucleotides directed toward the 5-HT$_6$ receptor sequence led to improvements in some measures of performance in the Morris water maze.[16] SB-271,046 treatment also led to improvements in the spatial alternation operant behavior test in aged rats.[24]

The compounds of the present invention are selective, high affinity antagonists of 5-HT$_6$, and thus, provide a valuable treatment for 5-HT$_6$ receptor mediated disorders.

BACKGROUND REFERENCES

1. Branchek, T. A., et al. (2000). Annu Rev Pharmacol Toxicol 40: 319-34.
2. Monsma, F. J., Jr., et al. (1993). Mol Pharmacol 43(3): 320-7.
3. Ruat, M., et al. (1993). Biochem Biophys Res Commun 193(1): 268-76.
4. Kohen, R., et al. (1996). J Neurochem 66(1): 47-56.
5. Ward, R. P., et al. (1996). J Comp Neurol 370(3): 405-14.
6. Ward, R. P., et al. (1995). Neuroscience 64(4): 1105-11.
7. Gerard, C., et al. (1997). Brain Res 746(1-2): 207-19.
8. Gerard, C., et al. (1996). Synapse 23(3): 164-73.
9. Glennon, R. A., et al. (2000). J Med Chem 43(5): 1011-8.
10. Roth, B. L., et al. (1994). J Pharmacol Exp Ther 268(3): 1403-10.
11. Sleight, A. J., et al. (1998). Br J Pharmacol 124(3): 556-62.
12. Routledge, C., et al. (2000). Br. J. Pharmacol. 130(7): 1606.
13. Hirst, W. D., et al. (1999). Br. J. Pharmacol. Suppl. ((in press)).
14. Hirst, W. D., et al. (2000). Br. J. Pharmacol. 130: 1597.
15. Bourson, A., et al. (1995). J Pharmacol Exp Ther 274(1): 173-80.
16. Bentley, J. C., et al. (1999). Br J Pharmacol 126(7): 1537-42.
17. Bourson, A., et al. (1998). Br J Pharmacol 125(7): 1562-6.
18. Routledge, C., et al (1999). Br. 3. Pharmacol. 127(Suppl.): 21P.
19. Goldberg, T. E., et al. (1993). Br J Psychiatry 162: 43-8.
20. Hagger, C., et al. (1993). Biol Psychiatry 34(10): 702-12.
21. Lee, M. A., et al. (1994). J Clin Psychiatry 55 Suppl B: 82-7.
22. Purdon, S. E., et al. (2000). Arch Gen Psychiatry 57(3): 249-58.
23. Parada, M. A., et al. (1997). 3 Pharmacol Exp Ther 281(1): 582-8.
24. Rogers, D. C., et al. (1999). Br J Pharamcol 127(suppl.): 22P.
25. Dawson, L. A., et al. (2000). Br J Pharmacol 130(1): 23-6.
26. Dudkin, K. N., et al. (1996). Neurosci Behav Physiol 26(6): 545-51.
27. Koechlin, B., et al. (1999). Nature 399(6732): 148-51.

The present invention provides compounds of formula I:

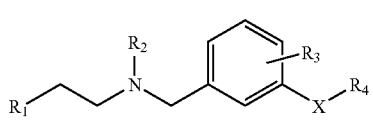

formula I wherein

X is selected from the group consisting of —O—, —NH—, —S—, —SO$_2$—, —CH$_2$—, —CH(F)—, —CH(OH)—, and —C(O)—;

R$_1$ is selected from the group consisting of optionally substituted phenyl, optionally substituted naphthyl, optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused;

R$_2$ is selected from the group consisting of hydrogen and C$_1$-C$_3$ alkyl;

R$_3$ is selected from the group consisting of hydrogen, fluoro, and methyl;

R$_4$ is selected from the group consisting of hydrogen, allyl, C$_2$-C$_4$ alkyl, fluorinated C$_2$-C$_4$ alkyl, optionally substituted phenyl, optionally substituted phenylsulfonyl, optionally substituted benzyl, and optionally substituted 5 to 6 membered monocyclic aromatic heterocycle having one or two heteroatoms selected from the group consisting of nitrogen, oxygen, and sulfur, provided that R$_4$ is not optionally substituted phenylsulfonyl when X is —SO$_2$—, CH$_2$—, —CH(F)—, —CH(OH)—, or —C(O)—; and pharmaceutically acceptable salts thereof.

The present invention also provides compounds of formula II:

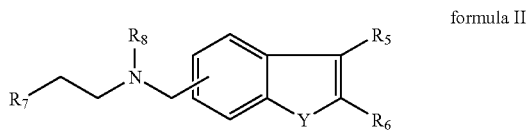

formula II wherein

Y is selected from the group consisting of O, NH, and NR$_9$, wherein R$_9$ is selected from the group consisting of C$_1$-C$_4$ alkyl, and optionally substituted phenyl;

R$_5$ and R$_6$ are hydrogen or taken together with the atoms to which they are attached form a benzo ring, provided that R$_5$ and R$_6$ are hydrogen when Y is NR$_9$;

R$_7$ is selected from the group consisting of optionally substituted phenyl, optionally substituted naphthyl, optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused;

R$_8$ is selected from the group consisting of hydrogen and C$_1$C$_3$ alkyl; and pharmaceutically acceptable salts thereof.

The present invention also provides for novel pharmaceutical compositions, comprising: a compound of the formula I or II and a pharmaceutically acceptable diluent.

Because the compounds of formula I and II are antagonists of 5-HT$_6$ receptor, the compounds of formula I and II are useful for the treatment of a variety of disorders. Thus, in another embodiment the present invention provides methods of treating disorders associated with 5-HT$_6$, comprising: administering to a patient in need thereof an effective amount of a compound of formula I or II. That is, the present invention provides for the use of a compound of formula I or II and pharmaceutical compositions thereof for the treatment disorders associated with 5-HT$_6$. More specifically, the present invention provides a method of treating disorders selected from the group consisting of cognitive disorders, age-related cognitive disorder, mild cognitive impairment, mood disorders (including depression, mania, bipolar disorders), psychosis (in particular schizophrenia), anxiety (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, amylotrophic lateral sclerosis, and multiple sclerosis, comprising: administering to a patient in need thereof an effective amount of a compound of formula I or an effective amount of a compound of formula II.

In addition, the present invention also provides processes for preparing the compounds of formula I and II and intermediate thereof.

As used herein, the following terms have the meanings indicated:

The term "$C_1$-$C_3$ alkyl" refers to a straight or branched alkyl chain having from one to three carbon atoms, and includes methyl, ethyl, propyl, and iso-propyl.

The term "optionally substituted phenyl" refers to a radical of the formula

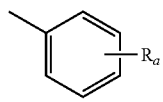

wherein $R_a$ is from 1 to 3 groups independently selected from the group consisting of hydrogen, hydroxy, $C_1$-$C_4$ alkyl, $C_1$-$C_4$ alkoxy, halogen, benzyloxy, carboxy, $C_1$-$C_4$ alkoxycarbonyl, amido, N—$C_1$-$C_4$ alkyl)amido, sulfonylamido, cyano, trifluoromethyl, trifluoromethoxy, nitro, and phenyl optionally substituted with $C_1$-$C_4$ alkyl, $C_1$-$C_4$ alkoxy, halogen, cyano, and trifluoromethyl.

The term "optionally substituted naphthyl" refers to a radical of the formula

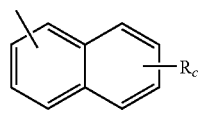

wherein $R_c$ is from 1 to 2 groups independently selected from the group consisting of hydrogen, $C_1$-$C_4$ alkyl, $C_1$-$C_4$ alkoxy, halogen, cyano, trifluoromethyl, and nitro.

The term "optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused" refers to radicals of the formula

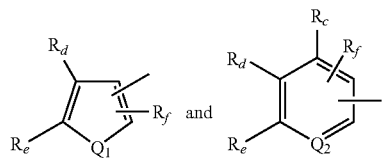

wherein $Q_1$ is selected from the group consisting of —O—, —S—, and —$NR_g$— wherein $R_g$ is selected from the group consisting of hydrogen and $C_1$-$C_4$ alkyl; and $Q_2$ is —N═, $R_d$, each $R_e$, and $R_f$ are each independently selected from the group consisting of hydrogen, $C_1$-$C_4$ alkyl, $C_1$-$C_4$ alkoxy, halogen, cyano, and trifluoromethyl, or $R_d$ and $R_e$ (or one of $R_e$) are taken together with the atoms to which they are attached to form an benzo ring which benzo ring is optionally substituted with 1 to 4 substituents independently selected from the group consisting of hydrogen, hydroxy, $C_1$-$C_4$ alkyl, $C_1$-$C_4$ alkoxy, trifluoromethoxy, 2,2,2-trifluoroethoxy, trifluoromethyl, halogen, carboxy, $C_1$-$C_4$ alkoxycarbonyl, amido, N—($C_1$-$C_4$ alkyl)amido, amino, ($C_1$-$C_4$ alkyl)amino, acylamino wherein the acyl group is selected from the group consisting of $C_1$-$C_4$ alkyl and phenyl; cyano, nitro, sulfonylamido, phenyl optionally substituted with $C_1$-$C_4$ alkyl, $C_1$-$C_4$ alkoxy, halogen, cyano, and trifluoromethyl; phenoxy, benzyloxy, —NHS(O)$_2$R$_h$, wherein $R_h$ is selected from the group consisting of $C_1$-$C_4$ alkyl and phenyl; and —S(O)$_p$R$_i$, wherein p is 0, 1, or 2 and $R_i$ is selected from the group consisting of $C_1$-$C_4$ alkyl and phenyl optionally substituted with $C_1$-$C_4$ alkyl, $C_1$-$C_4$ alkoxy, halogen, cyano, and trifluoromethyl; and $R_f$ is selected from the group consisting of hydrogen, $C_1$-$C_4$ alkyl, $C_1$-$C_4$ alkoxy, trifluoromethyl, and halogen. The term specifically includes furyl, thienyl, pyrrolyl, pyridyl, benzofuryl, benzothienyl, indolyl and quinolinyl; each optionally substituted as described above.

The term "fluorinated $C_2$-$C_4$ alkyl" refers to a straight or branched alkyl chain having from two to four carbon atoms substituted with one or more fluorine atoms. The term includes 2-fluoroethyl, 2,2-difluoroethyl, 2,2,2-trifluoroethyl, 3-fluoropropyl, 3,3-difluoropropyl, 3,3,3-trifluoropropyl, 2,2,3,3,3-pentafluoropropyl, 2,2,3,3-tetrafluoropropyl, 4,4,4-trifluorobutyl, 3,3,4,4,4-pentafluorobutyl, and the like.

The term "optionally substituted phenylsulfonyl" refers to a radical of the formula

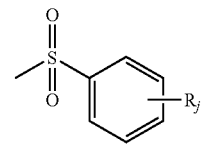

wherein $R_j$ is from 1 to 3 groups independently selected from the group consisting of hydrogen, $C_1$-$C_4$ alkyl, $C_1$-$C_4$ alkoxy, halogen, cyano, trifluoromethyl, nitro, and phenyl.

The term "optionally substituted benzyl" refers to a radical of the formula

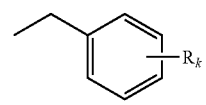

wherein $R_k$ is form 1 to 3 groups independently selected from the group consisting of hydrogen, $C_1$-$C_4$ alkyl, $C_1$-$C_4$ alkoxy, cyano, nitro, trifluoromethyl, and halogen.

The term "optionally substituted 5 to 6 membered monocyclic aromatic heterocycle having one or two heteroatoms selected from the group consisting of nitrogen, oxygen, and sulfur" refers to radicals of the formula

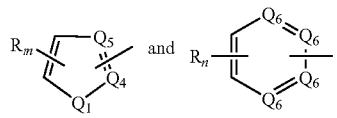

wherein $Q_3$ is selected from the group consisting of —O—, —S—, and —$NR_g$— wherein $R_g$ is selected from the group consisting of hydrogen and $C_1$-$C_4$ alkyl; and $Q_4$ and $Q_5$ are —$CR_m$, wherein each $R_m$ is independently selected from the group consisting of hydrogen, $C_1$-$C_4$ alkyl, halogen, and trifluoromethyl or one or both of $Q_4$ and $Q_5$ is —N═; and wherein one or two of $Q_6$ are —N═, while the others are $CR_n$; wherein each $R_n$ is independently selected from the group consisting of hydrogen, $C_1$-$C_4$ alkyl, $C_1$-$C_4$ alkoxy, halogen, cyano, nitro, and trifluoromethyl. The term specifically includes furyl, thienyl, thiazolyl, pyrazolyl, imidazolyl, triazolyl, oxazolyl, thiazolyl, isoxazolyl, thioisoxazolyl, pyridyl, pyrimidyl, pyridazinyl, and pyrazidinyl; each optionally substituted as described above.

The term "$C_1$-$C_4$ alkyl" refers to a straight or branched alkyl chain having from one to four carbon atoms, and includes methyl, ethyl, propyl, iso-propyl, butyl, sec-butyl, iso-butyl, and t-butyl.

The term "$C_2$-$C_4$ alkyl" refers to a straight or branched alkyl chain having from two to four carbon atoms, and includes ethyl, propyl, iso-propyl, butyl, sec-butyl, iso-butyl, and t-butyl.

The term "$C_1$-$C_4$ alkoxy" refers to a straight or branched alkyl chain having from one to four carbon atoms attached to an oxygen atom, and includes methoxy, ethoxy, propoxy, iso-propoxy, butoxy, iso-butoxy, sec-butoxy, and t-butoxy.

The term "halogen" refers to a chloro, fluoro, bromo or iodo atom.

The term "pharmaceutically-acceptable addition salt" refers to an acid addition salt.

The compound of formula I or II and the intermediates described herein form pharmaceutically acceptable acid addition salts with a wide variety of organic and inorganic acids and include the physiologically acceptable salts which are often used in pharmaceutical chemistry. Such salts are also part of this invention. A pharmaceutically-acceptable addition salt is formed from a pharmaceutically-acceptable acid as is well known in the art. Such salts include the pharmaceutically acceptable salts listed in *Journal of Pharmaceutical Science*, 66, 2-19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

As with any group of pharmaceutically active compounds, some groups are preferred in their end use application. Preferred embodiments of the present invention are given for the compounds of formula I below:

Compounds in which wherein X is selected from the group consisting of —O—, —NH—, and —S— are preferred, with compounds in which X is —O— being more preferred.

Compounds in which $R_1$ is optionally substituted phenyl or optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused are preferred.

When $R_1$ is optionally substituted phenyl preferred substituents are 1 to 3 groups independently selected from the group consisting of hydrogen, $C_1$-$C_4$ alkyl, halogen, benzyloxy, carboxy, $C_1$-$C_4$ alkoxycarbonyl, amido, N—($C_1$-$C_4$ alkyl)amido, sulfonylamido, cyano, trifluoromethyl, trifluoromethoxy, nitro, and phenyl optionally substituted with $C_1$-$C_4$ alkyl, $C_1$-$C_4$ alkoxy, halogen, cyano, and trifluoromethyl.

When $R_1$ is optionally substituted phenyl more preferred substituents are 1 to 3 groups independently selected from the group consisting of hydrogen, $C_1$-$C_4$ alkyl, halogen, cyano, and trifluoromethyl.

Compounds in which $R_3$ is hydrogen or fluorine are preferred.

Compound in which $R_1$ is optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused, the compounds which are benzo fused are preferred, with indolyl being preferred, and indol-3-yl being even more preferred.

When $R_1$ is indol-3-yl, preferred groups are depicted as the radical below:

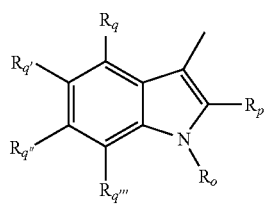

a) $R_o$ is selected from the group consisting of hydrogen and $C_1$-$C_4$ alkyl, with hydrogen being more preferred;
b) $R_p$ is selected from the group consisting of hydrogen and $C_1$-$C_4$ alkyl, with hydrogen being more preferred;
c) $R_q$ is selected from the group consisting of hydrogen, $C_1$-$C_4$ alkyl, $C_1$-$C_4$ alkoxy, and halogen, with hydrogen being more preferred;

d) $R_{q'}$ is selected from the group consisting of hydrogen, $C_1$-$C_4$ alkyl, $C_1$-$C_4$ alkoxy, trifluoromethoxy, 2,2,2-trifluoroethoxy, trifluoromethyl halogen, and —$S(O)_pR_i$ wherein p is 2 and $R_1$ is phenyl optionally substituted with $C_1$-$C_4$ alkyl, $C_1$-$C_4$ alkoxy, trifluoromethyl, with halogen being more preferred;

e) $R_{q''}$ is selected from the group consisting of hydrogen, $C_1$-$C_4$ alkyl, $C_1$-$C_4$ alkoxy, halogen, nitro, cyano, trifluoromethyl, and —$S(O)_pR_i$, wherein p 2 and $R_1$ is phenyl optionally substituted with $C_1$-$C_4$ alkyl, with halogen being more preferred; and f) $R_{q'''}$ is selected from the group consisting of hydrogen, $C_1$-$C_4$ alkyl, $C_1$-$C_4$ alkoxy, halogen, trifluoromethyl, cyano, and nitro, with hydrogen and halogen being preferred.

Compounds in which $R_4$ is selected from the group consisting of $C_2$-$C_4$ alkyl, fluorinated $C_2$-$C_4$ alkyl and optionally substituted phenyl are preferred.

When $R_4$ is $C_2$-$C_4$ alkyl, particularly preferred groups include propyl, isopropyl, and butyl.

When $R_4$ is fluorinated $C_2$-$C_4$ alkyl, preferred groups include 2,2-difluoroethyl, 2,2,2-trifluoroethyl, 3-fluoropropyl, 3,3-difluoropropyl, 3,3,3-trifluoropropyl, 2,2,3,3,3-pentafluoropropyl, and 2,2,3,3-tetrafluoropropyl.

When $R_4$ is optionally substituted phenyl preferred groups include 1 to 3 groups independently selected from the group consisting of hydrogen, $C_1$-$C_4$ alkyl, $C_1$-$C_4$ alkoxy, halogen, cyano, and trifluoromethyl.

Preferred embodiments of the present invention are given for the compounds of formula II below:

Compounds in which $R_7$ is optionally substituted phenyl or optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused are preferred.

When $R_7$ is optionally substituted phenyl preferred substituents are 1 to 3 groups independently selected from the group consisting of hydrogen, $C_1$-$C_4$ alkyl, $C_1$-$C_4$ alkoxy, halogen, cyano, trifluoromethoxy, and trifluoromethyl.

Compounds in which $R_7$ is optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused, the compounds which are benzo fused are preferred, with indolyl being preferred, and indol-3-yl being even more preferred, with the indol-3-yl depicted above for formula I being more preferred.

Preferred compounds of formula II having the points of attachment depicted below:

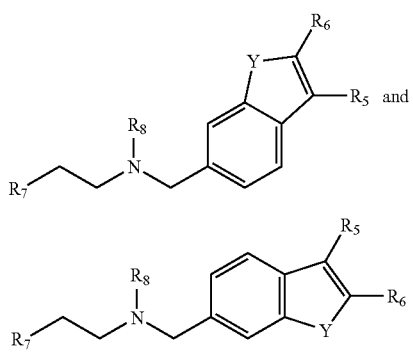

While only compounds of formula I are depicted, the compounds of formula I and II are prepared as described in Schemes A and B below. In the Schemes below all substituents, unless otherwise indicated, are as previously defined, and all starting materials and reagents are well known and appreciated in the art and readily available or prepared by methods described herein. In the Schemes below, it is understood that protecting groups can be used, where appropriate to allow for elaboration of a portion of the compounds Of formula I or II. The selection, use, and removal of suitable protecting groups is well known and appreciated in the art (*Protecting Groups in Organic Synthesis*, Theodora Greene (Wiley-Interscience)).

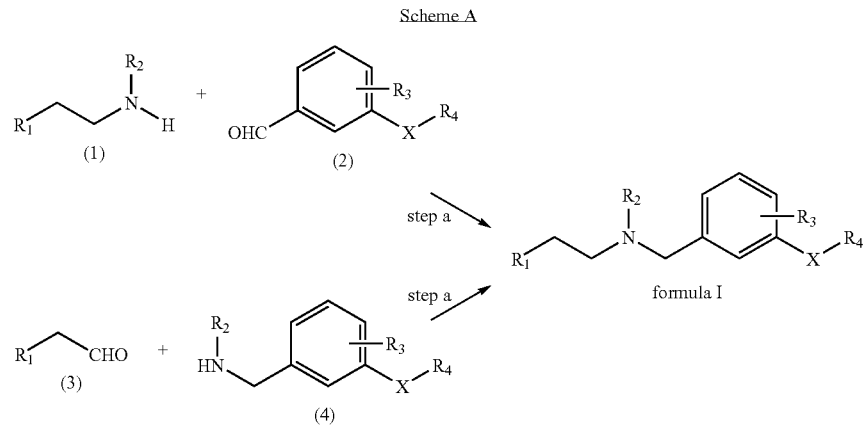

Scheme A depicts alternative methods for the preparation of compounds of formula I by reductive amination.

In one alternative of Scheme A, step a, an appropriate compound of formula (1) is contacted with an appropriate compound of formula (2) in a reductive amination reaction to give a compound of formula I. An appropriate compound of formula (1) is one in which $R_1$ and $R_2$ are as desired in the final product of formula I or give rise to groups desired in the final product of formula I. An appropriate compound of formula (2) is one in which X, $R_3$, and $R_4$ are as desired in the final product of formula I, or give rise to groups desired in the final product of formula I.

In another alternative of Scheme A, step a, an appropriate compound of formula (3) is contacted with an appropriate compound of formula (4) in a reductive amination reaction to give a compound of formula I. An appropriate compound of formula (3) is one in which $R_1$ and $R_2$ are as desired in the final product of formula I or give rise to groups desired in the final product of formula I. An appropriate compound of formula (4) is one in which X, $R_3$, and $R_4$ are as desired in the final product of formula I, or give rise to groups desired in the final product of formula I.

The reductive amination depicted in Scheme A, step a, can be carried out under a variety of conditions, such as by hydrogenation using a suitable catalyst or using a suitable reducing agent.

For example, an appropriate amine of formula (1) is contacted with an appropriate aldehyde of formula (2) (or alternately an appropriate amine of formula (4) and an appropriate aldehyde of formula (3)) and a suitable reducing agent to give a compound of formula I. The reaction is carried out in a suitable solvent, such as methanol, ethanol, tetrahydrofuran, or mixtures of methanol or ethanol and tetrahydrofuran, dichloromethane, and 1,2-dichloroethane. The reaction may be carried out in the presence of a drying agent, such as sodium sulfate, cupric sulfate, or molecular sieves. The reaction is carried out in the presence of from about 1 to 20 molar equivalents of a suitable reducing agent, such as, sodium borohydride, sodium cyanoborohydride, and sodium triacetoxyborohydride. It may be advantageous to allow Schiff base formation to proceed before addition of the suitable reducing agent. When sodium cyanoborohydride is used it may be advantageous to monitor and adjust the pH during the course of the reaction as is known in the art. The reaction is generally carried out at temperatures of from 0° C. to the refluxing temperature of the solvent. Generally, the reactions require 1 to 72 hours. The product can be isolated and purified by techniques well known in the art, such as filtration, extraction, evaporation, trituration, chromatography, and recrystallization.

Scheme A, optional step b, not shown, an acid addition salt of a compound of formula I is formed using a pharmaceutically-acceptable acid. The formation of acid addition salts is well known and appreciated in the art.

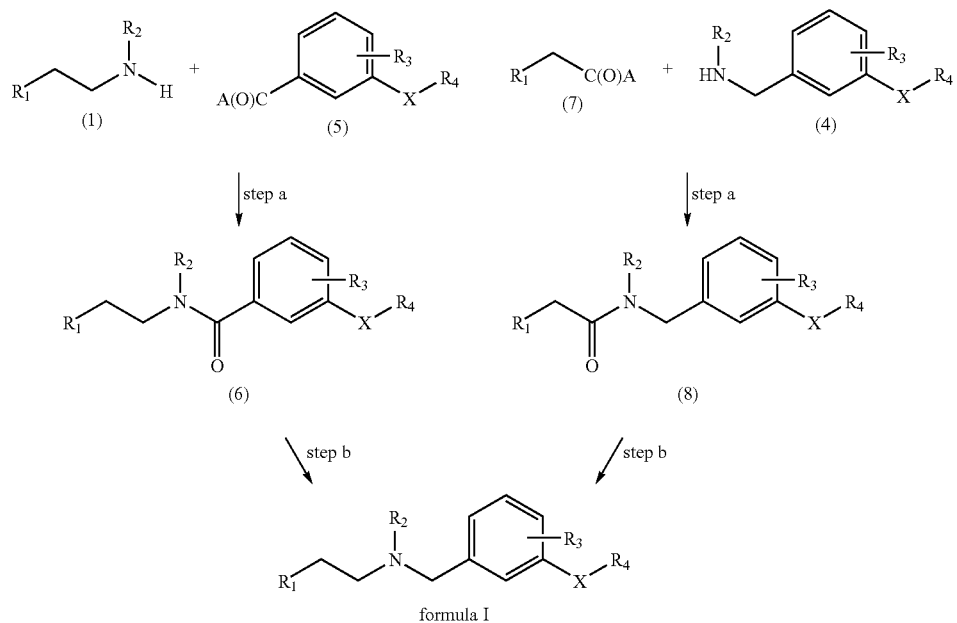

Scheme B depicts alternative methods for the preparation of compounds of formula I by formation and reduction of an amide.

In one alternative, Scheme B, step a, depicts contacting an appropriate compound of formula (1) with an appropriate compound of formula (5) in a amide forming reaction to give a compound of formula (6). An appropriate compound of formula (1) is as described in Scheme A. An appropriate compound of formula (5) is one in which A is an activating group, talking the form of an acid halide, activated ester, activated amide, or anhydride, and X, $R_3$, and $R_4$ are as desired in the final product of formula I, or give rise to groups desired in the final product of formula I.

In another alternative, Scheme B, step a, depicts contacting an appropriate compound of formula (7) with an appropriate compound of formula (4) in a amide forming reaction to give a compound of formula (8). An appropriate compound of formula (7) is one in which A is an activating group as described above and $R_1$ is as desired in the final product of formula I. An appropriate compound of formula (4) is as described in Scheme A. Appropriate compounds of formula (4) and (7) are generally available from commercial sources and can also be prepared by methods described herein and by methods described in the art.

The amide formation reaction depicted in Scheme B, step a, is readily accomplished by a number of methods readily available to the skilled person, including those which are conventionally conducted for peptide synthesis. Such methods can be carried out on the acid, acid halide, activated esters, activated amides, and anhydrides.

For example, well known coupling reagents such as a carbodiimides with or without the use of well known additives such as N-hydroxysuccinimide, 1-hydroxybenzotriazole, etc. can be used to facilitate amide formation. Such coupling reactions are typically use about 1 to 1.5 molar ratios of acid, amine, and coupling reagent and are conventionally conducted in an inert aprotic solvent such as pyridine, dimethylformamide, dichloromethane, chloroform, 1,2-dichloroethane, acetonitrile, tetrahydrofuran and the like. It may be advantageous to use a suitable base, such as triethylamine or N,N-diisopropylethylamine, in such coupling reactions. The reaction is preferably conducted at from about 0° C. to about 60° C. until reaction completion which typically occurs within 1 to about 48 hours. Upon reaction completion, the product can be isolated and purified by techniques well known in the art, such as filtration, extraction, evaporation, trituration, chromatography, and recrystallization.

Alternatively, for example, an acid halide can be employed in the reaction. It may be advantageous to use a suitable base to scavenge the acid generated during the reaction, suitable bases include, by way of example, triethylamine, N,N-diisopropylethylamine, N-methylmorpholine, pyridine, and the like. Typically, about 1 to 1.5 molar ratios of the acid halide and amine are used. The reaction can be carried out in a variety of inert aprotic solvents such as pyridine, dichloromethane, chloroform, 1,2-dichloroethane, tetrahydrofuran, and the like. The reaction is preferably conducted at from about 0° C. to about 60° C. until reaction completion which typically occurs within 1 to about 12 hours. Upon reaction completion, the product can be isolated and purified by techniques well known in the art, such as filtration, extraction, evaporation, trituration, chromatography, and recrystallization.

Alternatively, for example, an acid halide can be employed in the reaction under Schotten-Baumann conditions. Typically, under such conditions 1 to 10 molar equivalents of amine are used. Such couplings generally use a suitable base to scavenge the acid generated during the reaction, such as sodium hydroxide, potassium hydroxide, sodium carbonate, potassium carbonate, sodium bicarbonate, potassium bicarbonate, and the like. The reaction can be carried out in a variety of mixed solvent systems such as dichloromethane, chloroform, ethyl acetate, tetrahydrofuran and the like; and water. The reaction is preferably conducted at from about 0° C. to about 80° C. until reaction completion which typically occurs within 1 to about 6 hours. Upon reaction completion, the product can be isolated and purified by techniques well known in the art, such as filtration, extraction, evaporation, trituration, chromatography, and recrystallization.

Alternatively, for example, an anhydride (either symmetrical or mixed) can be employed in the reaction. Such anhydrides are formed by numerous methods known in art. Typically, about 1 to 1.5 molar equivalents of the anhydride and amine are used. It may be advantageous to use a suitable base to scavenge the acid generated during the reaction. Suitable bases include, by way of example, triethylamine, N,N-diisopropylethylamine, N-methylmorpholine, pyridine, sodium carbonate, potassium carbonate, sodium bicarbonate, and the like. The reaction can be carried out in a variety of solvents. The reaction is preferably conducted at from about 0° C. to about 60° C. until reaction completion which typically occurs within 1 to about 12 hours. Upon completion, the product can be isolated and purified by techniques well known in the art, such as filtration, extraction, evaporation, trituration, chromatography, and recrystallization.

Scheme B, steps b, depicts reduction of a compound of formula (6) or (8) to give a compound of formula I.

For example, a compound of formula (6) or (8) is contacted with a suitable reducing agent to give a compound of formula I. Suitable reducing agents are those which are capable of reducing an amide to an amine and include, borane reagents, such as borane dimethyl sulfide complex, hydride transfer reagents, such as aluminum hydride and lithium aluminum hydride, and the like. The reaction is carried out in a solvent, such as tetrahydrofuran or diethyl ether, typically using 1 to 10 equivalents of reducing agent. The reaction is generally conducted at from about 0° C. the refluxing temperature of the selected solvent and typically occurs within 1 to about 48 hours. The product can be isolated and purified by techniques well known in the art, such as quenching, filtration, extraction, evaporation, trituration, chromatography, and recrystallization.

Scheme B, as an optional step, not shown, an acid addition salt of a compound of formula I is formed using a pharmaceutically-acceptable acid. The formation of acid addition salts is well known and appreciated in the art.

In Schemes A and B, as an optional step, not shown, as will be appreciated by the skilled person, a compound of formula I in which $R_2$ is hydrogen can be alkylated to give a compound in which $R_2$ is not hydrogen. Methods for alkylating such secondary amines are will known in the art and discussed in Scheme C, step c, below.

In Schemes A and B, as will be appreciated by the skilled person, compounds of formula II are also prepared by the methods described in Schemes A and B using compounds of the formula (9) and (10), below:

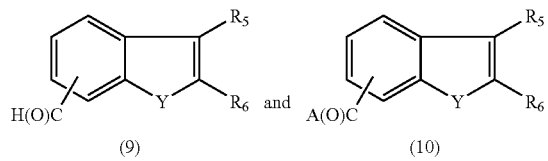

An appropriate compound of formula (9) is one in which Y, $R_5$ and $R_6$ are as desired in the final product of formula II and an appropriate compound of formula (10) is one in which A is an activating group, as described above, and Y, $R_5$ and $R_6$ are as desired in the final product of formula II.

Starting material for Schemes A and B are prepared in the Schemes below. In the Schemes below all substituents, unless otherwise indicated, are as previously defined, and all starting material and reagents are well known and appreciated in the art.

Scheme C describes methods for preparing compounds of formula (1).

Scheme C

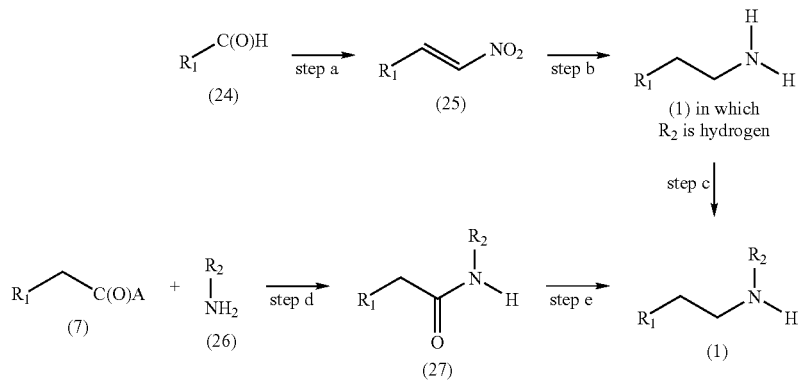

Scheme C, step a, depicts the reaction of an appropriate aldehyde of formula (24) and nitromethane to give the compound of formula (25). An appropriate aldehyde of formula (24) is one in which $R_1$ is as desired in the final product of formula I. The reaction of the anion of nitromethane with aldehydes to give nitro olefins is well known and appreciated in the art. Modern Synthetic Reactions, H. O. House (2nd ed. The Benjamin/Cummings Publishing Company 1972).

For example, an appropriate aldehyde of formula (24) is condensed with nitromethane to give the compound of formula (25). Typically the reaction is carried out in the presence of an excess of nitromethane. The reaction is performed in a suitable solvent, such as tetrahydrofuran, nitromethane, and dimethyl sulfoxide. The reaction is performed using from about 1.1 to about 3 molar equivalents of a suitable base, such as sodium bis(trimethylsilyl)amide, potassium t-butoxide, sodium hydride, sodium acetate, triethylamine, N,N-diisopropylethylamine, ammonium salts, such as ammonium acetate. The reaction is carried out at temperatures of from about $-20°$ C. to the reflux temperature of the selected solvent and generally require from 6 hours to 48 hours. The product of the coupling reaction can be isolated and purified using techniques well known in the art, including extraction, evaporation, chromatography and recrystallization.

Scheme C, step b, depicts the reduction of a compound of formula (25) to give a compound of formula (1) in which $R_2$ is hydrogen.

For example, an appropriate compound of formula (25) is hydrogenated over a suitable catalyst, such as Raney® nickel or a palladium catalyst. When Raney nickel is used, the reaction is carried out in a suitable solvent, such as ethanol, methanol, water, and mixtures thereof. It may be advantageous to carry out the hydrogenation under acidic conditions, for example, using hydrochloric or sulfuric acid. When a palladium catalyst is used palladium-on-carbon is preferred and the reaction is carried out in a suitable solvent, such as ethanol, methanol, tetrahydrofuran, water, and mixtures thereof. It may be advantageous to carry out the hydrogenation under acidic conditions, for example, using hydrochloric, trifluoroacetic acid, or sulfuric acid. The reaction is generally carried out at temperatures of from ambient temperature to 70° C. The reaction is carried out with hydrogen at pressures of from 15 psi to 120 psi in an apparatus designed for carrying out reactions under pressure, such as a Parr® hydrogenation apparatus. The product can be isolated by carefully removing the catalyst by filtration and evaporation. The product can be purified by extraction, evaporation, trituration, chromatography, and recrystallization.

Alternately, for example, an appropriate compound of formula (25) is contacted with a suitable reducing agent. Suitable reducing agents include hydride transfer reagents, such as aluminum hydride and lithium aluminum hydride, and the like. The reaction is carried out in a solvent, such as tetrahydrofuran or diethyl ether, typically using 1 to 10 equivalents of reducing agent. The reaction is generally conducted at from about 0° C. the refluxing temperature of the selected solvent and typically occurs within 1 to about 48 hours. The product can be isolated and purified by techniques well known in the art, such as quenching, filtration, extraction, evaporation, trituration, chromatography, and recrystallization.

Additionally, an appropriate compound of formula (25) can be reduced in two steps to a compound of formula (1). For example, the vinyl group of a compound of formula (25) can be reduced using reagents such as sodium borohydride. The reaction is typically carried out using an excess of borohydride in a solvent, such as methanol, ethanol, isopropanol, water, and the like. The intermediate 2-nitroethyl compound can be isolated and purified by techniques well known in the art, such as quenching, filtration, extraction, evaporation, trituration, chromatography, and recrystallization. The intermediate 2-nitroethyl compound can then be reduced using a variety of methods, such as the hydrogenation and hydride transfer reagents as discussed above. Also, the intermediate 2-nitroethyl compound can be reduced using metals such as zinc to give the desired amine of formula (1) in which $R_2$ is hydrogen.

Scheme C, step c, depicts the optional alkylation of a compound of formula (1) in which $R_2$ is hydrogen to give a compound of formula (1) in which $R_2$ is not hydrogen.

For example, a compound of formula (1) in which $R_2$ is hydrogen is contacted with a suitable alkylating agent. A suitable alkylating agent is one which transfers a group $R_2$ as is desired in the final product of formula I. Suitable alkylating agents include $C_1$-$C_3$ alkyl halides. The reaction is carried out in a suitable solvent, such as dioxane, tetrahydrofuran, tetrahydrofuran/water mixtures, or acetonitrile. The reaction is carried out in the presence of from 1.0 to 6.0 molar equivalents of a suitable base, such as sodium carbonate, sodium bicarbonate, potassium carbonate, potassium bicarbonate, triethylamine, or N,N-diisopropylethylamine. The reaction is generally carried out at temperatures of from $-78°$ C. to the refluxing temperature of the solvent. Generally, the reactions require 1 to 72 hours. The product can be isolated and purified by techniques well known in the art, such as extraction, evaporation, trituration, chromatography, and recrystallization.

Alternately, for example, a compound of formula (1) in which $R_2$ is hydrogen undergoes a reductive amination with an aldehyde or ketone which gives a compound of formula (1) in which $R_2$ is not hydrogen. Suitable aldehydes include formaldehyde, acetaldehyde, propionaldehyde, and acetone. The reaction is carried out as described in Scheme A, step a.

In another alternate, for example, a compound of formula (1) in which $R_2$ is hydrogen undergoes amide or carbamate formation followed by reduction to give a compound of formula (1) in which $R_2$ is not hydrogen. Suitable aldehydes include formaldehyde, acetaldehyde, propionaldehyde, and acetone. The reaction is carried out as described in Scheme A, step a.

Scheme C, steps d and e, depict an alternative approach to preparing the compounds of formula (1) via formation of an amide using an appropriate compound of formula (7) and an appropriate amine of formula (26) to give an amide of formula (27), followed by reduction to give a compound of formula (1). An appropriate compound of formula (7) is as described in Scheme B. An appropriate amine of formula (26) is one which gives $R_2$ as desired in final compound of formula I. The skilled person will recognize that many of the amides of formula (27) are commercially available and available in the art.

The amide formation and reduction in Scheme C are carried out as described in the Scheme B.

Scheme D describes methods for preparing compounds of formula (1) in which $R_1$ is optionally substituted indol-3-yl.

For example, an appropriate indole of formula (28) is contacted with about 1 to 2 molar equivalents of oxalyl chloride to give an intermediate keto-acid chloride. The reaction is carried out in a suitable solvent, such a diethyl ether or tetrahydrofuran. The reaction is generally carried out at temperatures of from 0° C. to 40° C. and generally require from 6 hours to 48 hours. The intermediate keto-acid chloride product can be isolated and purified using techniques well known in the art, including extraction, evaporation, chromatography and recrystallization. Generally, the intermediate keto-acid chloride product is used directly after isolation. The intermediate keto-acid chloride product is contacted with an appropriate amine, $R_2NH_2$, as defined above and using the procedures described above.

Scheme D, step b, depicts the reduction of a compound of formula (29) to give a compound of formula (1) in which $R_1$ is optionally substituted indol-3-yl.

For example, a compound of formula (29) is reduced using a suitable reducing reagent such as, lithium aluminum hydride to give a compound of formula (1) which $R_1$ is optionally substituted indol-3-yl. The reaction is carried out in a solvent, such as tetrahydrofuran or diethyl ether, typically using 1 to 12 molar equivalents of reducing agent. The reaction is generally conducted at from about 0° C. the refluxing temperature of the selected solvent and typically occurs within 12 to about 48 hours. The product can be isolated and purified by techniques well known in the art, such as quenching, filtration, extraction, evaporation, trituration, chromatography, and recrystallization.

In Scheme D, step c, an appropriate indole of formula (28) is formylated to give a compound of formula (30). An appropriate indole of formula (28) is as described in step a, above.

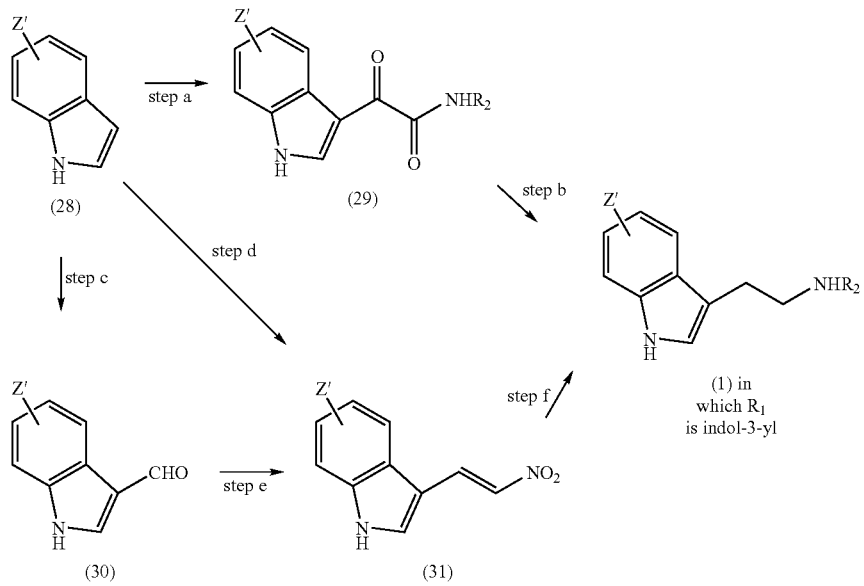

Scheme D

Scheme D, step a, depicts the two-step reaction of an appropriate indole of formula (28) with oxalyl chloride followed by an appropriate amine of formula (26), $R_2NH_2$ to give a compound of formula (29). An appropriate indole of formula (28) is one in which Z' represents optional substituents on the indole 2- and 4- to 7-positions as desired in the final product of formula I. An appropriate amine of formula (26) is as described in Scheme C, above.

For example, an appropriate indole of formula (28) is reacted with a suitable formyl transfer reagent, such as the Vilsmeier reagent formed from dimethylformamide. Generally, about 1 molar equivalent of formyl transfer reagent is used. The reaction is performed in a suitable solvent, such as benzene, dimethylformamide, tetrahydrofuran, or diethyl ether. The reaction is carried out at temperature of from about −70° C. to about 20° C. and generally require from 1 hours to 6 hours. The product of the reaction can be isolated and purified using techniques well known in the art. These techniques include extraction, evaporation, chromatography and recrystallization.

In Scheme D, step d, an appropriate indole of formula (28) is contacted with $(CH_3)_2N-CH=CH-NO_2$ to give a compound of formula (30). An appropriate indole of formula (28) is as described in step a, above.

For example, an appropriate indole of formula (28) is reacted with 1-dimethylamino-2-nitroethylene. Generally, about 1 equimolar amounts of reagents. The reaction is performed in a suitable solvent, such as trifluoroacetic acid or dichloromethane containing about 2 to 15 equivalents of trifluoroacetic acid. The reaction is carried out at temperature of from about −70° C. to about 20° C. and generally require from 1 hours to 24 hours. The product of the reaction can be isolated and purified using techniques well known in the art. These techniques include extraction, evaporation, chromatography and recrystallization.

Scheme D, steps e and f, depict an the reaction of an aldehyde of formula (30) to give a nitro olefin of formula (31) and the reduction of the nitro olefin to give a compound of formula (1) in which $R_1$ is optionally substituted indol-3-yl. These steps can be carried out using the methods described in Scheme C.

As will be appreciated by the skilled person, in steps not shown, the indole nitrogen of a compound of formula (1) can be substituted, as desired, using suitable amine protecting groups to give compounds in which $R_1$ is 1-substituted indol-3-yl. Also as will be appreciated by the skilled person, in steps described in Scheme C, $R_2$ groups which are not hydrogen can be introduced by various methods.

Scheme E describes methods for preparing compounds of formula (2) in which X is —O— or —S—.

formula I. Such acetal formation reactions are readily accomplished by methods well known in the art. (*Protecting Groups in Organic Synthesis*, Theodora Greene (Wiley-Interscience)).

For example, a compound formula (11) is contacted under acid catalysis with an appropriate alcohol, HOR. An appropriate alcohol is one which gives an acetal with is stable to the reaction in step b and can be removed in step c to give a compound of formula (2). Appropriate alcohols include methanol, ethanol, propanol, 1,3-propane diol, ethylene glycol, and the like.

In Scheme E, step b, an appropriate compound of formula (11), (12), or (14) is reacted with an $R_4$ group transfer reagent, as desired, to give a compound of formula (2), (13), or (15); respectively. Appropriate compounds of formula (11), (12), and (14) are ones in which X and $R_3$ are as desired in the final product of formula I. A variety of reagents that transfers an $R_4$ as desired in the final product are available and suitable for the reaction depicted in Scheme E. Such reagents include halopyridines, halopryidine N-oxides, allyl halides, $C_2$-$C_4$ alkanols, $C_2$-$C_4$ alkyl halides and sulfonates, fluorinated $C_2$-$C_4$ alkanols, fluorinated $C_2$-$C_4$ alkyl halides and sulfonates, optionally substituted phenyl having at least one fluoro or chloro atom, optionally substituted phenylsulfonyl halides or anhydrides, and optionally substituted benzyl halides.

For example, where the appropriate $R_4$ group transfer reagent is a halide, sulfonate, or anhydride, an appropriate compound of formula (11), (12), or (14) is coupled under basic conditions to give a compound of formula (2), (13), or (15); respectively. The reaction is performed in a suitable solvent, such as acetonitrile, dimethylformamide, dimethylacetamide, tetrahydrofuran, pyridine, and dimethyl sulfoxide. The reaction is carried out in the presence of from about

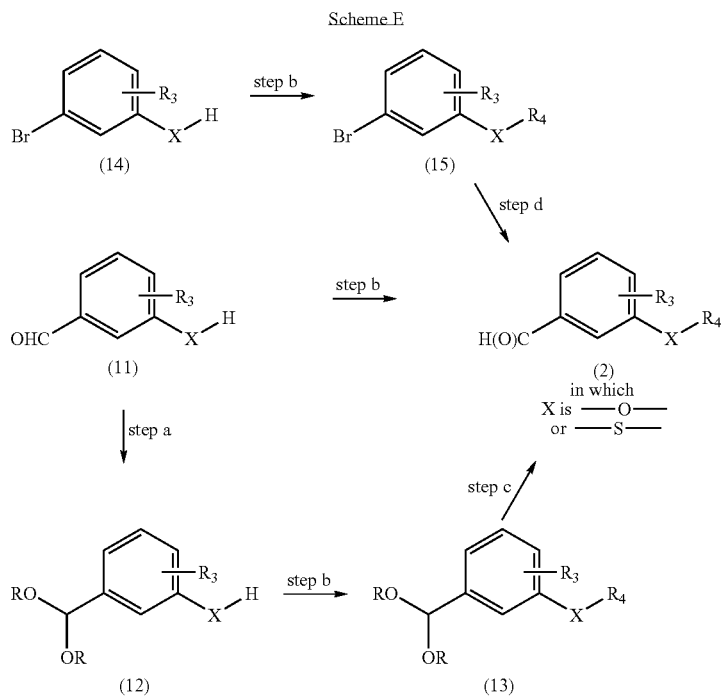

Scheme E, step a, depicts the formation of an acetal of an appropriate compound of formula (11) to give a compound of formula (12). An appropriate compound of formula (11) is one in which X and $R_3$ are as desired in the final compound of 1 to about 3 molar equivalents of a suitable base, such as potassium hydride, sodium hydroxide, sodium hydride, sodium carbonate, potassium carbonate, cesium carbonate, N,N-diisopropylethylamine, triethylamine, and the like. The reaction is carried out at temperature of from about −30° C. to about 100° C. and generally require from 6 hours to 48 hours. The product of the reaction can be isolated and purified using techniques well known in the art. These techniques include extraction, evaporation, chromatography and recrystallization.

Of course, when a halopyridine N-oxide is used the N-oxide is remove by reduction to give the $R_4$ as desired in the final product of formula I. Such reductions are readily accomplished by the skilled person, and include catalytic reduction over palladium catalysts using hydrogen or ammonium formate in a suitable solvent such as methanol, ethanol, water, and mixtures thereof.

Alternately, for example, where the appropriate $R_4$ group transfer reagent is an alkanol, the coupling can be carried out under Mitsunobu conditions which are well known in the art. The reaction is carried out in a suitable solvent, such as tetrahydrofuran and diethyl ether using a phosphine, such as triphenylphosphine or a resin bound phosphine and a dialkyl azodicarboxylate, such as diethyl azodicarboxylate, diisopropyl azodicarboxylate or di-t-butyl azodicarboxylate. The reaction is generally carried out at temperatures of from ambient temperatures to 60° C. The reaction generally requires from 1 hour to 12 hours. The product can be isolated by techniques well known in the art, such as extraction and evaporation. The product can then be purified by techniques well known in the art, such as distillation, chromatography, or recrystallization.

Scheme E, step c, depicts the deprotection of an acetal of formula (13) to give a compound of formula (2). Such deprotections are readily accomplished by methods well known in the art. (*Protecting Groups in Organic Synthesis*, Theodora Greene (Wiley-Interscience)).

For example, a compound formula (13) is contacted under acid under aqueous conditions to give a compound of formula (2).

In Scheme E, step d, a bromo compound of formula (15) is formylated to give a compound of formula (2).

For example, a compound of formula (15) is metalated by treatment with a metalation reagent such as butyl lithium. The reaction is performed in a suitable solvent, such as hexane, benzene, toluene, tetrahydrofuran or diethyl ether. The reaction is typically carried out in the presence of from about 1 to about 1.5 molar equivalents of a metalating reagent. The metalation reaction is carried out at temperature of from about −70° C. to about 20° C. and generally require from 1 hours to 6 hours. The metalated species is then treated with a formyl transfer reagent such as dimethylformamide or an alkyl chloroformate to give a compound of formula (2) or a alkoxycarbonyl compound which can be elaborated to an aldehyde as described herein. The product of the reaction can be isolated and purified using techniques well known in the art. These techniques include extraction, evaporation, chromatography and recrystallization.

Scheme F describes methods for preparing compounds of formula (2) from the versatile intermediate, compound (17), which readily prepared by acetal formation as described above.

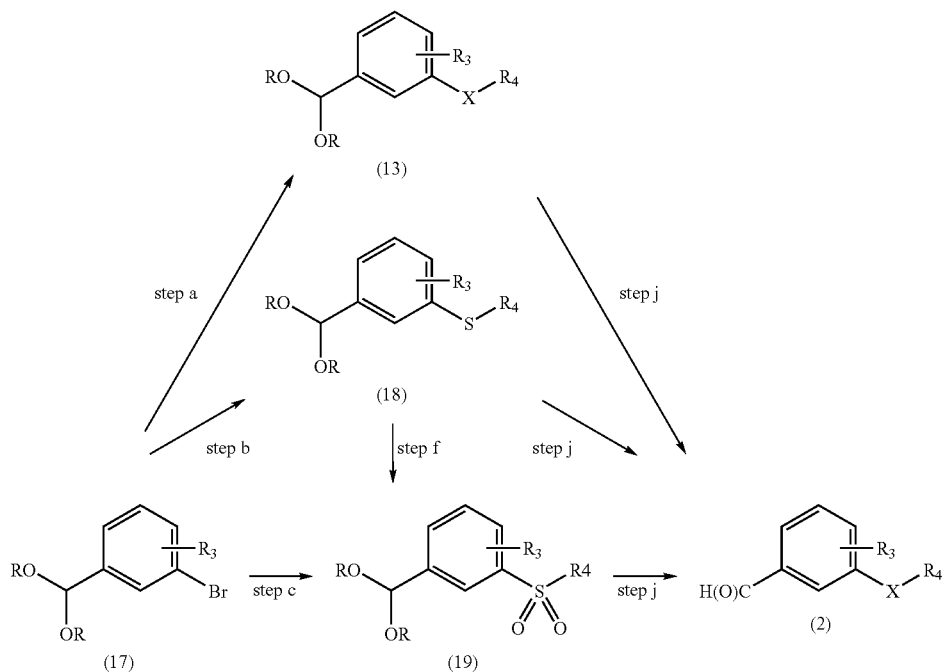

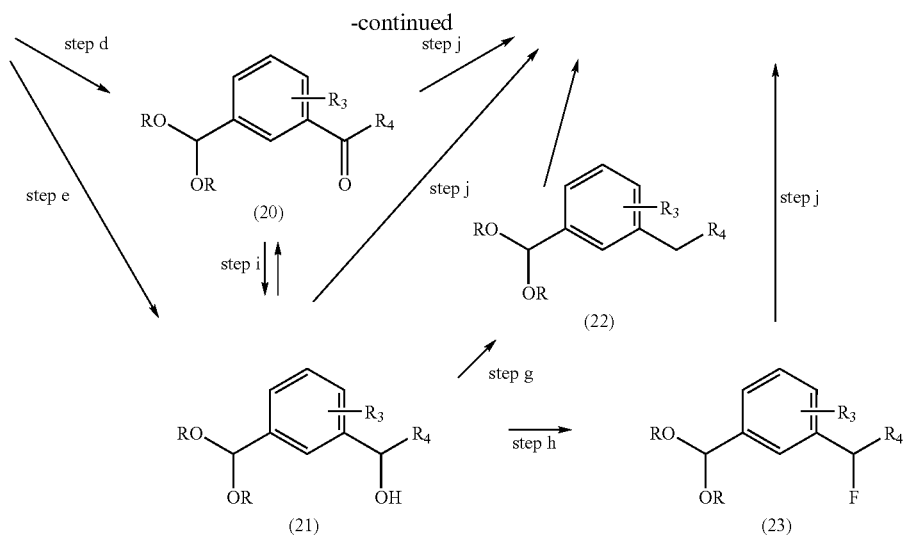

Scheme F, step a, depicts an aromatic displacement reaction of an appropriate compound of formula (17) and an appropriate alcohol ($R_4OH$) or an appropriate thiol ($R_4SH$) to give a compound of formula (13) in which X is —O— or —S— are defined above in Scheme E. An appropriate compound of formula (17) is one in which $R_3$ is as desired in the final product of formula I. In an appropriate alcohol ($R_4OH$) or an appropriate thiol ($R_4SH$), $R_4$ is as desired in the final product of formula I, and includes $C_2$-$C_4$ alkyl alcohols and thiols, fluorinated $C_2C_4$ alkyl alcohols and thiols, optionally substituted phenols and thiophenols, optionally substituted benzyl alcohols and thiols.

For example, an appropriate compound of formula (17) and an appropriate alcohol ($R_4OH$) or an appropriate thiol ($R_4SH$) are coupled give a compound of formula (13). The reaction is performed in a suitable solvent, such as dimethylformamide, dimethylacetamide, and dimethyl sulfoxide. The reaction is performed using from about 1.1 to about 3 molar equivalents of an appropriate alcohol or thiol. The reaction is carried out in the presence of from about 1 to about 6 molar equivalents of a suitable base, such as potassium hydride, sodium hydroxide, potassium carbonate, sodium carbonate, or sodium hydride. The coupling is performed using a suitable catalyst, such as copper salts. The reaction generally requires from 6 hours to 48 hours. The product of the coupling reaction can be isolated and purified using techniques well known in the art. These techniques include extraction, evaporation, chromatography and recrystallization.

Scheme F, steps b-e, depict a number of reactions of an appropriate compound of formula (17), after metalation as described in Scheme E, step d, to give compounds of formula (18)-(21), respectively. In these steps an appropriate compound of formula (17) is one in which $R_3$ is as desired in the final product of formula I and is not adversely affected by the metalation conditions of the reaction. Generally, these reactions are performed in the solvent used and at the temperature used to form the metalated species. The products of these reactions can be isolated and purified using techniques well known in the art, include quenching, extraction, evaporation, trituration, chromatography, and recrystallization.

For example, in Scheme F, step b, a metalated compound of formula (17) is contacted with an appropriate disulfide ($R_4S$—)$_2$, to give a compound of formula (18). An appropriate disulfide is one that gives $R_4$ as desired in the final product of formula I and gives rise to compounds in which X is —S—. Appropriate disulfides include $C_1$-$C_4$ alkyl disulfides, optionally substituted phenyl disulfides, and optionally substituted benzyl disulfides. The reaction is performed using from about 1 to about 2 molar equivalents of an appropriate disulfide. The reaction is typically carried out in the same solvent used for the metallation and at temperatures of about −78° C. to about 50° C. The reaction generally require from 12 hours to 48 hours.

For example, in Scheme F, step c, a metalated compound of formula (17) is contacted with an appropriate sulfonyl fluoride ($R_4SO_2F$) to give a compound of formula (19). An appropriate sulfonyl fluoride is one that transfers $R_4$ as desired in the final product of formula I and gives rise to compounds in which X is —$SO_2$—. Appropriate sulfonyl fluorides include an optionally substituted phenyl sulfonyl fluoride. The reaction is performed using from about 1 to about 3 molar equivalents of an appropriate sulfonyl fluoride. The reaction is typically carried out in the same solvent used for the metallation and at temperatures of about −78° C. to about 0° C. The reaction generally require from 2 hours to 12 hours.

For example, in Scheme F, step d, a metalated compound of formula (17) is contacted with an appropriate acid chloride ($R_4C(O)Cl$) to give a compound of formula (20). An appropriate acid chloride is one that transfers $R_4$ as desired in the final product of formula I and gives rise to compounds in which X is —C(O)—. Appropriate acid chlorides include $C_2$-$C_4$ alkyl acid chlorides, fluorinated $C_2$-$C_4$ alkyl acid chlorides, optionally substituted phenyl acid chlorides, optionally substituted benzyl acid chlorides, and optionally substituted 5 to 6 membered monocyclic aromatic heterocycle acid chlorides. The reaction is performed using from about 0.8 to about 1.2 molar equivalents of an appropriate acid chloride. The reaction is typically carried out in the same solvent used for the metallation and at temperatures of about −78° C. to about 50° C. The reaction generally require from 1 hours to 12 hours.

For example, in Scheme F, step e, a metalated compound of formula (17) is contacted with an appropriate aldehyde ($R_4C(O)H$) to give a compound of formula (21). An appropriate aldehyde is one that transfers $R_4$ as desired in the final product of formula I and gives rise to compounds in which X is —CH(OH)—. Appropriate aldehydes include $C_2$-$C_4$ alkyl aldehyde, fluorinated $C_2$-$C_4$ alkyl aldehyde, optionally substituted phenyl aldehyde, optionally substituted benzyl aldehyde, and optionally substituted 5 to 6 membered monocyclic aromatic heterocycle aldehyde. The reaction is performed using from about 1 to about 3 molar equivalents of an appropriate aldehyde. The reaction is typically carried out in the same solvent used for the metallation and at temperatures of about −50° C. to about 50° C. The reaction generally requires from 4 hours to 24 hours.

As will be appreciate by the skilled person, compounds of formula (18)-(21) can undergo a number of other transformations which are depicted in Scheme F, steps f-i, to give, ultimately, compounds of formula I having various groups at X. These transformations are trivial and well within the ability of the skilled person. These transformations include oxidation of sulfides (step f) which can be accomplished by peroxide, peracids, and other reagents known in the art; reduction of a benzyl alcohol (step g) which can be accomplished by a variety of reagents, such as triethylsilane/trifluoroacetic acid; halogenation of a benzyl alcohol to give fluoro (step h) using reagents such as DAST and fluorinating reagents; reduction of a ketone (step i) using various hydride transfer reagents or oxidation of a benzylic alcohol (step i) which can be accomplished by manganese dioxide or Swern conditions.

In Scheme F, step j, compounds of the formula (13) and (18)-(23) are deprotected to give an aldehyde of formula (2) as described in Scheme E, step c.

Scheme G describes methods for preparing compounds of formula (5).

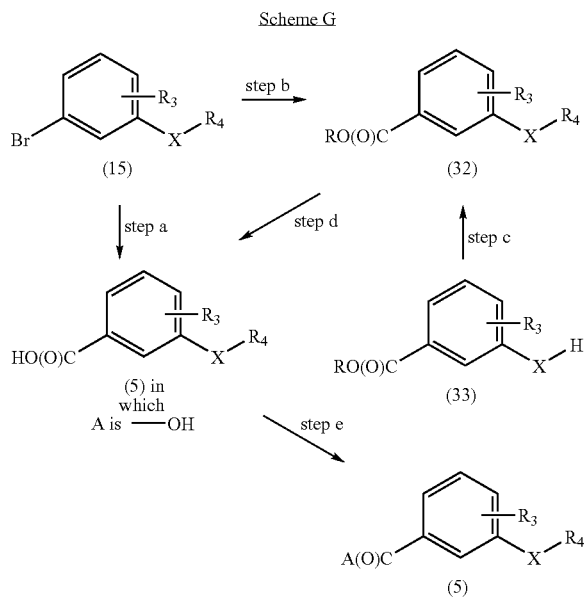

Scheme G

Scheme G, step a, a bromo compound of formula (15) is carboxylated to give a compound of formula (5) in which A is —OH.

For example, a compound of formula (15) is metalated as described in Scheme E, step d, and the metalated species is then treated with carbon dioxide to give a compound of formula (5) in which A is —OH. The product of the reaction can be isolated and purified using techniques well known in the art. These techniques include extraction, evaporation, chromatography and recrystallization.

Scheme G, step b, a bromo compound of formula (15) is alkoxyformylated using an appropriate chloroformate or carbonate to give a compound of formula (32). An appropriate chloroformate or carbonate is one that transfers an RO(O)C— group in which R is methyl, ethyl, or benzyl.

For example, a compound of formula (15) is metalated as described in Scheme E, step d, and the metalated species is then treated with about 1 to 3 molar equivalents of an appropriate chloroformate or carbonate. The reaction is typically carried out in the same solvent used for the metallation and at temperatures of about −78° C. to about 50° C. The reaction typically requires from 1 to 24 hours. The product of the reaction can be isolated and purified using techniques well known in the art. These techniques include extraction, evaporation, chromatography and recrystallization.

In Scheme G, step c, an appropriate compound of formula (33) is reacted with an $R_4$ group transfer reagent, as desired, to give a compound of formula (32). An appropriate compound of formula (33) is one in which X and $R_3$ are as desired in the final product of formula I. Reagents that transfers an $R_4$ are as described in Scheme E.

For example, where the appropriate $R_4$ group transfer reagent is a halide or anhydride, an appropriate compound of formula (34) is coupled under basic conditions with to give a compound of formula (33). The reaction is performed in a suitable solvent, such as dimethylformamide, tetrahydrofuran, or pyridine. The reaction is typically carried out in the presence of from about 1 to about 3 molar equivalents of a suitable base, such as sodium carbonate, potassium carbonate, cesium carbonate, N,N-diisopropylethylamine, triethylamine, and the like. The reaction is carried out at temperature of from about −30° C. to about 100° C. and generally require from 6 hours to 48 hours. The product of the reaction can be isolated and purified using techniques well known in the art. These techniques include extraction, evaporation, chromatography and recrystallization.

Alternately, for example, where the appropriate $R_4$ group transfer reagent is an alkanol, the coupling can be carried out under Mitsunobu conditions which are well known in the art and described in Scheme E.

Scheme G, step d, an ester of formula (32) is deprotected to give a compound of formula (5) in which A is —OH. Such deprotections are readily accomplished by methods well known in the art. (*Protecting Groups in Organic Synthesis*, Theodora Greene (Wiley-Interscience)).

Scheme G, step e, a compound of formula (5) in which A is —OH is converted to a compound of formula (5) in which A is an activating group, such as acid halide, activated ester, activated amide, or anhydride. The formation of such activated intermediates is well known and appreciated in the art.

For example, an acid halide can be prepared by a variety of reagent such as oxalyl chloride, oxalyl bromide, thionyl chloride, thionyl bromide, phosphorous oxychloride, phosphorous trichloride, and phosphorous pentachloride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid; an activated ester, such as phenol ester, p-nitrophenol ester, N-hydroxysuccinimide ester, N-hydroxyphthalimide ester, 1-hydroxybenzotriazole ester; or activated amide, such as imidazole, dimethylpyrazole, triazole; are prepared by method which are well known and appreciated in the art. Such activated intermediates may be prepared and used directly or are prepared and isolated before use in the schemes above.

Scheme H describes methods for preparing compounds of formula (4).

Scheme H

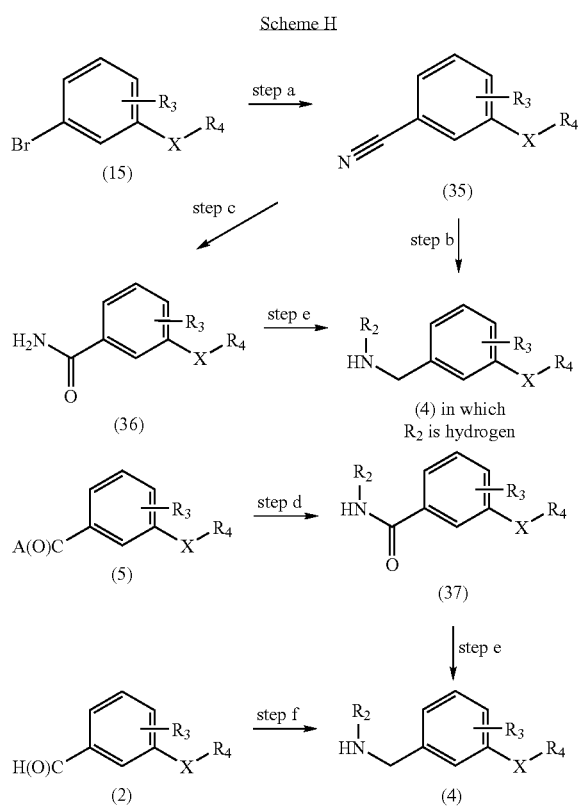

Scheme H, step a, a bromo compound of formula (15) is converted to a nitrile of formula (35).

For example, a compound of formula (15) is treated with copper (I) cyanide to give a compound of formula (35). The reaction is performed in a suitable solvent, such as dimethylformamide. The reaction is typically carried out in the presence of from about 1 to about 3 molar equivalents of copper (I) cyanide. The reaction is carried out at temperature of from about ambient temperature to about 100° C. and generally require from 6 hours to 48 hours. The product of the reaction can be isolated and purified using techniques well known in the art. These techniques include extraction, evaporation, chromatography and recrystallization.

Scheme H, step b, a nitrile compound of formula (35) reduced to give a compound formula (4) in which $R_2$ is hydrogen.

For example, a nitrile compound of formula (35) is contacted with sodium borohydride in the presence of cobalt chloride. The reaction is carried out in a suitable solvent, such as methanol, or ethanol. The reaction is generally carried out at temperatures of from 0° C. to 50° C. Generally, the reactions require 1 to 72 hours. The product can be isolated and purified by techniques well known in the art, such as extraction with aqueous acid, evaporation, trituration, chromatography, and recrystallization.

Alternately, for example, a nitrile compound of formula (35) is hydrogenated over a suitable catalyst, such as Raney® nickel. The reaction is carried out in a suitable solvent, when Raney® nickel is used as the catalyst, suitable solvents will generally contain ammonia, such as ethanol/ammonium hydroxide. The reaction is generally carried out at temperatures of from ambient temperature to 50° C. The reaction is carried out at pressures of from 15 psi (103 kPa) to 120 psi (827 kPa) in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

Scheme H, step c, a nitrile compound of formula (35) is converted to a amide of formula (36).

For example, a compound of formula (35) is treated with acid or base under hydrolysis conditions to give a compound of formula (36). The reaction is performed in a suitable solvent, such as ethanol, isopropanol, dimethylsulfoxide, each containing water. The hydrolysis of an aromatic nitrile to an amide is well known and appreciated in the art. The product of the reaction can be isolated and purified using techniques well known in the art. These techniques include extraction, evaporation, chromatography and recrystallization.

Scheme H, step d, depicts formation of an amide of formula (37) by reacting a compound of formula (5) and an appropriate amine of formula $H_2NR_2$ in a amide forming reaction. An appropriate amine of formula $H_2NR_2$ is one which gives $R_2$ as desired in the final product of formula I. Suitable methods of forming amides are well known in the art and are described in Scheme B, above.

Scheme H, step e, a amide compound of formula (36) or (37) is reduced to a compound of formula (4). Such reductions of amides are readily carried out as described in Scheme B, above, and as known in the art.

Scheme H, step f, a compound of formula (2) and an appropriate amine of formula $H_2NR_2$ undergo reductive amination to give a compound of formula (4). Such reductive aminations are readily carried out as described in Scheme B, above, and by other methods known in the art.

As will be appreciated by the skilled person, the compounds of formula II are readily prepared by methods analogous to those described above.

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "N" refers to normal or normality; "M" refers to molar or molarity; "mmol" refers to millimole or millimoles; "g" refers to gram or grams; "mL" refers milliliter or milliliters; "mp" refers to melting point; "brine" refers to a saturated aqueous sodium chloride solution; etc. In the $^1H$ NMR, all chemical shifts are given in δ, unless otherwise indicated.

Example 1

2-(3-(4-Fluorophenoxy)phenyl)-(1,3)dioxolane

Combine 4-fluorophenol (3.0 g, 227.8 mmol), 2-(3-bromophenyl)-1,3-dioxolane (5.0 ml, 33.3 mmol), potassium carbonate (anhydrous, 8.0 g, 55.6 mmol), and dry pyridine (50 ml). Heat to 90° C. and add copper oxide (5.5 g, 69.5 mmol). Heat at reflux. After 24 hours, cool to room temperature, dilute with dichloromethane, and filter. Concentrate the filtrate in vacuum to give a yellow oil. Chromatograph the oil on silica gel eluting with 95:5 hexane:EtOAc to give the title compound.

By the method of Example 1 the following compounds were prepared: a) 2-(3-(2-Fluorophenoxy)phenyl)(1,3)dioxolane;

b) 2-(3-(3-Fluorophenoxy)phenyl)-(1,3)dioxolane;

c) 2-(3-(Naphth-2-yloxy)phenyl)-(1,3)dioxolane;

d) 2-(3-(Naphth-1-yloxy)phenyl)-(1,3)dioxolane;
e) 2-(3-(Pyrid-3-yloxy)phenyl)-(1,3)dioxolane;
f) 3-(Pyridin-3-yloxy)benzaldehyde;
g) 3-(Pyrimidin-5-yloxy)benzaldehyde; and
h) 3 (Pyridin-4-yloxy)benzaldehyde.

Example 2

3-[1,3]-Dioxolan-2-ylphenyl)phenylamine

Combine 2-(3-bromophenyl)-1,3-dioxolane (0.7 ml, 4.3 mmol), aniline (0.4 ml, 4.7 mmol), sodium t-butoxide (0.6 g, 6.0 mmol), BINAP (10.0 mg, 0.03 mol), $Pd_2(dba)_3$ (30.0 mg, 0.01 mmol) and toluene (20 ml). Heat at 80° C. After 18 hours, cool to room temperature, dilute with ether (40 ml), filter, and concentrate to give a residue. Chromatograph the residue on silica gel eluting with 9:1 hexane:EtOAc to give the title compound.
By the method of Example 2 the following compounds were prepared: a) Benzyl-(3-[1,3]dioxolan-2-ylphenyl)-amine;
b) (3-[1,3]Dioxolan-2-ylphenyl)-pyridin-3-ylamine;
c) (3-[1,3]Dioxolan-2-ylphenyl)-pyridin-4-ylamine; and
d) (3-[1,3]Dioxolan-2-ylphenyl)-pyridin-2-ylamine.

Example 3

2-(3-Phenylsulfanylphenyl)[1,3]-dioxolane

Combine 2-3-bromophenyl)-1,3-dioxolane (3.0 ml, 20.0 mmol) and tetrahydrofuran (100 ml). Cool to about −78° C. Add dropwise a solution of n-butyllithium, 1.6 M solution in hexane (13.4 ml, 21.0 mmol). After 10 minutes, add phenyl disulfide (4.3 g, 20.0 mmol) as a solution in tetrahydrofuran (50 ml). After 1 hour, warm to room temperature over 1 hour then quenched with water (150 ml) and extract with ether. Extract the combined organic layers sequentially with distilled water and brine and then dry ($Na_2SO_4$), filter, and concentrate to give a residue. Chromatograph the residue eluting with 9:1 hexane:EtOAc gives the title compound.
By the method of Example 3 the following compounds were prepared: a) 2-(3-p-Tolylsulfanylphenyl)-[1,3]-dioxolane.

Example 4

2-(3-Benzenesulfonylphenyl)-[1,3]-dioxolane

Combine 2-(3-phenylsulfanylphenyl)-[1,3]-dioxolane (1.0 g, 3.6 mmol) and dichloromethane (15 ml). Cool to about −78° C. Add a slurry of m-chloroperbenzoic acid (2.3 g, 7.2 mmol) in dichloromethane (10 ml). After 30 minutes, warm to room temperature then add a solution 1N of sodium thiosulfate (20 ml). After 15 minutes, add a solution of saturated sodium bicarbonate. Separate the organic layer and extract the aqueous layer with dichloromethane, combine the organic layers and wash sequentially with distilled water and brine and then dry ($Na_2SO_4$), filter, and concentrate to give a residue. Chromatograph the residue eluting with EtOAc to give the title compound.
By the method of Example 4 the following compounds were prepared: a) 2-(3-(Toluene-4-sulfonyl)-phenyl)-[1,3]-dioxolane.

Example 5

(3-[1,3]Dioxolan-2-ylphenyl)phenylmethanol

Combine 2-(3-bromophenyl)-1,3-dioxolane (10.0 ml, 66.0 mmol) and tetrahydrofuran (100 ml) and cool to about −78° C. Add dropwise a solution of n-butyllithium, 1.6 M solution in hexane (44.0 ml, 66.0 mmol). After 10 min, add a solution of benzaldehyde (7.6 ml, 66.0 mmol) in tetrahydrofuran (50 ml) via cannula. After 1 hour, warm to room temperature. After 18 hours, quench into water and extract with dichloromethane. Combine the organic layers and wash sequentially with distilled water and brine and then dry ($Na_2SO_4$), filter, and concentrate to give a residue. Chromatograph the residue eluting with 7:3 hexane:EtOAc to give the title compound.

Example 6

(3-[1,3]Dioxolan-2-ylphenyl)phenylmethanone

Combine (3-[1,3]dioxolan-2-ylphenyl)phenyl-methanol (5.0 g, 18.5 mmol) and 18-crown-6 (160 mg, 0.6 mmol) in dichloromethane. Add potassium permanganate (8.8 g, 55.5 mmol). Heat to about 40° C. After 4 hours, cool to room temperature add water and sodium hydrogensulfite (6.0 g). Basify with a solution of 1N sodium hydroxide (about 60 ml) and extract with dichloromethane. Combine the organic layers and wash sequentially with distilled water and brine and then dry ($Na_2SO_4$), filter, and concentrate to give a residue. Chromatograph the residue eluting with EtOAc to give the title compound.

Example 7

3-Benzylbenzaldehyde

Combine (3-[1,3]dioxolan-2-ylphenyl)-phenyl-methanol (2.3 g, 8.7 mmol) and sodium iodide (5.3 g, 35.0 mmol) in acetonitrile (25 ml). Add dichloromethylsilane (2.1 ml, 17.4 mmol) via syringe. After 10 min, dilute with EtOAc and wash with water, saturated sodium bicarbonate, 10% sodium thiosulfate, and then brine. Dry the organic layers ($Na_2SO_4$), filter, and concentrate to give a residue. Chromatograph the residue eluting with 9:1 hexane:EtOAc to give the title compound.

Example 8

2-(3-(α-Fluorobenzyl)phenyl)-[1,3]-dioxolane

Combine (3-[1,3]-dioxolan-2-ylphenyl)phenylmethanol (2.3 g, 8.9 mmol) and dichloromethane (50 ml). Cool to about −78° C. Add dropwise a solution of (diethylamino)sulfur trifluoride (1.7 ml, 12.9 mmol). After 10 minutes, quench with water and extract with dichloromethane. Combine the organic layers and wash sequentially with distilled water and brine and then dry ($Na_2SO_4$), filter, and concentrate to give a residue. Chromatograph the residue eluting with 7:3 hexane: EtOAc to give the title compound.

Example 9

3-Nitrodibenzofuran

Combine dibenzofurane (20.0 g, 0.11 mol) and acetic acid (80 ml). Heat to 65° C. Add 98% nitric acid (20.0 g, 11.8 mol). After 3 hours, cool to room temperature to give a solid. Collect the solid by filtration, rinse with water, and dry to give the title compound.

Example 10

N-Dibenzofuran-3-ylamine

Combine 3-nitrodibenzofuran (22.0 g, 0.1 mol) and Raney nickel (2.75 g), and ethanol (365 ml) and hydrogenate at room temperature and 40 psi (276 kPa). After 18 hours, filter and concentrate the filtrate to residue. Chromatograph the residue eluting with 9:1 hexane:EtOAc to give the title compound.

Example 11

3-Bromodibenzofuran

Combine N-dibenzofuran-3-ylamine (2.0 g, 10.8 mmol), water (20 ml), and conc. hydrobromic acid (6 ml). Cool to 0° C. Add a solution of sodium nitrite (0.7 g, 10.8 mmol) in water (16 ml). After 15 minutes add the mixture above to a mixture of copper bromide (1.7 g, 12.3 mmol) in water (9.2 ml) and hydrobromic acid (4 ml). Warm to ambient temperature. After 18 hours, add water and extract with dichloromethane. Combine the organic layers and wash sequentially with distilled water and brine and then dry ($Na_2SO_4$), filter, and concentrate to give a residue. Chromatograph the residue eluting with 8:2 hexane:EtOAc to give the title compound.

Example 12

Dibenzofuran-3-carbaldehyde

Combine 3-bromodibenzofuraan (0.5 g, 2.0 mmol) and tetrahydrofuran (30 ml). Cool to about −78° C. Add a solution of t-butyllithium, 1.6 M solution in hexane (2.2 ml, 3.0 mmol), then warm to about 0° C. for 10 min. Cool to about −78° C. and add dimethylformamide (0.5 ml, 5.9 mmol). Warm to room temperature, quench with water, and extract with dichloromethane. Combine the organic layers and wash sequentially with distilled water and brine and then dry ($Na_2SO_4$), filter, and concentrate to give a residue. Chromatograph the residue eluting with 8:2 hexane:EtOAc to give the title compound.

Example 13

3-(Thiazol-2-yloxy)benzaldehyde

In a sealed tube, combine 2-bromo-thiazole (2.0 ml, 22.2 mmol), 3-hydroxy-benzaldehyde (1.8 g, 15.0 mmol) and potassium carbonate (2.1 g, 15.0 mmol) in dimethylformamide (20 ml). Heat to 100° C. After 48 hours, cool, pour into water (150 ml), and extract with ether. Combine the organic layers and wash sequentially with distilled water and brine and then dry, ($Na_2SO_4$), filter, and concentrate to give a residue. Chromatograph the residue eluting with 9:1 hexane:EtOAc to give the title compound.

Example 14

6-Bromo-1H-indole

Combine 4-bromo-2-nitrotoluene (5.0 g, 23.1 mmol), dimethylformamide (50 ml), DMF-dimethylacetal (9.0 ml, 69.4 mmol), and pyrrolidine (2.0 ml, 23.1 mmol). Heat to 110° C. After 3 hours, cool to room temperature, dilute with ether, and wash with water. Combine the organic layers, and concentrate to give a residue. Combine the residue and 80% aq. acetic acid (120 ml) and heat at 75° C. Add zinc dust (13.1 g, 200.5 mmol) portionwise. Heat to 85° C. After 2 hours, cool and filter. Dilute the filtrate with ether, wash with water dry (Na2SO4), and concentrate to give a residue. Chromatograph the residue eluting with 9:1 hexane:EtOAc to give the title compound.

By the method of Example 14 the following compounds were prepared: 4-Bromo-1H-indole.

Example 15

1H-Indole-6-carbaldehyde

Combine hexane washed potassium hydride (1.3 g, 10.7 mmol) and ether (20 ml). Cool to about 0° C. and add a solution of 6-bromo-1H-indole (2.1 g, 10.7 mmol) in ether (5 ml). After 15 min, cool to about −78° C. and add a solution of t-butyllithium, 1.4 M solution in hexane (14.0 ml, 10.7 mmol). After 10 min, add dimethylformamide (1.7 ml, 20.0 mmol) in ether (5 ml). Slowly, warm to room temperature and then pour into a ice cold solution of 1M phosphoric acid and extract with EtOAc. Combine the organic layers and wash sequentially with distilled water and brine and then dry ($Na_2SO_4$), filter, and concentrated to give a residue. Chromatograph the residue eluting with 9:1 hexane:EtOAc to give the title compound.

By the method of Example 15 the following compounds were prepared; 1H-Indole-4-carbaldehyde.

Example 16

1-Phenyl-1H-indole-6-carbaldehyde

Combine in a sealed tube 1H-indole-6-carbaldehyde 0.9 g, 6.2 mmol), copper(I) trifluoromethanesulfate-complex (0.2 g, 0.3 mmol), phenanthroline (1.3 g, 6.2 mmol), transdibenzylidenacetone (0.1 g, 0.3 mmol), cesium carbonate (2.6 g, 7.9 mmol) and iodobenzene (1.6 ml, 14.3 mmol) in xylene (40 ml). Heat at about 110° C. After 24 hours, cool to room temperature, dilute with dichloromethane and saturated ammonium chloride. Separate the layer and Extract the aqueous layer with dichloromethane. Combine the organic layers and wash sequentially with distilled water and brine and then dry ($Na_2SO_4$), filter, and concentrated to give a residue. Chromatograph the residue eluting with 8:2 hexane:EtOAc to give the title compound.

By the method of Example 16 the following compounds were prepared: 1-Phenyl-1H-indole-4-carbaldehyde.

Example 17

3-Phenylsulfanylbenzaldehyde

Combine 2-(3-phenylsulfanylphenyl)-[1,3]-dioxolane (0.3 g, 1.1 mmol) and acetonitrile (8.0 ml) add a solution of hydrochloric acid (1N, 2.0 ml). After 18 hours, concentrate in vacuum to remove most of the acetonitrile, dilute with water and extract with ether. Combine the organic extracts and wash once with saturated sodium bicarbonate, then with brine. Dry ($Na_2SO_4$) the organics, filter, and concentrated to give the title compound.

By the method of Example 17 the following compounds were prepared: a) 3-Benzenesulfonylbenzaldehyde;
  b) 3-p-Tolylsulfanylbenzaldehyde;
  c) 3-(p-Tosyl)benzaldehyde;
  d) 3-Benzylaminobenzaldehyde;
  e) 3-Phenylaminobenzaldehyde;
  f) 3-Benzoylbenzaldehyde;

g) 3-(α-Fluorobenzyl)benzaldehyde;
h) 3-(4-Fluorophenoxy)benzaldehyde;
i) 3-(2-Fluorophenoxy)benzaldehyde;
j) 3-(3-Fluorophenoxy)benzaldehyde;
k) 3-(Naphth-2-yloxy)benzaldehyde;
l) 3-(Naphth-1-yloxy)benzaldehyde;
m) 3-(Pyridin-3-ylamino)benzaldehyde;
n) 3-(Pyridin-4-ylamino)benzaldehyde;
o) 3-(Pyridin-2-ylamino)benzaldehyde; and
p) 3-(Pyridin-2-yloxy)benzaldehyde.

Example 18

2-Naphth-2-ylethylamine

Combine naphth-2-ylacetonitrile (1.0 g, 6.0 mmol) and nickel (II) chloride hexahydrate (0.7 g, 3.0 mmol) and tetrahydrofuran (30 ml). Add dropwise borane-tetrahydrofuran complex, 1M solution in tetrahydrofuran (24.0 ml, 24.0 mmol). After 1 hour, evaporate to give a residue. Chromatograph on silica gel eluting with 8:2 EtOAc:MeOH+2% $NH_4OH$) to give the title compound.

By the method of Example 18 the following compounds were prepared: 2-Naphth-1-ylethylamine.

Example 19

5-Methanesulfonyltryptamine

Combine 2-(3-Chloropropyl)-(1,3)-dioxolane (6.69 g, 44.5 mmol), (4-methanesulfonylphenyl) hydrazine hydrochloride (9.92 g, 44.5 mmol), and $Na_2HPO_4$ (1.58 g, 11.1 mmol) in 300 ml of methanol/water (1:1). Heat to reflux. After 4.5 hours, cool to ambient temperature, then evaporate to residue. Dissolve the residue in 1 N NaOH and extract with dichloromethane. Combine the organic extracts, wash with brine, dry ($Na_2SO_4$), filter, then concentrate to residue. Chromatograph the residue on silica gel eluting with dichloromethane/2N $NH_3$(methanol) (84/16) to give the title compound as a light brown solid: mp 134-138° C., MS (ACPI): m/e 239.1 (M+1). Analysis for $C_{11}H_{14}N_2O_2S$: Calcd: C, 55.44; H, 5.92; N, 11.76. found: C, 55.33; H, 5.97; N, 11.48.

Example 20

N-t-Butoxycarbonyl-2-(6-chloro-1H-indol-3-yl)ethylamine

Combine di-tert-butyl dicarbonate (1.2 g, 5.34 mmol), 6-chlorotryptamine (866.4 mg, 4.45 mmol) d and $NaHCO_3$ (598.2 mg) in dioxane (50 ml). Stir at ambient temperature. After 15 hours, evaporate to residue, partition the residue between water and dichloromethane. Separate the layer and extract the aqueous layer with dichloromethane. Combine the organic extracts, wash with brine, dry ($Na_2SO_4$), filter and then evaporated to give the title compound as a light yellow oil.

Example 21A

N-Methyl-2-(6-chloro-1H-indol-3-yl)ethylamine

Combine N-t-butoxycarbonyl-2-(6-chloro-1H-indol-3-yl) ethylamine (1.3 g, 4.41 mmol) and dry THF (20 ml) and add dropwise to an ice bath cooled suspension of $LiAlH_4$ (1.0 g, 26.5 mmol) in dry THF (30 ml). Heat to reflux. After 2 hours, cool to, ambient temperature and stir. After 15 hours, quench with saturated $NaSO_4$ (100 ml/mol), stir for 1 hour at ambient temperature, then filter under vacuum. Wash precipitate with THF and evaporated filtrate and washes to residue. Chromatograph the residue on silica gel eluting with dichloromethane/2N $NH_3$(methanol) (84/16) to give the title compound: MS (ACPI): m/e 209.0 (M+1).

Example 21B 5-(4-Fluorophenyl)-1H-indole

Combine 5-bromoindole (5.00 g, 25.50 mmol) and $Pd(Ph_3P)_4$ (1.47 g, 1.28 mmol) in toluene (510 ml). After 30 minutes, add a solution of 4-fluorobenzeneboronic acid (5.35 g, 38.26 mmol) in ethanol (153 ml) then add saturated $NaHCO_3$ (255 ml). Heat to reflux. After 4 hours, cool to ambient temperature, pour into saturated NaCl (250 ml), and separate the organic layer. Extract the aqueous layer with ethyl acetate. Combine the organic extracts, wash with brine, dried, then evaporate to residue. Chromatograph the residue on silica gel eluting with ethyl acetate/hexanes (10/90) to give the title compound: mp 84-89° C. MS (ACPI): m/e 212.0 (M+1). Analysis for $C_{14}H_{10}FN$: Calcd: C, 79.60; H, 4.77; N, 6.63. found: C, 79.33; H, 4.92; N, 6.64.

By the method of Example 21 the following compounds were prepared: a) 5-Phenyl-1H-indole: mp 71-74° C. MS (ACPI): m/e 194.0 (M+1). Analysis for $C_{14}H_{11}N$: Calcd: C, 87.01; H, 5.74; N, 7.25. found: C, 86.67; H, 5.82; N, 7.31.

b) 4-Phenylphenethylamine hydrochloride: (Exception-Chromatograph the residue on silica gel using dichloromethane/2N $NH_3$(methanol) (90/10) to give the final product. The HCl salt was prepared in ethyl acetate: MS (ACPI): m/e 198.1 (M+1). Analysis for $C_{14}H_{16}ClN$: Calcd: C, 71.94; H, 6.90; N, 5.99. found: C, 71.66; H, 6.90; N, 5.94.

Example 22

7-Cyano-1H-indole

Combine 7-bromoindole (4.72 g, 24.0 mmol) and copper cyanide (4.30 g, 48.1 mmol) in 1-methyl-2-pyrrolidine (40 mL). Heat to 200° C. After 2.5 hours, cool to room temperature, add water-ethyl acetate (200 mL, 1/1) to give a solid. Filter through the celite, extract the filtrate with ethyl acetate, combine the organic layers, wash with brine, dry over $Na_2SO_4$, filter and evaporate in vacuo to give a residue. Chromatograph the residue on silica gel eluting with hexanes:ethyl acetate (10:1) to give (1.87 g) of the title compound as a yellow solid: $^1$H NMR (300 MHz, DMSO-$d_6$)) 6.64-6.66 (m, 1H), 7.17 (t, 1H, J=7.6 Hz), 7.51-7.53 (m, 1H), 7.60-7.62 (m, 1H), 7.94 (d, 1H, J=8.0H), 12.03 (br, 1H).

Example 23

3-Formyl-5-cyano-1H-indole

Add phosphorous oxychloride (11.76 g, 76.67 mmol) dropwise to DMF (24.3 ml) wile maintaining the temperature at less than 10° C. Warm to ambient temperature and stir for 15 minutes at ambient temperature. Add dropwise 5-cyanoindole (10.00 g, 70.34 mmol) as a solution in DMF (30 ml) while keeping the temperature below 35°. After 1 hour, pour the reaction mixture into ice/water (300 ml) and then add 5N NaOH (54 ml) with stirring Add slowly an additional amount of 5N NaOH (19.7 ml) and then heated to 90° for 1 minute and then cooled to ambient temperature to give a precipitate. Filter the precipitate and washed with water and dry to give the title compound: mp 248-250° C. MS (ACPI): m/e 171.0 (M+1). Analysis for $C_{10}H_6N_2O$: Calcd: C, 70.58; H, 3.55; N, 16.46. found: C, 70.41; H, 3.53; N, 16.33.

By the method of Example 23 the following compounds were prepared: a) 3-Formyl-5-(4-fluorophenyl)-1H-indole; mp 215-217° C. MS (ACPI): m/e 239.1 (M+1). Analysis for $C_{15}H_{10}FNO$: Calcd: C, 75.30; H, 4.21; N, 5.85. found: C, 74.94; H, 4.17; N, 5.84.

b) 3-Formyl-5-phenyl-1H-indole; mp>250° C. MS (ACPI): m/e 222.1 (M+1). Analysis for $C_{15}H_{11}NO$: Calcd: C, 81.43; H, 5.01; N, 6.33. found: C, 81.04; H, 5.05; N, 6.36;

c) 3-Formyl-6-methyl-1H-indole; mp 178-180° C. MS (ACPI): m/e 159.9 (M+1). Analysis for $C_{10}H_6NO$: Calcd: C, 75.45; H, 5.70; N, 8.80. found: C, 75.60; H, 5.78; N, 8.97;

d) 3-Formyl-6-cyano-1H-indole; mp 246° C. MS (ACPI): m/e 171.0 (M+1). Analysis for $C_{10}H_6N_2O$: Calcd: C, 70.58; H, 3.55; N, 16.46. found: C, 70.51; H, 3.59; N, 16.40; and e) 3-Formyl-6-trifluoromethoxy-1H-indole; mp 189-192° C. MS (ACPI): m/e 230.0 (M+1). Analysis for $C_{10}H_6F_3NO_2$: Calcd: C, 52.41; H, 2.64; N, 6.11. found: C, 52.31; H, 2.61; N, 6.09.

f) 3-Formyl-7-cyano-1H-indole; $^1$H NMR (300 MHz, DMSO-$d_6$) δ 7.41 (t, 1H, J=7.6 Hz), 7.80-7.82 (m, 1H), 8.42-8.50 (m, 2H), 10.02 (s 1H), 13.06 (br, 1H).

g) 3-Formyl-6-bromo-1H-indole; mp 197-200° C. Analysis for $C_9H_6BrNO$: Calcd: C, 48.25; H, 2.70; N, 6.25. found: C, 47.87; H, 2.68; N, 6.17.

h) 3-Formyl-7-fluoro-1H-indole; mp 211-214° C. MS (ACPI): m/e 163.9 (M+1). Analysis for $C_9H_6FNO$: Calcd: C, 66.26; H, 3.71; N, 8.59. found: C, 66.12; H, 3.67; N, 8.56.

Example 25

3-(2-Nitrovinyl)-5-cyano-1H-indole

Combine 3-formyl-5-cyano-1H-indole (10.60 g, 63.32 mmol) and a solution of ammonium acetate (10.60 g) in nitromethane (660 ml). Heat to 90° C. After 2 hours, cool to ambient temperature to give a precipitate. Collect the precipitate by filtration, wash with 1:1 MeOH/water (500 ml), and dry to give the title compound: mp 247-251° C. MS (ACPI): m/e 214.0 (M+1).

By the method of Example 25 the following compounds were prepared: a) 3-(2-Nitrovinyl)-5-(4-fluorophenyl)-1H-indole; mp 217-220° C. MS (ACPI): m/e 282.2 (M+1). Analysis for $C_{15}H_{10}FN_2O_2$: Calcd: C, 68.08; H, 3.93; N, 9.92. found: C, 67.73; 14, 3.92; N, 9.73;

b)$_{3-2}$-Nitrovinyl)-5-phenyl-1H-indole; MS (ACPI): m/e 265.1 (M+1);

c) 3-(2-Nitrovinyl)-6-methyl-1H-indole; MS (ACPI): m/e 203.1 (M+1);

d) 3-(2-Nitrovinyl)-6-cyano-1H-indole; mp>250° C. MS (ACPI): m/e 212.0 (M−1). Analysis for $C_{11}H_7N_3$(h: Calcd: C, 61.97; H, 3.31; N, 19.71. found: C, 62.09; H, 3.34; N, 20.06. and e) 3-(2-Nitrovinyl)-6-trifluororo methoxy-1H-indole; mp 139-143° C. MS (ACPI): m/e 273.0 (M+1).

f) 3-(2-Nitrovinyl)-6-phenoxy-11H-indole; $^1$H NMR (DMSO $d_6$) 12.1 (s, 1H), 8.38-8.34 (d, 1H), 8.20-8.19 (m, 1H), 8.01-7.97 (m, 2H), 7.39-7.35 (m, 2H), 7.14-7.07 (m, 2H), 7.02-7.00 (m, 2H), 6.95-6.92 (m, 1H).

g) 3-(2-Nitro-vinyl)-5-(pyridin-3-yloxy)-1H-indole: ISMS 282 (M+1); $^1$H NMR (DMSO-$d_6$) 9.5 (bs, 1H), 8.36-8.32 (m, 2H), 8.26-8.24 (m, 2H), 7.98-7.95 (m, 1H), 7.79-7.78 (m, 1H), 7.55-7.53 (m, 1H), 7.34-7.31 (m, 1H), 7.27-7.24 (m, 1H), 7.02-7.00 (m, 1H).

h) 3-(2-Nitro-vinyl)-7-cyano-1H-indole: $^1$H NMR (300 MHz, CDCl$_3$) δ 7.36 (t, 1H, J=7.7 Hz), 7.76 (d, 1H, J=7.2 Hz), 8.09-8.14 (m, 1H), 8.36-8.46 (m, 3H); MS (electrospray), m/e: 212.1 (M−1)

i) 3-(2-Nitrovinyl)-6-bromo-1H-indole; mp 210° C., dec. Analysis for $C_{10}H_7BrN_2O_2$: Calcd: C, 44.97; Hp 2.64; N, 10.49. found: C, 44.62; H, 2.70; N, 10.49.

j) 3-(2-Nitrovinyl)-7-fluoro-1H-indole; mp 176-180° C. MS (ACPI): n/e 207.1 (M+1). Analysis for $C_{10}H_7FN_2O_2$: Calcd: C, 58.26; H, 3.42; N, 13.59. found: C, 58.01; H, 3.31; N, 13.26.

Example 26

3-2-Nitroethyl)-5-cyano-1H-indole

Add sodium borohydride (25.65 g, 678 mmol) to an ice bath cooled solution of 3-(2-nitrovinyl)-5-cyano-1H-indole (12.68 g, 59.5 mmol) in 1:1 MeOH/DMF (600 ml). After 1.5 hours, add brine (600 ml) then adjust the pH to approximately 7 with 5N HCl. Evaporate under reduced pressure to remove the methanol and then extract with dichloromethane. Combine the organic extracts, wash with brine, dry ($Na_2SO_4$), then evaporate to residue. Chromatograph the residue on silica gel eluting with dichloromethane to give, after evaporation, the title compound as colorless prisms: mp 132-136° C. MS (ACPI): m/e 215.0 (M+1). Analysis for $C_{11}H_9N_3O_2$: Calcd: C, 61.39; H, 4.22; N, 19.52. found: C, 61.09; H, 4.10; N, 19.16.

By the method of Example 26 the following compounds were prepared: a) 3-(2-nitro-ethyl)-7-cyano-1H-indole; $^1$H NMR (300 MHz, DMSO-$d_6$) 3.39 (t, 2H, J=6.9 Hz), 4.87 (t, 2H, J=7.0 Hz), 7.17 (t, 1H, J=7.4 Hz), 7.38 (m, 1H), 7.63 (d, 1H, J=7.4 Hz), 7.99 (d, 1H, J=7.9 Hz), 11.96 (br, 1H). MS (electrospray), m/e: 214.1 (M−1).

Example 27

5-Cyanotryptamine

Add zinc powder (16.22 g, 248.1 mmol) in four portions to 2N HCl (300.0 ml). Add dropwise 3-(2-nitroethyl)-5-cyano-1H-indole (2.25 g, 10.5 mmol) as a solution in methanol (300.0 ml). Heat to reflux. After 2.5 hours, cool to ambient temperature and adjust the pH to 11 using 5N NaOH, filter through Celite, wash with water, then extract the filtrate with dichloromethane. Combine the organic extracts, wash with brine, dry ($Na_2SO_4$), then evaporated to give the title compound: mp 102-105° C., MS (ACPI): m/e 186.1 (M+1). Analysis for $C_{11}H_{11}N_3$: Calcd: C, 71.33; H, 5.99; N, 22.69. found: C, 71.03; H, 5.91; N, 22.64.

By the method of Example 27 the following compounds were prepared: a) 3-(2-aminoethyl)-7-cyano-1H-indole; $^1$H NMR (300 MHz, DMSO-$d_6$) 2.76-2.82 (m, 4H), 7.15 (t, 1H, J=7.6 Hz), 7.31 (s, 1H), 7.58 (d, 1H, J=7.4 Hz), 7.91-7.94 (m, 1H), 11.80 (br, 1H); MS (electrospray), m/e: 186.1 (M+1), 184.1 (m−1).

By the method of Example 27 the following compound was prepared: a) 6-Bromotryptamine; mp 114-116° C. Analysis for $C_{10}H_{11}BrN_2$: Calcd: C, 50.23; H, 4.64; N, 11.72. found: C, 49.96; H, 4.49; N, 11.47.

Example 28

N-t-Butoxycarbonyl-2-(5-cyano-1H-indol-3-yl)ethylamine

Combine di-tert-butyl dicarbonate and a solution of 5-cyanotryptamine (1.33 g, 7.15 mmol) and 2N NaOH (4.2 ml) in THF (60 ml). After 3 hours at ambient temperature, evaporate to residue. Dissolve the residue in water and extract with dichloromethane. Combine the organic extracts, wash with brine, dry ($Na_2SO_4$), and evaporate to residue. Chromatograph the residue on silica gel eluting with dichloromethane/2N $NH_3$(methanol) (97/3)) to give the title compound: mp 129-132° C. MS (ACPI): m/e 286.2 (M+1). Analysis for $C_{16}H_{19}N_3O_2$: Calcd: C, 67.35; H, 6.71; N, 14.73. found: C, 67.16; H, 6.68; N, 14.46.

By the method of Example 28 the following compounds were prepared: a) N-t-Butoxycarbonyl-2-(6-cyano-1H-indol-3-yl)ethylamine.

Example 29

N-t-Butoxycarbonyl-2-(5-amido-1H-indol-3-yl)ethylamine

Combine water (64.0 ml) and NaOH (8.53 g) and cool to about 5° C. in an ice bath. Add a solution of N-t-butoxycarbonyl-2-(5-cyano-1H-indol-3-yl)ethylamine (1.85 g, 6.50 mmol) in ethanol (128.0 ml) then added to the chilled solution. Add dropwise 30% peroxide (6.4 ml) while keeping the temperature below 5° C. After 30 minutes, warm to ambient temperature. After 22 hours, decompose the excess peroxide by adding a 20% sodium bisulfite solution (45.0 ml) with stirring. After 30 minutes, evaporate under reduced pressure to remove the ethanol and extract the resulting aqueous solution with ethyl acetate. Combine the organic extracts, wash with brine, dry ($Na_2SO_4$), then evaporate to residue. Chromatograph the residue on silica gel eluting with dichloromethane/2N $NH_3$(methanol) (96/4) to give, after evaporation, the title compound: mp 65-68° C. MS (ACPI): in/e 304.2 (M+1). Analysis for $C_{16}H_{21}N_3O_3$: Calcd: C, 63.35; H, 6.98; N, 13.85. found: C, 63.26; H, 6.99; N, 13.71.

By the method of Example 28 the following compounds were prepared: a) N-t-Butoxycarbonyl-2-(6-amido-1H-indol-3-yl)ethylamine: MS (ACPI): m/e 302.3 (M−1).

Example 30

5-Amidotryptamine

Dissolve N-t-butoxycarbonyl-2-(5-amido-1H-indol-3-yl)ethylamine (1.83 g, 6.04 mmol) in dioxane (25.0 ml). Add dropwise a 4M HCl in dioxane (7.5 ml). After 18 hours, collect the solid by filtration and wash with diethyl ether to give, after drying, the title compound as the hydrochloride: mp 192-195° C. MS (ACPI): m/e 202.0 (M+1).

By the method of Example 30 the following compounds were prepared: a) 6-Amidotryptamine: mp 169-173° C. MS (ACPI): m/e 204.1 (M+1).

Example 32

5-(4-Fluorophenyl)tryptamine

Combine $LiAlH_4$ (2.66 g, 70.17 mmol) and dry THF (70.0 ml) and cool the suspension in an ice bath. Add dropwise a solution of 5-(4-fluorophenyl)-3-(2-nitrovinyl)-1H-1-indole (3.30 g, 11.69 mmol) in dry THF (30.0 ml). Heat to reflux. After 1 hour, cool to ambient temperature and stir. After 15 hours, quench with saturated $Na_2SO_4$ (100 ml/mol) and stir at ambient temperature. After 1 hour, filter, rinse the precipitate with THF, and evaporate the filtrate to residue. Chromatograph the residue on silica gel eluting with dichloromethane/2N $NH_3$(methanol) (80/20) to give the title compound.

Prepare the HCl salt in diethyl ether: mp>250° C. MS (ACPI): m/e 255.0 (M+1). Analysis for $C_{16}H_{11}ClFN_2$: Calcd: C, 66.09; H, 5.55; N, 9.63. found: C, 65.78; H, 5.48; N, 9.58.

By the method of Example 32 the following compounds were prepared: a) 5-Phenyltryptamine; mp 244-246° C. MS (ACPI): m/e 237.1 (M+1). Analysis for $C_{16}H_{17}ClN_2$: Calcd: C, 70.45; H, 6.28; N, 10.27. Found: C, 70.75; H, 6.33; N, 10.27. (isolated as the hydrochloride);

b) 6-Methyltryptamine; mp 139-141° C. MS (ACPI): m/e 175.0 (M+1). Analysis for $C_{11}H_{14}N_2$: Calcd: C, 75.82; H, 8.10; N, 16.08. Found: C, 76.05; H, 8.26; N, 16.12.

c) 6-Trifluoromethoxtryptamine; MS (ACPI): m/e 245.0 (M+1). Analysis for $C_{11}H_{11}F_3N_2O$: Calcd: C, 54.10; H, 4.54; N, 11.47. Found: C, 53.92; H, 4.50; N, 11.06.

d) 7-Fluorotryptamine; MS (ACPI): m/e 179.0 (M+1). Analysis for $C_{10}H_{11}FN_2$: Calcd: C, 67.40; H, 6.22; N, 15.72. Found: C, 67.06; H, 6.11; N, 15.48.

Example 33

6-Ethoxycarbonyl-1H-indole

Combine 6-carboxy-1H-indole and ethanol (110 ml) and cool to 5° C. Add dropwise concentrated $H_2SO_4$ (96%, 11.08 ml) while keeping the temperature below 10° C. Heat to reflux. After 4 hours, cool and pour onto ice/water, adjust the pH to about pH 9 and extract with ethyl acetate. Combine the organic extracts, wash with brine, dry $Na_2SO_4$), then concentrate to residue. Chromatograph the residue on silica gel eluting with chloroform to give, after evaporation, the title compound: mp 72-75° C. MS (ACPI): m/e 189.9 (M+1).

Example 34

3-(2-Nitrovinyl)-6-ethoxycarbonyl-1H-indole

Combine 1-dimethylamino-2-nitroethylene (1.93 g, 16.58 mmol) and TFA (110.0 ml) and stir until dissolved. Add 6-ethoxycarbonyl-1H-indole (3.14 g, 16.58 mmol) and stir at ambient temperature. After 1 hour, pour the reaction mixture into ice/water, extract with ethyl acetate, then evaporate to residue. Stir the residue in warm ethanol, cool to ambient temperature, then filter and dry to give the title compound as a dark yellow powder: mp 241° C. MS (ACPI): m/e 261.1 (M+1). Analysis for $C_{13}H_{12}N_2O_4$: Calcd: C, 60.00; H, 4.65; N, 10.76. found: C, 59.99; H, 4.63; N, 10.59.

Example 35

3-(2-Nitroethyl)-6-ethoxycarbonyl-1H-indole

Combine 3-(2-nitrovinyl)-6-ethoxycarbonyl-1H-indole (4.0 g, 15.37 mmol) and $NaBH_4$ (726.7 mg, 19.21 mmol) in 100 ml of THF/Methanol (9:1) and stir at ambient temperature. After 1.5 hours, concentrate to residue. Partition the residue between brine and ethyl acetate, wash with brine, combine the organic layers, dry ($Na_2SO_4$), then evaporate to give the title compound as a yellow powder: mp 124-127° C. MS (ACPI): m/e 263.0 (M+1). Analysis for $C_{13}H_{14}N_2O_4$: Calcd: C, 59.54; H, 5.38; N, 10.68. found: C, 59.40; H, 5.36; N, 10.53.

By the method of Example 35 the following compounds were prepared: a) 3-(2-Nitroethyl)-6-cyano-1H-indole: m/e 214.1 (M−1). Analysis for $C_{11}H_9N_3O_2$: Calcd: C, 61.39; H, 4.22; N, 19.52. found: C, 61.05; H, 4.09; N, 19.19.

b) 3-(2-Nitroethyl)-6-bromo-1H-indole;

c) 3-(2-Nitroethyl)-6-methanesulfonyl-1H-indole; mp 162-164° C. MS (ACPI): m/e 269.1 (M+1).
d) 3-2-Nitroethyl)-6-benzenesulfonyl-1H-indole (exception: 75 ml of THF was used).

Example 36

6-Ethoxycarbonyltryptamine

Combine $Pt_2O$ (440 mg) and a solution of 3-(2-nitroethyl)-6-ethoxycarbonyl-1H-indole (3.55 g, 13.54 mmol) in ethyl acetate (100 ml). Hydrogenate at 60 psi (410 kPa) and ambient temperature. After 4 hours, filter through celite and concentrate the filtrate to residue. Chromatograph the residue on silica gel eluting with dichloromethane/2N $NH_3$ (methanol) (85/15) to give, after evaporation, the title compound as an off-white powder: mp 127-131° C. MS (ACPI): m/e 233.0 (M+1). Analysis for $C_{13}H_{16}N_2O_2$: Calcd: C, 67.22; H, 6.94; N, 12.06. found: C, 66.87; H, 6.86; N, 11.86.

By the method of Example 36 the following compounds were prepared: a) 6-Cyanotryptamine: mp 144-147° C. MS (ACPI): m/e 186.0 (M+1). Analysis for $C_{11}H_{11}N_3$: Calcd: C, 71.33; H, 5.99; N, 22.69. found: C, 71.10; H, 5.89; N, 22.38.
b) 6-Methanesulfonyltryptamine: mp 149-153° C. MS (ACPI): mile 239.1 (M+1). Analysis for $C_{11}H_{14}N_2O_2S$: Calcd: C, 55.44; H, 5.92; N, 11.76. found: C, 55.12; H, 5.82; N, 11.97.
c) 6-Benzenesulfonyltryptamine: mp 169-172° C. MS (ACPI): m/e 301.0 (M+1).

Example 38

6-Trifluoromethoxy-1H-indole

Combine 1-methyl-4-trifluoromethoxybenzene (5.44 g, 30.87 mmol) and $H_2SO_4$ (96%, 30.9 ml). Cool to about 0° C. Add dropwise fuming $HNO_3$ (2.06 g, 32.72 mmol) while maintaining the temperature below 10° C. When the addition is complete, warm to ambient temperature. After 2.5 hours, pour the mixture onto ice/water, extract with dichloromethane. Combine the organic extracts, wash with brine, dry ($Na_2SO_4$), then concentrate to residue. Chromatograph the residue on silica gel eluting with hexanes/ethyl acetate (75/25) to give, after evaporation, 1-methyl-2-nitro-4-trifluoromethoxybenzene: MS (ACPI): m/e 220.1 (M-1).

Combine 1-methyl-2-nitro-4-trifluoromethoxybenzene (3.73 g, 16.86 mmol), pyrrolidine (1.32 g, 18.55 mmol), N,N-dimethylformamide dimethyl acetal (6.03 g, 50.58 mmol), and dry DMF (35 ml). Heat to about 105°. After 19 hours, remove the DMF under reduced pressure to give an oily residue. Combine the residue and ethyl acetate, wash with brine, dry ($Na_2SO_4$), then concentrate to give N,N-dimethyl-2-(2-nitro-4-trifluoromethoxyphenyl)vinylamine.

Combine N,N-dimethyl-2-(2-nitro-4-trifluoromethoxyphenyl)vinylamine (4.64 g, 16.8 mmol) and Raney® nickel (900 mg) in ethanol (100 ml). Hydrogenate at 60 psi (410 kPa) and ambient temperature. After 18 hours, filter through celite, concentrate the filtrate to residue, and chromatograph on silica gel eluting with hexanes/ethyl acetate (30/70) to give, after evaporation, the title compound as an off-white powder: mp 59° C. MS (ACPI): m/e 200.0 (M-1).

Example 39

2-Phenylphenethylamine

Combine 2-phenylphenylacetonitrile (4.69 g, 24.26 mmol) and diethyl ether (10 ml) and add dropwise to a cooled (−10°) solution of $LiAlH_4$ (2.76 g, 72.81 mmol) in diethyl ether (100 ml). Warm to ambient temperature. After 2 hours, quench with saturated sodium sulfate (100 mL/mol). Filter to remove the precipitate, dry ($Na_2SO_4$) the filtrate, filter, and concentrate to residue. Chromatograph the residue on silica gel eluting with dichloromethane/2N $NH_3$(methanol) (95/5) to give the title compound as a yellow oil. Prepare the HCl salt in diethyl ether: mp 197-199° C. MS (ACPI): m/e 198.1 (M+1). Analysis for $C_{14}H_{16}ClN$: Calcd: C, 71.94; H, 6.90; N, 5.99. found: C, 72.15; H, 6.84; N, 6.09.

Example 40

7-Chloro-1H-indole

By the method of *J. Med. Chem.* 1990, 33, 2777), add dropwise 2-chloroaniline (5.8 g, 45.45 mmol) in anhydrous toluene (80 mL) to a cold 1M solution of $BCl_3$ (50 mL) in dichloromethane. After addition, allow the reaction to stir at 0° C. for 10 minutes. After 10 minutes at 0° C., add chloroacetonitrile (13.72 g, 11.53 mL, 181.8 mmol, 4 eq) and aluminum trichloride (6.67 g, 50 mmol, 1.1 eq) in 5 equal portions over 45 minutes and then heat to reflux (~65° C.). After 6 hours, cool to room temperature. After 16 hours, cool the reaction in an ice bath and add 2N HCl (61.4 mL) and then heat the reaction to reflux. After 45 minutes, cool in an ice bath, neutralize the acid with 2N NaOH keeping the temperature of the reaction below 15° C. until the pH is about 5. Transfer the reaction to a separatory funnel and remove the organic layer. Extract the aqueous layer with dichloromethane (2×200 mL). Combine the organic layers, dry over $MgSO_4$, filter, and remove the solvent in vacuo to give 1-(2-amino-3-chlorophenyl)-2-chloroethanone which may be used without further purification.

Dissolve 1-(2-amino-3-chlorophenyl)-2-chloroethanone (7.0 g, 34.30 mmol) in 10% aqueous 1,4-dioxane (75 mL). Carefully add NaBH (2.6 g, 68.6 mmol, 2 eq.) as a solid. Heat to reflux. After 4 hours, cool to room temperature, dilute with water (300 mL), and extract with dichloromethane (2×200 mL). Combine the organic layers, dry over $MgSO_4$, filter, and remove the solvent in vacuo leaving a light brown oil in the flask. Purify the oil by HPLC (silica gel mobile phase: 100% hexane to 50% EtOAc in hexanes over 50 minutes), to give the title compound as a brown oil: $^1H$ NMR (300 MHz, d6-DMSO-d6): 5.16 (m, 1H), 5.39 (d, 1H), 5.70 (bs, 1H), 6.59 (t, 1H), 7.09 (m, 2H); MS (ES+): m/z 154, 152 (M+H)$^+$.

By the method of Example 40 the following compounds were prepared: a) 5-Bromo-7-ethyl-1H-indole: $^1H$ NMR (300 MHz, d6-DMSO-d6): 1.25 (t, 3H), 2.85 (m, 2H), 6.41 (m, 1H), 7.02 (M, 1H), 7.36 (m, 1H), 7.55 (m, 1H), 11.28 (bs, 1H); MS (ES+): m/z 224, 226 (M+H)$^+$; Analysis for $C_{10}H_{10}BrN$: Calcd.: C, 53.60; H, 4.50; N, 6.25. found: C, 53.50; H, 4.34; N, 6.22.

Example 42

6-Trifluoromethyl-1H-indole

Combine 2-bromo-5-trifluoromethylphenylamine (27.06 g, 112.74 mmol) and 200 mL of pyridine. Cool in an ice bath and add ethyl chloroformate (18.35 g, 169.11 mL, 1.5 eq). After addition was complete, allow the reaction to gradually warming to room temperature. After 18 hours, evaporate it vacuo to give a residue. Dissolve the residue in $Et_2O$/water and transfer to a separatory funnel. Separate the layer and extract the aqueous layer with $Et_2O$ (2×300 mL), combine the organic layers, dry over $MgSO_4$, filter, and evaporate in vacuo to give N-(2-bromo-5-trifluoromethylphenyl)carbamic acid ethyl ester which may be used without further purification.

Following the procedure described in *J. Org. Chem.* 1997, 62, 6507, combine N-(2-bromo-5-trifluoromethylphenyl) carbamic acid ethyl ester (34.33 g, 110 mmol), triethylamine (300 mL), dichlorobis (triphenylphosphine)palladium(II) (5.4 g, 7.7 mmol), and copper (I) iodide (1.47 g, 7.7 mmol). Evacuate the dark solution and fill with $N_2$ twice and then quickly add (trimethylsilyl)acetylene (16.21 g, 165 mmol, 23.32 mL) with vigorous stirring. Heat to 80° C. When TLC indicates absence of the starting material, add water and $Et_2O$ and filter through celite and evaporate the filtrate in vacuo to give a residue. Dilute residue with water and extract with $Et_2O$, combine the organic layers and remove the evaporate to give a dark brown oil. Absorb the oil onto silica gel and load onto a short column of silica gel equilibrated with 100% hexanes. Wash with 100% hexanes (2 L) and elute the product with 1% EtOAc in hexanes. Pool fractions containing the product and remove in vacuo the solvent to give 5-trifluoromethyl-2-trimethylsilanylethynyl phenylamine as a red/brown oil; MS (IS): m/z 330 $(M+H)^+$.

Carefully add NaH (10.83 g, 60% in oil, 270.8 mmol, 4 eq.) to EtOH (200 mL). When cool, add a solution of 5-trifluoromethyl-2-trimethylsilanylethynylphenylamine (22.3 g, 67.7 mmol) in EtOH (400 mL) with vigorous stirring. After 2 hours, heat to reflux. After 4 hours, evaporate in vacuo to remove the EtOH and dilute the residue obtained with water and extract with $Et_2O$. Combine the organic layers and wash with brine, dry over $MgSO_4$, filter, and evaporate to give a dark oil. Absorbed the oil onto silica gel and load onto short column of silica gel. Elute with 20% EtOAc in hexanes. Pool fractions containing the product and remove the solvent leaving a dark brown oil. Further purification of the oil by HPLC (silica column) using a gradient 1% $Et_2O$ in hexanes to 15% $Et_2O$ in hexanes. Pool fractions containing the product and remove the solvent to give the title compound as an orange solid: $^1H$ NMR (300 MHz, d6-DMSO-d6): 6.58 (m, 1H), 7.28 (m, 1H), 7.61 (t, 1H), 7.74 (m, 2H), 11.51 (bs, 1H); MS (EI+): m/z 185 (M+).

By the method of Example 42 the following compounds were prepared: a) 5-Ispropyl-1H-indole: MS (ES+): m/z 160 $(M+H)^+$; (ES)–: m/z 158 $(M-H)^-$.

Example 44

6-Fluoro-5-methoxy-1H-indole

Dissolve fuming nitric acid (24 mL) in concentrated $H_2SO_4$ in a round bottom flask. Add 3,4-difluorobromobenzene (20 g, 104 mmol) dropwise via pipette with vigorous stirring. After addition, stir the reaction at room temperature for 2 hours, pour the reaction into ice water and extract with $Et_2O$ (2×250 mL). Collect and combine the organic layers, dry over $MgSO_4$, filter, and remove the solvent to give 1-bromo-4,5-difluoro-2-nitrobenzene as a light yellow oil.

Add 1-bromo-4,5-difluoro-2-nitrobenzene (24 g, 100 mmol) to a solution of sodium methoxide (1.2 eq) in MeOH. After addition, stir the reaction at room temperature for 2.5 hours. Remove the solvent in vacuo and dilute the residue with water and extract with $Et_2O$ (2×250 mL). Combine the organic layers, dry over $MgSO_4$, filter, and the remove solvent in vacuo to give 1-bromo-4-fluoro-5-methoxy-2-nitrobenzene as a yellow solid: $^1H$ NMR (300 MHz, $CDCl_3$): 3.99 (s, 3H), 7.26 (m, 1H), 7.83 (d, 1H); MS (ED+): m/z 249, 251 (M+); Analysis for $C_7H_5BrFNO_3$: Calcd.: C, 33.63; H, 2.02; N, 5.60. found: C, 33.79; H, 1.98; N, 5.62.

Combine 1-bromo-4-fluoro-5-methoxy-2-nitrobenzene (20.5 g, 82 mmol) and Pt-on-carbon (sulfided) in THF (600 mL) and hydrogenate at 60 psi (414 kPa) over for 4 hours. Filter the reaction through celite to remove the catalyst and remove the solvent to give 2-bromo-5-fluoro-4-methoxyaniline as a brown solid which may taken on without further purification.

Using 2-bromo-5-fluoro-4-methoxyaniline, the method of Example 42 gives N-(2-bromo-5-fluoro-4-methoxyphenyl) carbamic acid ethyl ester as a brown solid: $^1H$ NMR (300 MHz, $CDCl_3$): 1.33 (t, 3H), 3.85 (s, 3H), 4.23 (q, 2H), 7.09 (d, 1H), 7.97 (bd, 1H); MS (FD+): m/z 291, 293 (M+); N-(5-fluoro-4-methoxy-2-trimethylsilanylethynylphenyl)carbamic acid ethyl ester as a yellow solid: MS (ES+): m/z 310 $(M+1H)^+$; (ES–): m/z 308 $(M-H)^-$; and the title compound as a solid: $^1H$ NMR (300 MHz, $CDCl_3$): 3.93 (s, 3H), 6.48 (m, 1H), 7.15 (m, 3H), 8.11 (bs, 1H); MS (ES+): m/z 166 $(M+H)^+$; (ES–): m/z 164 $(M-H)^-$; Analysis for $C_9H_8FNO$: Calcd.: C, 65.45; H, 4.88; N, 8.48. found: C, 65.17; H, 4.97; N, 8.70.

Example 45

5,6-Difluoro-1H-indole

Using the method of Example 42 gives 2-bromo-4,5-difluoroaniline; which gives N-(2-bromo-4,5-difluorophenyl) carbamic acid ethyl ester; which gives N-(4,5-Difluoro-2-trimethylsilanylethynylphenyl)carbamic acid ethyl ester; which gives the title compound as an orange solid: $^1H$ NMR (300 MHz, d6-DMSO-d6): 6.43 (m, 1H), 7.38 (m, 2H), 7.50 (m, 1H), 11.25 (bs, 1H); MS (ES–): m/z 152 $(M-H)^-$; Analysis for $C_8H_5F_2N$: Calcd.: C, 62.75; H, 3.29; N, 9.15. found: C, 62.41; H, 3.12; N, 8.98.

Example 46

5-Trifluoromethoxy-1H-indole

Using the method of Example 42 and 2-bromo-4-(trifluoromethoxy)aniline gives N-(2-bromo-4-trifluoromethoxyphenyl)carbamic acid ethyl ester: $^1H$ NMR (300 MHz, $CDCl_3$): 1.34 (t, 3H), 4.25 (m, 2H), 7.19 (m, 1H), 7.41 (m, 1H), 8.20 (d, 1H); MS (ES–): m/z 326, 328 $(M-H)^-$; Analysis for $C_{10}H_9BrF_3NO_3$: Calcd.: C, 36.6096; H, 2.7650; N, 4.2692. found: C, 36.50; H, 2.67; N, 3.97. which gives N-(4-Trifluoromethoxy-2-trimethylsilanylethynylphenyl) carbamic acid ethyl ester, which gives the title compound as a yellow oil: MS (ES–): m/z 200 $(M-H)^-$.

Example 47

4-Phenyl-1H-indole

Using the method of Carrera and Sheppard in *Synlett.* 1994, 93-94, 4-bromoindole gives the title compound: $^1H$ NMR (300 MHz, d6-DMSO-d6): 6.56 (m, 1H), 7.08 (m, 1H), 7.17 (m, 1H), 7.43 (m, 5H), 7.67 (m, 2H), 11.27 (bs, 1H); MS (ES+): m/z 194 $(M+H)^+$; (ES–): m/z 192 $(M-H)^-$.

Example 48

(2-Nitro-5-trifluoromethylphenyl)-acetonitrile

By the method of Liebigs Ann. Chem. 1988, 203-208, using 4-nitrobenzotrifluoride (15 g, 78.49 mmol) gives the title compound: MS (ES–): m/z 229 $(M-H)^-$.

Example 49

5-Trifluoromethyl-1H-indole

By the method of Liebigs Ann. Chem. 1988, 203-208 using (2-nitro-5-trifluoromethylphenyl)acetonitrile gives the title compound as a white solid: $^1$H NMR (300 MHz, d6-DMSO-d6): 6.60 (m, 1H), 7.36 (m, 1H), 7.53 (m, 1H), 7.57 (m, 1H), 7.94 (m, 1H), 11.51 (bs, 1H); MS (ES–): m/z 184 (M–H)$^-$.

Example 50

3-Formyl-4-methoxy-1H-indole

Add phosphorus oxychloride (1.1 eq.) with vigorous stirring to DMF (cooled in an ice bath). After the addition is complete, allow to stir in the ice bath for ~10 minutes, then add a solution of 4-methoxy-1H-indole (5 g) in anhydrous DMF with vigorous stirring. Allow to stir at 0° C. After 1 hour, warm to room temperature. After 16 hours, carefully add 4 eq. of 2N NaOH with vigorous stirring. Heat to about 80° C. and then cool. Pour the reaction mixture into cold water with vigorous stirring to give a solid. Collect the solid by filtration and dry in a vacuum oven at room temperature to give the title compound. Acidify the filtrate and extract with EtOAc. Combine the organic layers and wash with 50% brine. Collect the organic layer, dry (MgSO$_4$) filter, and remove the solvent to give the title compound as a light purple solid. Total yield of the title compound is 5.44 g: MS (ES+): m/z 175 (M+H)$^+$, 160 (M–CH$_3$)$^+$; (ES–): m/z 174 (M–H)$^-$.

By the method of Example 50 the following compounds were prepared: a) 3-Formyl-6-methoxy-1H-indole, $^1$H NMR (300 MHz, d6-DMSO): 3.79 (s, 3H); 6.85 (dd, 1H); 6.98 (m, 1H); 7.92 (d, 1H); 8.15 (s, 1H); 9.86 (s, 1H); 11.92 (bs, 1H); MS (ES+): m/z 176 (M+H)$^+$; (ES–): m/z 174 (M–H);

b) 3-Formyl-7-methoxy-1H-indole;

c) 3-Formyl-4-chloro-1H-indole;

d) 3-Formyl-6-chloro-1H-indole, $^1$H NMR (300 MHz, d6-DMSO-d6): 7.24 (dd, 1H), 7.56 (d, 1H), 8.06 (d, 1H), 8.33 (s, 1H), 9.93 (s, 1H), 12.21 (bs, 1H); MS (ES+): m/z 182, 180 (M+H)$^+$; (ES–): m/z 180, 178 (M–H)$^-$;

e) 3-Formyl-7-chloro-1H-indole, $^1$H NMR (300 MHz, d6-DMSO): 7.23 (t, 1H), 7.35 (d, 1H), 8.05 (d, 1H), 8.38 (bs, 1H), 9.95 (s, 1H), 12.54 (bs, 1H); MS (ES+): m/z 182, 180 (M+H)$^+$; (ES–): m/z 180, 178 (M–H)$^-$;

f) 3-Formyl-4-fluoro-1H-indole, $^1$H NMR (300 MHz, d6-DMSO): 7.01 (m, 1H), 7.24 (m, 1H), 7.36 (d, 1H), 8.30 (s, 1H), 10.03 (d, 1H), 12.48 (bs, 1H); MS (ES+): m/z 164 (M+H)$_4$; (ES–): m/z 162 (M–H)$^-$;

g) 3-Formyl-5-methoxy-6-trifluoromethyl-1H-indole, $^1$H NMR (300 MHz, d6-DMSO): 3.91 (s, 3H), 7.77 (dd, 1H), 7.95 (bs, 1H), 8.42 (s, 1H), 9.96 (s, 1H), 12.29 (bs, 1H); MS (ES+): m/z 244 (M+H)$^+$; (ES–): m/z 242 (M–H)$^-$;

h) 3-Formyl-6-chloro-5-methoxy-1H-indole, $^1$H NMR (300 MHz, d6-DMSO): 3.88 (s, 3H), 7.58 (s, 1H), 7.71 (s, 1H), 8.26 (s, 1H), 9.91 (s, 1H), 12.08 (bs, 1H); MS (ES–): m/z 210, 212 (M+H)$^+$; (ES–): m/z 208, 210 (M–H)$^-$;

i) 3-Formyl-4-chloro-5-methoxy-1H-indole, $^1$H NMR (300 MHz, d6-DMSO): 3.89 (s, 3H), 7.13 m (dd, 1H), 7.47 (dd, 1H), 8.23 (s, 1H), 10.5 (s, 1H), 12.39 (bs, 1H); MS (ES+): m/z 210, 212 (M+H)$^+$ (ES–): m/z 208, 210 (M–H)$^-$;

j) 3-Formyl-6-trifluoromethyl-1H-indole, $^1$H NMR (300 MHz, d6-DMSO): 7.52 (d, 1H), 8.27 (d, 1H), 8.51 (m, 1H), 9.99 (s, 1H), 12.47 (bs, 1H). MS (ES+): m/z 214 (M+H)$^+$, (ES–): m/z 212 (M–H)$^-$;

k) 3-Formyl-5-methoxy-2-methyl-1H-indole, $^1$H (300 MHz, d6-DMSO): 2.65 (s, 3H), 3.76 (s, 3H), 6.78 (dd, 1H), 7.27 (d, 1H), 7.56 (m, 1H), 10.00 (s, 1H), 11.85 (bs, 1H); MS (ES+): m/z 190 (M+H)$^+$; (ES–): m/z 188 (M–H)$^-$;

l) 3-Formyl-6-fluoro-5-methoxy-1H-indole, $^1$H NMR (300 MHz, d6-DMSO): 3.87 (s, 3H), 7.35 (d, 1H), 7.71 (d, 1H), 8.21 (s, 1H), 9.89 (s, 1H), 12.03 (bs, 1 h); MS (ES+): m/z 194 (M+H)$^+$; (ES–): m/z 192 (M–H);

m) 3-Formyl-5,6-difluoro-1H-indole, $^1$H NMR (300 MHz, d6-DMSO): 7.56 (m, 1H), 7.92 (m, 1H), 8.36 (s, 1H), 9.92 (s, 1H), 12.25 (bs, 1H); MS (ES+): m/z 182 (M+H)$^+$ (ES–): m/z 180 (M–H)$^-$;

n) 3-Formyl-6-chloro-5-fluoro-1H-1H-indole, $^1$H NMR (300 MHz, d6-DMSO): 7.72 (d, 1H), 7.91 (d, 1H), 8.40 (s, 1H), 9.93 (s, 1H), 12.29 (bs, 1H); MS (ES+): m/z 198 (M+H)$^+$; (ES–): m/z 196 (M–H)$^-$;

o) 3-Formyl-5-trifluoromethoxy-1H-indole, $^1$H NMR (300 MHz, d6-DMSO): 7.24 (m, 1H), 7.61 (m, 1H), 7.97 (bs, 1H), 8.42 (d, 1H), 9.95 (s, 1H), 12.35 (bs, 1H); MS (ES+): m/z 230 (M+H)$^+$; (ES–): m/z 228 (M–H)$^-$; Analysis for $C_{10}H_6F_3NO_2$: Calcd.: C, 52.4138; H, 2.6391; N, 6.1122. found: C, 52.70; HA 2.73; N, 6.13;

p) 3-Formyl-4,6-difluoro-5-methoxy-1H-indole, MS (ES+): 212 (M+H)$^+$; (ES–): 210 (M–H)$^-$;

q) 3-Formyl-4-phenyl-1H-indole, $^1$H NMR (300 MHz, d6-DMSO): 7.07 (m, 1H), 7.30 (m, 1H), 7.46 (m, 6H), 7.53 (m, 1H), 8.20 (s, 1H), 9.37 (s, 1H), 12.40 (bs, 1H). MS (ES+): m/z 222 (M+H)$^+$; (ES–): m/z 220 (M–H);

r) 3-Formyl-6-phenyl-1H-indole, $^1$H NMR (300 MHz, d6-DMSO): 7.35 (m, 1H), 7.49 (m, 3H), 7.71 (m, 3H), 8.15 (m, 1H), 8.33 (d, 1H), 9.96 (s, 1H), 12.20 (bs, 1H). MS (EI+): m/z 221 (M)$^+$;

s) 3-Formyl-5-isopropyl-1H-indole, $^1$H NMR (300 MHz, d6-DMSO): 1.24 (d, 6H), 2.99 (m, 1H), 7.15 (m, 1H), 7.41 (m, 1H), 7.94 (m, 1H), 8.22 (m, 1H), 9.90 (s, 1H), 12.02 (bs, 1H); MS (ES+): 188 (M+H)$^+$; (ES–): m/z 186 (M–H);

t) 3-Formyl-4,6-difluoro-5-methoxy-1-methyl-1H-indole: $^1$H NMR (300 MHz, CDCl$_3$): 3.81 (s, 3H), 4.02 (s, 3H), 6.92 (m, 1H), 7.77 (s, 1H), 10.14 (d, 1H); MS (ES+): m/z 226 (M+H)$^+$; and u) 3-Formyl-4,6-difluoro-1-methyl-1H-indole: $^1$H NMR (300 MHz, d6-DMSO): 3.87 (s, 3H), 7.10 (m, 1H), 7.41 (m, 1H), 8.32 (s, 1H), 9.93 (d, 1H); MS (ES+): 196 (M+H)$^+$.

Example 51

3-(2-Nitrovinyl)4-methoxy-1H-indole

Combine ammonium acetate (dried from treatment with toluene and removal of the toluene in vacuo) as a solid (0.75 eq.), nitromethane (20 eq.), and 4-methoxy-1H-indole-3-carbaldehyde (5.4 g; 30.82 mmol). Heat to about 65° C. After the reaction is judged to be near completion (by TLC), add silica gel and evaporate in vacuo to remove the nitromethane. Load the silica gel from the reaction mixture on top of short column of silica gel and elute with 25% acetone in hexanes to give, after evaporation, the title compound which may be used in the next step without further purification.

By the method of Example 51 the following compounds were prepared: a) 3-(2-Nitrovinyl)-6-methoxy-1H-indole, b) 3-(2-Nitrovinyl)-7-methoxy-1H-indole, $^1$H NMR (300 MHz; d6-DMSO): 3.95 (s, 3H), 5.02 (m, 1H), 6.86 (d, 1H), 7.17 (t, 1H), 7.50 (d, 1H), 8.38 (d, 1H), 12.40 (bs, 1H); MS (ES+): m/z 219 (M+H)$^+$; (ES–): m/z 217 (M–1)$^-$;

c) 3-(2-Nitrovinyl)-4-chloro-1H-indole, $^1$H NMR (300 MHz, d6-DMSO): 5.08 (m, 1H), 7.24 (m, 2H), 7.51 (dd, 1H), 8.12 (d, 1H), 8.92 (d, 1H), 12.6 (bs, 1H); MS (ES–): m/z 221, 223 (M–H);

d) 3-(2-Nitrovinyl)-6-chloro-1H-indole, $^1$H NMR (300 MHz, d6-DMSO): 5.03 (m, 1H), 7.22 (dd, 1H), 7.58 (d, 1H), 8.03 (m, 2H), 8.38 (d, 1H), 12.23 (bs, 1H); MS (ES−): m/z 223, 221 (M−H)$^-$;

e) 3-(2-Nitrovinyl)-7-chloro-1H-indole, $^1$H NMR (300 MHz, d6-DMSO): 7.23 (t, 1H), 7.36 (d, 1H), 7.97 (d, 1H), 8.06 (d, 1H), 8.33 (bs, 1H), 8.40 (d, 1H), 12.58 (bs, 1H); MS (ES+): m/z 225, 223 (M+H)$^+$; (ES−): m/z 223, 221 (M−H)$^-$;

f) 3-2-Nitrovinyl)-4-fluoro-1H-indole, g) 3-(2-Nitrovinyl)-5-methoxy-trifluoromethyl-1H-indole, MS (ES+): m/z 286 (M+); (ES−): m/z 285 (M−H)$^-$;

h) 3-(2-Nitrovinyl)-6-chloro-5-methoxy-1H-indole, i) 3-(2-Nitrovinyl)-4-chloro-5-methoxy-1H-indole, $^1$H NMR (300 MHz, d6-DMSO): 3.88 (s, 3H), 5.03 (m, 2H), 7.13 (d, 1H), 7.46 (d, 1H), 8.08 (d, 1H), 12.42 (bs, 1H); MS (ES−): m/z 151, 153 (M−H);

j) 3-(2-Nitrovinyl)-6-trifluoromethyl-1H-indole, MS (ES+): m/z 257 (M+H)$^+$; (ES−): m/z 255 (M−H)$^-$;

k) 3-(2-Nitrovinyl)-5-methoxy-2-methyl-1H-indole, $^1$H NMR (300 MHz, d6-DMSO): 2.58 (s, 3H), 3.84 (s, 3H), 6.82 (m, 1H), 7.28 (m, 2H), 7.89 (d, 1H), 8.29 (d, 1H), 12.14 (bs, 1H); MS (ES+): nl/z 233 (M+H)$^+$; (ES−): m/z 231 (M−H)$^-$;

l) 3-(2-Nitrovinyl)-6-fluoro-5-methoxy-1H-indole;

m) 3-(2-Nitrovinyl)-5,6-difluoro-1H-indole;

n) 3-(2-Nitrovinyl)-6-chloro-5-fluoro-1H-indole;

o) 3-(2-Nitrovinyl)-5-trifluoromethoxy-1H-indole;

p) 3-(2-Nitrovinyl)-4,6-difluoro-5-methoxy 1H-indole;

q) 3-(2-Nitrovinyl)-4-phenyl-1-1H-indole;

r) 3-(2-Nitrovinyl)-6-phenyl-1H-indole;

s) 3-(2-Nitrovinyl)-5-isopropyl-1H-indole;

t) 3-(2-Nitrovinyl)-4,6-difluoro-5-methoxy-1-methyl-1H-indole: $^1$H NMR (300 MHz, d6-DMSO): 3.82 (t, 3H), 3.92 (s, 3H), 7.53 (m, 1H), 7.84 (m, 1H), 8.30 (m, 2H); MS (ES+): m/z 269 (M+H)$^+$; and u) 3-(2-Nitrovinyl)-4,6-difluoro-1-methyl-1H-indole.

Example 52

4-Methoxytryptamine

Combine LiAlH$_4$ (6.78 g; 178.74 mmol; 6 eq) and anhydrous THF. Dissolve 3-(2-nitrovinyl)-4-methoxy-1H-indole (6.5 g; 29.79 mmol) in anhydrous THF and add dropwise to the LiAlH$_4$ solution with vigorous stirring. After the addition is complete, heat to reflux. After 1 hour cool to ambient temperature and stir. After 16 hours, quench the excess LiAlH$_4$ as described in *J. Med. Chem.* 1995, 38, 2050. Filter the gray suspension through celite and rinse the celite with ethyl acetate. Evaporate the filtrate in vacuo to residue. Chromatograph the residue on silica gel eluting with 1 L of CHCl$_3$MeOH/NH$_4$OH (95:10:1) and then 1 L of CHCl$_3$/MeOH/NH$_4$OH (90:10:1) as the mobile phase. Pool fractions containing the product and evaporate to give the title compound as a tan solid: $^1$H NMR (300 MHz, d$_6$-DMSO): 2.96 (t, 2H); 3.42 (t, 2H), 3.83 (s, 3H); 6.42 (dd, 1H); 6.93 (m, 3H); 10.7 (s, 1H); MS (ES+): m/z 191 (M+H)$^+$; 174 (M−NH$_2$)$^+$; 159 (M−OCH$_3$)$^+$; (ES−): m/z 189 (M−H)$^-$.

By the method of Example 52 the following compounds were prepared: a) 6-Methoxytryptamine, $^1$H NMR (300 MHz; d6-DMSO): 2.86 (t, 2H); 3.42 (t, 2H); 3.75 (s, 3H); 6.62 (dd, 1H); 6.83 (m, 1H); 6.97 (bs, 1H); 7.37 (m, 1H); 10.55 (s, 1H); MS (ES+): m/z 191 (M+H)$^+$; 174 (M−NH$_2$)$^+$; (ES−): m/z 189 (M−H)$^-$;

b) 7-Methoxytryptamine, $^1$H NMR (300 MHz, d6-DMSO): 2.88 (t, 2H), 3.42 (t, 2H), 3.89 (s, 3H), 6.61 (d, 1H), 6.89 (t, 1H), 7.02 (m, 1H), 7.10 (d, 1H), 10.85 (bs, 1H); MS (ES+): m/z 191 (M+H)$^+$, 174 (M−NH$_2$)$^+$; (ES−): m/z 189 (M−H)$^-$;

c) 4-Chlorotryptamine, $^1$H NMR (300 MHz, d6-DMSO): 3.11 (t, 2H), 3.44 (t, 2H), 6.99 (m, 2H), 7.22 (m, 1H), 7.30 (d, 1H), 11.19 (bs, 1H); MS (ES+): m/z 178, 180 (M+H)$^+$; (ES−): m/z 193 (M−H)$^-$;

d) 6-Chlorotryptamine, $^1$H NMR (300 MHz, d6-DMSO): 2.89 (t, 2H), 3.42 (t, 2H), 6.96 (dd, 1H), 7.17 (bs, 1H), 7.35 (m, 1H), 7.52 (d, 1H), 10.91 (bs, 1H); MS (ES+): m/z 197, 195 (M+H)$^+$, 180, 178 (M−NH$_2$)$^+$; (ES−): m/z 195, 193 (M−H)$^-$;

e) 7-Chlorotryptamine, $^1$H NMR (300 MHz, d6-DMSO): 2.91 (t, 2H), 3.43 (t, 2H), 6.98 (t, 1H), 7.13 (d, 1H), 7.20 (bs, 1H), 7.51 (d, 1H), 11.15 (bs, 1H); MS (ES+): m/z 197, 195 (M+H)$^+$, 180, 178 (M−NH$_2$)$^+$; (ES−): m/z 195, 193 (M−H)$^-$;

f) 4-Fluorotryptamine, g) 5-Methoxy-6-trifluoromethyltryptamine, h) 6-Chloro-5-methoxytryptamine, $^1$H NMR (300 MHz, d6-DMSO): 2.89 (t, 2H), 3.42 (t, 2H), 3.84 (s, 3H), 7.12 (bs, 1H), 7.19 (s, 1H), 7.36 (s, 1H), 8.01 (bs, 1H); MS (ES+): m/z 225, 227 (M+H)$^+$, 208, 210 (M−NH2)$^+$; (ES−): m/z 223, 225 (M−H)$^-$;

i) 4-Chloro-5-methoxytryptamine, $^1$H NMR (300 MHz, d6-DMSO): 3.10 (t, 2H), 3.43 (t, 2H), 3.81 (s, 3H), 6.95 (d, 1H), 7.18 (m, 1H), 7.25 (dd, 1H), 10.93 (bs, 1H); MS (ES+): m/z 208, 210 (M−NH$_2$)$^+$ (ES−): m/z 223, 225 (M−H)$^-$;

j) 6-Trifluoromethyltryptamine, k) 5-Methoxy-2-methylatyptamine, $^1$H NMR (300 MHz, d6-DMSO): 2.28 (s, 3H), 2.80 (t, 2H), 3.31 (bt, 2H), 6.59 (dd, 1H), 6.88 (d, 1H), 7.09 (d, 1H); MS (ES+): m/z 188 (M−NH$_2$)$^+$ (ES−): m/z 203 (M−H)$^-$;

l) 6-Fluoro-5-methoxytryptamine;

m) 5,6-Difluorotryptamine;

n) 6-Chloro-5-fluorotryptamine;

o) 5-Trifluoromethoxytryptamine;

p) 4,6-Difluoro-5-methoxytryptamine;

q) 4-Phenyltryptamine;

r) 6-Phenyltryptamine;

s) 5-Isopropyltryptamine;

t) 4,6-Difluoro-5-methoxy-1-methyltryptamine: $^1$H NMR (300 MHz, CDCl$_3$): 3.0 (m, 4H), 3.67 (s, 3H), 3.98 (s, 3H), 6.85 (m, 2H); and u) 4,6-Difluoro-5-methoxy-1-methyltryptamine: $^1$H NMR (300 MHz, d6-DMSO): 2.92 (t, 2H), 3.39 (t, 2H), 3.69 (s, 3H), 6.75 (m, 1H), 7.13 (m, 2H); MS (ES+): m/z 211; (M+H)$^+$ 194 (M−NH$_2$)$^+$.

Example 53

4-Methoxytryptamine hydrochloride

Dissolve 4-methoxytryptamine (1 g, 5.26 mmol) in MeOH and add of NH$_4$Cl (0.97 eq, 0.27 g, 5.10 mmol). After 30 minutes, evaporate in vacuo to remove the MeOH leaving a thick orange oil. Dissolve the oil in MeOH and add dropwise to Et$_2$O (200 mL) with vigorous stirring giving a gummy white precipitate. Stir with heating to give the title compound as a solid: $^1$H NMR (d$_6$-DMSO, 300 MHz): 3.06 (bs, 4H); 3.86 (s, 3H); 6.46 (dd, 1H); 7.06-6.9 (m, 3H); 7.93 (bs, 1H); 10.9 (s, 1H); MS (ES+): m/z 191 (M+H)$^+$; 175 (M−CH$_3$)$^+$; 174 (M−NH$_2$)$^+$; (ES−): 189 (M−H)$^-$; Analysis for C$_{11}$H$_{15}$ClN$_2$O: Calcd.: C, 58.2788; H, 6.6692; N, 12.3566. found C, 58.18; H, 6.73; N, 12.15.

Example 54

5,6-Difluorotryptamine hydrochloride

Prepare by the method of Example 53 to give the title compound: $^1$H NMR (300 MHz, d6-DMSO): 2.97 (m, 4H), 7.27 (m, 1H), 7.36 (m, 1H), 7.53 (m, 1H), 11.20 (bs, 1H); MS (ES+): m/z 197 (M+H)$^+$, 180 (M−NH$_2$)$^+$; (ES−): m/z 195 (M−H)$^−$.

Example 55

4-Phenyltryptamine hydrochloride

Add a solution of HCl (4.6 mL of 4 M HCl in 1,4-dioxane) dropwise to a solution of 4-phenyltryptamine (3.33 g, 14.09 mmol) in EtOAc/Et$_2$O to give a solid. Collect the solid by filtration and dry overnight in a vacuum oven at room temperature to give the title compound as an off white solid: $^1$H NMR (300 MHz, d6-DMSO): 2.54 (m, 4H), 6.82 (m, 1H), 7.14 (t, 1H), 7.27 (m, 1H), 7.41 (m, 5H), 7.68 (bs, 2H), 11.28 (bs, 1H); MS (ES+): m/z 237 (M+H)$^+$, 220 (M−NH2)$^+$; (ES−): m/z 235 (M−H)$^−$; Analysis for C$_{16}$H$_{17}$ClN$_2$; Calcd.: C, 70.4517; H, 6.2818; N, 10.2696. found: C, 70.26; H, 6.16; N, 10.20.

Example 56

5-Chloro-6-fluorotryptamine hydrochloride

Prepare by the method of Example 55 to give the title compound: $^1$H NMR (300 MHz, d6-DMSO): 3.00 (m, 4H), 7.37 (m, 1H), 7.53 (d, 1H), 7.59 (d, 1H), 11.28 (bs, 1H); MS (ES+): m/z 213 (M+H)$^+$, 196, 198 (M−NH$_2$)$^+$; (ES−): m/z 211, 213 (M−H)$^−$.

Example 57

4-Chlorotryptamine oxalate

Add dropwise oxalic acid (1.32 g, 1.3 eq.) in MeOH to a solution of 4-chlorotryptamine in EtOAc (2.2 g, 11.3 mmol) with vigorous stirring. When addition was complete, add Et$_2$O to the cloud point and place flask in the freezer to give a solid. Collect the solid by filtration and wash with ether. Dry in a vacuum oven at room temperature to give the title compound as an off-white solid: $^1$H NMR (300 MHz, d6-DMSO): 3.11 (m, 2H), 3.2 (m, 2H), 7.04 (m, 2H), 7.34 (m, 2H), 11.44 (bs, 1H); MS (ES+): m/z 195 (M+H)$^+$, 178 (M−NH$_2$)$^+$; (ES−): m/z 193 (M−H)$^−$; Analysis for C$_{12}$H$_{13}$ClN$_2$O$_4$: Calcd.: C, 50.6263; H, 4.6026; N, 9.8396. found: C, 50.56; H, 4.57; N, 9.66.

Using the method of Example 57 gives the following compounds: a) 6-Phenyltryptamine oxalate: 3.05 (m, 4H), 7.31 (m, 3H), 7.45 (t, 2H), 7.65 (m, 4H), 11.10 (bs, 1H). MS (ES+): m/z 237 (M+H)$^+$, 220 (M−NH2)$^+$; (ES−): m/z 235 (M−H);

b) 4,6-Difluoro-5-methoxytryptamine oxalate: 1H NMR (300 MHz, d6-DMSO): 3.04 (m, 4H), 3.85 (s, 3H), 7.10 (m, 1H), 7.22 (m, 1H), 11.29 (bs, 1H); MS (ES+): m/z 227 (M+H)$^+$; (ES−): m/z 225 (M−H)$^−$; Analysis for C$_{13}$H$_{14}$F$_2$N$_2$O$_5$: Calcd.: C, 49.3718; H, 4.4620; N, 8.8576. found: C, 49.68; H, 4.57; N, 8.60. and c) 5-Isopropyltryptamine oxalate: $^1$H NMR (300 MHz, d6-DMSO): 1.25 (d, 6H), 3.01 (m, 4H), 6.99 (m, 1H), 7.17 (m, 1H), 7.27 (m, 1H), 7.36 (bs, 1H), 10.85 (bs, 1H); MS(ES+): m/z 203 (M+H)$^+$, 186 (M−NH2)+; (ES−): m/z 201 (M−H)$^−$.

Example 58

5-Trifluoromethoxytryptamine oxalate

Add oxalic acid (1.3 eq.) in acetone to a solution of 5-trifluoromethoxytryptamine in acetone. Warm and add Et$_2$O to the cloud point and then placed in the freezer overnight to obtain the title compound as a white crystalline solid: $^1$H NMR (300 MHz, d6-DMSO): 3.02 (m, 4H), 7.06 (m, 1H), 7.39 (m, 1H), 7.45 (d, 1H), 7.55 (m, 1H), 11.30 (bs, 1H). MS (ES+): m/z 245 (M+H)$^+$, 228 (M−NH$_2$)$^+$; (ES−): m/z 243 (M−H); Analysis for C$_{11}$H$_{11}$F$_3$N$_2$O: Calcd.: C, 46.7144; H, 3.9203; N, 8.3809. found: C, 46.55; H, 3.62; N, 8.27.

Using the method of Example 58 gives the following compounds: a) 4,6-Difluoro-5-methoxytryptamine oxalate: $^1$H NMR (300 MHz, d6-DMSO): 3.04 (m, 4H), 3.85 (s, 3H), 7.10 (m, 1H), 7.22 (m, 1H), 11.29 (bs, 1H); MS (ES+): m/z 227 (M+H)$^+$; (ES−): m/z 225 (M−H)$^−$; Analysis for C$_{13}$H$_{14}$F$_2$N$_2$O$_5$: Calcd.: C, 49.3718; H, 4.4620; N, 8.8576. found: C, 49.68; H, 4.57; N, 8.60.

Example 60

4-Fluorotryptamine oxalate

Add dropwise oxalic acid (1.44 g, 1.2 eq.) in acetonitrile to an acetonitrile solution of 4-fluorotryptamine with vigorous stirring. Warm add MeOH to make a solution. Add Et$_2$O to the cloud point and cool the solution in the freezer to give a solid. Collect the solid by filtration and dry in a vacuum oven overnight at 45° C. to give the title compound as a tan solid: $^1$H NMR (300 MHz, d6-DMSO): 3.07 (m, 4H), 6.73 (m, 1H), 7.04 (m, 1H), 7.22 (m, 2H), 11.30 (bs, 1H); MS (ES+): m/z 179 (M+H)$^+$; (ES−): m/z 177 (M−H)$^−$.

Example 61

6-Fluoro-5-methoxytryptamine oxalate

Add oxalic acid (3.91 g, 1.2 eq.) in MeOH dropwise to an EtOAc/MeOH solution of 6-fluoro-5-methoxytryptamine with vigorous stirring. Add Et$_2$O to give a solid and collect the solid by filtration and dry overnight in a vacuum oven at 60° C. to give the title compound: $^1$H NMR (300 MHz, d6-DMSO): 3.0 (m, 4H), 3.85 (s, 3H), 7.21 (m, 3H), 10.89 (bs, 1H); MS (ES+): m/z 209 (M+H)$^+$; Analysis for C$_{13}$H$_{15}$FN$_2$O$_5$: Calcd.: C, 52.3496; H, 5.0690; N, 9.3919. Found: C, 52.06; H, 4.91; N, 9.20.

Example 62

2-(2-(7-Fluoro 1H-indol-3-yl)ethyl)isoindole-1,3-dione

Combine 2-fluorohydrazine hydrochloride (3.25 g, 20 mmol) and 2-(4,4-diethoxy-butyl)-isoindole-1,3-dione (6.99 g, 24 mmol) and dissolve in 4% aqueous H$_2$SO$_4$. Heat the reaction to reflux. After 2 hours, cool to ambient temperature. Basify the reaction mixture with 30% aqueous NH$_4$OH to pH of about 11. Extract with dichloromethane (2×100 mL). Combine the organic phases, dry over MgSO$_4$, filter, and remove the solvent leaving an orange oil. Absorb the oil onto silica gel and load on top short column of silica gel equilibrated with 15% EtOAc in hexanes. Eluent with 15% EtOAc in hexanes (1500 mL) and then 30% EtOAc in hexanes (2000 mL) to give, after evaporation, the title compound as a yellow solid: $^1$H NMR (300 MHz, d6-DMSO): 3.03 (t, 2H), 3.85 (t, 2H), 6.91 (m, 2H), 7.25 (m, 1H), 7.36 (d, 1H), 7.83 (m, 4H), 11.32 (bs, 1H); MS (FD): m/z 308 (M+).

Example 63

7-Fluorotryptamine oxalate

Dissolve 2-(2-(7-fluoro-1H-indol-3-yl)ethyl)isoindole-1,3-dione in 25 mL of THF. Add ethanolamine (63.4 g, 62.65 mL, 1038 mmol, 100 eq.) with vigorous stirring and heat to 70° C. After 1.5 hours, cool to room temperature. After 18 hours, pour reaction mixture into of water (250 mL) containing of 5N NaOH (3 mL) and extract with Et$_2$O (2×200 mL). Combine the organic layers and wash with 0.1 N NaOH. Collect the organic layer, dry over MgSO$_4$, filter, and remove the solvent in vacuo to give the title compound as a yellow oil.

Add oxalic acid (0.62 g, 1.2 eq.) in MeOH dropwise to an EtOAc solution of the base (1.02 g, 5.72 mmol) with vigorous stirring. Heat the cloudy suspension to reflux for 30 minutes and then cool to give a solid. Collect the solid by filtration and dry overnight in a vacuum oven at 60° C. to give the title compound as an off-white solid: $^1$H NMR (300 MHz, d6-DMSO): 3.04 (m, 4H), 6.96 (m, 2H), 7.30 (m, 1H), 7.38 (d, 1H), 11.51 (bs, 1H); MS (ES+): m/z 179 (M+H)$^+$, 162 (M−NH$_2$)$^+$; (ES−): m/z 177 M−H)$^−$; Analysis for C$_{12}$H$_{13}$FN$_2$O$_4$: Calcd.: C, 53.7318; H, 4.8849; N, 10.4431. found: C, 53.50; H, 4.86; N, 10.32.

Example 64

6-Trifluoromethyltryptamine oxalate

Add 6-trifluoromethyltryptamine to 1:1 acetone/Et$_2$O. Add dropwise of oxalic acid (1.2 eq.) in acetone to give a solid. Collect the solid by filtration and dry overnight in the vacuum oven to obtain the title compound: MS (ES+): m/z 212 (M−NH$_2$)$^+$; (ES−): m/z 227 (M−H)$^−$.

Example 65

4,6-Difluoro-5-methoxy-1H-indole

Dissolve 2,6-difluoro-4-nitrophenol (J. Heterocyclic. Chem. 1976, 13, 1253; 10 g, 57.11 mmol) in 300 mL of benzene. Add dropwise a solution of 1-methyl-3-p-tolyltriazene (9.37 g, 62.82 mmol, 1.1 eq.) in benzene (150 mL). After TLC indicates absence of starting material, transfer the reaction mixture to a separator funnel and wash with 1 N HCl, then saturated NaHCO$_3$, and then water. Dry the organic layer over MgSO$_4$, filter, and remove the solvent to give a residue. Crystallize the residue from MeOH/water to give 1,3-difluoro-2-methoxy-5-nitrobenzene as white needles: $^1$H NMR (300 MHz, CDCl$_3$): 4.25 (t, 3H), 7.80 (d, 2H).

Combine 1,3-difluoro-2-methoxy-5-nitrobenzene (10.12 g, 53.51 mmol) and 4-chlorophenoxyacetonitrile (11.21 g, 66.89 mmol 1.25 eq.) in DMSO (150 mL). Add dropwise to a suspension of solid NaOH (powdered, 10.70 g, 267.55 mmol, 5 eq.) over 5 hours. After 18 hours, pour the reaction mixture into cold, aqueous HCl and extract with Et$_2$O (2×150 mL). Combine the organic layers, wash with brine, and evaporate to give a residue. Chromatograph the residue on silica gel and eluting with 20% EtOAc in hexanes to give, after evaporation, (2,4-difluoro-3-methoxy-6-nitrophenyl)acetonitrile as a yellow oil: MS (ES−): m/z 227 (M−H)$^−$.

Using (2,4-difluoro-3-methoxy-6-nitrophenyl)acetonitrile in the cyclization as described in Israel J. Chem. 1966, 4, 155-159 gives an oil. Chromatograph the oil on silica gel eluting with 20% EtOAc in hexanes to give, after evaporation, the title compound as a purple solid; $^1$H NMR (300 MHz, d6-DMSO): 3.85 (bs, 3H), 6.46 (m, 1H), 7.12 (d, 1H), 7.36 (m, 1H), 11.35 (bs, 1H); MS (ES−): m/z 182 (M−H)$^−$.

Using the method of Example 65 gives the following compounds: a) 4,6-Difluoro-1H-indole: $^1$H NMR (300 MHz, CDCl$_3$): 4.68 (d, 2H), 6.14 (m, 2H), 6.57 (bs, 2H); MS (ES+): m/z 205, 207 (M+H)$^+$ which gives the title compound.

Example 66

4,6-Difluoro-5-methoxy-1-methyl-1H-indole

Combine 4,6-difluoro-5-methoxy-1H-indole (7.5 g, 40.95 mmol) and cold DMF (100 mL) and treat with NaH (1.8 g, 45.05 mmol, 1.1 eq.) and with vigorously stirring. After about 10 minutes, add dropwise iodomethane (11.62 g, 81.90 mmol, 2 eq.). After the addition was complete, allow the reaction to stir at room temperature for several hours until TLC indicates the absence of starting material. Dilute the reaction with water and extract with Et$_2$O (2×150 mL). Combine the organic layers, dry over MgSO$_4$, filter, and remove the solvent leaving an oil. Chromatograph the oil on silica gel eluting with 10% EtOAc in hexanes to give, after evaporation, the title compound as a light yellow oil: $^1$H NMR (300 MHz, CDCl$_3$): 3.72 (s, 3H), 3.97 (s, 3H), 6.50 (d, 1H), 6.84 (d, 1H), 6.98 (d, 1H); MS (ES+): m/z 198 (M+H)$^+$; Analysis for C$_{10}$H$_9$F$_2$NO: Calcd.: C, 60.91; H, 4.60; N, 7.10. found: C, 60.93; H, 4.63; N, 7.25.

Using the method of Example 66 gives the following compounds: a) 4,6-Difluoro-1-methyl-1H-indole.

Example 67

N-(2-(5-Methoxy-1H-indol-3-yl)ethyl)-3-phenoxy-benzylamine

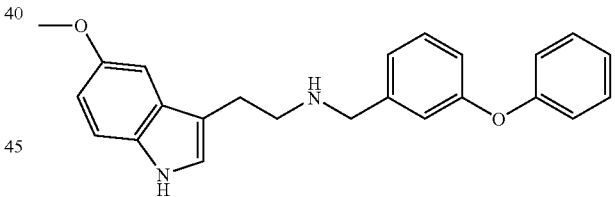

Combine 3-phenoxybenzaldehyde (5.6 ml, 26.7 mmol), 5-methoxytryptamine (5.0 g, 26.7 mmol) and 3 Å molecular sieves (1.0 g) in methanol (50 ml) and under argon and heat at reflux for 4 hours. Remove the molecular sieves by filtration and then slowly add sodium borohydride (3.0 g, 60.0 mmol) portionwise. Stir at room temperature for 1 hour and concentrate under reduced pressure, dissolve the concentrated reaction mixture in sodium hydroxide 1N (100 ml) and extract with dichloromethane (3×50 ml). Combine organic layers and wash sequentially with distilled water (50 ml) and brine (50 ml), dry (Na$_2$SO$_4$) the organic layer, and concentrate to give a residue. Chromatograph the residue on silica gel eluting with 9:1 EtOAc:MeOH with 2% NH4OH gives the title compound.

Formation of oxalate salt: Add a solution of the free base (8.7 g, 23.5 mmol) in EtOAc (50 ml) to a solution of oxalic acid (2.1 g, 23.5 mmol) in EtOAc (5 ml) to give a precipitate. Collect the precipitate and recrystallize from methanol/diethyl ether to give a solid. Collect the solid by filtration, rinse with diethyl ether, and dry in a vacuum oven at 50° C. overnight to give the title compound as the oxalate, mp 188-190° C., RMN consistent, Mass: m/z 373.2 (M+), Anal. Calcd for $C_{26}H_{26}N_2O_6$: C, 67.52; H, 5.67; N, 6.06. Found: C, 67.38; H, 5.46; N, 6.04.

By the method of Example 67 the following compounds were prepared, isolated as the oxalate except where noted:

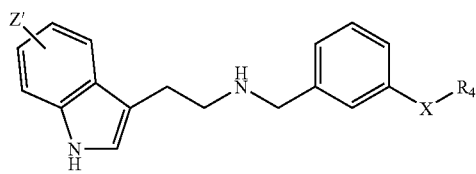

| No. | Z' | X | R₄ | Data |
|---|---|---|---|---|
| 68 | H | —O— | phenyl | mp 203-205° C., Mass: m/z 343.1 (M⁺), Anal. Calcd for $C_{25}H_{24}N_2O_5$: C, 69.43; H, 5.59; N, 6.48 Found: C, 69.25; H, 5.42; N, 6.37 |
| 69 | H | —S— | phenyl | mp 106-108° C., Mass: m/z 359.2 (M⁺), Anal. Calcd for $C_{22}H_{24}N_2O_4S$: C, 66.95; H, 5.39; N, 6.25 Found: C, 66.19; H, 5.49; N, 6.13 |
| 70 | H | —SO₂— | phenyl | mp 203-205° C., Mass: m/z 391.2 (M⁺), Anal. Calcd for $C_{25}H_{24}N_2O_6S$: C, 62.49; H, 5.03; N, 5.83 Found: C, 62.05; H, 5.21; N, 5.82 |
| 71 | 5-methoxy | —S— | phenyl | mp 198-200° C., Mass: m/z 389.3 (M⁺), Anal. Calcd for $C_{26}H_{26}N_2O_5S$: C, 65.25; H, 5.48; N, 5.85 Found: C, 64.50; H, 5.63; N, 5.73 |
| 72 | 5-methoxy | —SO₂— | phenyl | mp 142-144° C., Mass: m/z 421.1 (M⁺), Anal. Calcd for $C_{26}H_{26}N_2O_7S$: C, 61.16; H, 5.13; N, 5.49 Found: C, 61.14; H, 5.38; N, 5.25 |
| 73 | H | —S— | 4-methylphenyl | mp 190-192° C., Mass: m/z 373.2 (M⁺), Anal. Calcd for $C_{26}H_{26}N_2O_4S$: C, 67.51; H, 5.67; N, 6.06 Found: C, 67.44; H, 5.69; N, 6.13 |
| 74 | H | —SO₂— | 4-methylphenyl | mp 212-214° C., Mass: m/z 405.4 (M⁺), Anal. Calcd for $C_{26}H_{26}N_2O_6S$: C,63.14; H, 5.30; N, 5.66 Found: C, 62.59; H, 5.70; N, 5.29 |
| 75 | 5-methoxy | —CH(F)— | phenyl | mp 214-216° C., Mass: m/z 389.3 (M⁺), Anal. Calcd for $C_{27}H_{27}FN_2O_5$: C, 67.77; H, 5.69; N, 5.85 Found: C, 67.52; H, 5.77; N, 5.64 |
| 76 | H | —CH(F)— | phenyl | mp 216-218° C., Mass: m/z 359.2 (M⁺), Anal. Calcd for $C_{26}H_{25}FN_2O_4$: C, 69.63; H, 5.62; N, 6.25 Found: C, 69.55; H, 5.36; N, 5.95 |
| 77 | 5-methoxy | —CH₂— | phenyl | mp 199-202° C., Mass: m/z 371.1 (M⁺), Anal. Calcd for $C_{27}H_{28}N_2O_5$: C, 70.42; H, 6.13; N, 6.08 Found: C, 69.73; H, 6.25; N, 6.05 |
| 78 | H | —CH₂— | phenyl | mp 222-224° C., Mass: m/z 341.2 (M⁺), Anal. Calcd for $C_{26}H_{26}N_2O_4$: C, 72.54; H, 6.09; N, 6.51 Found: C, 72.23; H, 6.08; N, 6.37 |
| 79 | 5-methoxy | —CH(OH)— | phenyl | mp 146-148, Mass: m/z 387.2, Anal. Calcd for $C_{27}H_{28}N_2O_5$: C, 68.05; H, 5.92; N, 5.88 Found: C, 67.29; H, 6.03; N, 5.51 |
| 80 | H | —CH(OH)— | phenyl | mp 167-169° C., Mass: m/z 357.3 (M⁺), Anal. Calcd for $C_{26}H_{26}N_2O_5$: C, 69.94; H, 5.87; N, 6.27. Found: C, 68.11; H, 6.07; N, 6.06 |
| 81 | 5-methoxy | —NH— | phenyl | mp 170-172° C., Mass: m/z 372.3 (M⁺), Anal. Calcd for $C_{26}H_{27}N_3O_5$: C, 67.67; H, 5.90; N, 9.10 Found: C, 67.24; H, 6.08; N, 8.54 |
| 82 | H | —NH— | phenyl | mp 196-198° C., Mass: m/z 342.2 (M⁺), Anal. Calcd for $C_{25}H_{25}N_3O_4$: C, 69.59; H, 5.84; N, 9.74 Found: C, 67.57; H, 6.06; N, 8.84 |
| 83 | 5-methoxy | —NH— | benzyl | mp 203-205° C., Mass: m/z 386.2 (M⁺), Anal. Calcd for $C_{27}H_{29}N_3O_5$: |

-continued

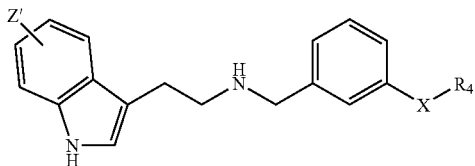

| No. | Z' | X | R₄ | Data |
|---|---|---|---|---|
| | | | | C, 68.20; H, 6.15; N, 8.84 Found: C, 67.46; H, 6.14; N, 8.79 |
| 84 | H | —NH— | benzyl | mp 204-206° C., Mass: m/z 356.3 (M⁺), Anal. Calcd for $C_{26}H_{27}N_3O_4$: C, 70.10; H, 6.11; N, 9.43. Found: C, 68.48; H, 5.95; N, 9.26. |
| 85 | 5-methoxy | —O— | H | mp 126-128° C., Mass: m/z 297.5 (M⁺), Anal. Calcd for $C_{18}H_{20}N_2O_2$: C, 72.94; H, 6.80; N, 9.45. Found: C, 71.78; H, 6.71; N, 9.20. (isolated as the base) |
| 86 | H | —O— | H | mp 143-145° C., Mass: m/z 267.3 (M⁺), Anal. Calcd for $C_{17}H_{18}N_2O$: C, 76.66; H, 6.81; N, 10.51. Found: C, 75.11; H, 6.61; N, 10.22 (isolated as the base) |
| 87 | 5-fluoro | —O— | phenyl | mp 204-206° C., Mass: m/z 361.1 (M⁺), Anal. Calcd for $C_{25}H_{23}FN_2O_5$: C, 66.66; H, 5.15; N, 6.22. Found: C, 66.83; H, 5.17; N, 6.30. |
| 88 | 5-methoxy | —O— | naphth-1-yl | mp 196-198° C., Mass: m/z 423.1 (M⁺), Anal. Calcd for $C_{30}H_{26}N_2O_6$: C, 70.30; H, 5.51; N, 5.47. Found: C, 68.11; H, 5.56; N, 5.52. |
| 89 | H | —O— | naphth-1-yl | mp 210-212° C., Mass: m/z 393.2 (M⁺), Anal. Calcd for $C_{29}H_{24}N_2O_5$: C, 72.19; H, 5.43; N, 5.81. Found: C, 72.10; H, 5.40; N, 6.66. |
| 90 | 5-methoxy | —O— | 3-fluoro phenyl | mp 186-188° C., Mass: m/z 391.2 (M⁺), Anal. Calcd for $C_{26}H_{25}FN_2O_6$: C, 64.99; H, 5.24; N, 5.83. Found: C, 63.10; H, 5.11; N, 5.67. |
| 91 | H | —O— | 3-fluoro phenyl | mp 217-219° C. in 75% yield, RMN consistent, Mass: m/z 361.1 (M⁺), Anal. Calcd for $C_{25}H_{23}FN_2O_5$: C, 66.66; H, 5.15; N, 6.22. Found: C, 66.12; H, 5.22; N, 6.34. |
| 92 | 5-methoxy | —O— | 2-fluoro phenyl | mp 184-186° C., Mass: m/z 391.2 (M⁺), Anal. Calcd for $C_{26}H_{25}FN_2O_6$: C, 64.99; H, 5.24; N, 5.83. Found: C, 65.06; H, 5.23; N, 5.85. |
| 93 | H | —O— | 2-fluoro phenyl | mp 206-208° C., Mass: m/z 361.1 (M⁺), Anal. Calcd for $C_{25}H_{23}FN_2O_5$: C, 66.66; H, 5.15; N, 6.22. Found: C, 66.30; H, 4.97; N, 6.21. |
| 94 | 5-methoxy | —O— | 4-fluoro phenyl | mp 184-186° C., Mass: m/z 391.2 (M⁺), Anal. Calcd for $C_{26}H_{25}FN_2O_6$: C, 64.99; H, 5.24; N, 5.83. Found: C, 63.99; H, 4.95; N, 5.75. |
| 95 | H | —O— | 4-fluoro phenyl | mp 222-224° C., Mass: m/z 361.1 (M⁺), Anal. Calcd for $C_{25}H_{23}FN_2O_5$: C, 66.66; H, 5.15; N, 6.22. Found: C, 65.74; H, 4.81; N, 6.13. |
| 96 | 5-methoxy | —O— | naphth-2-yl | mp 198-200° C., Mass: m/z 423.1 (M⁺), Anal. Calcd for $C_{30}H_{26}N_2O_6$: C, 70.30; H, 5.51; N, 5.47. Found: C, 68.97; H, 5.43; N, 5.44. |
| 97 | H | —O— | naphth-2-yl | mp 219-221° C., Mass: m/z 393.2 (M⁺), Anal. Calcd for $C_{29}H_{24}N_2O_5$: C, 72.19; H, 5.43; N, 5.81. Found: C, 71.65; H, 5.32; N, 5.91. |
| 98 | 5-methoxy | —O— | benzyl | mp 204-206° C., Mass: m/z 387.2 (M⁺), Anal. Calcd for $C_{27}H_{28}N_2O_6$: C, 68.05; H, 5.92; N, 5.87. Found: C, 67.26; H, 5.80; N, 5.86. |
| 99 | H | —O— | benzyl | mp 211-213° C., Mass: m/z 357.3 (M⁺), Anal. Calcd for $C_{26}H_{26}N_2O_5$: C, 69.94; H, 5.86; N, 6.27. Found: C, 69.46; H, 5.75; N, 6.16. |

-continued

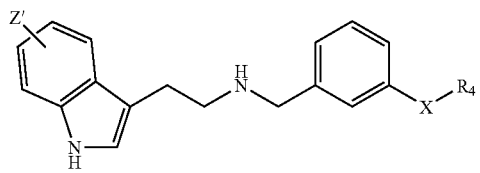

| No. | Z' | X | R4 | Data |
|-----|-----|-----|-----|-----|
| 100 | 5-hydroxy | —O— | phenyl | mp 188-190° C., Mass: m/z 359.2 (M+), Anal. Calcd for C25H24N2O6: C, 66.95; H, 5.39; N, 6.24. Found: C, 63.56; H, 5.01; N, 5.86. |
| 101 | 5-methoxy | —O— | pyrimid-5-yl | mp 191-193° C., Mass: m/z 375.2 (M+), Anal. Calcd for C24H24N4O6: C, 62.06; H, 5.20; N, 12.06. Found: C, 61.66; H, 5.41; N, 10.87. |
| 102 | H | —O— | pyrimid-5-yl | mp 188-190° C., Mass: m/z 345.1 (M+), Anal. Calcd for C23H22N4O5: C, 63.58; H, 5.10; N, 12.89. Found: C, 62.52; H, 5.28; N, 11.58. |
| 103 | 5-methoxy | —O— | pyrid-4-yl | mp 124-126° C., Mass: m/z 374.2 (M+), Anal. Calcd for C23H25Cl2N3O2: C, 61.88; H, 5.64; N, 9.41. Found: C, 61.26; H, 5.70; N, 9.14. (isolated as the hydrochloride) |
| 104 | H | —O— | pyrid-4-yl | mp 147-149° C., Mass: m/z 344.2 (M+), Anal. Calcd for C22H23Cl2N3O: C, 63.46; H, 5.56; N, 10.09. Found: C, 61.47; H, 5.33; N, 9.43. (isolated as the hydrochloride) |
| 105 | 6-chloro | —O— | pyrid-4-yl | mp 150-152° C., Mass: m/z 378.2 (M+), Anal. Calcd for C22H22Cl3N3O: C, 58.61; H, 4.91; N, 9.32. Found: C, 57.28; H, 4.61; N, 8.85. |
| 106 | 5-methoxy | —O— | pyrid-3-yl | mp 178-180° C., Mass: m/z 374.2 (M+), Anal. Calcd for C25H25N3O6: C, 64.78; H, 5.43; N, 9.06. Found: C, 63.02; H, 5.30; N, 8.87. |
| 107 | H | —O— | pyrid-3-yl | mp 190-192° C., Mass: m/z 344.1. (M+), Anal. Calcd for C24H23N3O5: C, 66.50; H, 5.34; N, 9.69. Found: C, 65.69; H, 5.21; N, 9.20. |
| 108 | 5-fluoro | —O— | pyrid-3-yl | mp 135-137° C., Mass: m/z 362.3 (M+), Anal. Calcd for C22H22Cl2FN3O: C, 60.83; H, 5.10; N, 9.67. Found: C, 61.49; H, 5.31; N, 9.70. (isolated as the hydrochloride) |
| 109 | 6-chloro | —O— | pyrid-3-yl | mp 160-162° C., Mass: m/z 378.1 (M+), Anal. Calcd for C22H22Cl3N3O: C, 58.61; H, 4.91; N, 9.32. Found: C, 58.18; H, 4.89; N, 9.01. (isolated as the hydrochloride) |
| 110 | 5-methoxy | —O— | pyrid-2-yl | mp 202-204° C., Mass: m/z 374.2 (M+), Anal. Calcd for C23H25Cl2N3O2: C, 61.88; H, 5.64; N, 9.41. Found: C, 60.57; H, 6.35; N, 10.89. (isolated as the hydrochloride) |
| 111 | H | —O— | pyrid-2-yl | mp 196-198° C., Mass: m/z 344.2 (M+), Anal. Calcd for C22H23Cl2N3O: C, 63.46; H, 5.56; N, 10.09. Found: C, 63.69; H, 6.09; N, 11.62. (isolated as the hydrochloride) |
| 112 | 6-chloro | —O— | pyrid-2-yl | mp 149-151° C., Mass: m/z 378.1 (M+), Anal. Calcd for C22H22Cl3N3O: C, 58.61; H, 4.91; N, 9.32. Found: C, 61.96; H, 4.91; N, 9.73. (isolated as the hydrochloride) |
| 113 | 5-methoxy | —O— | thiazol-2-yl | mp 180-182° C., Mass: m/z 380.3 (M+), Anal. Calcd for C23H23N3O6S: C, 58.83; H, 4.93; N, 8.94. Found: C, 58.11; H, 4.79; N, 8.84. |
| 114 | H | —O— | thiazol-2-yl | mp 203-205° C., Mass: m/z 350.3 (M+), Anal. Calcd for C22H21N3O5S: C, 60.12; H, 4.81; N, 9.56. Found: C, 59.73; H, 4.83; N, 9.36. |
| 115 | 5-methoxy | —O— | 2,6-difluoro | mp 137-139° C., Mass: m/z 473.1 |

-continued

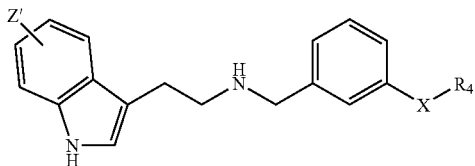

| No. | Z' | X | R₄ | Data |
|---|---|---|---|---|
| | | | phenylsulfonyl | (M⁺), Anal. Calcd for $C_{26}H_{24}F_2N_2O_8S$: C, 55.51; H, 4.30; N, 4.97. Found: C, 55.90; H, 4.47; N, 5.12. |
| 116 | H | —O— | 2,6-difluoro phenylsulfonyl | mp 185-187° C., Mass: m/z 443.2 (M⁺), Anal. Calcd for $C_{25}H_{22}F_2N_2O_7S$: C, 56.38; H, 4.16; N, 5.26. Found: C, 56.96; H, 4.39; N, 5.31. |
| 117 | 5-methoxy | —NH— | pyrid-2-yl | mp 174-176° C., Mass: m/z 373.1 (M⁺), Anal. Calcd for $C_{23}H_{26}Cl_2N_4O_6$: C, 62.02; H, 5.88; N, 12.57. Found: C, 61.45; H, 5.91; N, 12.22. (isolated as the hydrochloride) |
| 118 | H | —NH— | pyrid-2-yl | mp 168-170° C., Mass: m/z 343.1 (M⁺), Anal. Calcd for $C_{22}H_{24}Cl_2N_4$: C, 63.61; H, 5.82; N, 13.48. Found: C, 62.18; H, 6.12; N, 12.11. (isolated as the hydrochloride) |
| 119 | 6-chloro | —NH— | pyrid-2-yl | mp 164-166° C., Mass: m/z 377.1 (M⁺), Anal. Calcd for $C_{22}H_{23}Cl_3N_4$: C, 58.74; H, 5.15; N, 12.45. Found: C, 57.75; H, 5.07; N, 11.94. (isolated as the hydrochloride) |
| 120 | 5-methoxy | —NH— | pyrid-3-yl | mp 150-154° C., Mass: m/z 373.2 (M⁺), Anal. Calcd for $C_{23}H_{26}Cl_2N_4O_6$: C, 62.02; H, 5.88; N, 12.57. Found: C, 61.30; H, 6.58; N, 10.87. (isolated as the hydrochloride) |
| 121 | H | —NH— | pyrid-3-yl | mp 140-142° C., Mass: m/z 343.2 (M⁺), Anal. Calcd for $C_{22}H_{22}N_4$: C, 77.16; H, 6.47; N, 16.36. Found: C, 75.73; H, 6.54; N, 15.58. (isolated as the base) |
| 122 | 6-chloro | —NH— | pyrid-3-yl | mp 172-174° C., Mass: m/z 377.2 (M⁺), Anal. Calcd for $C_{22}H_{23}Cl_3N_4$: C, 58.74; H, 5.15; N, 12.45. Found: C, 57.05; H, 5.16; N, 11.84. (isolated as the hydrochloride) |
| 123 | 5-methoxy | —NH— | pyrid-4-yl | mp 170-172° C., Mass: m/z 373.3 (M⁺), Anal. Calcd for $C_{23}H_{26}Cl_2N_4O_6$: C, 62.02; H, 5.88; N, 12.57. Found: C, 61.05; H, 6.08; N, 11.97. (isolated as the hydrochloride) |
| 124 | H | —NH— | pyrid-4-yl | mp 174-176° C., Mass: m/z 343.4 (M⁺), Anal. Calcd for $C_{22}H_{24}Cl_2N_4$: C, 63.61; H, 5.82; N, 13.48. Found: C, 62.32; H, 6.20; N, 12.44. (isolated as the hydrochloride) |
| 125 | 6-chloro | —NH— | pyrid-4-yl | mp 158-160° C., Mass: m/z 377.2 (M⁺), Anal. Calcd for $C_{22}H_{23}Cl_3N_4$: C, 58.74; H, 5.15; N, 12.45. Found: C, 57.17; H, 5.19; N, 11.69. (isolated as the hydrochloride) |
| 126 | 5-methoxy-6-fluoro | —NH— | 2,2,2-trifluoroethyl | mp 151-153° C., Mass: m/z 397.2 (M⁺), Anal. Calcd for $C_{24}H_{24}F_4N_2O_6$: C, 56.25; H, 4.72; N, 5.46. Found: C, 56.38; H, 4.76; N, 5.53. (isolated as the maleate) |
| 127 | 5-methoxy-6-fluoro | —NH— | 2,2,3,3,3-pentafluoro propyl | mp 145-147° C., Mass: m/z 447.2 (M⁺), Anal. Calcd for $C_{25}H_{24}F_6N_2O_6$: C, 53.38; H, 4.30; N, 4.98. Found: C, 53.36; H, 4.29; N, 5.00. (isolated as the maleate) |
| 128 | 5-methoxy-6-fluoro | —O— | 2,2,3,3-tetrafluoro propyl | mp 143-145° C., Mass: m/z 429.2 (M⁺), Anal. Calcd for $C_{25}H_{25}F_5N_2O_6$: C, 55.14; H, 4.62; N, 5.14. Found: C, 55.10; H, 4.62; N, 5.18. (isolated as the maleate) |

-continued

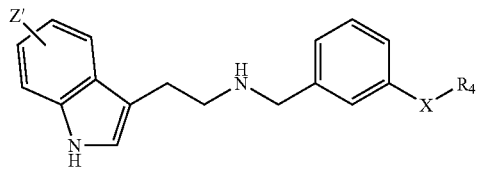

| No. | Z' | X | R₄ | Data |
|---|---|---|---|---|
| 129 | 5-methoxy | —C(O)— | phenyl | mp 163-166°, Mass: m/z 385.2 (M⁺), Anal. Calcd for $C_{27}H_{26}N_2O_6$: C, 68.34; H, 5.52; N, 5.90. Found: C, 66.64; H, 5.56; N, 5.90. |
| 130 | H | —C(O)— | phenyl | mp 168-170° C., Mass: m/z 355.3 (M⁺), Anal. Calcd for $C_{26}H_{24}N_2O_5$: C, 70.26; H, 5.44; N, 6.30. Found: C, 69.51; H, 5.52; N, 6.22. |
| 130 A | 6-fluoro | —O— | pyrid-4-yl | mp: 123.4-124.9° C. Mass (ES+): m/z 363.0 (M + 1). Anal. Calcd. for $C_{22}H_{20}FN_3O$: C, 73.11; H, 5.58; N, 11.63. Found: C, 73.36; H, 5.41; N, 11.57. (isolated as the free base) |
| 130 B | 6-fluoro | —O— | pyrid-3-yl | mp 169.0-170.8° C. Mass (APCI): m/z 362.1 (M + 1). Anal. Calcd for $C_{22}H_{20}F_1N_3O \cdot 1.0\ C_4H_4O_4$: C, 65.40; H, 5.07; N, 8.80. Found: C, 65.45; H, 5.12; N, 8.70. (isolated as the maleate salt) |
| 130 C | 5-methoxy 6-fluoro | —O— | 2,2,2 trifluoro ethyl | mp 151-153° C. Mass: m/z 397.2 (M⁺), Anal. Calcd for $C_{24}H_{24}F_4N_2O_6$: C, 56.25; H, 4.72; N, 5.46. Found: C, 56.38; H, 4.76; N, 5.53. (isolated as the maleate salt) |

By the method of Example 67 the following compounds were prepared, isolated as the oxalate except where noted:

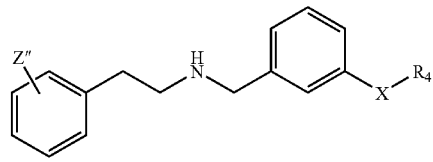

| No. | Z' | X | R₄ | Data |
|---|---|---|---|---|
| 131 | 3-chloro | —O— | phenyl | mp 222-224° C., Mass: m/z 338.2 (M⁺), Anal. Calcd for $C_{23}H_{22}ClNO_5$: C, 64.56; H, 5.18; N, 3.27. Found: C, 64.24; H, 5.02; N, 3.89. |
| 132 | 3-trifluoro methyl | —O— | phenyl | mp 220-222° C., Mass: m/z 372.2 (M⁺), Anal. Calcd for $C_{24}H_{22}F_3NO_5$: C, 62.47; H, 4.81; N, 3.04. Found: C, 62.69; H, 4.78; N, 3.10. |
| 133 | 4-methoxy | —O— | phenyl | mp 221-223° C., Mass: m/z 334.2 (M⁺), Anal. Calcd for $C_{24}H_{25}NO_6$: C, 68.07; H, 5.95; N, 3.31. Found: C, 67.98; H, 5.92; N, 3.29. |
| 134 | 3,4-dimethoxy | —O— | phenyl | Mp 209-211° C., Mass: m/z 364.2 (M⁺), Anal. Calcd for $C_{25}H_{27}NO_7$: C, 66.21; H, 6.00; N, 3.09. Found: C, 66.28; H, 6.07; N, 3.27. |
| 135 | 3-methoxy | —O— | phenyl | Mp 210-212° C., Mass: m/z 334.1 (M⁺), Anal. Calcd for $C_{24}H_{25}NO_6$: C, 68.07; H, 5.95; N, 3.31. Found: C, 68.31; H, 5.78; N, 3.36. |
| 136 | 3,4-dichloro | —O— | phenyl | mp 219-221° C., Mass: m/z 372.1 (M⁺), Anal. Calcd for $C_{23}H_{21}Cl_2NO_5$: C, 59.75; H, 4.58; N, 3.03. Found: C, 58.98; H, 4.63; N, 3.66. |
| 137 | 3-chloro | —O— | 3- | mp 214-216° C., Mass: m/z 406.4 |

-continued

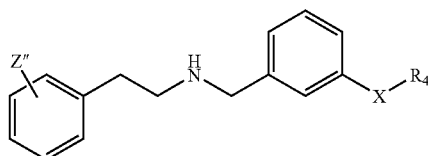

| No. | Z' | X | R₄ | Data |
|-----|-----|-----|-----|------|
| | | | trifluoromethyl phenyl | (M⁺), Anal. Calcd for $C_{27}H_{30}ClNO_5$: $C_{24}H_{21}ClF_3NO_5$: C, 58.13; H, 4.27; N, 2.82. Found: C, 58.28; H, 4.53; N, 2.86. |
| 138 | 3-chloro | —O— | 4-t-butyl phenyl | mp 221-223° C., Mass: m/z 394.2 (M⁺), Anal. Calcd for $C_{27}H_{30}ClNO_5$: C, 67.00; H, 6.25; N, 2.89. Found: C, 66.36; H, 5.83; N, 2.94. |
| 139 | 3-chloro | —O— | 4-chloro phenyl | mp 212-214° C., Mass: m/z 372.1 (M⁺), Anal. Calcd for $C_{23}H_{21}Cl_2NO_5$: C, 59.75; H, 4.58; N, 3.03. Found: C, 61.50; H, 4.77; N, 3.20. |
| 140 | 3-chloro | —O— | 4-methoxy phenyl | mp 207-209° C., Mass: m/z 368.2 (M⁺), Anal. Calcd for $C_{24}H_{24}ClNO_6$: C, 62.95; H, 5.28; N, 3.06. Found: C, 63.17; H, 5.32; N, 3.19. |
| 141 | 3-chloro | —O— | 4-methyl phenyl | mp 206-208° C., Mass: m/z 352.4 (M⁺), Anal. Calcd for $C_{24}H_{24}ClNO_5$: C, 65.23; H, 5.47; N, 3.17. Found: C, 67.52; H, 5.68; N, 3.30. |
| 142 | 3-chloro | —O— | 3,5-dichloro phenyl | mp 223-225° C., Mass: m/z 406.3 (M⁺), Anal. Calcd for $C_{23}H_{20}Cl_3NO_5$: C, 55.61; H, 4.06; N, 2.82. Found: C, 56.08; H, 3.83; N, 2.26. |
| 143 | 3-chloro | —O— | 3,4-dichloro phenyl | mp 217-219° C., Mass: m/z 406.4 (M⁺), Anal. Calcd for $C_{23}H_{20}Cl_3NO_5$: C, 55.61; H, 4.06; N, 2.82. Found: C, 55.73; H, 4.38; N, 3.02. |
| 144 | H | —O— | phenyl | mp 162-164° C., Mass: m/z 304.2 (M⁺), Anal. Calcd for $C_{23}H_{23}NO_5$: C, 70.22; H, 5.89; N, 3.56. Found: C, 70.70; H, 5.38; N, 3.78. |
| 145 | 4-chloro | —O— | phenyl | mp 222-224° C., Mass: m/z 338.2 (M⁺), Anal. Calcd for $C_{23}H_{22}ClNO_5$: C, 64.56; H, 5.18; N, 3.27. Found: C, 63.65; H, 5.18; N, 3.25. |
| 146 | 3-chloro | —S— | phenyl | mp 122-124° C., Mass: m/z 354.3 (M⁺), Anal. Calcd for $C_{23}H_{22}ClNO_4S$: 62.23; H, 4.99; N, 3.15. Found: C, 63.08; H, 5.09; N, 3.15. |
| 147 | 3-chloro | —SO₂— | phenyl | mp 110-112° C., Mass: m/z 386.1 (M⁺), Anal. Calcd for $C_{23}H_{22}ClNO_6S$: C, 58.04; H, 4.66; N, 2.94. Found: C, 58.91; H, 4.78; N, 3.05. |
| 148 | H | —S— | phenyl | mp 111-113° C., Mass: m/z 320.1 (M⁺), Anal. Calcd for $C_{23}H_{23}NO_4S$: C, 67.46; H, 5.66; N, 3.42. Found: C, 67.66; H, 5.77; N, 3.41. |
| 149 | H | —SO₂— | phenyl | mp 127-129° C., Mass: m/z 352.4 (M⁺), Anal. Calcd for $C_{23}H_{23}NO_6S$: C, 62.57; H, 5.25; N, 3.17. Found: C, 62.75; H, 5.16; N, 3.26. |
| 150 | 3-chloro | —S— | 4-methyl phenyl | mp 222-224° C., Mass: m/z 368.1 (M⁺), Anal. Calcd for $C_{24}H_{24}ClNO_4S$: C, 62.94; H, 5.28; N, 3.06. Found: C, 63.11; H, 5.35; N, 3.11. |
| 151 | 3-chloro | —SO₂— | 4-methyl phenyl | mp 226-228° C., Mass: m/z 400.1 (M⁺), Anal. Calcd for $C_{24}H_{24}ClNO_6S$: C, 58.83; H, 4.94; N, 2.86. Found: C, 58.79; H, 4.94; N, 2.93. |
| 152 | 3-chloro | —NH— | benzyl | mp 206-208° C., Mass: m/z 351.5 (M⁺), Anal. Calcd for |

-continued

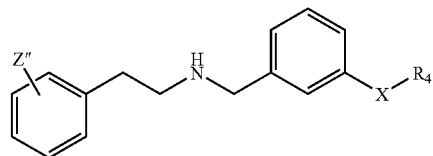

| No. | Z' | X | R₄ | Data |
|---|---|---|---|---|
| | | | | $C_{24}H_{25}ClN_2O_4$: C, 65.38; H, 5.72; N, 6.35. Found: C, 65.23; H, 5.86; N, 6.29. |
| 153 | 3-chloro | —NH— | phenyl | mp 196-198° C., Mass: m/z 337.2 (M⁺), Anal. Calcd for $C_{23}H_{23}ClN_2O_4$: C, 64.71; H, 5.43; N, 6.56. Found: C, 56.60; H, 4.90; N, 5.64. |
| 154 | 3-chloro | —CH(OH)— | phenyl | mp 193-195° C., Mass: m/z 352.4 (M⁺), Anal. Calcd for $C_{24}H_{24}ClN_2O_5$: C, 65.23; H, 5.47; N, 3.17. Found: C, 64.96; H, 5.60; N, 3.32. |
| 155 | 3-chloro | —CH₂— | phenyl | mp 220-222° C., Mass: m/z 336.1 (M⁺), Anal. Calcd for $C_{24}H_{24}ClNO_4$: C, 67.68; H, 5.68; N, 3.29. Found: C, 67.65; H, 5.83; N, 3.42. |
| 156 | 3-chloro | —CH(F)— | phenyl | mp 182-184° C., Mass: m/z 354.3 (M⁺), Anal. Calcd for $C_{24}H_{23}ClFNO_4$: C, 64.94; H, 5.22; N, 3.16. Found: C, 65.21; H, 5.26; N, 3.09. |
| 157 | 3-chloro | —O— | 4-fluoro phenyl | mp 218-220° C., Mass: m/z 356.2 (M⁺), Anal. Calcd for $C_{23}H_{21}ClFNO_5$: C, 61.96; H, 4.75; N, 3.14. Found: C, 60.56; H, 4.67; N, 3.17. |
| 158 | 3-trifluoro methyl | —O— | 4-fluoro phenyl | mp 221-223° C., Mass: m/z 390.2 (M⁺), Anal. Calcd for $C_{24}H_{21}F_4NO_5$: C, 60.13; H, 4.42; N, 2.92. Found: C, 59.18; H, 4.30; N, 2.91. |
| 159 | 3-chloro | —O— | 2-fluoro phenyl | mp 214-216° C., Mass: m/z 356.2 (M⁺), Anal. Calcd for $C_{23}H_{21}ClFNO_5$: C, 61.96; H, 4.75; N, 3.14. Found: C, 61.42; H, 4.68; N, 3.21. |
| 160 | 3-trifluoro methyl | —O— | 2-fluoro phenyl | mp 218-220° C., Mass: m/z 390.2 (M⁺), Anal. Calcd for $C_{24}H_{21}F_4NO_5$: C, 60.13; H, 4.42; N, 2.92. Found: C, 59.83; H, 4.34; N, 2.96. |
| 161 | 3-chloro | —O— | 3-fluoro phenyl | mp 219-221° C., Mass: m/z 356.2 (M⁺), Anal. Calcd for $C_{23}H_{21}ClFNO_5$: C, 61.96; H, 4.75; N, 3.14. Found: C, 61.26; H, 4.74; N, 3.11. |
| 162 | 3-trifluoro methyl | —O— | 3-fluoro phenyl | mp 221-223° C., Mass: m/z 390.2 (M⁺), Anal. Calcd for $C_{24}H_{21}F_4NO_5$: C, 60.13; H, 4.42; N, 2.92. Found: C, 58.79; H, 4.28; N, 2.88. |
| 163 | 3-chloro | —O— | naphth-2-yl | mp 229-231° C., Mass: m/z 388.1 (M⁺), Anal. Calcd for $C_{27}H_{24}ClNO_5$: C, 67.85; H, 5.06; N, 2.93. Found: C, 67.71; H, 5.02; N, 3.03. |
| 164 | 3-trifluro methyl | —O— | naphth-2-yl | mp 225-227° C., Mass: m/z 422.0 (M⁺), Anal. Calcd for $C_{28}H_{24}F_3NO_5$: C, 65.75; H, 4.73; N, 2.74. Found: C, 65.72; H, 4.84; N, 2.88. |
| 165 | 3-chloro | —O— | naphth-1-yl | mp 208-210° C., Mass: m/z 388.1 (M⁺), Anal. Calcd for $C_{27}H_{24}ClNO_5$: C, 67.85; H, 5.06; N, 2.93. Found: C, 66.71; H, 5.11; N, 3.26. |
| 166 | 3-trifluroro methyl | —O— | naphth-1-yl | mp 211-213° C., Mass: m/z 422.0 (M⁺), Anal. Calcd for $C_{28}H_{24}F_3NO_5$: C, 65.75; H, 4.73; N, 2.74. Found: C, 64.30; H, 4.76; N, 2.90. |
| 167 | 3-chloro | —O— | H | mp 96-98° C., Mass: m/z 262.0 (M⁺), Anal. Calcd for $C_{15}H_{15}ClNO$: C, 68.83; H, 6.16; N, 5.35. Found: C, 68.59; H, 5.99; N, 5.37. (isolated as |

-continued

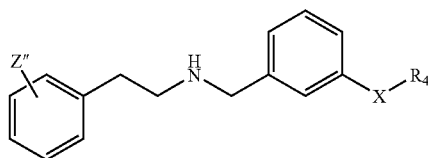

| No. | Z' | X | R4 | Data |
|---|---|---|---|---|
| 168 | 3-trifluromethyl | —O— | H | mp 101-103° C., Mass: m/z 296.3 (M+), Anal. Calcd for $C_{16}H_{16}F_3NO$: C, 65.07; H, 5.46; N, 4.74. Found: C, 65.06; H, 5.42; N, 4.80. (isolated as the base) |
| 169 | 3-trifluromethyl | —O— | benzyl | mp 223-225° C., Mass: m/z 386.1 (M+), Anal. Calcd for $C_{25}H_{24}F_3NO_5$: C, 63.15; H, 5.08; N, 2.94. Found: C, 63.22; H, 4.97; N, 3.02. |
| 170 | 3-chloro | —O— | 2,4-difluorophenylsulfonyl | mp 201-203° C., Mass: m/z 438.0 (M+), Anal. Calcd for $C_{23}H_{20}ClF_2NO_7S$: C, 52.32; H, 3.81; N, 2.65. Found: C, 52.26; H, 3.80; N, 2.71. |
| 171 | 3-trifluromethyl | —O— | 2,4-difluorophenylsulfonyl | mp 202-204° C., Mass: m/z 472.2 (M+), Anal. Calcd for $C_{24}H_{20}F_5NO_7S$: C, 51.34; H, 3.59; N, 2.49. Found: C, 51.61; H, 3.65; N, 2.54. |
| 172 | 3-chloro | —O— | thiazol-2-yl | m p 216-218° C., Mass: m/z 345.0 (M+), Anal. Calcd for $C_{20}H_{19}ClN_2O_5S$: C, 55.23; H, 4.40; N, 6.44. Found: C, 55.15; H, 4.16; N, 6.43. |
| 173 | 3-trifluromethyl | —O— | thiazol-2-yl | mp 222-224° C., Mass: m/z 379.4 (M+), Anal. Calcd for $C_{21}H_{19}F_3N_2O_5S$: C, 53.84; H, 4.08; N, 5.98. Found: C, 53.71; H, 3.95; N, 5.96. |
| 174 | 3-chloro | —O— | pyrid-3-yl | mp 213-215° C., Mass: m/z 339.1 (M+), Anal. Calcd for $C_{22}H_{21}ClN_2O_5$: C, 61.61; H, 4.93; N, 6.53. Found: C, 60.40; H, 4.89; N, 6.74. |
| 175 | 3-trifluromethyl | —O— | pyrid-3-yl | mp 221-223° C., Mass: m/z 373.1 (M+), Anal. Calcd for $C_{23}H_{21}F_3N_2O_5$: C, 59.74; H, 4.57; N, 6.05. Found: C, 59.17; H, 4.47; N, 6.93. |
| 176 | 3-methoxy | —O— | pyrid-3-yl | mp 101-103° C., Mass: m/z 335.2 (M+), Anal. Calcd for $C_{21}H_{24}Cl_2N_2O_2$: C, 61.92; H, 5.93; N, 6.87. Found: C, 61.43; H, 6.07; N, 6.25. (isolated as the hydrochloride) |
| 177 | 3-chloro | —O— | pyrid-4-yl | mp 154-156° C., Mass: m/z 339.1 (M+), Anal. Calcd for $C_{20}H_{21}Cl_3N_2O$: C, 58.34; H, 5.14; N, 6.80. Found: C, 58.35; H, 5.18; N, 6.69. (isolated as the hydrochloride) |
| 178 | 3-trifluromethyl | —O— | pyrid-4-yl | mp 208-210° C., Mass: m/z 373.1 (M+), Anal. Calcd for $C_{21}H_{21}Cl_2F_3N_2O$: C, 56.64; H, 4.75; N, 6.29. Found: C, 56.57; H, 4.68; N, 6.20 (isolated as the hydrochloride) |
| 179 | 3-chloro | —O— | pyrimid-5-yl | mp 205-207° C., Mass: m/z 340.1 (M+), Anal. Calcd for $C_{21}H_{20}ClN_3O_5$: C, 58.67; H, 4.68; N, 9.77. Found: C, 57.66; H, 4.70; N, 8.17. |
| 180 | 3-trifluromethyl | —O— | pyrimid-5-yl | mp 218-220° C., Mass: m/z 374.1 (M+), Anal. Calcd for $C_{22}H_{20}F_3N_3O_5$: C, 57.02; H, 4.35; N, 9.06. Found: C, 56.55; H, 4.44; N, 8.89. |
| 181 | 3-chloro | —O— | pyrid-2-yl | mp 93-95° C., Mass: m/z 339.1 (M+), Anal. Calcd for $C_{20}H_{21}Cl_3N_2O$: C, 58.34; H, 5.14; N, 6.80. Found: C, 62.31; H, 5.30; N, 7.36. (isolated as |

-continued

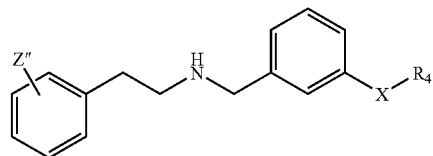

| No. | Z' | X | R₄ | Data |
|---|---|---|---|---|
| 182 | 3-trifluoro methyl | —O— | pyrid-2-yl | the hydrochloride) mp 86-88° C., Mass: m/z 373.1 (M⁺), Anal. Calcd for $C_{21}H_{21}Cl_2F_3N_2O$: C, 56.64; H, 4.75; N, 6.29. Found: C, 60.00; H, 4.92; N, 6.76 (isolated as the hydrochloride) |
| 183 | 3-chloro | —NH— | pyrid-3-yl | mp 158-160° C., Mass: m/z 338.3 (M⁺), Anal. Calcd for $C_{22}H_{22}ClN_3O_4$: C, 61.75; H, 5.18; N, 9.82. Found: C, 58.90; H, 4.64; N, 8.87. |
| 184 | 3-trifluro methyl | —NH— | pyrid-3-yl | mp 182-184° C., Mass: m/z 372.3 (M⁺), Anal. Calcd for $C_{23}H_{22}F_3N_3O_4$: C, 59.86; H, 4.80; N, 9.10. Found: C, 58.33; H, 4.44; N, 8.60. |
| 185 | 3-chloro | —NH— | pyrid-4-yl | mp 156-158° C., Mass: m/z 338.3 (M⁺), Anal. Calcd for $C_{20}H_{22}Cl_3N_3$: C, 58.48; H, 5.39; N, 10.22. Found: C, 57.13; H, 5.49; N, 9.80. (isolated as the hydrochloride) |
| 186 | 3-trifluro methyl | —NH— | pyrid-4-yl | mp 142-144° C., Mass: m/z 372.3 (M⁺), Anal. Calcd for $C_{21}H_{22}Cl_2F_3N_3$: C, 56.76; H, 4.99; N, 9.45. Found: C, 55.05; H, 4.88; N, 9.33 (isolated as the hydrochloride) |
| 187 | 3-chloro | —NH— | pyrid-2-yl | mp 142-144° C., Mass: m/z 338.0 (M⁺), Anal. Calcd for $C_{20}H_{22}Cl_3N_3$: C, 58.48; H, 5.39; N, 10.22. Found: C, 58.12; H, 5.39; N, 10.08. (isolated as the hydrochloride) |
| 188 | 3-trifluro methyl | —NH— | pyrid-2-yl | mp 144-146° C., Mass: m/z 372.1 (M⁺), Anal. Calcd for $C_{21}H_{22}Cl_2F_3N_3$: C, 56.76; H, 4.99; N, 9.45. Found: C, 56.60; H, 5.04; N, 9.32. (isolated as the hydrochloride) |
| 189 | 3-chloro | —O— | benzyl | MS m/e 351.9 (m + 1) |
| 190 | 3-trifluoro methyl | —NH— | phenyl | mp = 205-207° C., ms: m + 1 = 371.1 |

By the method of Example 67 the following compounds were prepared, isolated as the oxalate except where noted:

| No. | R₁ | Data |
|---|---|---|
| 191 | pyrid-4-yl | mp 176-178° C., Mass: m/z 305.2 (M⁺), Anal. Calcd for $C_{22}H_{22}N_2O_5$: C, 66.99; H, 5.62; N, 7.10. Found: C, 67.55; H, 5.70; N, 7.24. |
| 192 | pyrid-3-yl | mp 198-200° C., Mass: m/z 305.2 (M⁺), Anal. Calcd for $C_{22}H_{22}N_2O_5$: C, 66.99; H, 5.62; N, 7.10. Found: C, 64.98; H, 5.43; N, 6.86. |
| 193 | thien-2-yl | mp 234-236° C., Mass: m/z 310.2 (M⁺), Anal. Calcd for $C_{21}H_{21}NO_5S$: C, 63.14; H, 5.29; N, 3.50. Found: C, 62.25; H, 5.18; N, 3.53. |
| 194 | imidazol-4-yl | mp 194-196° C., Mass: m/z 294.2 (M⁺), Anal. Calcd for $C_{20}H_{20}N_3O_5$: C, 62.65; H, 5.52; N, 10.95. Found: C, 59.94; H, 5.30; N, 10.12. |
| 195 | naphth-2-yl | mp 223-225° C., Mass: m/z 354.4 (M⁺), Anal. Calcd for $C_{27}H_{25}NO_5$: C, 73.12; H, 5.68; N, 3.16. Found: C, 73.38; H, 5.94; N, 3.40. |
| 196 | naphth-1-yl | mp 223-225° C., Mass: m/z 354.4 (M⁺), Anal. Calcd for $C_{27}H_{25}NO_5$: C, 73.12; H, 5.68; N, 3.16. Found: C, 73.18; H, 5.52; N, 3.23. |

By the method of Example 67 the following compounds were prepared, isolated as the oxalate except where noted:

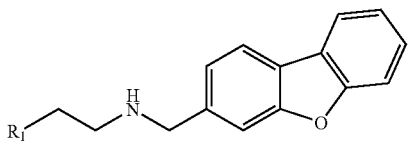

| No. | R₁ | Data |
|---|---|---|
| 197 | 3-chlorophenyl | mp 240-242° C., Mass: m/z 336.0 (M⁺), Anal. Calcd for $C_{23}H_{20}ClNO_5$: C, 55.23; H, 4.40; N, 6.44. Found: C, 55.15; H, 4.16; N, 6.43. |
| 198 | 3-trifluoromethyl phenyl | mp 255-257° C., Mass: m/z 370.0 (M⁺), Anal. Calcd for $C_{24}H_{20}F_3NO_5$: C, 62.74; H, 4.38; N, 3.04. found: C, 62.95; H, 4.27; N, 3.08. |
| 199 | 5-methoxy-1H-indol-3-yl | mp 232-234° C., Mass: m/z 371.1 (M⁺), Anal. Calcd for $C_{26}H_{24}N_2O_6$: C, 67.81; H, 5.25; N, 6.08. Found: C, 67.46; H, 4.44; N, 5.44. |
| 200 | 1H-indol-3-yl | mp 221-223° C., Mass: m/z 341.1 (M⁺), Anal. Calcd for $C_{25}H_{22}N_2O_5$: C, 69.75; H, 5.15; N, 6.50. Found: C, 71.99; H, 4.48; N, 6.40. |

By the method of Example 67 the following compounds were prepared, isolated as the oxalate except where noted:

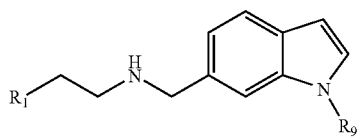

| No. | R₁ | R₉ | Data |
|---|---|---|---|
| 201 | 3-chlorophenyl | phenyl | mp 225-227° C., Mass: m/z 361.1 (M+), Anal. Calcd for $C_{25}H_{23}ClN_2O_4$: C, 66.59; H, 5.14; N, 6.21. Found: C, 66.21; H, 5.02; N, 6.14. |
| 202 | 3-trifluoromethyl phenyl | phenyl | mp 216-218° C., Mass: m/z 395.1 (M+), Anal. Calcd for $C_{25}H_{25}F_3N_2O_4$: C, 64.45; H, 4.78; N, 5.78. Found: C, 63.98; H, 4.67; N, 5.76. |
| 203 | 5-methoxy-1H-indol-3-yl | phenyl | mp 208-210° C., Mass: m/z 394.2 (M+), Anal. Calcd for $C_{28}H_{27}N_3O_5$: C, 69.26; H, 5.60; N, 8.62. Found: C, 67.78; H, 5.29; N, 8.42. |
| 204 | 1H-indol-3-yl | phenyl | mp 227-229° C., Mass: m/z 364.3 (M+), Anal. Calcd for $C_{27}H_{25}N_3O_4$: C, 71.19; H, 5.53; N, 9.22. Found: C, 70.02; H, 5.33; N, 8.95. |
| 205 | 5-methoxy-1H-indol-3-yl | H | mp 170-172° C., Mass: m/z 318.2 (M+), Anal. Calcd for $C_{22}H_{23}N_3O_5$: C, 64.53; H, 5.62; N, 10.26. Found: C, 56.16; H, 4.98; N, 8.75. |

By the method of Example 67 the following compounds were prepared, isolated as the oxalate except where noted:

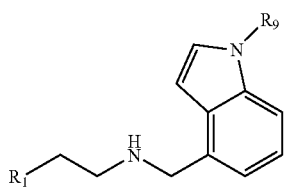

| No. | R₁ | R₉ | Data |
|---|---|---|---|
| 206 | 3-chlorophenyl | phenyl | mp 237-239° C., Mass: m/z 361.1 (M⁺), Anal. Calcd for $C_{25}H_{23}ClN_2O_4$: C, 66.59; H, 5.14; N, 6.21. Found: C, 66.55; H, 5.16; N, 6.20. |
| 207 | 3-trifluoromethyl | phenyl | mp 239-241° C., Mass: m/z 395.1 (M⁺), Anal. Calcd for $C_{25}H_{25}F_3N_2O_4$: C, 64.45; H, 4.78; N, 5.78. Found: C, 64.59; H, 4.83; N, 5.83. |
| 208 | 5-methoxy-1H-indol-3-yl | phenyl | mp 194-196° C., Mass: m/z 396.2 (M⁺), Anal. Calcd for $C_{28}H_{27}N_3O_5$: C, 69.26; H, 5.60; N, 8.62. Found: C, 68.33; H, 5.37; N, 8.52. |
| 209 | 1H-indol-3-yl | phenyl | mp 206-208° C., Mass: m/z 366.2 (M⁺), Anal. Calcd for $C_{27}H_{25}N_3O_4$: C, 71.19; H, 5.53; N, 9.22. Found: C, 69.23; H, 5.42; N, 8.86. |
| 210 | 5-methoxy-1H-indol-3-yl | H | mp 186-188° C., Mass: m/z 318.2 (M⁺), Anal. Calcd for $C_{22}H_{23}N_3O_5$: C, 64.53; H, 5.66; N, 10.26. Found: C, 62.88; H, 4.61; N, 9.27. |

Example 220

N-(2-(3-Chlorophenyl)ethyl)-3-benzoylbenzylamine

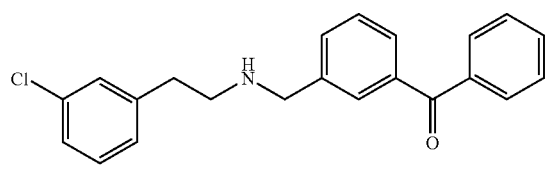

Combine 3-benzoylbenzaldehyde (0.45 g, 2.1 mmol), and (3-chlorophenyl)ethylamine (0.3 ml, 2.1 mmol) and 3 Å molecular sieves (1.0 g) in MeOH (30 ml). Heat to reflux. After 3 hours, cool, filter, and concentrate to give a residue. Dissolve the residue in dichloroethane (20 ml), add acetic acid (0.12 ml, 2.1 mmol) and sodium triacetoxyborohydride (0.6 g, 2.94 mmol) and stir at ambient temperature. After 2 hours, concentrate the reaction mixture and add dichloromethane (90 ml) and extract sequentially with distilled water (50 ml) and then brine (50 ml). Dry the organic layer over $Na_2SO_4$ and give a residue. Chromatograph the residue on silica gel eluting with EtOAc to give the title compound as the base.

The oxalate using the method of Example 67 to give the title compound: mp 196-198° C., Mass: m/z 350.4 M+), Anal. Calcd for $C_{24}H_{22}ClNO_5$: C, 65.53; H, 5.04; N, 3.18. Found: C, 65.27; H, 5.20; N, 3.13.

Example 221

N-(2-(3-Chlorophenyl)ethyl)-3-ethoxybenzylamine

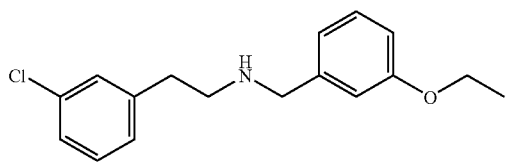

Combine 3-ethoxybenzaldehyde (3.38 g, 22.5 mmol), 2-(3-chlorophenyl)ethylamine (2.33 g, 15.0 mol), and 3 Å molecular sieves (2.88 g) in ethanol (230 ml). Stir the reaction mixture at reflux for 4 hours. Filter to remove the molecular sieves and then slowly add sodium borohydride (1.70 g, 45.0 mmol) to the filtrate and stir at ambient temperature. After 15 hours, concentrate the reaction mixture to a residue, dissolve the residue in 1 N NaOH, and extract with dichloromethane. Combine organic extracts, wash with brine, dry over $Na_2SO_4$, and concentrate to a residue. Chromatograph the residue on silica gel eluting with ethyl acetate to give the title compound. The HCl salt was prepared in ethyl acetate to give the title compound: mp 178-180° C.; MS (ACPI): m/e 290.1 (M+1); Analysis for $C_{17}H_{21}Cl_2NO$: Calcd: C, 62.58; H, 6.49; N, 4.29. Found: C, 62.65; H, 6.53; N, 4.32.

By the method of Example 221 the following compounds were prepared, isolated as the maleate except where noted:

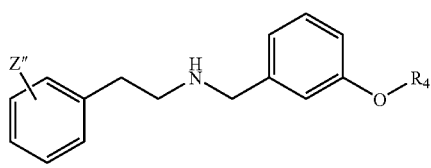

| No. | Z″ | $R_4$ | Data |
|---|---|---|---|
| 222 | 3-chloro | propyl | mp 138-140° C. MS (ACPI): m/e 304.1 (M + 1). Analysis for $C_{18}H_{23}Cl_2NO$: Calcd: C, 63.53; H, 6.81; N, 4.12; found: C, 63.74; H, 6.81; N, 4.22. (isolated as the hydrochloride) |
| 223 | 3-trifluoromethyl | propyl | mp 145-147° C. MS (ACPI): m/e 338.1 (M + 1). Analysis for $C_{23}H_{26}F_3NO_5$: Calcd: C, 60.92; H, 5.78; N, 3.09; found: C, 60.77; H, 5.60; N, 3.12. |
| 224 | 3-trifluoromethyl | ethyl | mp 164-166° C. MS (ACPI): m/e 324.2 (M + 1). Analysis for $C_{18}H_{21}ClF_3NO$: Calcd: C, 60.09; H, 5.88; N, 3.89; found: C, 60.42; H, 5.80; N, 3.93. (isolated as the hydrochloride) |
| 225 | 2-phenyl | 2,2,2-trifluoro ethyl | mp 181-183° C. MS (ACPI): m/e 386.2 (M + 1). Analysis for $C_{27}H_{26}F_3NO_5$: Calcd: C, 64.67; H, 5.23; N, 2.79; found: C, 64.52; H, 5.01; N, 2.85. |
| 226 | 4-phenyl | 2,2,2-trifluoro ethyl | mp 39° C. MS (ACPI): m/e 386.2 (M + 1). (Exception- one equivalent of triethylamine in the reaction) (isolated as the free base) |

By the method of Example 221 the following compounds were prepared, isolated as the maleate except where noted:

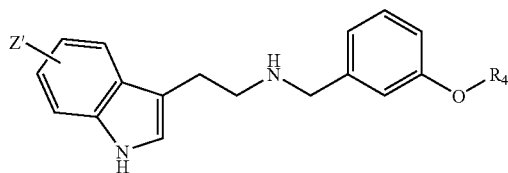

| No. | Z′ | $R_4$ | Data |
|---|---|---|---|
| 227 | 5-chloro | ethyl | mp 153-156° C., MS (ACPI): m/e 329.1 (M + 1). Analysis for $C_{23}H_{25}ClN_2O_5$: Calcd: C, 62.09; H, 5.66; N, 6.30; found: C, 62.27; H, 5.38; N, 6.19 |
| 228 | 5-chloro | propyl | mp 163-166° C. MS (ACPI): m/e 343.1 (M + 1). Analysis for $C_{24}H_{27}ClN_2O_5$: Calcd: C, 62.81; H, 5.93; N, 6.10; found: C, 63.07; H, 5.80; N, 6.07. |
| 229 | 5-chloro | 2,2,2-trifluoroethyl | mp 178-181° C., MS (ACPI): m/e 383.1 (M + 1). Analysis for $C_{23}H_{22}ClF_3N_2O_5$: Calcd: C, 55.37; H, 4.44; N, 5.62; found: C, 55.71; H, 4.39; N, 5.66. |
| 230 | 5-chloro | 3-fluoropropyl | mp 167-170° C., MS (ACPI): m/e 361.1 (M + 1). Analysis for $C_{24}H_{26}ClFN_2O_5$: Calcd: C, 60.44; H, 5.49; N, 5.87; found: C, 60.30; H, 5.25; N, 5.78. |
| 231 | 5-chloro | 2,2,3,3,3-pentafluoro propyl | mp 170-173° C. MS (ACPI): m/e 433.1 (M + 1). Analysis for $C_{24}H_{22}ClF_5N_2O_5$: Calcd: C, 52.52; H, 4.04; N, 5.10; foun d: C, 52.49; H, 4.06; N, 5.16. |
| 232 | 5-chloro | 2,2,3,3-tetrafluoro propyl | mp 163-167° C. MS (ACPI): m/e 415.1 (M + 1). Analysis for $C_{24}H_{23}ClF_4N_2O_5$: Calcd: C, 54.30; H, 4.37; N, 5.28; found: C, 54.47; H, 4.36; N, 5.33. |
| 233 | 5- | 2,2,2- | mp 179-182° C., MS (ACPI): m/e 379.1 (M + 1). |

-continued

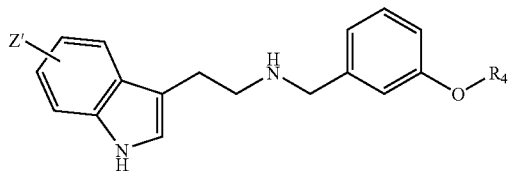

| No. | Z' | R4 | Data |
|---|---|---|---|
|  | methoxy | trifluoroethyl | Analysis for $C_{24}H_{25}F_3N_2O_6$: Calcd: C, 58.30; H, 5.10; N, 5.67; found: C, 58.26; H, 5.09; N, 5.69. |
| 234 | 6-chloro | 2,2,3,3-tetrafluoro propyl | mp 156-160° C., MS (ACPI): m/e 415.1 (M + 1). Analysis for $C_{24}H_{23}ClF_4N_2O_5$: Calcd: C, 54.30; H, 4.37; N, 5.28; found: C, 54.31; H, 4.34; N, 5.31. |
| 235 | 5-cyano | 2,2,2-trifluoroethyl | mp 176-1178° C. MS (ACPI): m/e 374.0 (M + 1). Analysis for $C_{20}H_{19}ClF_3N_3O$: Calcd: C,58.61; H, 4.67; N, 10.25; found: C, 58.52; H, 4.61; N, 10.17. (isolated as the hydrochloride) |
| 236 | 5-methyl sulfonyl | 2,2,2-trifluoro ethyl | mp 193-195° C. MS (ACPI): m/e 429.9 (M + 1). Analysis for $C_{24}H_{25}F_3N_2O_7S$: Calcd: C, 53.13; H, 4.64; N, 5.16; found: C, 53.12; H, 4.58; N, 5.20. |
| 237 | 5-cyano | 3,3,3-trifluoro propyl | mp 150-154° C. MS (ACPI): m/e 387.9 (M + 1). Analysis for $C_{25}H_{24}F_3N_3O_5$: Calcd: C, 59.64; H, 4.80; N, 8.35; found: C, 59.55; H, 4.77; N, 8.38. |
| 238 | 5-methyl sulfonyl | 3,3,3-trifluoro propyl | mp 178-181° C. MS (ACPI): m/e 440.9 (M + 1). Analysis for $C_{25}H_{27}F_3N_2O_7S$: Calcd: C, 53.95; H, 4.89; N, 5.03; found: C, 53.87; H, 4.86; N, 5.04. |
| 239 | 4-fluoro | 2,2,2-trifluoro ethyl | mp 199-202° C. MS (ACPI): m/e 367.2 (M + 1). Analysis for $C_{19}H_{19}ClF_4N_2O$: calcd: C, 56.65; H, 4.75; N, 6.95; found: C, 56.82; H, 4.65; N, 6.84. (isolated as the hydrochloride) |
| 240 | 4-fluoro | 2,2,3,3,3-pentafluoro propyl | mp 118-121° C. MS (ACPI): m/e 417.2 (M + 1). Analysis for $C_{24}H_{22}F_6N_2O_5$: Calcd: C, 54.14; H, 4.16; N, 5.26; found: C, 54.39; H, 4.25; N, 5.30. |
| 241 | 4-fluoro | 2,2,3,3-tetrafluoro propyl | mp 188-191° C. MS (ACPI): m/e 399.0 (M + 1). Analysis for $C_{20}H_{20}ClF_5N_2O$: Calcd: C, 55.24; H, 4.64; N, 6.44; found: C, 55.03; H, 4.53; N, 6.34. (isolated as the hydrochloride) |
| 242 | 7-fluoro | 2,2,2-trifluoro ethyl | mp 157-160° C. MS (ACPI): m/e 367.2 (M + 1). Analysis for $C_{23}H_{22}F_4N_2O_5$: Calcd: C, 57.26; H, 4.60; N, 5.81; found: C, 57.34; H, 4.39; N, 6.11. |
| 243 | 7-fluoro | 2,2,3,3,3-pentafluoro propyl | mp 166-168° C. MS (ACPI): m/e 417.2 (M + 1). Analysis for $C_{24}H_{22}F_6N_2O_5$: Calcd: C, 54.14; H, 4.16; N, 5.26; found: C, 53.99; H, 3.98; N, 5.61. |
| 244 | 7-fluoro | 2,2,3,3-tetrafluoro propyl | mp 170-173° C. MS (ACPI): m/e 399.2 (M + 1). Analysis for $C_{24}H_{24}F_5N_2O_5$: Calcd: C, 56.03; H, 4.51; N, 5.45; found: C, 55.73; H,4.30; N, 5.66. |
| 245 | 5-amido | 3,3,3-trifluoro propyl | mp 143-147 C. MS (ACPI): m/e 406.1 (M + 1). Analysis for $C_{21}H_{22}F_3N_3O_2$: Calcd: C, 62.22; H, 5.47; N, 10.36; found: C, 61.96; H, 5.42; N, 10.13. (isolated as the base) |
| 246 | 5-amido | 2,2,2-trifluoro ethyl | mp 125-130° C. MS (ACPI): m/e 392.1 (M + 1). Analysis for $C_{20}H_{21}ClF_3N_3O_2$: Calcd: C, 56.15; H, 4.95; N, 9.82; found: C, 55.80; H, 4.93; N, 9.71. (isolated as the hydrochloride) |
| 247 | 6-phenyl | 2,2,2-trifluoro ethyl | mp 117-120° C. MS (ACPI): m/e 425.1 (M + 1). Analysis for $C_{26}H_{23}F_3N_2O$: Calcd: C, 70.74; H, 5.46; N, 6.60; found: C,70.75; H, 5.42; N, 6.66. (isolated as the base) |
| 248 | 6-methyl | 2,2,3,3,3-pentafluorro propyl | m.p. 168-170° C. MS (ACPI): m/e 413.2 (M + 1). Analysis for $C_{21}H_{22}F_5N_2O$: Calcd: C, 56.82; H, 4.77; N, 5.30; found: C, 57.21; H, 4.46; N, 5.33 |
| 249 | 6-phenyl | 2,2,3,3,3-pentafluoro propyl | mp 110.5-113.5° C. MS (ACPI): m/e 475.1 (M + 1). Analysis for $C_{26}H_{23}F_5N_2O$: Calcd: C, 65.82; H, 4.89; N, 5.90; found: C, 65.70; H, 4.84; N, 5.93. (isolated as the base) |
| 250 | 6-phenyl | 2,2,3,3-tetrafluoro propyl | mp 94-98° C. MS (ACPI): m/e 457.1 (M + 1). Analysis for $C_{26}H_{24}F_4N_2O$: calcd: C, 68.41; H, 5.30; N, 6.14; found: C, 68.18; H, 5.28; N, 6.06 (isolated as the base) |
| 251 | 6-methyl | 2,2,2-trifluoro ethyl | mp 176-178° C. MS (ACPI): m/e 363.1 (M + 1). Analysis for $C_{20}H_{22}ClF_3N_2O$: Calcd: C, 60.23; H, 5.56; N, 7.02; found: C, 60.16; H, 5.43; N, 6.98. (isolated as the hydrochloride) |
| 252 | 6-methyl | 2,2,3,3-tetrafluoro propyl | mp 156-158° C. MS (ACPI): m/e 395.1 (M + 1). Analysis for $C_{21}H_{23}ClF_4N_2O$: Calcd: C, 58.54; H, 5.38; N, 6.50; found: C, 58.60; H, 5.32; N, 6.55. (isolated as the hydrochloride) |

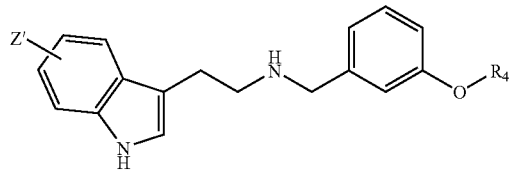

| No. | Z' | R₄ | Data |
|---|---|---|---|
| 253 | 6-ethoxy carbonyl | 2,2,3,3-tetrafluoro propyl | mp 166-168° C. MS (ACPI): m/e 453.1 (M + 1). Analysis for $C_{23}H_{25}ClF_4N_2O_3$: Calcd: C,56.50; H, 5.15; N, 5.73; found: C,56.18; H, 5.00; N, 5.66. (isolated as the hydrochloride) |
| 254 | 6-ethoxy carbonyl | 2,2,2-trifluoro ethyl | mp 169.5-171.5° C. MS (ACPI): m/e (421.2 (M + 1). Analysis for $C_{26}H_{27}F_3N_2O_7$: Calcd: C, 58.21; H, 5..07; N, 5.22; found: C, 58.43; H, 4.85; N, 5.27. |
| 255 | 6-cyano | 2,2,2-trifluoro eethyl | mp 175-177° C. MS (ACPI): m/e 374.1 (M + 1). Analysis for $C_{24}H_{22}F_3N_3O_5$: Calcd: C, 58.90; H, 4.53; N, 8.59; found: C, 58.62; H, 4.48; N, 8.50. |
| 256 | 6-cyano | 2,2,3,3-tetrafluoro propyl | mp 167-169° C. MS (ACPI): m/e 406.1 (M + 1). Analysis for $C_{25}H_{23}F_4N_3O_5$: Calcd: C, 57.58; H, 4.45; N, 8.06; found: C, 57.31; H, 4.35; N, 8.08. |
| 257 | 6-amido | 2,2,2-teetrafluoro ethyl | mp 102° C. MS (ACPI): m/e 392.2 (M + 1). Analysis for $C_{20}H_{20}F_3N_3O_2$: Calcd: C, 61.38; H, 5.15; N, 10.74; found: C, 61.68; H, 5.11; N, 10.65. (isolated as the base) |
| 258 | 6-amido | 2,2,3,3-tetrafluoro propyl | mp 120° C. MS (ACPI): m/e 424.3 (M + 1). Analysis for $C_{21}H_{21}F_4N_3O_2$: Calcd: C, 59.57; H, 5.00; N, 9.92; found: C, 59.333; H, 4.82; N, 9.79. (isolated as the base) |
| 259 | 6-trifluoro methoxy | 2,2,3,3-tetrafluoro propyl | mp 132-134° C. MS (ACPI): m/e 465.1 (M + 1). Analysis for $C_{21}H_{20}ClF_7N_2O_2$: Calcd: C, 50.36; H, 4.033; N, 5.59; found: C, 50.25; H, 3.96; N, 5.58. (isolated as the hydrochloride) |
| 260 | 6-trifluoro methoxy | 2,2,2-trifluoro ethyl | mp 160-164° C. MS (ACPI): m/e 433.1 (M + 1). Analysis for $C_{20}H_{19}ClF_6N_2O_2$: Calcd: C, 51.24; H, 4.08; N, 5.98; found: C, 51.26; H, 3.99; N, 5.96. (isolated as the hydrochloride) |
| 260A | 7-chloro | 2,2,3,3-teetrafluoro propyl | mp 153.6-154.4° C. MS (ACPI): m/e 415.1 (M + 1). Anal. Calcd. for $C_{20}H_{19}ClF_4N_2O \cdot 1.0$ HCl: C, 53.23; H, 4.47; N, 6.21. Found: C, 52.89; H, 4.40; N, 6.18. (isolated as the hydrochloride) |
| 260B | 7-chloro | 2,2,2-trifluoroethyl | mp 193.4-194.9° C. Mass (ES+): m/z 3383.17 (M + 1). Anal. Calcd. for $C_{19}H_{18}ClF_3N_2O \cdot 1.0$ HCl: C, 54.43; H, 4.57; N, 6.68. Found: C, 54.66; H, 4.39; N, 6.66. (isolated as the hydrochloride) |

Example 261

N-(2-(7-Fluoro-1H-indol-3-ylethyl)-3-(2,2,3,3-tetrafluoropropoxy)benzylamine hydrochloride Add acetyl chloride (2.4 mL, 33.8 mmol) dropwise to anhydrous ethanol (50 mL) and stir the solution for 10 min at ambient temperature and add to a solution of N-(2-(7-fluoro-1H-indol-3-yl)ethyl)-3-(2,2,3,3-tetrafluoropropoxy)benzylamine (12.0 g, 30.1 mmol) in ethyl acetate. Concentrate the resulting solution under reduced pressure to give a yellow solid. Recrystallize the yellow solid from ethyl acetate/ethanol/diethyl ether to give the title compound: mp 142-143° C. MS (m/e): 399 (M+1), 397 (M−1). Calculated for $C_{20}H_{19}F_5N_2O\cdot HCl$: Calcd: C, 55.24; H, 4.64; N, 6.44. Found: C, 55.44; H, 4.66; N, 6.46.

Example 262

(N-(2-(7-Fluoro-1H-indol-3-yl)ethyl)-3-(2,2,3,3-tetrafluoropropoxy)benzylamine hydrochloride L(+) tartrate Add L-(+)-tartaric acid (49 mg, 0.33 mmol) and methanol to a solution of (N-(2-(7-fluoro-1H-indol-3-yl)ethyl)-3-(2,2,3,3-tetrafluoropropoxy)benzylamine (130 mg, 0.33 mmol) in ethyl acetate. Evaporate the solvent to give a gum. Crystallize the gum from diethyl ether/ethyl acetate to give the title compound: mp 192-194° C.

Example 263

N-(2-(7-Fluoro-1H-indol-3-yl)ethyl)-3-(2,2,2-trifluoroethoxy)benzylamine hydrochloride Add dropwise acetyl chloride (2.3 ml, 32.4 mmol) to anhydrous ethanol (50 mL) and stir for 10 min at ambient temperature and add to a solution N-(2-(7-fluoro-1H-indol-3-yl)ethyl)-3-(2,2,2-trifluoroethoxy)benzylamine (10.7 g, 29.2 mmol) in diethyl ether. Concentrate the resulting solution under reduced pressure to give a yellow solid. Recrystallize the yellow solid from ethyl acetate/methanol to give the title compound: mp 163-164° C.; MS (m/e): 367 (M−1), 365 (M−1); Calculated for $C_{19}H_{18}F_4N_2O$ HCl: Calcd: C, 56.65; H, 4.75; N, 6.95. Found: C, 56.45; H, 4.54; N, 6.90.

Example 264

N-(2-(7-Fluoro-1H-indol-3-yl)ethyl)-3-(2,2,2-trifluoroethoxy)benzylamine L(+)tartrate Add L-(+)-tartaric acid (295 mg, 1.96 mmol) in methanol to a solution of N-(2-(7-fluoro-1H-indol-3-yl)ethyl)-3-(2,2,2-trifluoroethoxy)benzylamine (720 mg, 1.96 mmol) in ethyl acetate. Concentrate under reduced pressure the resulting solution to give a clear colorless oil. Crystallize the oil from diethyl ether to give the title compound: mp 118-119° C. MS (m/e): 367 (M+1), 365 (M−1). Calculated for $C_{19}H_{18}F_4N_2O \cdot C_4H_6O_6$: Calcd: C, 53.49; H, 4.68; N, 5.42. Found: C, 53.21; H, 4.55; N, 5.41.

Example 270

N-(2-(5-Fluoro-1H-indol-3-yl)ethyl)-3-propoxybenzylamine hydrochloride

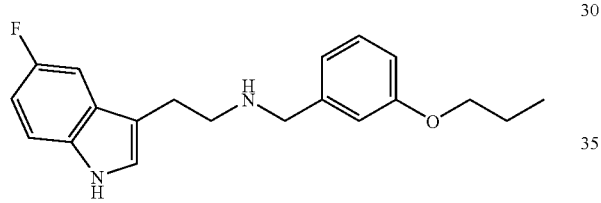

Combine 3-propoxybenzaldehyde (2.96 g, 18.0 mmol), 5-fluorotryptamine hydrochloride (2.58 g, 12.0 mol), triethylamine (1.15 g), and 3 Å molecular sieves (2.27 g) in ethanol (200 ml). Stir the reaction mixture at reflux for 4 hours. Filter to remove the molecular sieves and then slowly add sodium borohydride (1.36 g, 36.0 mmol) to the filtrate and stir at ambient temperature. After 15 hours, concentrate the reaction mixture to a residue, dissolve the residue in 1 N NaOH, and extract with dichloromethane. Combine organic extracts, wash with brine, dry over $Na_2SO_4$, and concentrate to a residue. Chromatograph the residue on silica gel eluting with ethyl acetate yielded 3.31 g of an oil. The HCl salt was prepared in diethyl ether: mp 197-199° C.; MS (ACPI): m/e 327.2 (M+1); Analysis for $C_{20}H_{24}ClFN_2O$: Calcd: C, 66.20; H, 6.67; N, 7.72. found: C, 66.06; H, 6.63; N, 7.76.

By the method of Example 270 the following compounds were prepared, isolated as the maleate except where noted:

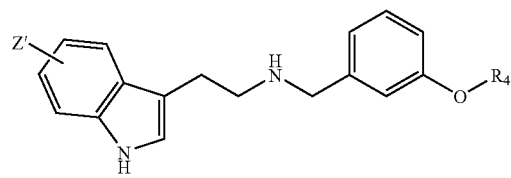

| No. | Z' | R4 | Data |
|---|---|---|---|
| 271 | 5-fluoro | ethyl | mp 196-198° C., MS (ACPI): m/e 313.1 (M + 1). Analysis for $C_{19}H_{22}ClFN_2O$: Calcd: C, 65.42; H, 6.36; N, 8.03; found: C, 65.48; H, 6.30; N, 8.04. (isolated as the hydrochloride) |
| 272 | 5-trifluoro methyl | ethyl | mp 156-160° C., MS (ACPI): m/e 363.1 (M + 1). Analysis for $C_{24}H_{25}F_3N_2O_5$: Calcd: C, 60.25; H, 5.27, N, 5.85; found: C, 60.47; H, 5.26; N, 5.79. |
| 273 | 5-trifluoro methyl | propyl | mp 169-172° C., MS (ACPI): m/e 377.1 (M + 1). Analysis for $C_{25}H_{27}F_3N_2O_5$: Calcd: C, 60.97; H, 5.53; N, 5.69; found: C, 60.95; H, 5.54; N, 5.70 |
| 274 | 5-trifluoro methyl | 2,2,2-trifluoro ethyl | mp 180-184° C. MS (ACPI): m/e 417.1 (M + 1). Analysis for $C_{24}H_{22}F_6N_2O_5$: Calcd: C, 54.14; H, 4.16; N, 5.26; found: C, 53.99; H, 4.07; N, 5.61. |
| 275 | 5-trifluoro methyl | 3,3,3-trifluoro propyl | mp 158-161° C., MS (ACPI): m/e 431.1 (M + 1). Analysis for $C_{25}H_{24}F_6N_2O_5$: Calcd: C, 54.95; H, 4.43; N, 5.13; found: C, 54.84; H, 4.46; N, 5.03. |
| 276 | 4-methoxy | 2,2,3,3-tetrafluoro propyl | mp 144-147° C. MS (ACPI): m/e 411.1 (M + 1). Analysis for $C_{25}H_{26}F_4N_2O_6$: Calcd: C, 57.03; H, 4.98; N, 5.32; found: C, 56.84; H, 4.94; N, 5.34. |
| 277 | 5-cyano | 2,2,3,3- | mp 172-174° C. MS (ACPI): m/e 406.2 (M + 1). |

-continued

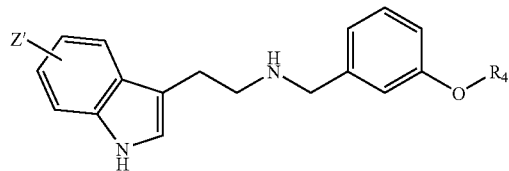

| No. | Z' | R₄ | Data |
|---|---|---|---|
| 278 | 5-cyano | 2,2,3,3-tetrafluoro propyl | Analysis for $C_{25}H_{23}F_4N_3O_5$: Calcd: C, 57.58; H, 4.45; N, 8.06; found: C, 57.91; H, 4.13; N, 8.34. mp 168-170° C. MS (ACPI): m/e 424.1 (M + 1). |
| 279 | 5-(4-fluorophenyl) | 2,2,3,3,3-pentafluoro propoxy | Analysis for $C_{25}H_{22}F_5N_3O_5$: Calcd: C, 55.66; H, 4.11; N, 7.79; found: C, 55.54; H, 4.16; N, 7.71. p 161-165° C. MS (ACPI): m/e 475.1 (M + 1). Analysis for $C_{26}H_{24}ClF_5N_2O$: Calcd: C, 61.12; H, 4.73; N, 5.48; found: C, 61.18; H, 4.64; N, 5.50. (isolated as the hydrochloride) |
| 280 | 5-(4-fluorophenyl) | 2,2,3,3,3-pentafluoro propoxy | (isolated as the hydrochloride) mp 168-171° C. MS (ACPI): m/e 493.1 (M + 1). Analysis for $C_{25}H_{23}ClF_6N_2O$: Calcd: C, 59.04; H, 4.38; N, 5.30; found: C, 59.15; H, 4.28; N, 5.30. (isolated as the hydrochloride) |
| 281 | 5-phenyl | 2,2,3,3-tetrafluoro propyl | mp 148-151° C. MS (ACPI): m/e 457.1 (M + 1). Analysis for $C_{26}H_{25}ClF_4N_2O$: Calcd: C, 63.35; H, 5.11; N, 5.68; found: C, 63.16; H, 4.99; N, 5.67. (isolated as the hydrochloride) |
| 282 | 5-phenyl | 2,2,3,3,3-pentafluoro prop | mp 65-70° C., dec. MS (ACPI): m/e 475.1 (M + 1). Analysis for $C_{26}H_{24}ClF_5N_2O$: Calcd: C, 61.12; H, 4.73; N, 5.48; found: C, 60.98; H, 4.66; N, 5.41. (isolated as the hydrochloride) |
| 283 | 5-(4-fluorophenyl) | 2,2,2-trifluoro ethyl | mp 214-216° C. MS (ACPI): m/e 443.1 (M + 1). Analysis for $C_{25}H_{23}ClF_4N_2O$: Calcd: C, 62.70; H, 4.84; N, 5.85; found: C, 62.47; H, 4.71; N, 5.79. (isolated as the hydrochloride) |
| 284 | 5-phenyl | 2,2,2-trifluoro ethyl | mp 171-174° C., dec. MS (ACPI): m/e 425.1 (M + 1). Analysis for $C_{25}H_{24}ClF_3N_2O$: Calcd: C, 65.15; H, 5.25; N, 6.08; found: C, 65.46; H, 5.17; N, 6.10. (isolated as the hydrochloride) |
| 285 | 4-phenyl | 2,2,3,3,3-pentafluoro propyl | mp 55° C., dec. MS (ACPI): m/e 475.1 (M + 1). Analysis for $C_{26}H_{24}ClF_5N_2O$: Calcd: C, 61.12; H, 4.73; N, 5.48; found: C, 61.11; H, 4.83; N, 5.40. (isolated as the hydrochloride) |
| 286 | 4-phenyl | 2,2,2-trifluoro ethyl | mp 60° C., dec. MS (ACPI): m/e 425.1 (M + 1). Analysis for $C_{25}H_{24}ClF_3N_2O$: Calcd: C, 65.15; H, 5.25; N, 6.08; found: C, 65.08; H, 5.42; N, 5.93. (isolated as the hydrochloride) |
| 287 | 4-phenyl | 2,2,3,3-tetrafluoro propyl | mp 56° C., dec. MS (ACPI): m/e 457.1 (M + 1). Analysis for $C_{26}H_{25}ClF_4N_2O$: Calcd: C, 63.35; H, 5.11; N, 5.68; found: C, 63.60; H, 5.35; N, 5.48. (isolated as the hydrochloride) |
| 288 | 7-fluoro | pyrid-4-yl | mp 212-214° C. MS (ACPI): m/e 362.2 (M + 1). (isoalted as the oxalate) |
| 289 | 7-fluoro | pyrid-3-yl | mp 167-169° C. MS (ACPI): m/e 362.1 (M + 1). (isolated as the oxalate) |
| 299 | 7-phenyl | 2,2,2-trifluoro ethyl | mp 116-120° C. MS (ACPI): m/e 425.3 (M + 1). Analysis for $C_{29}H_{27}F_3N_2O_5$: Calcd: C, 64.44; H, 5.03; N, 5.18; found: C, 64.47; H, 4.96; N, 5.24. |
| 300 | 7-phenyl | 2,2,3,3-tetrafluoro propyl | mp 108-111° C. MS (ACPI): m/e 457.3 (M + 1). Analysis for $C_{30}H_{28}F_4N_2O_5$: Calcd: C, 62.93; H, 4.93; N, 4.89; found: C, 63.02; H, 4.91; N, 4.96. |

Example 301

N-(2-(6-Chloro-1H-indol-3-yl)ethyl-N-methyl-3-(2,2,3,3-tetrafluoropropoxy)benzylamine maleate

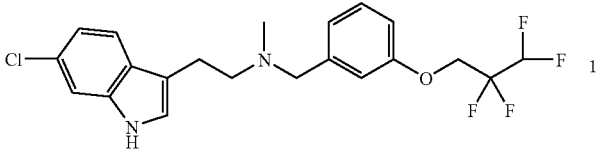

Add 3-(2,2,3,3-tetrafluoropropoxy)benzaldehyde (232.6 mg, 0.98 mmol) to a solution of N-(2-(6-chloro-1H-indol-3-yl)ethyl)-N-methylamine (205.6 mg, 0.98 mmol) and sodium triacetoxy borohydride (305.3 mg, 1.37 mmol) in dichloroethane (50 ml). Stir at ambient temperature. After 24 hours, evaporate to residue and dissolve the residue in 1N NaOH then extract with dichloromethane. Combine the organic extracts, washed with brine, dry (Na$_2$SO$_4$), filter, and evaporate to a residue. Chromatograph the residue on silica gel eluting with ethyl acetate to give the title compound. The maleate salt was prepared in diethyl ether: mp 125-128° C. MS (ACPI): m/e 429.3 (M+1). Analysis for C$_{25}$H$_{25}$ClF$_4$N$_2$O$_5$: Calcd: C, 55.10; H, 4.62; N, 5.14. found: C, 55.13; H, 4.59; N, 5.09.

By the method of Example 301 the following compounds were prepared:

Example 306

N-(2-(6-Carboxy-1H-indol-3-yl)ethyl)-3-(2,2,3,3-tetrafluoropropoxy)benzylamine

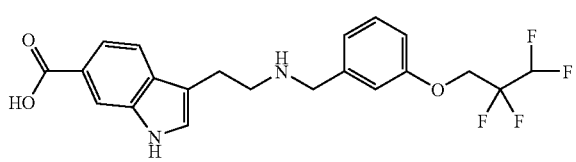

Combine N-(2-(6-ethoxycarbonyl-1H-indol-3-yl)ethyl)-N-(2,2,3,3-tetrafluoropropoxybenzyl)amine (1.09 g, 2.4 mmol) and 2N NaOH (4.8 ml) in ethanol (4.8 ml). Heat to reflux. After 2 hours, cool to ambient temperature, evaporate under vacuum to remove the ethanol, and then neutralize with 5N HCl (1.92 ml) to give a solid. Collect the solid by filtration

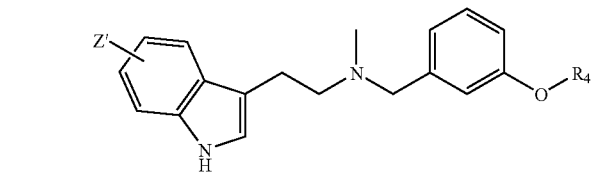

| No. | Z' | R$_4$ | Data |
|---|---|---|---|
| 302 | 5-methoxy | 2,2,2-trifluoroethyl | mp 144-147° C. MS (ACPI): m/e 393.1 (M + 1). Analysis for C$_{23}$H$_{25}$F$_3$N$_2$O$_6$: Calcd: C, 57.26; H, 5.22; N, 5.81; found: C, 56.89; H, 5.16; N, 5.82. (isolated as the oxalate) |
| 303 | 4-methoxy | 2,2,3,3-tetrafluoropropyl | mp 104-109° C. MS (ACPI): m/e 425.2 (M + 1). Analysis for C$_{24}$H$_{26}$F$_4$N$_2$O$_6$: Calcd: C, 56.03; H, 5.09; N, 5.45; found: C, 55.85; H, 5.05; N, 5.43. (isolated as the oxalate) |
| 304 | 4-fluoro | 2,2,2-trifluoroethyl | mp 199-202° C. MS (ACPI): m/e 367.2 (M + 1). Analysis for C$_{19}$H$_{19}$ClF$_4$N$_2$O: Calcd: C, 56.65; H, 4.75; N, 6.95; found: C, 56.82; H, 4.65; N, 6.84. (isolated as the hydrochloride) |
| 305 | 6-phenyl | 2,2,3,3-tetrafluoropropyl | mp 94-98° C. MS (ACPI): m/e 457.1 (M + 1). Analysis for C$_{26}$H$_{24}$F$_4$N$_2$O: Calcd: C, 68.41; H, 5.30; N, 6.14; found: C, 68.18, H, 5.28; N, 6.06. (isolated as the base) |

Example 307

N-(2-(6-Carboxy-1H-indol-3-yl)ethyl)-3-(2,2,2-trifluoroethoxy)benzylamine

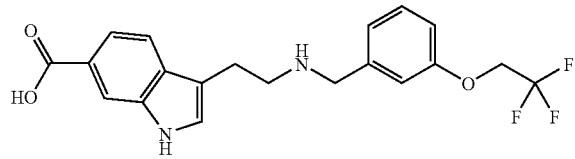

The method of Example 306 gives the title compound: mp 232-235° C. MS (ACPI): m/e 393.2 (M+1).

Example 310

5-Phenoxy-1H-indole

Combine potassium hydroxide (3 g, 0.054 mol) and phenol (15 g, 0.16 mol), and heat to 110° C. until the potassium hydroxide is dissolved. Cool the mixture to room temperature and add 5-fluoro-2-nitrotoluene (7.75 g, 0.05 mol) in one aliquot. Heat the reaction mixture to 130° C. for 30 min, cool to room temperature, and then pour into 10% NaOH (200 mL). Extract the aqueous solution with ether (2×100 mL), combine the organic layers and wash with 10% NaOH (2×100 mL), water (2×100 mL), dry over $Na_2SO_4$ and concentrate in vacuo. Chromatograph on silica gel eluting with hexanes/ethyl acetate to give 2-nitro-5-phenoxytoluene as a solid: $^1$H NMR (300 MHz, $CDCl_3$) 2.59 (s, 3H), 6.81-6.85 (m, 2H), 7.06-7.09 (m, 2H), 7.22-7.26 (m, 1H), 7.40-7.45 (m, 2H), 8.03-8.06 (m, 1H).

Combine 2-nitro-5-phenoxytoluene (1.15 g, 5.0 mmol) and tris(dimethylamino)methane (0.87 g, 6.0 mmol) in 10 mL dry toluene and heat to reflux under nitrogen. After 2 hours, cool the reaction mixture to room temperature and evaporate the toluene under reduced pressure to form a residue. Dissolve the residue in 15 mL EtOAc, mix with Pd/C (10%, 100 mg), stir at room temperature under 1 atmosphere of hydrogen for 1.5 days. Filter off catalyst and concentrate the filtrate. Chromatograph on silica gel eluting with hexanes/EtOAc give the title compound as a solid: $^1$H NMR (300 MHz, $CDCl_3$) 6.49-6.50 (m, 1H), 6.93-7.03 (m, 4H), 7.22-7.27 (m, 5H), 8.15 (br, 1H).

By the method of Example 310 the following compounds were prepared: a) 4-(p-Tolyloxy)-2-methylnitrobenzene: $^1$H NMR (300 MHz, $CDCl_3$) 2.35 (s, 3H), 2.57 (s, 3H), 6.77-6.80 (m, 2H), 6.93-7.03 (m, 2H), 7.18-7.24 (m, 2H), 8.00-8.03 (m, 1H);

b) 5-p-Tolyloxy-1H-indole: $^1$H NMR (300 MHz, $CDCl_3$) 2.31 (s, 3H), 6.48-6.49 (m, 1H), 6.87-6.96 (m, 3H), 7.07-7.10 (m, 2H), 7.20-7.35 (m, 3H), 8.15 (br, 1H);

c) 4-(o-Tolyloxy)-2-methylnitrobenzene: $^1$H NMR (400 MHz, $CDCl_3$) 2.16 (s, 3H), 2.57 (s, 3H), 6.50-6.78 (m, 2H), 6.93-7.03 (m, 3H), 7.18-7.35 (m, 1H), 8.00-8.03 (m, 1H);

d) 5-o-Tolyloxy-1H-indole: $^1$H NMR (400 MHz, $CDCl_3$) 2.31 (s, 3H), 6.45-6.46 (m, 1H), 6.78-6.80 (m, 1H), 6.90-6.00 (m, 2H), 7.01-7.10 (m, 2H), 7.13-7.24 (m, 2H), 7.32-7.34 (m, 1H), 8.11 (br, 1H);

e) 4-(m-Tolyloxy)-2-methylnitrobenzene: $^1$H NMR (300 MHz, $CDCl_3$) 2.37 (s, 3H), 2.60 (s, 3H), 6.80-6.88 (m, 4H), 7.03-7.06 (m, 1H), 7.27-7.32 (m, 1H), 8.03-8.06 (m, 1H);

f) 5-m-Tolyloxy-1H-indole: 6.0 g (54%) was obtained (red oil). 1H NMR (300 MHz, $CDCl_3$) 2.25 (s, 3H), 6.51-6.52 (m, 1H), 6.76-6.98 (m, 4H), 7.14-7.39 (m, 4H), 8.17 (br, 1H);

g) 4-(4-Fluorophenoxy)-2-methylnitrobenzene: $^1$H NMR (300 MHz, $CDCl_3$) 2.60 (s, 3H), 6.80-6.82 (m, 2H), 7.03-7.12 (m, 4H), 8.03-8.06 (m, 1H); and h) 5-(4-Fluorophenoxy)-1H-indole: 2.68 g (26%) was obtained (red oil). $^1$H NMR (300 MHz, $CDCl_3$) 6.50-6.52 (m, 1H), 6.91-7.01 (m, 5H), 7.24-7.38 (m, 3H), 8.18 (br, 1H) a) 5-p-tolyloxy-1H-indole.

Example 311

2-Oxo-(5-phenoxy-1H-indol-3-yl)acetyl chloride

Combine 5-phenoxy-indole (1.57 g, 7.5 mmol) and anhydrous ether (35 mL) and add oxalyl chloride (1.07 g, 8.25 mmol) in 8 mL ether. A precipitate forms. Stir the reaction over night. Collect the precipitate, dry in vacuo, to give the title compound: $^1$H NMR (300 MHz, DMSO-d6) 6.99-7.15 (m, 4H), 7.37-7.42 (m, 2H), 7.60 (d, 1H, J=8.7 Hz), 7.75 (d, 1H, J=2.4 Hz), 8.47 (d, 1H, J=3.2 Hz), 12.49, (br, 1H).

By the method of Example 311 the following compounds were prepared: a) 2-Oxo-(5-p-tolyloxy-1H-indol-3-yl)acetyl chloride;

b) 2-Oxo-(5-o-tolyloxy-1H-indol-3-yl)acetyl chloride: $^1$H NMR (300 MHz, $CDCl_3$) 2.83 (s, 3H), 6.86-6.89 (m, 1H), 7.03-7.16 (m, 5H), 7.26-7.27 (m, 1H). 7.40-7.44 (m, 1H), 7.87 (m, 1H), 8.20-8.32 (m, 2H), 8.90 (br, 1H);

c) 2-Oxo-(5-m-tolyloxy-1H-indol-3-yl)acetyl chloride; and d) 2-Oxo-(4-fluorophenoxy)-1H-indol-3-yl)acetyl chloride.

Example 312

2-Oxo-2-(5-phenoxy-1H-indol-3-yl)acetamide

Combine 2-oxo-(5-phenoxy-1H-indol-3-yl)acetyl chloride (2.15 g, 7.18 mmol), and ammonium hydroxide (28-30%, 32 ml, 680 mmol) and stir for 2 hours. Pour the reaction mixture into 10% (aq.) HCl, extract with dichloromethane, combine the organic layers and dry over $Na_2SO_4$, evaporate solvent in vacuo to give 1.94 g (96%) of title compound: $^1$H NMR (300 MHz, $CDCl_3$) 4.87 (s, 2H), 7.51-7.91 (m, 7H), 8.13-8.24 (m, 3H).

By the method of Example 312 the following compounds were prepared: a) 2-Oxo-2(5-p-tolyloxy-1H-indol-3-yl)acetamide;

b) 2-Oxo-2-(5-o-tolyloxy-1H-indol-3-yl)acetamide; and c) 2-Oxo-2-(5-m-tolyloxy-1H-indol-3-yl)acetamide.

Example 314

5-Phenoxytryptamine oxalate

Add 2-oxo-2-5-phenoxy-1H-indol-3-yl)acetamide (1.9 g, 6.86 mmol) in THF (60 mL) dropwise to a solution of $LiAlH_4$-THF (1.0 M, 41 mL, 41.0 mmol) in THF at room temperature. Heat the reaction mixture to reflux for 4 hours and cool to room temperature. Quench the reaction mixture with water (6 mL), followed by NaOH (2N, 3 mL). Collect the precipitate by filtration, and wash with ether (3×50 mL). Dry the filtrate over $Na_2SO_4$, concentrate in vacuo, purify the residue by flash chromatography (dichloromethane/MeOH/NH$_4$OH) to obtain 1.0 g (59%) of free amine of the title compound. The oxalic salt of the title compound gives: m.p. 156-157° C.; $^1$H NMR (300 MHz, DMSO-d6) 2.94 (t, 2H, J=7.3 Hz), 3.00 (t, 2H, J=7.3 Hz), 5.00 (br, 2H), 6.83-7.04 (m, 4H), 7.26-7.41 (m, 5H), 11.05 (br, 1H); MS (ELECTROSPRAY), m/e: 341.1 (M−1); Anal. Calcd. C$_{18}$H$_{18}$N$_2$O$_5$: C, 63.15; H, 5.30; N, 8.18. Found: C, 62.97; H, 5.25; N, 8.20.

By the method of Example 314 the following compounds were prepared and isolated as the oxalate, unless otherwise noted: a) 5-p-Tolyloxytryptamine: $^1$H NMR (300 MHz, CDCl$_3$) 2.31 (s, 3H), 2.83 (t, 2H, J=6.4 Hz), 2.98 (t, 2H, J=6.3 Hz), 6.86-6.96 (m, 3H), 7.07-7.10 (m, 3H), 7.24-7.33 (m, 2H), 8.02 (br, 1H) (isolated as the base);

b) 5-o-Tolyloxytryptamine: m.p. 187-188° C. $^1$H NMR (300 MHz, DMSO-d6) 2.27 (s, 3H), 2.90-3.05 (m, 4H), 6.66-4.68 (m, 1H), 6.76-6.79 (m, 1H), 6.93-6.98 (m, 1H), 7.06-7.16 (m, 2H), 7.24-7.39 (m, 3H), 7.66 (br, 2H), 11.05 (br, 1H); MS (ELECTROSPRAY) m/e: 265.1 (M−1-C$_2$H$_2$O$_4$); Anal. Calcd. C$_{19}$H$_{22}$N$_2$O$_5$: C, 64.04; H, 5.66; N, 7.86. Found: C, 63.90; H, 5.72; N, 7.83. and c) 5-m-Tolyloxytryptamine: m.p. 164-165° C.; $^1$H NMR (250 MHz, DMSO-d6) 2.26 (s, 3H), 2.89-3.07 (m, 4H), 4.52 (br, 2H), 6.68-6.72 (m, 2H), 6.82-6.86 (m, 2H), 7.17-7.42 (m, 4H), 11.06 (br, 1H); MS (ELECTROSPRAY) m/e: 265.1 (M−1-C$_2$H$_2$O$_4$).

Example 315

6-Chloro-7-fluoro-1H-indole

Combine boron trichloride (36.0 mL, 1.0 M solution in heptane, 36 mmol) and 1,2-dichloroethane (40 mL) and cool to 5° C. Add dropwise a solution of 2-fluoro-3-chloroaniline (4.36 g, 30.0 mmol) in 20 mL 1.2-dichloroethane. Warm the reaction mixture to room temperature and stir for 30 min. Add to the reaction mixture, chloroacetonitrile (2.71 g, 36.0 mmol), followed by TiCl$_4$ (6.83 g, 3.84 mL, 36.0 mmol). Heat the reaction mixture to reflux overnight. Cool the reaction mixture to room temperature, add 55.0 mL of 2.5 N HCl, heat to 85° C. for 30 min. Cool to room temperature, extract with dichloromethane (3×25 mL), combine the organic layers, wash with brine, dry over Na$_2$SO$_4$, concentrate in vacuo to give 5.1 g of 1-(2-amino-2-fluoro-3-chlorophenyl)-2-chloroethanone: $^1$H NMR (300 MHz, CDCl$_3$) 4.63 (s, 2H), 6.49 (br, 2H), 6.62-6.69 (m, 1H), 7.36-7.39 (m, 1H).

Dissolve 1-(2-amino-2-fluoro-3-chlorophenyl)-2-chloroethanone in 50 mL (10% water in 1,4-dioxane, v/v) and add NaBH$_4$ (0.86 g, 22.8 mmol) cautiously at room temperature. Reflux the reaction mixture for about 4 hour, cool to room temperature. Add 35 mL of 1N HCl and stir at room temperature for half an hour, extract with dichloromethane (20 mL×3), combine the organic layers and wash with H$_2$O and brine, dry over Na$_2$SO$_4$, and concentrate in vacuo. Chromatograph on silica gel eluting with EtOAc/hexanes to give the title compound 0.94 g (24%): $^1$H NMR (300 MHz, CDCl$_3$) 6.55-6.58 (m, 1H), 7.04-7.10 (m, 1H), 7.22-7.33 (m, 2H), 8.38 (br, 1H).

By the method of Example 315 the following compounds were prepared: a) 5,7-Difluoro-1H-indole: $^1$H NMR (300 MHz, CDCl$_3$) 6.55-6.56 (m, 1H), 6.71-6.78 (m, 1H), 7.01-7.11 (m, 1H), 7.26-7.28 (m, 1H), 8.34 (br, 1H);

b) 6,7-Difluoro-1H-indole: $^1$H NR (300 MHz, CDCl$_3$) 6.53-6.56 (m, 1H), 6.90-6.99 (m, 1H), 7.22-7.31 (m, 2H), 8.39 (br, 1H);

c) 5,6,7-Trifluoro-1H-indole: $^1$H NMR (300 MHz, CDCl$_3$) 6.52-6.55 (m, 1H), 7.13-7.20 (m, 1H), 7.26-7.27 (m, 1H), 8.35 (br, 1H) and d) 4,5,7-Trifluoro-1H-indole: $^1$H NMR (300 MHz, DMSO-d$_6$) 6.68-6.71 (m, 1H), 7.20-7.29 (m, 1H), 7.57-7.59 (m, 1H), 12.07 (br, 1H); MS (electrospray) m/e: 170.0 (M−1).

e) 4,7-Difluoro-1H-indole: $^1$H NMR (400 MHz, dmso-d$_6$): 11.91 (br s, 1H), 7.44 (t, 1H, J=2.8 Hz), 6.84-6.90 (m, 1H), 6.69-6.74 (m, 1H), 6.54-6.56 (m, 1H); MS (ES−): m/e 152.0 (M−1).

Example 316

3-Formyl-6-chloro-7-fluoro-1H-indole

Add phosphorus oxychloride (0.94 g, 6.16 mmol) to DMF (12 mL, cooled in an ice bath) with vigorous stirring. After about 10 minutes, add 6-chloro-7-fluoro indole (0.93 g, 5.6 mmol) in anhydrous DMF (4 mL), stir at 0° C. for 1 hour, warm to room temperature and stir overnight at room temperature (−16 hrs). Treat with 14.0 mL of 2N NaOH (4 eq.) with vigorous stirring. Heat the reaction to 80° C. for half an hour then cool. Pour the reaction into cold water with vigorous stirring to give a solid. Collect the solid by filtration and dry overnight in a vacuum oven at room temperature, to give the title compound: $^1$H NMR (300 MHz, CD$_3$COCD$_3$/CDCl$_3$) 7.09 (t, 1H, J=7.7 Hz), 7.83-7.86 (m, 2H), 9.89 (s, 1H). By the method of Example 316 the following compounds were prepared: a) 3-Formyl-5,7-difluoro-1H-indole: $^1$H NMR (300 MHz, CD$_3$COCD$_3$) 6.98-7.06 (m, 1H), 7.71-7.75 (m, 1H), 8.35 (s, 1H), 10.04 (s, 1H);

b) 3-Formyl-6,7-difluoro-1H-indole: $^1$H NMR (300 MHz, CDCl$_3$) 7.10-7.19 (m, 1H), 7.86-7.88 (m, 1H), 7.98-8.03 (m, 1H), 8.95 (br, 1H), 10.06 (s, 1H);

c) 3-Formyl-5,6,7-trifluoro-1H-indole: $^1$H NMR (300 MHz, CD$_3$COCD$_3$) 7.87-7.93 (m, 1H), 8.42 (s, 1H), 10.07 (s, 1H); and d) 3-Formyl-4,5,7-trifluoro-1H-indole: $^1$H NMR (300 MHz, DMSO-d$_6$) 7.46-7.55 (m, 1H), 8.49 (s, 1H), 10.02 (d, 1H, J=3.7 Hz), 13.19 (br, 1H).

e) 3-Formyl-4,7-difluoro-1H-indole: $^1$H NMR (400 MHz, dmso-d$_6$): δ 13.03 (br s, 1H), 10.00 (d, 1H, J=3.2 Hz), 8.36 (s, 1H), 7.07-7.13 (m, 1H), 6.94-7.00 (m, 1H); MS (APCI): m/e 182.0 (M+1).

f) 3-Formyl-4,5,6,7-tetrafluoro-1H-indole: $^1$H NMR (400 MHz, dmso-d$_6$): δ 13.33 (br s, 1H), 9.94 (d, 1H, J=4.4 Hz), 8.49 (s, 1H); MS (ES−): m/e 216.0 (M−1).

Example 317

3-(2-Nitrovinyl)-6-chloro-7-fluoro-1H-indole

Combine 3-formyl-6-chloro-7-fluoro-1H-indole (1.00 g, 5.06 mmol), ammonium acetate (292 mg, 3.8 mmol, 0.75 eq.) (dry by treating with toluene and remove the toluene in vacuo), and nitromethane (6.17 g, 101.2 mmol, 20 eq.). Warm to 65° C. When the reaction is complete (by TLC), add silica gel and remove the nitromethane in vacuo. Load the silica get on top of short column of silica gel and elute with 25% acetone in hexanes to give, after evaporation, the title compound.

By the method of Example 317 the following compounds were prepared: a) 3-(2-Nitrovinyl)-5,74-fluoro-1H-indole: $^1$H NMR (300 MHz, CDCl$_3$) 6.68-6.81 (m, 1H), 7.16-7.21 (m, 1H), 7.60 (d, 1H, J=13.5 Hz), 7.73 (d, 1H, J=2.7 Hz), 8.18 (d, 1H, J=13.5 Hz), 10.95 (br, 1H);

b) 3-(2-Nitrovinyl)-6,7-difluoro-1H-indole: $^1$H NMR (300 MHz, CDCl$_3$) 6.93-7.00 (m, 1H), 7.30-7.35 (m, 1H), 7.58 (d, 1H, J=13.5 Hz), 7.69 (d, 1H, J=2.9 Hz), 8.10 (d, 1H, J=13.5 Hz), 11.18 (br, 1H): MS (electrospray) m/e: 225 (M+1), 223 (M−1);

c) 3-(2-Nitrovinyl)-5,6,7-trifluoro-1H-indole.

d) 3-(2-Nitrovinyl)-4,5,7-trifluoro-1H-indole.

e) 3-(2-Nitrovinyl)-4,7-difluoro-1H-indole: MS (ES−): m/e 223.0 (M−1).

f) 3-(2-Nitrovinyl)-4,5,6,7-tetrafluoro-1H-indole: MS (ES−): nine 259.0 (M−1).

Example 318

6-Chloro-7-fluorotryptamine

Add dropwise 3-(2-nitrovinyl)-6-chloro-7-fluoro-1H-indole (1.20 g, 5.06 mmol) in anhydrous THF to a solution of lithium aluminum hydride (30.0 mL, 30.0 mmol, 1.0 M solution in THF). Heat to reflux for 2 hour and then cool to room temperature. Quench by carefully adding 1N NaOH to give a suspension. Filter the suspension through celite and rinse repeatedly with ether. Evaporate the filtrate in vacuo to give a residue. Chromatograph the residue on silica gel eluting with dichloromethane, methanol, and ammonium hydroxide (10:1:01) to give, after evaporation, the title compound: $^1$H NMR (300 MHz, CDCl$_3$) 2.87 (t, 2H, J=6.6 Hz), 3.02 (t, 2H, J=6.7 Hz), 7.03-7.08 (m, 2H), 7.26-7.29 (m, 1H), 8.51 (br, 1H).

By the method of Example 318 the following compounds were prepared: a) 5,7-Difluorotrrptamine: $^1$H NMR (300 MHz, CDCl$_3$) 2.46 (t, 2H, J=6.5 Hz), 3.01 (t, 2H, J=6.4 Hz), 6.69-6.77 (m, 1H), 7.03-7.11 (m, 2H), 8.29 (br, 1H);

b) 6,7-Difluorotryptamine: $^1$H NMR (300 MHz, CDCl$_3$) 2.87 (t, 2H, J=6.6 Hz), 3.02 (t, 2H, J=6.7 Hz), 6.88-6.97 (m, 1H), 7.04 (m, 1H), 7.20-7.25 (m, 1H), 8.64 (br, 1H);

c) 5,6,7-Trifluorotryptamine: $^1$H NMR (300 MHz, CDCl$_3$) 2.83 (t, 2H, J=6.6 Hz), 3.00 (t, 2H, J=6.7 Hz), 7.08-7.14 (m, 2H), 8.71 (br, 1H); MS (electrospray), m/e: 215.0 (M+1); and d)-4,5,7-Trifluorotryptamine: $^1$H NMR (300 MHz, CDCl$_3$) 2.93 (t, 2H, J=6.6 Hz), 3.03 (t, 2H, J=6.4 Hz), 6.73-6.82 (m, 1H), 7.02 (s, 1H), 8.58 (br, 1H); MS (electrospray), m/e: 215.0 (M+1), 213.0 (M−1).

f) 4,7-Difluorotryptamine: $^1$H NMR (400 MHz, dmso-d$_6$): 11.57 (br s, 1H), 7.19 (s, 1H), 6.80-6.85 (m, 1H), 6.61-6.67 (m, 1H), 2.79 (s, 4H). MS (ES+): m/e 197.0 (M+1) 180.0 (M−NH$_2$).

g) 4,5,6,7-Tetrafluorotryptamine: $^1$H NMR (400 MHz, dmso-d$_6$): δ 7.31 (s, 1H), 2.78 (s, 4H); MS (ES+): m/e 233.0 (M+1) 216.0 (M−16).

Example 319

N-(2-(5-Phenoxy-1H-indol-3-yl)ethyl)-3-phenoxybenzylamine

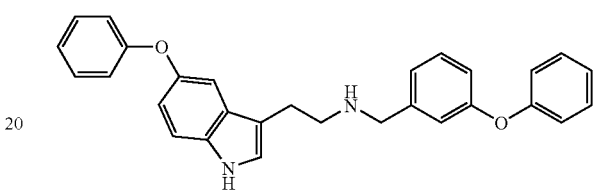

Combine 5-phenoxytryptamine (0.400 g, 1.59 mmol), 3-phenoxybenzaldehyde (0.377 g, 1.90 mmol) and molecular sieves 4 Å (0.40 g) in methanol (15 mL) and stir for 4 h. Filter and wash the molecular sieves several times with MeOH. Add NaBH$_4$ (61.5 mg, 1.59 mmol) in portions to the filtrate and stir at room temperature for 1 h. Remove the MeOH under vacuum to give a residue, dilute the residue with dichloromethane/water, separate the layers, extract the aqueous layer with dichloromethane, combine the organic layers, and dry over Na$_2$SO$_4$. Concentrate in vacuo and chromatograph on silica gel eluting with dichloromethane/MeOH the title compound. Form the oxalate salt of the title compound: m.p. 196-198° C.; $^1$H NMR (300 MHz, DMSO-d$_6$) 2.95-3.15 (m, 4H), 4.15 (s, 2H), 6.85-7.46 (m, 18H), 11.06 (br, 1H); MS (ELECTROSPRAY) m/e: 435.3 (M+1); HRMS (ES+) calcd for C$_{29}$H$_{27}$N$_2$O$_2$ (M+H) 435.2084 found 435.2073.

By the method of Example 319 the following compounds were prepared, isolated as the oxalate except where noted:

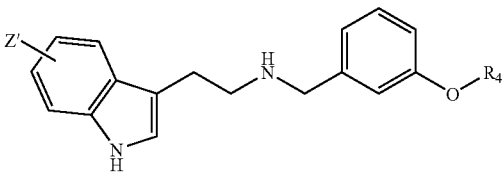

| No. | Z' | R$_4$ | Data |
|---|---|---|---|
| 320 | 5-p-tolyloxy | phenyl | m.p. 204-206° C.; $^1$H NMR (250 MHz, DMSO-d6) 2.25 (s, 3 H), 2.97-3.12 (m, 4 H), 4.01 (br, 2 H), 4.16 (s, 2 H), 6.78-6.84 (m, 3 H), 7.00-7.10 (m, 10 H), 7.13-7.43 (m, 4 H), 11.05 (br, 1 H); MS (ELECTROSPRAY) m/e: 449.1 (M + 1 − C$_2$H$_2$O$_4$); Analysis calcd: C$_{32}$H$_{30}$N$_2$O$_6$: C, 71.36; H, 5.61; N, 5.20. Found: C, 71.22; H, 5.59; H, 5.28 |
| 321 | 5-o-tolyloxy | phenyl | m.p. 191-192° C.; $^1$H NMR (300 MHz, DMSO-d6) 2.28 (s, 3 H), 2.99-3.15 (m, 4 H), 4.17 (s, 2 H), 6.63-6.66 (m, 1 H), 6.756.79 (m, 1 H), 6.92-7.42 (m, 15 H), 9.50 (br, 2 H), 11.05 (br, 1 H); MS (ELECTROSPRAY) m/e: 449.1 (M + 1 − C$_2$H$_2$O$_4$); Anal. calcd. C$_{32}$H$_{30}$N$_2$O$_6$: C, 71.36; H, 5.61; N, 5.20. Found C, 71.11; H, 5.59; N, 5.18 |
| 322 | 5-m-tolyloxy | phenyl | mp. 174-175° C. $^1$H NMR (250 MHz, DMSO- |

-continued

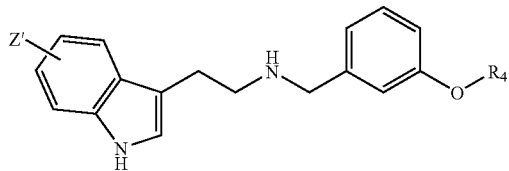

| No. | Z' | R₄ | Data |
|---|---|---|---|
| | | | d6) 2.51 (s, 3 H), 3.00-3.13 (m, 4 H), 4.15 (s, 2 H), 6.81-7.03 (m, 7 H), 7.11-7.42 (m, 11 H), 11.05 (br, 1 H); MS (ELECTROSPRAY) m/e: 449.1 (M + 1 − C₂H₂O₄) |
| 323 | 6-chloro-7-fluoro | 2,2,2-trifluoroethyl | mp 186-187° C. ¹H NMR (300 MHz, DMSO-d₆) 3.13 (s, 4 H), 4.15 s, 2 H), 4.78 (q, 2 H, J = 8.7 Hz), 7.07-7.12 (m, 2 H), 7.21-7.24 (m, 1 H), 7.37-7.45 (m, 4 H), 9.44 (br, 1 H), 11.72 (br, 1 H): ms (electrospray) m/e: 401.2 (M + 1 − HCl), 399.2 (M − 1 − HCl); Anal. calcd. C₁₉H₁₇ClF₄N₂O•HCl: C, 52.19; H, 4.15; N, 6.41. Found: C, 52.15; H, 4.14; N, 6.38 (isolated as the hydrochloride) |
| 324 | 6-chloro-7-fluoro | 2,2,3,3-tetrafluoropropyl | mp. 155-156° C.; 1H NMR (300 MHz, DMSO-d₆) 3.13 (s, 4 H), 4.16 (s, 2 H), 4.61 (t, 2 H, J = 13.5 Hz), 6.70 (tt, 1 H, J = 51.9 Hz, J = 5.5 Hz), 7.08-7.10 (m, 2 H), 7.11-7.12 (m ,1 H), 7.21-7.45 (m, 4 H), 9.41 (br, 1 H), 11.72 (br, 1 H); MS (electrospray) m/e: 433.2 (M + 1 − HCl), 431.2 (M − 1 − HCl); Anal. calcd. C₂₀H₁₈ClF₅N₂O•HCl: C, 51.19; H, 4.08; N, 5.97. Found: C, 51.27; H, 4.10; N, 6.07 (isolated as the hydrochloride) |
| 325 | 5,7-difluoro | 2,2,2-trifluoroethyl | m.p.: 179-180° C.; ¹H NMR (300 MHz, DMSO-d₆) 3.11 (s, 4 H), 4.16 (s, 2 H), 4.77 (q, 2 H, J = 8.7 Hz), 6.93-6.97 (m, 1 H), 7.00-7.14 (m, 1 H), 7.21-7.43 (m, 5 H), 9.41 (br, 1 H), 11.61 (br, 1 H); ms (electrospray) m/e: 385.2 (M + 1 − HCl), 383.2 (M − 1 − HCl); Anal. calcd. C₁₉H₁₇F₅N₂O•HCl•0.1H₂O: C, 54.00; H, 4.34; N, 6.63. Found: C, 53.71; H, 4.24; N, 6.70 (isolated as the hydrochloride) |
| 326 | 5,7-difluoro | 2,2,3,3-tetrafluoropropyl | mp. 109-110° C.; ¹H NMR (300 MHz, DMSO-d₆) 2.71-2.84 (m, 4 H), 3.71 (s, 2 H), 4.53 (t, 2 H, J = 13.5 Hz), 6.67 (tt, 1 H, J = 51.9 Hz, J = 5.5 Hz), 6.87-7.02 (m, 4 H), 7.12-7.28 (m, 3 H), 11.40 (br, 1 H); MS (electrospray) m/e: 417.0 (M + 1), 415.0 (M − 1); Anal. calcd. C₂₀H₁₈F₆N₂O•0.1H₂O: C, 57.45; H, 4.39; N, 6.70. Found: C, 57.24; H, 4.08; N, 6.68 |
| 327 | 6,7-difluoro | 2,2,2-trifluoroethyl | m.p.: 164-165° C.; ¹H NMR (300 MHz, DMSO-d₆) 3.13 (s, 4 H), 4.16 (s, 2 H), 4.77 (q, 2 H, J = 9.1 Hz), 7.00-7.13 (m, 2 H), 7.20-7.23 (m, 1 H), 7.33-7.43 (m, 4 H), 9.36 (br, 1 H), 11.57 (br, 1 H); MS (electrospray) m/e: 385.2 (M + 1 − HCl), 383.3 (M − 1 − HCl); Anal. calcd. C₁₉H₁₇F₅N₂O•HCl: C, 54.23; H, 4.31; N, 6.66. Found: C, 53.86; H, 4.28; N, 6.58 (isolated as the hydrochloride) |
| 328 | 6,7-difluoro | 2,2,3,3-tetrafluoropropyl | m.p.: 214-215° C.; ¹H NMR (300 MHz, DMSO-d₆) 3.02-3.17 (m, 4 H), 4.16 (s, 2 H), 4.59 (t, 2 H, J = 13.5 Hz), 6.68 (tt, 1 H, J = 51.9 Hz, J = 5.5 Hz), 7.00-7.17 (m, 5 H), 7.21-7.42 (m, 4 H), 11.65 (br, 1 H); MS (electrospray) m/e: 417.0 (M + 1 − C₄H₄O₄), 415.0 (M − 1 − C₄H₄O₄); Anal. calcd. C₂₀H₁₈F₆N₂O•C₄H₄O₄•0.9H₂O: C, 52.54; H, 4.37; N, 5.11. Found: C, 52.14; H, 3.95; N, 5.49 (isolated as the maleate) |
| 329 | 5,6,7-trifluoro | 2,2,2-trifluoroethyl | m.p.: 111-112° C.; ¹H NMR (300 MHz, DMSO-d₆) 2.72-2.81 (m, 4 H), 3.71 (s, 2 H), 4.68 (q, 2 H, J = 8.8 Hz), 6.87-7.00 (m, 3 H), 7.22-7.40 (m, 3 H), 11.58 (br, 1 H); MS (electrospray) m/e: 403.1 (M + 1), 401.2 (M − 1). Anal. calcd. C₁₉H₁₆F₆N₂O: C, 56.72; H, 4.01; N, 6.96. Found: C, 56.61; H, 3.92; N, 6.96 (isolated as the base) |
| 330 | 5,6,7-trifluoro | 2,2,3,3-tetrafluoropropyl | m.p.: 223-224° C.; ¹H NMR (300 MHz, DMSO-d₆) 3.11 (s, 4 H), 4.15 (s, 2 H), 4.61 (t, 2 H, J = 13.5 Hz), 6.70 (tt, 1 H, J = 51.9 Hz, J = 5.5 Hz), 7.08-7.12 (m, 1 H), 7.19-7.25 (m, 1 H), 7.36-7.43 (m, 3 H), 7.52-7.58 (m, 1 H), 9.50 (br, |

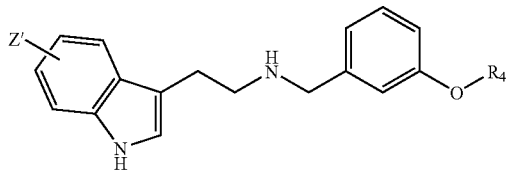

| No. | Z' | R₄ | Data |
|---|---|---|---|
| 331 | 4,5,7-trifluoro | 2,2,2-trifluoro ethyl | 1 H), 11.78 (br, 1 H); MS (electrospray) m/e: 435.1 (M + 1 − HCl), 433.1 (M − 1 − HCl); Anal. calcd. $C_{20}H_{18}F_6N_2O \cdot HCl \cdot 0.1H_2O$: C, 50.83; H, 3.88; N, 5.93. Found: C, 50.60; H, 3.74; N, 6.07 (isolated as the hydrochloride) m.p.: 243-244° C.; $^1$H NMR (300 MHz, DMSO-$d_6$) 3.16-3.21 (m, 4 H), 4.18 (s, 2 H), 4.75 (q, 2 H, J = 8.8 Hz), 7.11-7.25 (m, 3 H), 7.39-7.45 (m, 3 H), 9.37 (br, 1 H), 11.90 (br, 1 H); MS (electrospray) m/e: 403.1 (M + 1 − HCl), 401.0 (M − 1 − HCl); Anal. calcd. $C_{19}H_{16}$—$F_6N_2O \cdot HCl$: C, 52.00; H, 3.91; N, 6.38. Found: C, 51.83; H, 3.62; N, 6.55 (isolated as the hydrochloride) |
| 332 | 4,5,7-trifluoro | 2,2,3,3-tetrafluoro propyl | m.p.: 261-262° C.; $^1$H NMR (300 MHz, DMSO-$d_6$) 3.18 (s, 4 H), 4.17 (s, 2 H), 4.61 (t, 2 H, J = 13.5 Hz), 6.69 (tt, 1 H, J = 51.9 Hz, J = 5.5 Hz), 7.09-7.13 (m, 1 H), 7.17-7.26 (m, 2 H), 7.32-7.42 (m, 3 H), 9.37 (br, 1 H), 11.92 (br, 1 H); MS (electrospray) m/e: 435.1 (M + 1 − HCl), 433.1 (M − 1 − HCl); Anal. calcd. $C_{20}H_{17}F_7N_2O \cdot HCl$, C, 51.02; H, 3.85; N, 5.95. Found: C, 50.62; H, 3.79; N, 6.00 (isolated as the hydrochloride |
| 333 | 7-cyano | 2,2,2-trifluoro ethyl | mp. 241-242° C.; $^1$H NMR (300 MHz, DMSO-$d_6$) 3.15 (s, 4 H), 4.17 (s, 2 H), 4.78 (q, 2 H, J = 8.7 Hz), 7.10-7.22 (m, 3 H), 7.33-7.43 (m, 3 H), 7.60-7.62 (m, 1 H), 7.95-7.97 (m, 1 H), 9.29 (br, 2 H), 11.90 (br, 1 H); MS (electrospray) m/e: 374.2 (M + 1 − HCl), 372.0 (M − 1 − HCl); Anal. calcd. $C_{20}H_{18}F_3N_3O \cdot HCl \cdot 0.2 H_2O$: C, 58.10; H, 4.73; N, 10.16. Found: C, 57.91; H, 4.56; N, 10.88. |
| 334 | 7-cyano | 2,2,3,3-tetrafluoro ethyl | mp. 212-213° C.; $^1$H NMR (300 MHz, DMSO-$d_6$) 3.16 (s, 4 H), 4.16 (s, 2 H), 4.61 (t, 2 H, J = 13.6 Hz), 6.69 (tt, 1 H, J = 51.9 Hz, J = 5.5 Hz), 7.09-7.22 (m, 3 H), 7.33-7.43 (m, 3 H), 7.60-7.63 (m, 1 H), 7.96-7.98 (m, 1 H), 9.34 (br, 2 H), 11.92 (br, 1 H); MS (electrospray) m/e: 406.2 (M + 1 − HCl), 404.0 (M − 1 − HCl); Anal. calcd. $C_{21}H_{19}F_4N_3O \cdot HCl$, C, 57.08; H, 4.56; N, 9.51. Found: C, 57.12; H, 4.61; N, 9.53. |

Example 335

2-Fluoro-3-phenoxybenzaldehyde

Cool a solution of 2,2,6,6-tetramethylpiperidine (5.1 mL, 30.0 mmol) in THF (40 mL) to −78° C. Add dropwise n-Butyllithium (18.7 mL, 30.0 mmol, 1.6M in hexanes) and stir for 10 min at −78° C. Add dropwise 2-fluorophenyl phenyl ether (4.7 g, 25.0 mmol), stir 2 h at −78° C. Add N,N-dimethylformamide (2.3 mL, 30.0 mmol) dropwise over 15 min. Stir the resulting mixture for 3 h at −78° C. and allow to warm to ambient temperature over 16 h. Quench the reaction mixture with water (50 mL), extract with ethyl acetate, dry over $Na_2SO_4$, filter and concentrate under reduced pressure to give an oil. Crystallize the oil with hexanes to give a solid, collect and recrystallize from hexanes/ethyl acetate/methylene chloride to give the title compound: mp 75-77° C.; MS (m/e): 216 (M⁺); Calculated for $C_{13}H_9FO_2$: Calcd: C, 72.22; H, 4.20. Found: C, 72.41; H, 4.23. Purification of the mother liquors by silica gel chromatography (2-3% ethyl acetate/hexanes) gives an additional amount of the title compound: MS (m/e): 216 (M⁺).

By the method of Example 335 the following compound was prepared: a) 6-Fluoro-3-phenoxybenzaldehyde: MS (m/e): 216 (M⁺).

Example 336

3-Ethoxybenzaldehyde

Combine 3-hydroxybenzaldehyde (5.6 g, 46 mmol) and 1-iodoethane (10.7 g, 69 mmol) in DMSO (25 mL) and warm to 80° C. Treat with of cesium carbonate (22.4 g, 69 mmol) in portions. During the addition the temperature begin to rise so the bath is removed. Stir the reaction at 80° C. for 1 hour, pour into 200 mL brine and extract twice with 150 mL diethyl ether. Wash the combine extracts twice with 200 mL brine, dry over $MgSO_4$ and concentrate under vacuum to give an oil. Purification by chromatography ($SiO_2$; 2.5% EtOAc in hexanes) affords 5.73 g (38 mmol; 83%) of the title compound as an oil: $^1$H NMR (CDCl$_3$) 9.94 (s, 1H), 7.42-7.41 (m, 2H), 7.36-7.35 (m, 1H), 7.16-7.13 (m, 1H), 4.10-4.04 (q, 2H), 1.64-1.40 (t, 3H).

By the method of Example 336 the following compounds were prepared: a) 3-Propoxybenzaldehyde: $^1$H NMR (CDCl$_3$) 9.95 (s, 1H), 7.43-7.41 (m, 2H), 7.37-7.36 (m, 1H), 7.17-7.14 (m, 1H), 9.98-3.95 (t, 2H), 1.84-1.79 (m, 2H), 1.05-1.02 (t, 3H).

Example 337 p-Toluene-3-(2,2,3,3-tetrafluoropropoxy)tosylate

Add pyridine (1.9 L) (dried over molecular sieves 4 Å) to a round-bottomed flask (5 L), under inert atmosphere and equipped with a mechanical agitator and add 2,2,3,3-tetrafluoro-1-propanol (604.5 g, 4.58 mol). Cool the mixture to 0° C. with an ice-bath. Add p-toluenesulfonyl chloride (960 g, 5.04 mol) over 20 min it 4 portions to the reaction mixture and stir. After 20 min., cooling on an ice-bath), a precipitate is formed. Stir the reaction mixture for 1 h at 0° C. and 2 h at 20° C. Pour the reaction mixture, with agitation, over an ice-water mixture (1.44 L) and leave overnight (18 h) at 20° C. The crude tosylate derivative separates from the aqueous mixture as an oily material (1.34 kg) containing 14% w/w pyridine which corresponds to 1.15 kg of the tosylate (87.8%). The crude material is carried to the next reaction step without Ether purification: $^1$H-RMN is consistent.

Example 338

3-(2,2,3,3,3-Pentafluoropropoxy)benzaldehyde

Combine 3-hydroxybenzaldehyde (137.6 g, 1.127 mol), p-toluene-3-2,2,3,3,3-pentafluoropropoxy) tosylate (243 g, 0.799 mol), potassium carbonate (220 g, 1.597 mol) and dimethylformamide (2451 mL) in a double-wall 4 L reactor equipped with a reflux condenser and a mechanical agitator, and heat at 110° C. for 46.5 h under argon atmosphere. Cool the reaction mixture to room temperature and filter through a bed of 400 g of silica gel. Elute silica gel bed with 2.451 mL of ethyl acetate. Pour the combined organic layers over 7.3 L of ice-water. Add 10 N sodium hydroxide (500 mL) to this mixture and stir for 1 h. Separate the aqueous phase and extract with ethyl acetate (1000 mL). Pool the organic phase, wash with water (1000 mL) and brine (750 mL). Evaporation of the organic solvents under reduced pressure provides 159.79 g of a brown oily material containing the crude title compound. Purification by fractional distillation (two successive cycles) under reduced pressure (2 mm Hg) using a distillation apparatus equipped with a 30 cm length adiabatic column to gives a fraction of 52.4 g of the expected product (96.2% area by HPLC).

Example 339

3-(3,3,3-Trifluoropropoxy)benzaldehyde

Combine 3-hydroxybenzaldchyde (130.2 g, 1.066 mol), 3,3,3-trifluoropropoxy tosylate (143 g, 0.533 mol), potassium carbonate (147.35 g, 1,066 mol) and absolute ethanol (1430 mL) in a three-necked round-bottomed flask equipped with a reflux condenser and a magnetic stirred and reflux for 4 h under argon atmosphere. Concentrate the reaction mixture under reduced pressure. Pour the concentrated mixture over 1N sodium hydroxide (2145 mL), stir for 30 min and extract with dichloromethane (2145 mL). Decant the organic layer wash with 1N sodium hydroxide (2145 mL). After separation, wash the organic layer successively twice by 1 L water (pH aqueous phase=7), dry over 30 g magnesium sulfate, evaporate the dichloromethane organic layer to dryness under reduced pressure to yield 55.4 g of the title compound (0.254 mol, 47.6% yield) as a slightly yellow oily material.

Example 340

N-(2-(6-Fluoro-1H-indol-3-yl)ethyl)-2-fluoro-3-phenoxy-benzylamine

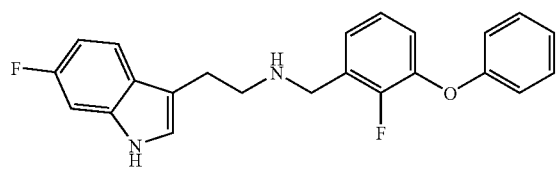

Combine 6-fluorotryptamine (419 mg, 2.35 mmol) and 2-fluoro-3-phenoxybenzaldehyde (610 mg, 2.82 mmol) in absolute ethanol (6 mL). Heat the mixture to 65° C. to give a homogeneous solution. Add 3 Å molecular sieves (400 mg) to the mixture and heat to reflux temperatures for 5 h. Cool the reaction mixture to ambient temperature and add sodium borohydride (267 mg, 7.1 mmol). Stir the mixture for 18 h at ambient temperature. Cool the reaction mixture on a water bath, quench with acetone, dilute with ethanol and acetone, and filter the molecular sieves. Concentrate the filtrate under reduced pressure, dilute with 1N NaOH, extract with ethyl acetate, wash with brine, dry (Na$_2$SO$_4$), filter and concentrate under reduced pressure to give 1.0 g of an oil. Chromatograph on silica gel eluting with 1%, 4% 2N ammonia in methanol/methylene chloride gives a clear colorless oil. Formation of the hydrochloride salt in ethyl acetate/methanol gives the hydrochloride of the title compound: mp 173-174.5° C.; MS (m/e): 379 (M+1), 377 (M−1); Calculated for C$_{23}$H$_{20}$F$_2$N$_2$O—HCl: Calcd: C, 66.59; H, 5.10; N, 6.75. Found: C, 66.50; H, 5.09; N, 6.73.

Example 341

N-(2-(6-Fluoro-1H-indol-3-yl)ethyl)-6-fluoro-3-phenoxy-benzylamine

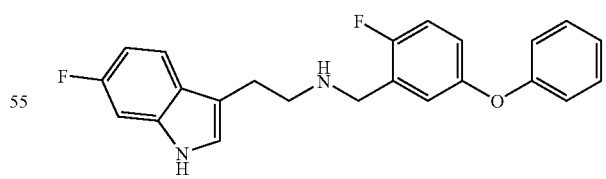

The method of Example 340 gives the hydrochloride of the title compound: mp 183.5-185.5° C.; MS (m/e): 379 (M+1), 377 (M−1); Calculated for C$_{23}$H$_{20}$F$_2$N$_2$O.HCl: Calcd: C, 66.59; H, 5.10; N, 6.75. Found: C, 66.54; H, 5.11; N, 6.68.

By the method of Example 340 the following compounds were prepared, isolated as the hydrochloride except where noted:

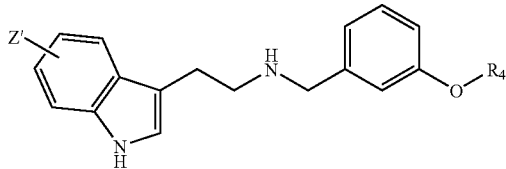

| No. | Z' | R$_4$ | Data |
|---|---|---|---|
| 342 | 5-methoxy | ethyl | ISMS 325 (M + 1); Analysis for C$_{20}$H$_{25}$ClN$_2$O$_2$ 0.2EtOH 0.1H$_2$O: calcd: C, 65.88; H, 7.16; N, 9.53; found: C, 65.90; H, 6.97; N, 7.16; $^1$H NMR (DMSO-d6) 10.85 (s, 1 H), 9.43 (bs, 2 H), 7.42-7.22 (m, 4 H), 7.18-7.10 (m, 2 H), 7.05-7.0 (m, 1 H), 6.32-6.25 (m, 1 H), 4.3-4.15 (m, 2 H), 4.15-4.05 (q, 2 H), 3.85 (s, 3 H), 3.15 (s, 4 H), 1.45-1.35 (t, 3 H) |
| 343 | 5-methoxy | propyl | ISMS 339 (M + 1); Analysis for C$_{21}$H$_{27}$ClN$_2$O$_2$: calcd: C, 67.28; H, 7.23; N, 7.47; found: C, 67.28; H, 7.30; N, 7.13; $^1$H NMR (DMSO-d6) 10.85 (s, 1 H), 9.43 (bs, 2 H), 7.35-7.15 (m, 4 H), 7.1-7.05 (m, 2 H), 7.0-6.92 (m, 1 H), 6.7-6.6 (m, 1 H), 4.15-4.05 (q, 2 H), 4.3-4.16 (m, 1 H), 4.15-4.05 (q, 2 H), 3.85 (s, 3 H), 3.15 (s, 4 H), 1.45-1.35 (t, 3 H) |
| 344 | 5-fluoro | 2,2,2-trifluoroethyl | ISMS 367 (M + 1); Analysis for C$_{19}$H$_{19}$ClF$_4$N$_2$O: calcd: C, 56.65; H, 4.75; N, 6.95; found: C, 56.37; H, 4.83; N, 6.81 (base) |
| 345 | 5-methoxy | 2,2,2-trifluoroethyl | Analysis for C$_{20}$H$_{22}$ClF$_3$N$_2$O$_2$: Calcd: C, 57.91; H, 5.34; N, 6.75; found: C, 57.72; H, 5.17; N, 6.61; ISMS 379 (M + 1) |
| 346 | 5-fluoro | 2,2,3,3,3-pentafluoropropyl | ISMS 417 (M + 1); Analysis for C$_{20}$H$_{18}$F$_6$N$_2$O C$_2$H$_2$O$_4$: calcd: C, 51.18; H, 3.98; N, 5.53; found: C, 51.18; H, 3.91; N, 5.51 (isolated as the oxalate) |
| 347 | 5-methoxy | 2,2,3,3,3-pentafluoropropyl | ISMS 429 (M + 1); Analysis for C$_{21}$H$_{21}$F$_5$N$_2$O$_2$ 1.2C$_2$H$_2$O$_4$ 0.8H$_2$O: calcd: C, 51.02; H, 4.57; N, 5.09; found: C, 50.64; H, 4.23; N, 5.15 (isolated as the oxalate) |
| 348 | 5-methoxy | 2,2,3,3-tetrafluoropropyl | ISMS 411 (M + 1) Analysis for C$_{21}$H$_{22}$F$_4$N$_2$O$_2$ C$_2$H$_2$O$_4$ 0.1H$_2$O: calcd: C, 55.0; H, 4.86; N, 5.58; found: C, 54.74; H, 4.74; N, 5.58 (isolated as the oxalate) |
| 349 | 5-methoxy | 3,3,3-trifluoropropyl | Analysis for C$_{21}$H$_{23}$F$_3$N$_2$O$_2$ HCl: calcd: C, 58.81; H, 5.64; N, 6.53; found: C, 58.42; H, 5.44; N, 6.51; ISMS 393 (M + 1) |
| 350 | 5-fluoro | 2,2,3,3-tetrafluoropropyl | Analysis for C$_{20}$H$_{20}$F$_4$N$_2$O HCl: calcd: C, 57.63; H, 5.08; N, 6.72; found: C, 57.49; H, 504; N, 6.76; ISMS 381 (M + 1) |
| 351 | 4-chloro-5-methoxy | 2,2,2-trifluoroethyl | Analysis for C$_{20}$H$_{20}$ClF$_3$N$_2$O$_2$ HCl: calcd: C, 53.47; H, 4.71; N, 6.24; found: C, 53.33; H, 4.65; N, 6.21; ISMS 413 (M + 1) |
| 352 | 4-chloro-5-methoxy | 2,2,3,3-tetrafluoropropyl | Analysis for C$_{21}$H$_{21}$ClF$_4$N$_2$O$_2$ HCl: calcd: C, 52.40; H, 4.61; N, 5.82; found: C, 52.25; H, 4.50; N, 5.80; ISMS 445 (M + 1) |
| 353 | 4-chloro-5-methoxy | 3,3,3-trifluoropropyl | Analysis for C$_{21}$H$_{22}$ClF$_3$N$_2$O$_2$ HCl: calcd: C, 54.4; H, 5.00; N, 6.05; found: C, 54.18; H, 4.86; N, 6.06; ISMS 427 (M + 1) |

By the method of Example 340 the following compounds were prepared, isolated as the hydrochloride except where noted:

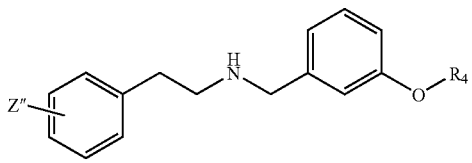

| No. | Z' | R4 | Data |
|-----|----|----|------|
| 360 | 3-chloro | 2,2,2-trifluoro ethyl | ISMS 344 (M + 1); Analysis for $C_{17}H_{18}ClF_3NO$ calcd: C, 53.70; H, 4.77; N, 3.68; found: C, 53.61; H, 4.96; N, 3.66 |
| 361 | 3-trifluoro methyl | 2,2,2-trifluoro ethyl | ISMS 378 (M + 1); Analysis for $C_{20}H_{19}F_6NO5$: calcd: C, 51.40; H, 4.10; N, 3.0; found: C, 51.26; H, 4.06; N, 3.07 (isolated as the oxalate) |
| 362 | 3-chloro | 2,2,3,3,3-pentafluoro propyl | ISMS 394 (M + 1); Analysis for $C_{18}H_{18}Cl_2F_5NO$: calcd: C, 50.25; H, 4.22; N, 3.26; found: C, 50.38; H, 4.03; N, 3.45 |
| 363 | 3-trifluoro methyl | 2,2,3,3,3-pentafluoro propyl | ISMS 428 (M + 1); Analysis for $C_{19}H_{17}F_8NOC_2H_2O_4$: calcd: C, 48.75; H, 3.70; N, 2.70; found: C, 48.76; H, 3.67; N, 2.79 (isolated as the oxalate) |
| 364 | 3-chloro | 2,2,3,3-tetrafluoro propyl | Analysis for $C_{18}H_{18}ClF_4NO \cdot C_2H_2O_4$: calcd: C, 51.57; H, 4.33; N, 3.01; found: C, 51.92; H, 4.29; H, 3.08; ISMS 376 (M + 1) |
| 365 | 3-trifluoro methyl | 2,2,3,3-tetrafluoro propyl | Analysis for $C_{19}H_{18}F_7NO \cdot C_2H_2O_4$: calcd: C, 50.51; H, 4.04; N, 2.81; found: C, 50.48; H, 4.02; N, 2.85; ISMS 410 (M + 1) (isolated as the oxalate) |
| 366 | 3-trifluoro methyl | 3,3,3-trifluoro propyl | Analysis for $C_{19}H_{19}F_6NO \cdot HCl$: calcd: C, 53.34; H, 4.71; N, 3.27; found: C, 53.23; H, 4.73; N, 3.28; ISMS 392 (M + 1) |
| 367 | 3-chloro | 3,3,3-trifluoro propyl | Analysis for $C_{18}H_{19}ClF_3NO \cdot HCl$: calcd: C, 54.84; H, 5.11; N, 3.55; found: C, 54.74; H, 5.02; H, 3.11; ISMS 358 (M + 1) |

Example 370

N-(2-(6-Fluoro-1H-indol-3-yl)ethyl)-3-(2,2,2-trifluoroethoxy)benzylamine

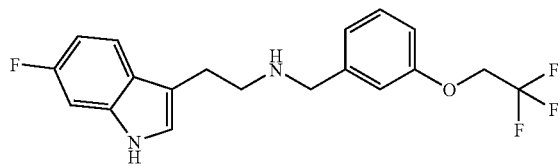

Combine 6-fluorotryptamine oxalate (350 mg, 1.3 mmol), N,N-diisopropylethylamine (506 mg, 3.9 mmol), 3-(2,2,2-trifluoroethoxy)benzaldehyde (266 mg, 1.3 mmol), and 4 Å molecular sieves (4 g) in EtOH (30 mL) and reflux for 7 hours. Decant the liquid into a separate flask and treat with NaBH4 (148 mg, 3.9 mmol). Stir 1 hour, concentrate the mixture in vacuo to give a residue. Partition the residue between 25 mL 5 N NaOH and 25 mL dichloromethane. Extract the aqueous layer with 25 mL dichloromethane, combine the organic layers, dry over MgSO4, and concentrate to approximately a 20 mL volume. Chromatograph on silica gel eluting with 1% MeOH in CHCl3 mixed with conc. NH4OH to give the title compound. Combine an EtOAc solution of the title compound with an EtOAc solution of one equivalent of oxalic acid to give a solid, filter, and dry under vacuum to give the oxalate salt of the title compound: ISMS 367 (M+1); Analysis for $C_9H_{19}ClF_4N_2O$: calcd: C, 55.27; H, 4.42; N, 6.14. found: C, 55.17; H, 4.38; N, 6.09.

By the method of Example 370 the following compounds were prepared, isolated as the hydrochloride except where noted:

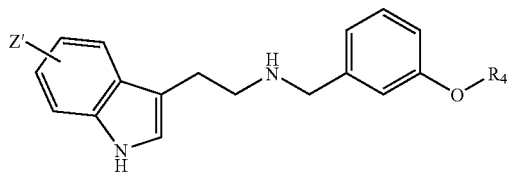

| No. | Z' | R$_4$ | Data |
|---|---|---|---|
| 372 | 5-fluoro | 2,2,3,3-tetrafluoropropyl | ISMS 399 (M + 1); Analysis for C$_{19}$H$_{17}$F$_8$NOC$_2$H$_2$O$_4$ H$_2$O: calcd: C, 53.51; H, 4.41; N, 5.67; found: C, 53.12; H, 4.21; N, 5.63 (isolated as the oxalate) |
| 373 | 6-fluoro | 2,2,3,3,3-pentafluoropropyl | Analysis for C$_{20}$H$_{18}$F$_6$N$_2$O HCl: calcd: C, 53.05; H, 4.23; N, 6.19; found: C, 52.88; H, 4.05; N, 6.12; ISMS 417 (M + 1) |
| 374 | 6-chloro-5-methoxy | 2,2,2-trifluoroethyl | Analysis for C$_{20}$H$_{20}$ClF$_3$N$_2$O$_2$ HCl: calcd: C, 53.47; H, 4.71; N, 6.24; found: C, 53.65; H, 4.85; N, 6.45; ISMS 413 (M + 1) (Form the salt in 50 mL 50/50 THF/EtOH using polyvinyl pyridine hydrochloride) |
| 375 | 6-chloro-5-methoxy | 2,2,3,3-tetrafluoropropyl | Analysis for C$_{21}$H$_{21}$ClF$_4$N$_2$O$_2$ HCl: calcd: C, 52.40; H, 4.61; N, 5.82; found: C, 52.15; H, 4.51; N, 5.69; ISMS 445 (M + 1) |
| 376 | 6-fluoro | 2,2,3,3-tetrafluoropropyl | Analysis for C$_{20}$H$_{19}$F$_5$N$_2$O HCl: calcd: C, 55.24; H, 4.64; N, 6.44; found: C, 55.06; H, 4.63; N, 6.44; ISMS 399 (M + 1) |
| 377 | 6-fluoro | 3,3,3-trifluoropropyl | Analysis for C$_{20}$H$_{20}$F$_4$N$_2$O HCl: calcd: C, 54.83; H, 5.11; N, 3.55; found: C, 54.74; H, 5.02; N, 3.11; ISMS 381 (M + 1) |
| 378 | 5-trifluoromethoxy | 2,2,3,3,3-pentafluoropropyl | Analysis for C$_{21}$H$_{18}$F$_8$N$_2$O$_2$ HCl: calcd: C, 48.62; H, 3.69; N, 5.40; found: C, 48.55; H, 3.48; N, 5.33; ISMS 483 (M + 1) |
| 379 | 5-trifluoromethoxy | 2,2,3,3-tetrafluoropropyl | Analysis for C$_{21}$H$_{19}$F$_7$N$_2$O$_2$ HCl: calcd: C, 50.36; H, 4.02; N, 5.59; found: C, 50.27; H, 3.92; N, 5.63; ISMS 465 (M + 1) |
| 380 | 5-trifluoromethoxy | 2,2,2-trifluoroethyl | Analysis for C$_{20}$H$_{18}$F$_6$N$_2$O$_2$ HCl: calcd: C, 51.24; H, 4.08; N, 5.98; found: C, 51.33; H, 4.09; N, 6.26; ISMS 433 (M + 1) |

Example 381

N-t-Butoxycarbonyl-2-(5-m-tolyloxy-1H-indol-3-yl)ethylamine

The method of Example 20 gives the title compound: $^1$H NMR (300 MHz, CDCl$_3$) 1.41 (s, 9H), 2.30 (s, 3H), 2.89 (t, 2H, J=6.7 Hz), 3.41 (m, 2H), 6.74-6.85 (m, 3H), 6.93-6.99 (m, 1H), 7.07-7.35 (m, 4H), 8.05 (br, 1H).

Example 382

N-Methyl-2-(5-n-tolyl)tryptamine

The method of Example 21 gives the title compound and formation of the oxalate salt gave: m.p. 182-183° C.; $^1$H NMR (250 MHz, DMSO-d6) 2.26 (s, 3H), 2.59 (s, 3H), 2.98-3.18 (m, 4H), 6.68-6.72 (m, 2H), 6.82-6.86 (m, 2H), 7.17-7.22 (m, 1H), 7.29-7.42 (m, 3H), 11.06 (br, 1H); MS (ELECTROSPRAY) m/e: 281.2 (M+1–C$_2$H$_2$O$_4$); Anal. calcd. C$_{20}$H$_{22}$N$_2$O$_5$: C, 64.85; H, 5.99; N, 7.56. Found: C, 65.01; H, 5.74; N, 7.71.

Example 383

N-Methyl-N-(2-(5-m-tolyloxy-1H-indol-3-yl)ethyl)-3-phenoxybenzylamine

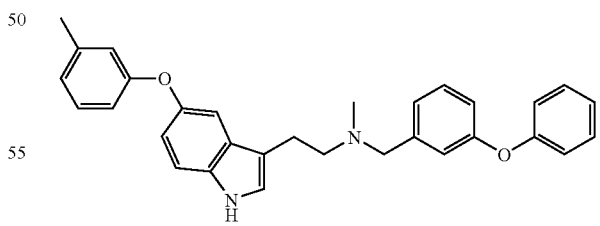

The method of Example 301 gives the title compound and formation of the oxalate salt gave: m.p. 142-144° C.; $^1$H NMR (250 MHz, DMSO-d6) 2.24 (s, 3H), 2.634 (s, 3H), 3.01-3.12 (m, 4H), 3.92 (br, 2H)), 4.16 (s, 2H), 6.65-6.70 (m, 2H), 6.81-6.84 (m, 2H), 6.99-7.03 (m, 3H), 7.12-7.26 (m, 6H), 7.34-7.43 (m, 4H), 11.00 (br, 1H); MS (ELECTROSPRAY) m/e: 463.4 (M+1–C$_2$H$_2$O$_4$); Anal. calcd. C$_{33}$H$_{32}$N$_2$O$_6$: C, 71.72; H, 5.84; N, 5.07. Found: C, 71.44; H, 5.89; N, 4.99.

Example 384

5-Nitrotryptamine

Warm mixture of 5-nitroindole (10 g, 62 mmol) and 200 mL glacial acetic acid to 70° C. and treat with Eschenmoser's salt (12 g, 65 mmol). Concentrate after 1 hour the reaction under vacuum to dryness. Mix the residue with 200 mL toluene, reconcentrate to dryness then partition between 200 mL concentrated ammonium hydroxide and 200 ml, EtOAc. When all solids dissolved, Separate the layers and extract the aqueous layer 200 mL EtOAc. Dry the combined organic layer over $MgSO_4$ and concentrate to give N,N-dimethyl-5-nitrotryptamine as a solid.

Dissolve the N,N-dimethyl-5-nitrotryptamine obtained above in 200 mL dry DMSO, treat with iodomethane (7.7 mL, 17.5 g, 124 mmol), and stir for 1 hour at ambient temperature. Add KCN (40 g, 621 mmol) and 18-crown-6 (0.5 g). Warm the reaction to 110° C. for 45 minutes, cool, poured onto ice then saturate with NaCl. Extract the quenched reaction mixture with EtOAc, combine the extracts, and wash 3 times with brine. Dry over $MgSO_4$ and concentrate under vacuum chromatograph on silica gel eluting with 1% MeOH in $CHCl_3$ to give (5-nitro-1H-indol-3-yl)acetonitrile as a solid: FDMS 201 (M+); Analysis for $C_{10}H_7N_3O_2$: calcd: C, 59.70; H, 3.51; N, 20.89. found: C, 59.32; H, 3.52; N, 20.56.

Dissolve (5-nitro-1H-indol-3-yl)-acetonitrile (9 g, 44.7 mmol) in 250 mL dry THF and treat with 90 mL 1 M $BH_3$ in THF at ambient temperature. Stir overnight and quench the reaction cautiously by the dropwise addition of 10 mL water. Concentrate to dryness under vacuum and partition the residue between 5 N HCl and EtOAc. Extract the aqueous layer with EtOAc and combine with the original EtOAc layer. Treat the aqueous layer with 5 N NaOH and extract 3 times with 10% MeOH in EtOAc. Purify by flushing the extracts through a pad of 100 g SCX ion exchange resin, rinsing with 2 liters of MeOH which was discarded, and then eluting with the 2 M $NH_3$ in MeOH and concentrating to give the title compound as a dark solid: ISMS 206 (M+1); Analysis for $C_{20}H_{18}F_6N_2O_2$ $0.3H_2O$ $0.1C_7H_8$: calcd: C, 57.34; H, 5.74; N, 19.29. found: C, 57.30; H, 5.38; N, 19.08. $^1$H NMR (DMSO-d6) 11.9-11.2 (bs, 1H), 8.50-8.49 (d, 1H), 7.95-7.92 (m, 1H), 7.47-7.45 (m, 1H), 7.38 (s, 1H), 2.79 (s, 4H), 2.2-1.3 (bs, 2H).

Example 385

6-Nitrotryptamine

The method of Example 384 gives (6-nitro-1H-indol-3-yl)-acetonitrile: ISMS 200 (M−1); Analysis for $C_{10}H_7N_3O_2$ $0.1H_2O$: calcd: C, 59.17; H, 3.58; N, 20.70. found: C, 59.04; H, 3.28; N, 20.39 which gives the title compound: ISMS 206 (M+1); $^1$H N (DMSO-d6) 11.5 (bs, 2H), 8.26 (s, 1H), 7.84-7.81 (m, 1H), 7.68-7.66 (m, 1H), 7.57 (s, 1H), 2.80-74 (m, 4H) (indole N—H not observable).

Example 390

N-(2-(5-Nitro-1H-indol-3-yl)ethyl)-3-phenoxybenzylamine

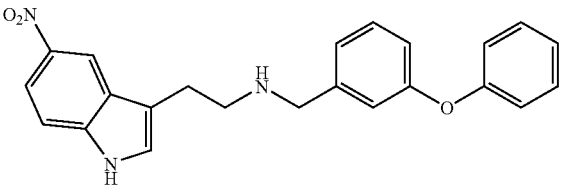

The method of Example 340 gives the title compound, salt formation in 10 mL EtOH with 0.25 mL 5 N HCl and 40 mL toluene then concentrating to a solid give the hydrochloride of the title compound: Analysis for $C_{23}H_{21}N_3O_3HCl$ 0.2 EtOH: calcd: C, 64.62; H, 5.17; N, 9.75. found: C, 64.89; H, 5.40; N, 9.75. ISMS 388 (M+1).

By the method of Example 390 the following compounds were prepared, isolated as the hydrochloride except where noted:

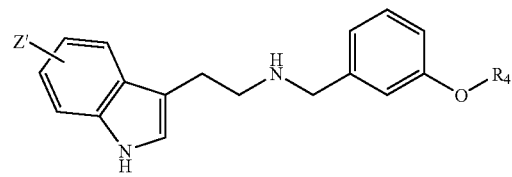

| No. | Z' | $R_4$ | Data |
|---|---|---|---|
| 391 | 5-nitro | 2,2,2-trifluoro ethyl | ISMS 444 (M + 1); Analysis for $C_{20}H_{20}ClF_4N_3O_3$•0.1 H2O: calcd: C, 52.87; H, 4.48; N, 9.74; found: C, 52.63; H, 4.34; N, 9.67 |
| 392 | 5-nitro | 2,2,3,3-tetrafluoro | ISMS 444 (M + 1); Analysis for $C_{20}H_{20}ClF_4N_3O_3$: calcd: C, 52.01; H, 4.36; N, |

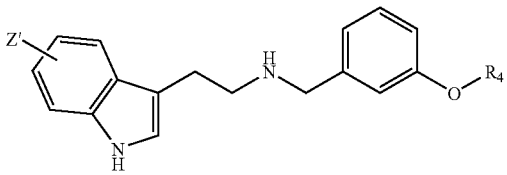

| No. | Z' | R₄ | Data |
|---|---|---|---|
| | | propyl | 9.10; found: C, 51.94; H, 4.19; N, 8.93 |
| 393 | 6-nitro | 2,2,2-trifluoro ethyl | ISMS 394 (M + 1); ¹H NMR (CDCl₃-freebase) 8.47 (bs, 1 H), 8.31-8.30 (m, 1 H), 8.01-7.98 (m, 1 H), 7.63-7.61 (m, 1 H), 7.32-7.31 (m, 1 H), 7.24-7.21 (m, 1 H), 6.94-6.92 (m, 1 H), 6.88 (s, 1 H), 6.80-6.77 (m, 1 H), 4.33-4.36 (m, 2 H), 3.79 (s, 2 H), 3.00-2.93 (m, 4 H), 1.54 (s, 1 H) |
| 394 | 6-nitro | 2,2,3,3-tetrafluoro propyl | ISMS 426 (M + 1); Analysis for $C_{20}H_{19}F_4N_3O_3$: calcd: C, 52.01; H, 4.36; N, 9.10; found: C, 51.96; H, 4.16; N, 8.76 |
| 395 | 6-nitro | 2,2,3,3,3-pentafluoro propyl | ISMS 444 (M + 1); Analysis for $C_{20}H_{18}F_5N_3O_3$: calcd: C, 50.06; H, 3.99; N, 8.76; found: C, 49.76; H, 3.86, N, 8.67 |

Example 396

N-(2-(5-Amino-1H-indol-3-yl)ethyl)-3-phenoxybenzylamine

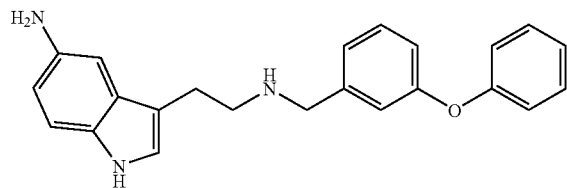

Combine N-(2-(5-nitro-1H-indol-3-yl)ethyl)-3-phenoxybenzylamine hydrochloride (250 mg, 0.64 mmol) and NiCl₂·6H₂O (460 mg, 1.9 mmol) in 30 mL MeOH and treat with NaBH₄ (73 mg, 1.9 mmol). After 1 hour concentrate to dryness, partition between EtOAc and concentrated NH₄OH. Extract the aqueous layer with EtOAc, combine the organic layer, dry over MgSO₄ and concentrate to dryness. Chromatograph on silica gel eluting with a stepwise gradient 20/75/5 THF/hexanes/Et₃N then 40/55/5 THF/hexanes/Et₃N gives the title compound as an oil. Additional chromatograph on silica gel eluting with 1% MeOH in CHCl₃ mixed with conc. NH₄OH gives the title compound as an oil. Treatment with in 10 mL EtOH with 0.25 mL 5 N HCl and 40 mL toluene then concentrating give the title compound as the hydrochloride: Analysis for $C_{23}H_{23}N_3O$ 2.6 HCl 0.6 EtOH: calcd: C, 59.66; H, 5.83; N, 9.07. found: C, 59.30; H, 5.48; N, 8.82. ISMS 358 (M+1).

By the method of Example 396 the following compounds were prepared, isolated as the hydrochloride except where noted:

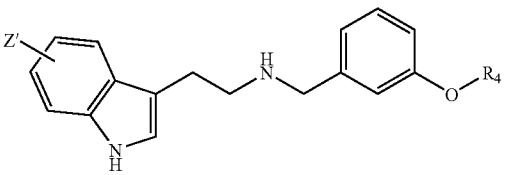

| No. | Z' | R₄ | Data |
|---|---|---|---|
| 397 | 5-amino | 2,2,2-trifluoro ethyl | Analysis for $C_{19}H_{20}F_3N_3O$ 2HCl 0.2 CHCl₃ 0.3 CH₃OH: calcd: C, 49.85; H, 5.02; N, 8.94; found: C, 50.05; H, 4.99; N, 8.73; ISMS 364 (M + 1) |
| 398 | 5-amino | 2,2,3,3-tetrafluoro propyl | ¹H NMR (DMSO-d6) 11.3 (bs, 1 H), 10.25 (bs, 3 H), 9.6 (bs, 2 H), 7.6 (s, 1 H), 7.5-7.35 (m, 4 H), 7.3-7.2 (m, 1 H), 7.2-7.0 (m, 2 H), 6.9-6.5 (d, 1 H), |

-continued

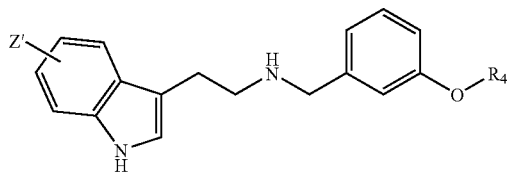

| No. | Z' | R₄ | Data |
|---|---|---|---|
| | | | 4.65-4.5 (t, 2 H), 4.25 (s, 2 H), 3.3 (s, 4 H); Analysis for $C_{20}H_{21}F_4N_3O$ 2HCl: calcd: C, 51.29; H, 4.95; N, 8.97; found: C, 51.26; H, 4.98; N, 8.26 |
| 399 | 6-amino | 2,2,2-trifluoro ethyl | ISMS 363 (M+); $C_{19}H_{22}Cl_2F_3N_3O$•0.4 H2O: calcd: C, 51.45; H, 5.18; N, 9.48; found: C, 51.45; H, 5.10; N, 9.63 |
| 400 | 6-amino | 2,2,3,3-tetrafluoro propyl | ISMS 393 (M+); $C_{20}H_{23}Cl_2F_4N_3O$•0.2 H2O: calcd: C, 50.90; H, 5.00; N, 8.90; found: C, 50.73; H, 4.82; N, 8.65 |

Example 401

6-Fluorotryptamine

Combine 6-fluoroindole (108 g, 0.8 mol) and dichloromethane (324 ml). Cool in an ice bath. Add trifluoroacetic acid (308 ml) over a few minutes (exothermic). Add a solution of Z-1-dimethylamino-2-nitroethylene (94.7 g, 0.816 mol) in dichloromethane (600 ml) during 40 minutes while maintaining the temperature at about 0-5° C. After 45 minutes, warm to about 20° C. After 2 hours, pour over 1.2 L ice water and stirring overnight with seeding to give a solid. Collect the solid by filtration, wash first with 100 ml of a mixture dichloromethane-cyclohexane 1/1, then with 750 ml of water and dry at 4° C. to give 3-(2-nitrovinyl)-6-fluoroindole.

Combine LiAlH₄ (48.8 g, 1.286 moles, 5 equiv.) and THF (848 ml) and cool in an ice-water bath to about 6° C. while keeping the temperature below 32° C. Add a solution of 3-(2-nitrovinyl)-6-fluoroindole (53 g, 0.257 mol, 1 equiv.) in THF (694 ml) while keeping the temperature below about 31° C. Allow to stir at ambient temperature. After 2.5 hours, quench with a mixture of 49 ml of water and 49 ml of THF, then with 49 ml of NaOH 15% and finally with 49 ml of water. Keep the temperature below ~32° C. during the quench. Stir for 1.5 hours, filter through a celite bed and wash with THF. Evaporate to residue, dissolve in 750 ml of diethyl ether and coot in an ice-water bath. Add a solution of HCl/diethyl ether to give a solid. Stir for 1 hour, collect the solid by filtration, wash with diethyl ether, and dry under reduced pressure at 45° C. to give the hydrochloride of the title compound.

Example 402

N-(2-(6-Fluoro-1-indol-3-yl)ethyl)-3-(2,2,3,3-tetrafluoropropoxy)benzylamine

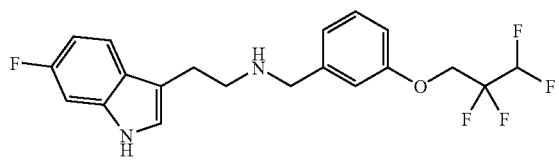

Combine 6-fluorotryptamine hydrochloride (90 g, 0.419 mol) and water (900 ml). Add an aqueous solution of NaOH (2N, 230 ml) and dichloromethane (900 ml). After 1 hour, separate the organic layer, extract the aqueous layer with dichloromethane, combine the organic layers, wash water, dry over MgSO₄, and evaporate to a residue. Combine the residue and toluene (200 ml) and evaporate to give 78.45 g of a brown oil. Combine the above 78.45 g with another 41.4 g hatch to provide 6-fluorotryptamine. Combine 6-fluorotryptamine (119.85) and ethanol (3.325 L), add 2,2,3,3-tetrafluoropropoxybenzaldehyde (176 g, 0.745 moles, 1.2 equiv.) and 150 g of molecular sieve 3A. Heat to reflux. After 2 hours, cool to RT room temperature and acid NaBH₄ (35.2 g, 0.93 mol, 1.5 equiv.). After 1 hour, filter through celite and wash with 500 nil of ethanol. Evaporate the filtrate under reduced pressure to give an oily residue. Partition the residue between water and dichloromethane. Separate the layers, extract the aqueous later with dichloromethane, combine organic layers, wash with brine and dry over MgSO₄. Filter and evaporate under reduced pressure to give the title compound.

The HCl salt is formed as follows: Combine N-(2-(6-fluoror-1H-indol-3-yl)ethyl)-3-(2,2,3,3-tetrafluoropropyl)benzylamine (387 g, 0.97 moles) and diethyl ether (3.95 L) of at room temperature. Add dropwise a solution of HCl/Et₂O (298 ml) over 15 minutes until the pH is about 3 to give a solid. Stir for 1 hour and collect the solid, wash with ether, and dry under reduced pressure for at 40° C. to give the title compound as the hydrochloride.

Example 410

(5-Bromo-1H-indol-3-yl)acetonitrile

The method of Example 384 using 5-bromoindole gives the title compound: ISMS 234 (M–1); Analysis for $C_{10}H_7BrN_2$ 0.1H₂O: calcd: C, 50.70; H, 3.06; N, 11.83. found: C, 50.69; H, 2.90; N, 11.64. ¹H NMR (CDCl₃) 8.22 (s, 1H), 7.70-7.69 (m, 1H), 7.33-7.31 (m, 1H), 7.24 (s, 1H), 7.23-7.22 (m, 1H), 3.78-3.77 (m, 4H).

Example 411

5-Bromotryptamine

Dissolve 5-bromo-1H-indole-3-carbonitrile (9.5 g, 40.4 mmol) in 200 mL dry THF and treat with 80 mL 1 M BH₃ in TIFF at ambient temperature. Stir overnight, the reaction and cautiously quench by dropwise addition of 5 mL water. Concentrate to dryness under vacuum and the residue. Partition between 1 N HCl and EtOAc. Extract the organic layer with 1 N HCl which was combined with the original aqueous layer. The Treat the aqueous layer with 5 N NaOH and extract with EtOAc. Saturate with NaCl and extract again with EtOAc. Combine the extracts dry over $MgSO_4$ and concentrate to dryness to give 4.72 g (19.7 mmol, 49%) of an oil which crystallized.

Conversion to the oxalate salt by treating an EtOAc solution of the compound with a solution of one equivalent of oxalic acid. Filter the resulting solid and dry under vacuum: Analysis for $C_{10}H_{11}BrN_2$ $C_2H_2O_2H_2O$: calcd: C, 43.08; H, 4.10; N, 8.37. found: C, 43.26; H, 3.91; N, 8.20. ISMS 240 (M+1).

Example 413

5-Methoxycarbonyl-1H-dole

Combine 5-carboxyindole (7.2 g, 44.7 mmol) in 400 mL dichloromethane and 100 mL MeOH and treat dropwise with 35 mL 2 M TMS diazomethane in hexanes. Stir overnight at ambient temperature. Concentration under vacuum to give the title compound as a solid: Analysis for $C_{10}H_9NO_2$ $0.1H_2O$: calcd: C, 67.86; H, 5.24; N, 7.91. found: C, 68.03; H, 5.15; N, 7.98. $^1$H NMR ($CDCl_3$) 8.44 (bs, 1H), 8.412-8.409 (m, 1H), 7.91-7.88 (m, 1H), 7.46-7.38 (m, 1H), 7.26-7.24 (m, 1H), 6.64-6.63 (m, 1H), 3.92 (s, 3H); ISMS 176 (M+1).

Example 414

3-Formyl-5-methoxycarbonyl-1H-indole

Place anhydrous DMF (25 mL) in a flask under an atmosphere of nitrogen, cool to 10° C. and treat dropwise with $POCl_3$ (8.22 g, 54 mmol) while keeping the temperature below 15° C. Add a solution of 5-methoxycarbonyl-1H-indole in 30 mL DMF portionwise keeping the temperature below 20° C. Remove the cooling bath and stir the mixture at ambient temperature for 1 hour then pour onto ice. Addition of 50 mL 5 N NaOH precipitated a solid which is filtered and rinsed with water and EtOAc to give the title compound: $^1$H NMR (DMSO-d6) 9.95 (s, 1H), 8.76 (s, 1H), 8.4 (s, 1H), 7.9-7.8 (m, 1H), 7.5-7.7 (d, 1H), 3.85 (s, 3H), 1.7 (s, 1H); ISMS 204 (M+1).

Example 415

3-(2-Nitroethyl)-5-methoxycarbonyl-1H-indole

The method of Example 317 to give the title compound: $^1$H NMR (DMSO-d6) 12.5 (bs, 1H), 8.38-8.37 (m, 1H), 8.37-8.34 (m, 1H), 8.23 (s, 1H), 7.87-7.84 (m, 1H), 7.80-7.77 (m, 1H), 7.57-7.55 (d, 1H), 3.85 (s, 3H); ISMS 246 (M+1).

Example 416

3-(2-Nitroethyl)-5-methoxycarbonyl-1H-indole

Treat a solution of 3-(2-nitrovinyl)-5-methoxycarbonyl-1H-indole (57 mg, 0.23 mmol) in 9 mL THF and 2 mL MeOH with $NaBH_4$ (26 mg 0.69 mmol). Stir at ambient temperature overnight, concentrate to dryness and partition between conc. $NH_4OH$ (10 mL) and dichloromethane. Extract the aqueous layer with dichloromethane, acidify with conc. HCl and extract twice with dichloromethane. Combine the organic layers, concentrate, and chromatograph on silica gel eluting with 1% MeOH in $CHCl_3$ to give the title compound as a solid: $^1$H NMR ($CDCl_3$) 8.35 (bs, 1H), 8.32 (s, 1H), 7.92-7.90 (m, 1H), 7.38-7.36 (d, 1H), 7.12-7.11 (m, 1H), 4.69-4.65 (t, 2H), 3.93 (s, 3H), 3.51-3.48 (t, 2H); ISMS 248 (M+).

Example 417

5-Methoxycarbonyltryptamine

Combine 3-(2-nitroethyl)-5-methoxycarbonyl-1H-indole (280 mg, 1.1 mmol), $PtO_2$ (200 mg) and 15 mL MeOH and hydrogenate at atmospheric pressure overnight. Filter reaction mixture through a pad of celite, concentrate the filtrate, and chromatograph on silica gel eluting with 5% MeOH in $CHCl_3$ mixed with conc. $NH_4OH$ to give the title compound as an oil: ISMS 219 (M+1); $^1$H NMR ($CDCl_3$) 9.01 (s, 1H), 8.36 (s, 1H), 7.88-7.85 (m, 1H), 7.32-7.24 (m, 1H), 7.05 (s, 1H), 3.91 (s, 3H), 3.05-3.01 (m, 2H), 2.93-2.89 (m, 2H), 1.22 (bs, 2H).

Example 418

2-(2-(5-Benzyloxy-1H-indol-3-yl)ethyl)isoindole-1,3-dione

Combine 5-benzyloxytrytamine hydrochloride (1 g, 3.3 mmol), phthalic anhydride (0.56 g, 4.0 mmol) and N,N-diisopropylethylamine (0.86 g, 6.6 mmol) in 25 mL anhydrous pyridine and reflux for 1 hour, cool to room temperature and treat with 4 g 3 Å molecular sieves. Refluxing was continued for 60 hours then the mixture was filtered. Concentrate under vacuum to give a residue which is mixed with 25 mL $CHCl_3$ and filtered to give a solid. Purification of the filtrate by chromatography on silica gel eluting with 1% MeOH in $CHCl_3$ to give an additional amount of title compound: ISMS 397 (M+1); Analysis for $C_{25}H_{20}N_2O_3$ $0.3H_2O$ $C_7H_8$: calcd: C, 75.09; H, 5.25; N, 6.82. found: C, 75.00; H, 5.22; N, 6.96.

By the method of Example 418 the following compounds were prepared:

a) 2-(2-(5-Hydroxy-1H-indol-3-yl)ethyl)isoindole-1,3-dione: (4.5 mmol, 95%); $^1$H NMR (DMSO-d6) 10.47 (s, 1H), 8.59 (bs, 1H), 7.84-7.78 (m, 4H), 7.09-7.06 (d, 1H), 7.03-7.02 (d, 1H), 6.85-6.84 (d, 1H), 6.56-6.54 (m, 1H), 3.79-3.75 (t, 2H), 2.91-2.87 (m, 2H).

Example 419

2-[2-(5-Hydroxy-1-triisopropylsilanyl-1H-indol-3-yl)ethyl]isoindole-1,3-dione

Combine a mixture of an oil dispersion of KH (40%, 1 g) in 30 mL anhydrous THF and a suspension of 2-(2-(5-benzyloxy-1H-indol-3-yl)ethyl)isoindole-1,3-dione (1.2 g, 3 mmol) in 30 mL THF portionwise. Stir for 1 hour at ambient temperature, cooled to 0° C., add triisopropylsilyltrifluoromethanesulfonate (1.85 g, 6 mmol) and stir an additional 1 hour at ambient temperature. Pour the reaction into a rapidly stirring solution of saturated $NaHCO_3$ and extract with 2×50 mL EtOAc. Combine the organic layer, day over $MgSO_4$ and concentrate to dryness and chromatograph on silica get eluting with 1% MeOH in $CHCl_3$ to give 2-(2-5-benzyloxy-1-triisopropylsilanyl-1H-indol-3-yl)ethyl)isoindole-1,3-dione as an oil.

Combine 2-(2-(5-benzyloxy-1-triisopropylsilanyl-1H-indol-3-yl)ethyl)isoindole-1,3-dione and EtOAc (40 mL) and hydrogenated overnight with 1 g 5% Pd/C at atmospheric pressure. Filter through celite, concentrate to dryness, and chromatograph on silica gel eluting stepwise with a gradient 10% EtOAc in hexanes to 30% EtOAc in hexanes to give the title compound as a solid: FDMS 462 (M+1) Analysis for $C_{27}F_{24}N_2O_3Si\,H_2O$: calcd: C, 69.55; H, 7.44; N, 6.01. Found: C, 69.44; H, 7.17; N, 6.00.

Example 420

2-(2-(5-Propoxy-1-triisopropylsilanyl-1H-indol-3-yl) ethyl)isoindole-1,3-dione

Combine 2-(2-(5-hydroxy-1-triisopropylsilanyl-1H-indol-3-yl)ethyl)isoindole-1,3-dione (0.7 g, 1.5 mmol), cesium carbonate (1 g, 3 mmol) and 1-iodopropane (0.4 g, 2.3 mmol) in DMF (25 mL) and stir at ambient temperature overnight Pour the reaction mixture into 50% EtOAc in hexanes and wash three times with brine. Dry the organic layer over $MgSO_4$ and concentrate under vacuum to give an oil. Chromatograph the oil on silica gel eluting with 5% EtOAc in hexanes to give the title compound: ISMS 505 (M+1); $^1H$ NMR ($CDCl_3$) 7.80-7.78 (m, 2H), 7.67-7.65 (m, 2H), 7.30-7.27 (d, 1H), 7.12-7.11 (d, 1H), 7.02 (s, 1H), 6.77-6.74 (m, 1H), 4.01-3.96 (m, 4H), 3.12-3.08 (m; 2H), 1.86-1.81 (m, 2H), 1.64-1.57 (m, 3H), 1.08-1.04 (m, 21H).

Example 421

5-Propoxy-1-triisopropylsilanyltryptamine

Combine 2-(2-(5-propoxy-1-triisopropylsilanyl-1H-indol-3-yl)ethyl)isoindole-1,3-dione (416 mg, 0.8 mmol) in 20 mL EtOH and 1 mL hydrazine hydrate. Reflux for 3 hours, filter through celite and concentrate to residue. Dissolve the residue in 10 mL MeOH and load onto a 12 g SCX ion exchange cartridge and rinse sequentially with MeOH, DMF, then MeOH. Elute the product with 2 M $NH_3$ in MeOH to give the title compound as an oil: ISMS 375 (M+1); $^1H$ NMR ($CDCl_3$) 7.34-7.32 (d, 1H), 7.02 (s, 1H), 7.00-6.99 (d, 1H), 6.80-6.77 (m, 1H), 3.97-3.94 (m, 2H), 3.01-2.98 (m, 2H), 2.86-2.83 (m, 2H), 1.88-1.76 (m, 2H), 1.70-1.58 (m, 3H), 1.3 (bs, 2H), 1.14-1.08 (m, 18H), 1.06-1.02 (t, 3H).

Example 422

6-Benzyloxytryptamine

Add to a mixture of LAH (6.2 g, 163.1 mmol) and 300 mL dry THF a solution of 3-2-nitrovinyl)-6-benzyloxy-1H-indole (9 g, 30.6 mmol) in 200 mL THF. Reflux the mixture overnight and then cool to 0° C. and quench sequentially with 6.2 mL water, 6.2 mL 15% aqueous NaOH and 18.6 mL water. After stirring 2 hours, filter through celite and concentrate to give 7.9 g (96%) of the title compound as an oil: $^1H$ NMR ($CDCl_3$) 8.06 (bs, 1H), 7.47-7.43 (m, 3H), 7.38-7.35 (t, 2H), 7.32-7.28 (m, 1H), 6.88-6.84 (m, 3H), 5.08 (s, 2H), 3.01-2.97 (m, 2H), 2.87-2.83 (m, 2H), 1.6 (bs, 2H).

Example 423

N-t-Butoxycarbonyl-2-(6-benzyloxy-1H-indol-3-yl) ethylamine

The method of Example 20 gives the title compound: $^1H$ NMR ($CDCl_3$) 7.84 (bs, 1H), 9.36 (s, 2H), 8.91 (s, 1H), 7.38-7.33 (m, 2H), 7.28-7.26 (m, 1H), 7.20-7.18 (m, 1H), 7.09-7.07 (m, 1H), 6.94-6.93 (m, 1H), 6.68-6.67 (m, 1H), 6.50-6.47 (m, 1H), 4.79-4.72 (m, 2H), 4.13 (s, 2H), 3.05-3.02 (m, 4H).

Example 425

N-t-Butoxycarbonyl-2-(6-hydroxy-1H-indol-3-yl) ethylamine

The method of Example 471 gives the title compound.

Example 428

2-(2-(5-Ethoxy-1H-indol-3-yl)ethyl)isoindole-1,3-dione

Combine 2-(2-(5-hydroxy-1H-indol-3-yl)ethyl)isoindole-1,3-dione (900 mg, 2.9 mmol), cesium carbonate (960 mg, 2.9 mmol) and 1-iodoethane (920 mg, 5.9 mmol) in N-methylpyrrolidinone (5 mL) and stir at ambient temperature for 4 hours, pour into brine and extract twice with EtOAc. Wash the combined extracts three times with brine, dry over $MgSO_4$, and concentrate under vacuum to give an oil. Chromatograph the oil on silica gel eluting with 20% EtOAc in hexanes to give the title compound as a white solid: ISMS 335 (M+1); Analysis for $C_{20}H_{18}N_2O_3$: calcd: C, 71.84; H, 5.43; N, 8.38. found: C, 71.97; H, 5.47; N, 8.36.

By the method of Example 428 the following compounds were prepared:

a) 2-(2-5-Isopropoxy-1H-indol-3-yl)ethyl)isoindole-1,3-dione: ISMS 348 (M+) $^1H$ NMR ($CDCl_3$) 7.94 (bs, 1H), 7.82-7.80 (m, 2H), 7.70-7.67 (m, 2H), 7.21-7.19 (d, 1H), 7.18 (s, 1H), 7.05-7.04 (d, 1H), 6.82-6.79 (m, 1H), 4.55-4.49 (m, 1H), 3.99-3.95 (m, 2H), 3.11-3.07 (m, 2H), 1.64-1.33 (d, 6H);

b) 2-(2-(5-(2,2,2-Trifluoroethoxy)-1H-indol-3-yl)ethyl) isoindole-1,3-dione: ISMS 389 (M+1); Analysis for $C_{20}H_{15}F_3N_2O_3$: calcd: C, 61.86; H, 3.89; N, 7.21. found: C, 61.77; H, 3.83; N, 7.20.

c) 2-(2-5-Butoxy-1H-indol-3-yl)ethyl)isoindole-1,3-dione: ISMS 363 (M+1); Analysis for $C_{22}H_{22}N_2O_3$: calcd: C, 72.91; H, 6.11; N, 7.73. found: C, 72.76; H, 6.09; N, 7.42. $^1H$ NMR ($CDCl_3$) 7.86-7.81 (m, 3H), 7.72-7.68 (m, 2H), 7.23-7.20 (m, 1H), 7.16-7.15 (m, 1H), 7.08-7.07 (m, 1H), 6.85-6.84 (m, 1H), 6.4.02-3.98 (m, 4H), 3.13-3.09 (m, 2H), 1.83-1.76 (m, 2H), 1.56-148 (m, 2H), 1.01-0.98 (t, 3H);

d) 2-(2-(5-Nitro-1H-indol-3-yl)ethyl)isoindole-1,3-dione: ISMS 334 (M−1); Analysis for $C_{18}H_{13}N_3O_4\,0.1H_2O$: calcd: C, 64.13; H, 3.95; N, 12.47. found: C, 64.05; H, 3.82; N, 12.27.

By the method of Example 421 the following compounds were prepared:

a) 5-Ethoxytryptamine: ISMS 205 (M+1); Analysis for $C_{12}H_{16}N_2O\,H_2O$: calcd: C, 69.33; H, 7.95; N, 13.48. found: C, 69.62; H, 7.75; N, 13.30.

b) 5-Isopropoxytryptamine: ISMS 219 (M+1); $^1H$ NMR ($CDCl_3$) 8.57 (bs, 1H), 7.20-7.18 (d, 1H), 7.08-7.07 (d, 1H), 6.95 (s, 1H), 6.84-6.82 (m, 1H), 4.54-4.48 (m, 1H), 3.01-2.98 (m, 2H), 2.86-2.83 (m, 2H), 1.38 (bs, 2H), 1.35-1.33 (d, 6H);

c) 5-(2,2,2-Trifluoroethoxy)tryptamine: ISMS 258 (M+); $^1H$ NMR ($CDCl_3$) 8.33 (bs, 1H), 7.26-7.24 (d, 1H), 7.09-7.08 (d, 1H), 7.03-7.02 (m, 1H), 6.90-6.87 (m, 1H), 4.40-4.34 (m, 2H), 3.03-3.00 (m, 2H), 2.87-2.84 (m, 2H), 1.44 (bs, 2H);

d) 5-Butyloxytryptamine: $^1H$ NMR ($CDCl_3$) 8.08 (bs, 1H), 7.23-7.21 (d, 1H), 7.03-7.02 (d, 1H), 7.03-7.02 (m, 1H), 6.98-6.83 (m, 1H), 4.01-3.98 (m, 2H), 3.02-2.99 (m, 2H), 2.87-2.84 (m, 2H), 1.82-1.74 (m, 2H), 1.56-1.50 (m, 2H), 1.32 (bs, 2H), 1.00-0.96 (t, 3H);

Example 429

5-1-Benzenesulfonyl-1H-indole

Place a 35% oil dispersion of KH (6 g) in a flask under nitrogen, rinse with 50 mL hexanes and dry under vacuum. Cool the solid suspension in 100 mL anhydrous DMF to 0° C. Add dropwise over 10 minutes a solution of 5-bromoindole (10.3 g, 52.5 mmol) in 25 mL DMF. Stir the mixture 1 hour at 0° C. then treat with triisopropylsilyltrifluoromethane sulfonate (32.2 g, 105.1 mmol). Remove the cooling bath and stir the reaction 72 hours before pouring into 500 mL water and extracting with EtOAc. Dilute the combined extracts with hexanes, wash with brine then dry over $MgSO_4$. Concentration under vacuum and chromatograph on silica gel eluting with 1% EtOAc in hexanes to give 5-Bromo-1-triisopropylsilanyl-1H-indole as a colorless oil: $^1$H NMR ($CDCl_3$) 7.73-7.72 (d, 1H), 7.36-7.34 (d, 1H), 7.24-7.23 (d, 1H), 7.21-7.19 (m, 1H), 6.55-6.54 (m, 1H), 1.72-1.61 (m, 3H), 1.13-1.10 (m, 18H).

Cool a solution of 5-bromo-1-triisopropylsilanyl-1H-indole (9 g, 25.5 mmol) in 550 mL anhydrous THF to −75° C. under argon and treat with 1.7 M t-butyl lithium (33 mL, 56.2 mmol) while keeping the temperature below −60° C. After the addition, recool the reaction mixture to about −73° C. before adding a solution of phenylsulfonyl fluoride (4.6 g, 28.7 mmol) in 30 mL THF. Stir the reaction at −78° C. for 1 hour then quench with saturated $NaHCO_3$ followed by brine. Separate the layers and extract the aqueous layer with EtOAc. Treat the combined organic layers with 1 M tetrabutylammonium fluoride (35 mL) in THF for 1 hour at ambient temperature, then concentrate to dryness. Combine the residue with EtOAc, wash twice with 1 N HCl, dry over $MgSO_4$, and concentrate to an oil. Chromatograph the oil on silica get eluting stepwise with 50% $CHCl_3$ in hexanes followed by 50% $CHCl_3$ in MeOH give an oily solid. Triturate the oily solid with $CHCl_3$ to give the title compound as a solid: Analysis for $C_{14}H_{11}NO_2S\ H_2O$: calcd: C, 64.89; H, 4.36; N, 5.41. found: C, 64.76; H, 4.45; N, 5.33. ISMS 257 (M+).

Example 430

242-(5-Amino-1H-indol-3-yl)ethyl)isoindole-1,3-dione

Combine a mixture of 2-(2-(5-nitro-1H-indol-3-yl)ethyl) isoindole-1,3-dione (1.8 g, 5.4 mmol), $PtO_2$ (500 mg), 100 mL MeOH and 100 mL THF and hydrogenate at atmospheric pressure overnight. Filter the reaction through a pad of celite and concentrate to dryness. Redissolve the residue in 50/50 chloroform/dichloromethane and refilter through a pad of celite. Concentration under vacuum give the title compound as a dark solid: ISMS 306 (M+1); Analysis for $C_{18}H_{13}N_3O_4$ $0.1C_7H_8$ 0.2 dichloromethane: calcd: C, 68.70; H, 4.89; N, 12.58. found: C, 69.08; H, 4.75; N, 12.69. $^1$H NMR ($CDCl_3$) 7.9-7.8 (m, 3H), 7.75-7.65 (m, 2H), 7.2-7.1 (m, 1H), 7.05-7.0 (m, 2H), 6.7-6.6 (m, 1H), 4.0-3.9 (m, 2H), 3.4 (bs, 2H), 3.1-3.0 (m, 2H).

Example 431

2-(2-(5-Benzoylamino-1H-indol-3-yl)ethyl)isoindole-1,3-dione

Combine 2-(2-(5-amino-1H-indol-3-yl)ethyl)isoindole-1, 3-dione (0.5 g, 1.64 mmol) and 4-dimethylaminopyridine (0.3 g, 2.5 mmol) and dissolve in 30 mL dichloromethane and cool to 0° C. Treat the reaction mixture with benzoyl chloride (276 mg, 1.96 mmol) and stir overnight during which the temperature was allowed to warn to room temperature. Concentrate to residue and chromatograph the residue on silica gel eluting with 0.5% MeOH in $CHCl_3$ to give the title compound as a solid: ISMS 410 (M+1); $^1$H NMR ($CDCl_3$) 7.86-7.85 (m, 2H), 7.79 (s, 1H), 7.72-7.68 (m, 2H), 7.60-7.57 (m, 2H), 7.46-7.42 (m, 1H), 7.4-7.36 (m, 3H), 7.13-7.11 (d, 1H), 6.89-6.88 (m, 1H), 3.88-3.84 (t, 2H), 3.00-2.97 (t, 2H).

By the method of Example 431 the following compounds were prepared:

a) 2-(2-(5-Methanesulfonylamino 1H-indol-3-yl)ethyl) isoindole-1,3-dione: ISMS 384 (M+1); $^1$H NMR ($CDCl_3$) 10.84 (s, 1H), 9.21 (s, 1H), 7.83-7.76 (m, 4H), 7.39-7.38 (m, 1H), 7.27-7.24 (m, 1H), 7.17-7.16 (m, 1H), 6.96-6.93 (m, 1H), 3.83-3.80 (m, 2H), 2.98-2.94 (m, 2H), 2.79 (s, 3H), 3.88-3.84 (t, 2H), 3.00-2.97 (t, 2H).

By the method of Example 421 the following compounds were prepared:

a) 5-Benzoylaminotryptamine: $^1$H NMR ($CD_3OD$) 7.94-7.92 (m, 2H), 7.85 (s, 1H), 7.54-7.47 (m, 3H), 7.34-7.29 (m, 2H), 7.08 (s, 1H), 4.86 (s, 2H), 3.33 (s, 2H), 2.95-2.86 (m, 4H); and b) 5-Methanesulfonylaminotryptamine: ISMS 253 (M+); $^1$H NMR ($CD_3OD$) 7.46-7.45 (d,1H), 7.31-7.29 (d,1H), 7.08 (s, 1H), 7.04-7.01 (m, 1H), 4.86 (s, 4H), 2.89-2.83 (m, 7H).

Example 432

5-Ethoxycarbonyl-1H-indole

Combine 5-carboxyindole (4.8 g, 29.8 mmol) in 150 mL THF and carbonyldiimidazole (9.7 g, 59.6 mmol) and stir overnight at ambient temperature. Treat the reaction mixture with 25 mL EtOH and 1.2 g (29.8 mmol) of a 60% oil dispersion of NaH and stir for 2 hours. Concentration under vacuum gives a residue. Partition the residue between 150 mL EtOAc and 100 mL brine. Separate the layers, dry the organic layer over $MgSO_4$, filter, and concentrated to an oil. Chromatograph on silica gel eluting with 1% MeOH in $CHCl_3$ to give 7.2 g of an oil. Crystallize the oil from toluene gives the title compound: Analysis for $C_{11}H_{11}NO_2$: calcd: C, 69.83; H, 5.86; N, 7.40. found: C, 69.82; H, 5.90; N, 7.38. ISMS 190 (M+1).

Example 433

5-(N-Butylamido)-1H-indole

Dissolve mixture of 5-carboxyindole (5 g, 31 mmol) in 150 mL THF and treat with carbonyldiimidazole (5 g, 31 mmol) and stir overnight at ambient temperature. Treat the reaction mixture with n-butylamine 4.5 g (62 mmol) and reflux for 1 hour. Concentration under vacuum gives a residue which is dissolved in EtOAc. Wash sequentially with 5 N HCl, 5 N NaOH, and then brine. Dry the organic layer over $MgSO_4$ and concentrated to give the title compound as an oil: $^1$H NMR ($CDCl_3$) 8.54 (bs, 1H), 8.07-8.06 (m, 1H), 7.63-7.61 (m, 1H), 7.39-7.37 (m, 1H), 7.26-7.24 (m, 1H), 6.60-6.59 (m, 1H), 6.14 (bs, 1H), 3.5-3.45 (m, 2H), 1.64-1.57 (m, 2H), 1.47-1.37 (m, 2H), 0.97-0.93 (m, 3H); EIMS 217 (M+1).

Example 434

5-(N-Propylamido)-1H-indole

The method of Example 433 gives the title compound: $^1$H NMR ($CDCl_3$) 8.07 (bs, 1H), 8.07 (s, 1H), 7.63-7.60 (m, 1H), 7.38-7.36 (m, 1H), 7.25-7.24 (m, 1H), 6.59-6.58 (m, 1H), 6.21 (bs, 1H), 3.46-3.41 (m, 2H), 1.69-1.60 (m, 2H), 1.00-0.96 (m, 3H); EIMS 203 (M+1).

By the method of Example 414 the following compounds were prepared:

a) 3-Formyl-5-benzenesulfonyl-1H-indole: ISMS 286 (M+1); $^1$H NMR (DMSO-d6) 9.83 (s, 1H), 8.55 (s, 1H), 7.89-7.86 (m, 2H), 7.61 (s, 2H), 7.59-7.52 (m, 3H), 1.70 (s, 3H).

b) 3-Formyl-5-ethoxycarbonyl-1H-indole: Analysis for $C_{12}H_{11}NO_3$: calcd: C, 66.35; H, 5.10; N, 6.45. found: C, 65.97; H, 5.17; N, 6.46. ISMS 218 (M+1);

c) 3-Formyl-N-butylamido-1H-indole: Analysis for $C_{14}H_{16}N_2O_2$ 0.1$H_2O$: calcd. C, 68.33; H, 6.64; N, 11.38. found: C, 68.35; H, 6.24; N, 11.30. ISMS 245 (M+1);

d) 3-Formyl-5-(N-propylamido)-1H-indole: Analysis for $C_{13}H_{14}N_2O_2$: calcd: C, 67.81; H, 6.13; N, 12.16. found: C, 67.42; H, 6.04; N, 12.10. $^1$H NMR (DMSO-d6) 9.95 (s, 1H), 8.6 (s, 1H), 8.48-8.45 (t, 1H), 8.36-8.35 (m, 1H), 7.76-7.73 (m, 1H), 7.52-7.50 (d, 1H), 3.32 (bs, 1H), 3.24-3.19 (m, 2H), 1.58-1.48 (m, 2H), 0.90-0.86 (m, 3H); EIMS 230 (M+);

e) 3-Formyl-6-benzyloxy-1H-indole: $^1$H NMR (DMSO-d6) 11.93 (s, 1H), 9.83 (s, 1H), 8.12-8.11 (m, 1H), 7.92-7.90 (m, 1H), 7.45-7.27 (m, 5H), 7.04-7.03 (m, 1H), 6.92-6.89 (m; 1H), 5.11 (s, 2H).

By the method of Example 415 the following compounds were prepared:

a) 5-Benzenesulfonyl-3-(2-nitrovinyl)-1H-indole: Analysis for $C_{16}H_{12}N_2O_4S$ 0.1$H_2O$: calcd: C, 58.42; H, 3.83; N, 8.31. found: C, 58.63; H, 3.52; N, 8.02. ISMS 229 (M+1);

b) 3-(2-Nitrovinyl)-5-ethoxycarbonyl-1H-indole: Analysis for $C_{16}H_{12}N_2O_4S$ 0.1$H_2O$: calcd: C, 58.42; H, 3.83; N, 8.31. found: C, 58.63; H, 3.52; N, 8.02. ISMS 229 (M+1);

c) 3-(2-Nitro-vinyl)-N-butylamido-1H-indole: Analysis for $C_{15}H_{17}N_3O_3$: calcd: C, 62.71; H, 5.96; N, 14.62. found: C, 62.46; H, 5.81; N, 14.38. ISMS 288 d) 3-(2-Nitro-vinyl)-N-propylamido 1H-indole:: ISMS 273 M(+1); $^1$H NMR (DMSO-d6) 12.38 (s, 1H), 8.62-8.59 (t, 1H), 8.43-8.39 (d, 1H), 8.37 (s, 1H), 8.31-8.30 (d, 1H), 8.18-8.15 (d, 1H), 7.84-7.82 (m, 1H), 7.55-7.53 (d, 1H), 3.31-3.24 (m, 2H), 1.61-1.52 (m, 2H), 0.92-0.89 (t, 3H); Analysis for $C_{14}H_{15}N_3O_3$ 0.1$H_2O$: calcd: C, 61.12; H, 5.57; N, 15.28. found: C, 61.06; H, 5.38; N, 15.05.

e) 3-(2-Nitro-vinyl)-6-benzyloxy-1H-indole: $^1$H NMR DMSO-d6) 11.85 (bs, 1H), 8.32-8.29 (m, 1H), 8.09 (s, 1H), 7.94-7.91 (m, 1H), 7.83-7.81 (m, 1H), 7.45-7.43 (m, 2H), 7.38-7.31 (m, 2H), 7.29-7.27 (m, 1H), 7.05-7.04 (m, 1H), 6.92-6.89 (m, 1H), 5.13 (s, 2H).

By the method of Example 416 the following compounds were prepared:

a) 5-Benzenesulfonyl-3-(2-nitroethyl)-1H-indole: Analysis for $C_{16}H_{14}N_2O_4S$ 0.1$H_2O$: calcd: C, 57.85; H, 4.31; N, 8.43. found: C, 57.72; H, 4.22; N, 8.25. ISMS 329 (M−1);

b) 3-(2-Nitroethyl)-5-ethoxycarbonyl-1H-indole: Analysis for $C_{15}H_{14}N_2O_4$: calcd: C, 59.54; H, 5.38; N, 10.68. found: C, 59.23; H, 5.25; N, 10.53. ISMS 263 (M+1);

c) 3-(2-Nitroethyl)-N-butylamido-1H-indole: Analysis for $C_{15}H_{19}N_3O_3$: calcd: C, 62.27; 1H, 6.62; N, 14.52. found: C, 61.98; H, 6.39; N, 14.42. ISMS 290 (M+1); and d) 3-(2-Nitroethyl)-N-propylamido-1H-indole:: $^1$H NMR ($CDCl_3$) 8.52 (bs, 1H), 8.06 (s, 1H), 7.58-7.55 (m, 1H), 7.35-7.33 (m, 1H), 7.10-7.09 (m, 1H), 6.23 (bs, 1H), 4.65-4.61 (t, 2H), 3.48-3.43 (m, 4H), 1.71-1.62 (m, 2H), 1.01-0.98 (t, 3H); Analysis for $C_{14}H_{17}N_3O_3$ 0.1$H_2O$: calcd: C, 60.68; H, 6.26; N, 15.16. found: C, 60.88; H, 6.05; N, 15.07.

By the method of Example 421 the following compounds were prepared:

a) 5-Benzenesulfonyltryptamine: ISMS 301 (M+1); 1H NMR (HCl-DMSO-d6) (s, 1H), 8.3 (s, 1H), 8.2 (bs, 2H), 8.0-8.9 (m, 2H), 7.4-7.2 (m, 5H), 7.1-7.0 (m, 1H), 3.2-3.0 (s, 4H);

b) 5-Ethoxycarbonyltryptamine (isolated as the oxalate salt): Analysis for $C_{13}H_{16}N_2O_2$ $C_2H_2O_4$: calcd: C, 55.90; H, 5.63; N, 8.69. found: C, 56.07; H, 5.54; N, 8.29. ISMS 233 (M+1); and c) 5-N-Butylamidotryptamine: Analysis for $C_{15}H_{21}N_3O$ 0.3$H_2O$: calcd: C, 68.05; H, 8.22; N, 15.87. found: C, 68.36; H, 8.11; N, 15.49. ISMS 260 (M+1); and d) 5-N-Propylamidotryptamine:(isolated as the oxalate salt): Analysis for $C_{14}H_{19}N_3O$ $C_2H_2O_4$ 0.1EtOAc: calcd: C, 57.23; H, 6.38; N, 12.21. found: C, 57.48; H, 6.53; N, 12.12. $^1$H NMR (DMSO-d6) 11.2 (s, 1H), 8.4 (t, 1H), 8.2 (s, 1H), 7.75-7.65 (m, 1H), 7.6 (bs, 4H), 7.4-7.35 (m, 1H), 7.3-7.25 (d, 1H), 3.3-3.2 (m, 2H), 3.15-3.0 (m, 4H), 1.6-1.45 (m, 2H), 0.9-0.8 (t, 3H); ISMS 246 (M+1).

Example 435

N-t-Butoxycarbonyl-2-(6-butoxy-1H-indol-3-yl)ethylamine

Combine N-t-butoxycarbonyl-2-(6-hydroxy-1H-indol-3-yl)ethylamine (250 mg, 0.9 mmol), cesium carbonate (295 mg, 0.9 mmol) and 1-iodobutane (200 mg, 1.1 mmol) and N-methylpyrrolidinone (10 mL) and stir at ambient temperature for 2 hours and pour into 75 mL brine. Extract the mixture twice with 25 mL EtOAc. Wash the combined extracts with brine 2×50 mL, dry over $MgSO_4$, and concentrate under vacuum to give an oil. Chromatograph the oil on silica gel eluting with 30% EtOAc in hexanes to give the title compound as a solid: ISMS 333 (M+1); Analysis for $C_{19}H_{28}N_2O_3$: calcd: C, 68.65; H, 8.49; N, 8.43. found: C, 68.83; H, 8.18; N, 8.33.

By the method of Example 435 the following compounds were prepared:

a) N-t-Butoxycarbonyl-2-(6-ethoxy-1H-indol-3-yl)ethylamine: ISMS 305 (M+1); Analysis for $C_{17}H_{24}N_2O_3$: calcd: C, 67.08; H, 7.95; N, 9.20. found: C, 66.85; H, 7.79; N, 9.14.

Example 436

6-Butoxytryptamine

Combine N-t-butoxycarbonyl-2-(6-butoxy-1H-indol-3-yl)ethylamine (430 mg, 1.3 mmol), 1 mL anisole and 5 mL trifluoroacetic acid and stir at room temperature for 2 hours. Concentrate the reaction to dryness under vacuum, mix with 10 mL concentrated $NH_4OH$ and extract with 20 mL dichloromethane. Dry the extract over $MgSO_4$ and concentrated to 300 mg oil (1.3 mmol, 100%).

By the method of Example 436 the following compounds were prepared:

a) 6-Ethoxytryptamine: ISMS 305 (M+1); Analysis for $C_{17}H_{24}N_2O_3$: calcd: C, 67.08; H, 7.95; N, 9.20. found: C, 66.85; H, 7.79; N, 9.14.

Example 437

N-t-Butoxycarbonyl-2-(6-phenylsulfonate-1H-indol-3-yl)ethylamine

Combine N-t-butoxycarbonyl-2-(6-hydroxy-1H-indol-3-yl)ethylamine (750 mg, 2.7 mmol) and pyridine (430 mg, 5.4 mmol) in dichloromethane (30 mL) and cool to 0° C. and treat with benzene sulfonyl chloride (480 mg, 2.7 mmol). Allow the reaction to warm to room temperature and stir overnight. Concentrate to dymess the mixture under vacuum, mix with dichloromethane and chromatograph on silica gel eluting with 30% EtOAc in hexanes to give N-t-butoxycarbonyl-2-(6-phenylsulfonate-1H-indol-3-yl)ethylamine as an oil: ISMS 415 (M−1); $^1$H NMR (CDCl$_3$) 8.14 (bs, 1H), 7.66-7.62 (m, 2H), 7.51-7.47 (m, 1H), 7.40-7.38 (m, 2H), 7.10 (s, 1H), 7.04-7.03 (m, 2H), 6.59-6.57 (m, 1H), 4.57 (bs, 1H), 3.40-3.80 (m, 2H), 2.89-2.86 (m, 2H), 1.41 (s, 9H).

Place N-t-butoxycarbonyl-2-(6-phenylsulfonate-1H-indol-3-yl)ethylamine (0.5 g, 1.2 mmol) in a flask with a stream of N$_2$ passing through it and heat to 200° C. overnight and cool to room temperature. Dissolve the residue in dichloromethane and chromatography on silica gel eluting with 2% MeOH in CHCl$_3$—NH$_4$OH to give the title compound as an oil.

By the method of Example 425 the following compounds were prepared and isolated as the hydrochloride except where noted:

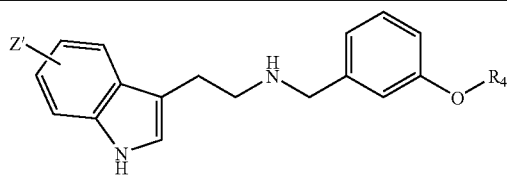

| No. | Z' | R$_4$ | Data |
|---|---|---|---|
| 438 | 5-propoxy | phenyl | ISMS 401 (M + 1); Analysis for C$_{20}$H$_{18}$N$_2$O$_3$ 0.1H$_2$O: calcd: C, 71.17; H, 6.71; N, 6.38; found: C, 71.02; H, 6.54; N, 6.33; $^1$H NMR (Free base-CDCl$_3$) 7.93 (bs, 1 H), 7.34-7.30 (m, 2 H), 7.35-7.28 (m, 2 H), 7.12-7.07 (m, 1 H), 7.06-6.96 (m, 6 H), 6.89-6.84 (m, 2 H), 3.97-3.94 (m, 2 H), 3.79 (s, 2 H), 2.97-2.94 (m, 4 H), 1.89-1.7 (m, 2 H), 1.51 (bs, 1 H), 1.07-1.04 (t, 3 H) |

Example 440

N-(2-(5-Propoxy-1H-indol-3-yl)ethyl)-3-(2,2,3,3-tetrafluoropropoxy)benzylamine

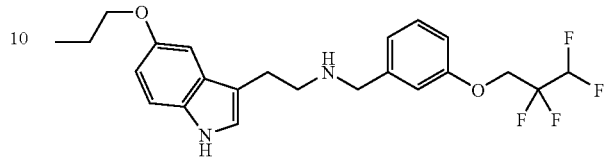

Combine 2-(5-propoxy-1-triisopropylsilanyltryptamine (138 mg, 0.37 mmol), 3-(2,2,3,3-tetrafluoropropoxy)benzaldehyde (87 mg, 1.8 mmol) and 1 g 3 Å molecular sieves in 25 mL EtOH and reflux overnight. Decant the liquid into a separate flask, cool to 0° C. and treat with 42 mg (1.1 mmol) NaBH$_4$. Stir the reaction at ambient temperature for 1 hour, treat with 0.74 mmol of tetrabutylammonium fluoride and stir for an additional hour. Concentrate under vacuum to give a residue. Chromatograph the residue on silica gel eluting with 10% MeOH in CHCl$_3$ to give the title compound. Treat the title compound with 10 mL EtOH with 0.25 mL 5 N HCl and 40 mL toluene then concentrating gives the hydrochloride of the title compound: ISMS 439 (M+1); $^1$H NMR (Free base-CDCl$_3$) 7.89 (bs, 1H), 7.23-7.21 (m, 1H), 7.03-7.02 (d, 1H), 6.99-6.98 (d, 1H), 6.94-6.92 (m, 1H), 6.89-6.83 (m, 2H), 6.78-6.75 (m, 1H), 6.18-5.90 (m, 1H), 4.29-4.23 (m, 2H), 3.95-3.91 (m, 2H), 3.78 (s, 2H), 2.95 (s, 4H), 1.85-1.75 (m, 2H), 1.51 (bs, 1H), 1.06-1.03 (t, 3H).

By the method of Example 440 the following compounds were prepared and isolated as the hydrochloride except where noted:

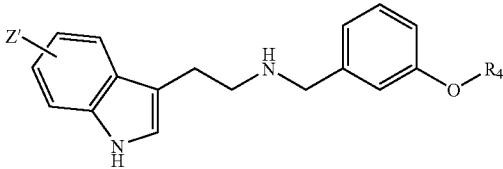

| No. | Z' | R$_4$ | Data |
|---|---|---|---|
| 441 | 5-n-propyl amido | 2,2,2-trifluoro ethyl | ISMS 434 (M + 1); C$_{23}$H$_{26}$F$_3$N$_3$O$_2$•HCl•0.8H$_2$O•0.1 C$_7$H$_8$: calcd: C, 57.67; H, 6.00; N, 8.51; found: C, 57.55; H, 5.77; N, 8.43 |
| 442 | 5-ethoxy carbonyl | 2,2,3,3-tetrafluoro propyl | ISMS 453 (M + 1); C$_{23}$H$_{27}$ClF$_3$N$_3$O$_2$: calcd: C, 56.50; H, 5.15; N, 5.73; found: C, 56.26; H, 5.04; N, 5.76 |
| 443 | 5-ethoxy carbonyl | phenyl | ISMS 415 (M + 1); C$_{26}$H$_{27}$ClN$_2$O$_3$•0.1H$_2$O: calcd: C, 68.97; H, 6.06; N, 6.19; found: C, 68.78; H, 5.87; N, 6.19 |
| 445 | 5-phenoxy | 2,2,3,3-tetrafluoro propyl | ISMS 473 (M + 1); C$_{26}$H$_{25}$ClF$_4$N$_2$O$_2$•0.5H$_2$O: calcd: C, 60.29; H, 5.06; N, 5.41; found: C, 60.27; H, 4.81; N, 5.33 (isolated as the base) |
| 456 | H | 2,2,2-trifluoro ethyl | ISMS 349 (M + 1); C$_{19}$H$_{20}$ClF$_3$N$_2$O•0.2H$_2$O: calcd: C, 58.75; H, 5.29; N, 7.21; found: C, |

-continued

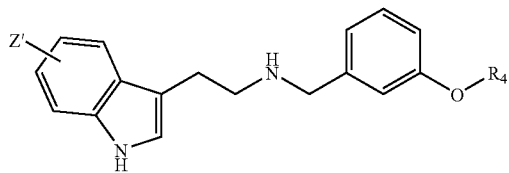

| No. | Z' | R$_4$ | Data |
|---|---|---|---|
| 457 | H | 2,2,3,3,3-pentafluoropropyl | 58.62; H, 5.04; N, 7.08 ISMS 385 (M + 1); C$_{19}$H$_{18}$ClF$_5$N$_2$O•0.2H$_2$O: calcd: C, 53.77; H, 4.37; N, 6.60; found: C, 53.81; H, 4.19; N, 6.59 |
| 458 | 5-phenyl | phenyl | Analysis for C$_{29}$H$_{26}$N$_2$O•HCl•0.2H$_2$O: calcd: C, 75.95; H, 6.02; N, 6.11; found: C, 76.01; H, 5.92; N, 5.97 ISMS 419 (M + 1) |
| 459 | 5-(4-fluorophenyl) | phenyl | Analysis for C$_{29}$H$_{25}$FN$_2$O•HCl•0.2H$_2$O: Calcd: C, 73.08; H, 5.58; N, 5.88; found: C, 72.99; H, 5.38; N, 5.83 ISMS 437 (M + 1) |
| 460 | 5-(N-butylamido) | 2,2,2-trifluoroethyl | Analysis for C$_{24}$H$_{28}$F$_3$N$_3$O$_2$•HCl•0.7H$_2$O: calcd: C, 58.05; H, 6.17; N, 8.46; found: C, 57.86; H, 5.98; N, 8.39 ISMS 448 (M + 1) |
| 461 | 5-hydroxy | 2,2,2-trifluoroethyl | ISMS 365 (M + 1) $^1$H NMR (DMSO-d6) 10.6 (bs, 1 H), 9.4 (bs, 2 H), 8.75 (s, 1 H), 7.45-6.6 (m, 7 H), 4.9-4.7 (m, 2 H), 4.2 (bs, 2 H), 3.2-2.9 (m, 4 H); |
| 462 | 5-benzyloxy | 2,2,3,3,3-pentafluuoropropyl | Analysis for C$_{27}$H$_{25}$F$_5$N$_2$O$_2$•HCl: calcd: C, 58.87; H, 4.95; N, 5.09; found: C, 59.02; H, 4.76; N, 5.1 ISMS 505 (M + 1)4 |
| 463 | 6-benzyloxy | 2,2,2-trifluoroethyl | ISMS 455 (M + 1) $^1$H NMR (CDCl$_3$-freebase) 7.88 (bs, 1 H), 7.48-7.45 (m, 3 H), 7.41-7.34 (m, 2 H), 7.35-7.30 (m, 1 H), 7.25-7.23 (m ,1 H), 6.95-6.93 (m, 1 H), 6.91-6.90 (m, 2 H), 6.88-6.86 (m, 2 H), 6.81-6.79 (m ,1 H), 5.10 (s, 2 H), 4.31-4.25 (m, 2 H), 3.79 (s, 2 H), 2.96 (s, 4 H), 1.65 (bs, 1 H) |
| 464 | 6-benzyloxy | 2,2,3,3-tetrafluoropropyl | ISMS 487 (M + 1) Analysis for C$_{27}$H$_{27}$F$_4$N$_2$O$_2$•HCl: calcd: C, 62.01; H, 5.20; N, 5.36; found: C, 61.69; H, 5.07; N, 5.33 |
| 465 | 6-butyloxy | 2,2,2-trifluoroethyl | $^1$H NMR (CDCl$_3$-freebase) 7.86 (bs, 1 H), 7.45-7.43 (m, 1 H), 7.23-7.19 (m, 1 H), 6.94-6.92 (m, 1 H), 6.89-6.88 (m, 1 H), 6.84-6.75 (m, 4 H), 4.29-4.23 (m, 2 H), 3.99-3.96 (m, 2 H), 3.78 (s, 2 H), 2.94 (s, 4 H), 1.81-1.74 (m, 2 H), 1.55-1.45 (m, 3 H), 0.99-0.95 (m, 3 H); Analysis for C$_{23}$H$_{27}$F$_3$N$_2$O$_2$ HCl: calcd: C, 60.46; H, 6.18; N, 6.13; found: C, 60.23; H, 5.99; N, 6.01 |
| 466 | 5-butyloxy | 2,2,3,3-tetrafluoropropyl | Analysis for C$_{24}$H$_{28}$F$_4$N$_2$O$_2$•HCl: calcd: C, 58.96; H, 5.98; N, 5.73; found: C, 58.62; H, 5.96; H, 5.77 ISMS 453 (M + 1) |
| 467 | 6-ethoxy | 2,2,2-trifluoroethyl | ISMS 393 (M + 1); Analysis for C$_{21}$H$_{23}$F$_3$N$_2$O$_2$ HCl: calcd: C, 58.81; H, 5.64; N, 6.53; found: C, 58.94; H, 5.58; N, 6.55 |
| 468 | 6-phenyl sulfonate | 2,2,2-trifluoroethyl | ISMS 505 (M + 1); Analysis for C$_{25}$H$_{23}$F$_3$N$_2$O$_4$S HCl: calcd: C, 55.51; H, 4.47; N, 5.18; found: C, 55.27; H, 4.41; N, 5.15 |
| 469 | 6-phenyl sulfonate | 2,2,3,3-tetrafluoropropyl | ISMS 536 (M + 1); Analysis for C$_{26}$H$_{24}$F$_4$N$_2$O$_4$S HCl: calcd: C, 54.50; H, 4.40; N, 4.89; found: C, 54.63; H, 4.41; N, 4.86 |
| 470 | 6-phenyl | phenyl | ISMS 419 (M + 1); Analysis for C$_{26}$H$_{24}$F$_4$N$_2$O$_4$S HCl 0.3H$_2$O: calcd: C, 75.65; H, 6.04; N, 6.08; found: C, 75.63; H, |

-continued

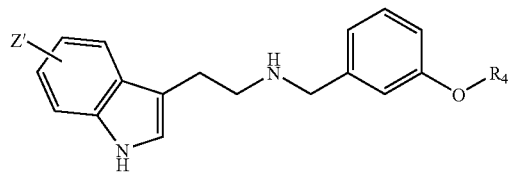

| No. | Z' | R₄ | Data |
|---|---|---|---|
| 470 A | 6-butyloxy | 2,2,3,3-tetrafluoro propyl | 5.89; N, 6.07 Analysis for $C_{23}H_{27}F_3N_2O_2$•HCl•HCl: Calcd: C, 58.52; H, 6.02; N, 5.69; found: C, 58.15; H, 5.64; N, 5.58. |

300 mg 5% Pd/C and hydrogenate at atmospheric pressure overnight. Filter the reaction through a pad of celite and concentrate to dryness then chromatograph on silica gel to give the title compound: ISMS 365 (M+1); $^1$H NMR (DMSO-d6) 10.6 (bs, 1H), 9.4 (bs, 2H), 8.75 (s, 1H), 7.45-6.6 (m,7H), 4.9-4.7 (m, 2H), 4.2 (bs, 2H), 3.2-2.9 (m, 4H).

By the method of Example 471 the following compounds were prepared and isolated as the hydrochloride except where noted:

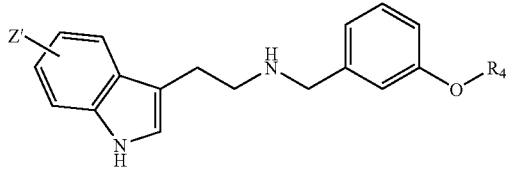

| No. | Z' | R₄ | Data |
|---|---|---|---|
| 472 | 5-hydroxy | 2,2,3,3-tetrafluoro propyl | ISMS 397 (M + 1); Analysis for $C_{20}H_{20}OF_4N_2O_2$ HCl H₂O: calcd: C, 53.28; H, 5.14; H, 6.21; found: C, 53.31; H, 4.91; N, 6.33 |
| 473 | 6-hydroxy | 2,2,2-trifluoro ethyl | ISMS 487 (M + 1); $^1$H NMR (DMSO-d6) δ10.52 (bs, 1 H), 9.36 (s, 2 H), 8.91 (s, 1 H), 7.38-7.33 (m, 2 H), 7.28-7.26 (m, 1 H), 7.20-7.18 (m, 1 H), 7.09-7.07 (m, 1 H), 6.94-6.93 (m, 1 H), 6.68-6.67 (m, 1 H), 6.50-6.47 (m, 1 H), 4.79-4.72 (m, 2 H), 4.13 (s, 2 H), 3.05-3.02 (m, 4 H) |
| 474 | 6-hydroxy | 2,2,3,3-tetrafluoro propyl | ISMS 397 (M + 1); Analysis for $C_{20}H_{20}F_4N_2O_2$ HCl H₂O: calcd: C, 53.28; H, 5.14; N, 6.21; found: C, 53.33; H, 4.76; N, 6.12 |

Example 471

N-(2-(5-Hydroxy-1H-indol-3-yl)ethyl)-3-(2,2,2-trifluoroethoxybenzylamine

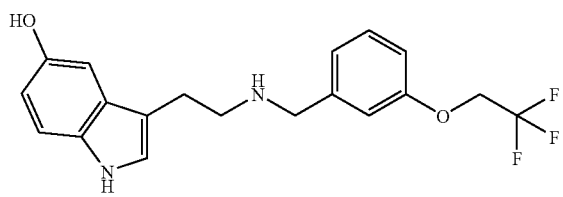

Combine N-(2-(5-benzyloxy-1H-indol-3-yl)ethyl)-3-(2,2,2-trifluoroethoxy)benzylamine hydrochloride (295 mg, 0.6 mmol) and 25 mL EtOH and treat with 0.3 mL 5 N HCl and Example 475

N-(2-(5-Carboxy-1H-indol-3-yl)ethyl)-3-(2,2,2-trifluoroethoxy)benzylamine

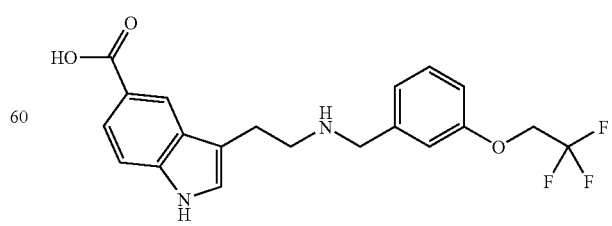

Combine N-(2-(5-methoxycarbonyl-1H-indol-3-yl)ethyl)-3-(2,2,2-trifluoroethoxy)benzylamine (200 mg, 0.5 mmol) in 50 mL THF and 1 mL 3 N NaOH. Reflux the mixture overnight, treat with 0.7 mL 5 N HCl and concentrate to dryness. Chromatograph to give the title compound: ISMS 393 (M+1); Analysis for $C_{20}H_{19}F_3N_2O_3$ $CF_3COOH$ 1.2$C_7H_8$ 2.1$H_2O$: calcd: C, 55.76; H, 5.20; N, 4.28. found: C, 55.51; H, 5.47; N, 4.50.

Example 480

3-(3-Fluoropropoxy)benzaldehyde

Combine 1-bromo-3-fluoropropane (10.0 g, 77.1 mmol) and 3-hydroxybenzaldehyde (10.4 g, 92.5 mmol) in dimethylformamide (220 mL) and stir at room temperature. Treat with potassium carbonate in portions (21.3 g, 144.2 mmol). Heat the reaction mixture at 100° C. for 36 hours, then pour into a 1:1 mixture of ice water and dichloromethane. Separate the phases and extract the aqueous layer with additional dichloromethane. Wash the combined organic extracts sequentially with 1.0 N sodium hydroxide, saturated sodium bicarbonate, brine, and then dry over sodium sulfate. Filtration and removal of the solvent in vacuo provides a residue. Chromatograph the residue on silica gel eluting with 40% ethyl acetate in hexanes to give the title compound as a yellow oil: $^1$H NMR (400 MHz, $CDCl_3$) 9.98 (s, 1H), 7.50-7.42 (m, 2H), 7.42-7.38 (m, 1H), 7.22-7.16 (m, 1H), 4.66 (dt, 2H, J=46.8, 5.8 Hz), 4.17 (t, 2H, J=6.0 Hz), 2.19 (d quintuplets, 2H, J=26.0, 6.0 Hz); MS (APCI): m/e 183.1 (M+1).

Example 481

2,2-Difluoroethyltosylate

Combine p-toluenesulfonyl chloride (12.9 g, 67.4 mmol) in pyridine (15 mL) at room temperature and treat dropwise with 2,2-difluoroethanol (5.0 g, 60.9 mmol) via syringe. Stir the reaction mixture under nitrogen for 72 hours, partition between water (20 mL) and dichloromethane (20 mL). Separate the aqueous phase and extract with additional dichloromethane (2×40 mL). Combine the organic extracts and wash sequentially with 1 N hydrochloric acid (2×50 mL), sodium bicarbonate (2×50 mL), and brine (2×50 mL). Dry the organic layer over sodium sulfate and concentrate in vacuo to give the title compound as a yellowish oil: $^1$H NMR (300 MHz, $CDCl_3$): 7.82 (d, 2H, J=9.0 Hz), 7.40 (d, 2H, J=9.0 Hz), 5.92 (tt, 1H, J=55.0, 0.4 Hz), 4.19 (td, 2H, J=12.6, 4.0 Hz), 2.48 (s, 3H).

Example 482

3-(2,2-Difluoroethoxy)benzaldehyde

The method of Example 480 gives the title compound as a yellow oil. $^1$H NMR (400 MHz, $CDCl_3$): 9.97 (s, 1H), 7.56-7.44 (m, 2H), 7.41-7.37 (m, 1H), 7.21 (ddd, 1H, J=8.0, 2.8, 1.2 Hz), 6.11 (tt, 1H, J=55.0, 4.0 Hz), 4.24 (td, 2H, J=12.6, 4.0 Hz).

Example 483

N-(2-(6-Chloro-1H-indol-3-yl)ethyl)-3-(3-fluoropropoxy)benzylamine

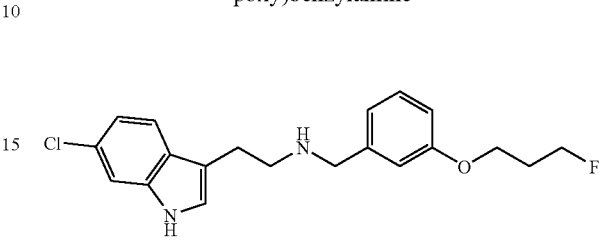

Combine 6-chlorotryptamine (1.4 g, 7.2 mmol), 3-(3-fluoropropoxy)benzaldehyde (1.3 g, 7.2 mmol), and molecular sieves in ethanol (150 mL), and heat at 78° C. overnight. Filter the reaction mixture through a plug of celite, and treat the resulting filtrate with sodium borohydride (817 mg, 21.6 mmol) and stir overnight at room temperature. Evaporate the solvent in vacuo to give a residue. Chromatograph the residue on silica gel eluting with 9:1 mixture of dichloromethane and 1N ammonia in methanol to give a residue. Chromatograph that residue on 10 g SCX column (wash column with methanol then elute with 1 N ammonia in methanol) and concentrate in vacuo to give a light yellow oil. Dissolve the oil in methanol and treated with a methanolic solution of ammonium chloride (112 mg, 2.1 mmol). Sonicate the resulting mixture for 10 minutes, remove the solvent in vacuo, and triturate the resulting residue with ether containing a few drops of acetonitrile to give a solid. Collect the solid by filtration to give the title compound as the hydrochloride: mp 177.8-178.9° C.; $^1$H NMR (400 MHz, dmso-$d_6$): 11.15 (br s, 1H), 9.41 (br s, 2H), 7.57 (d, 1H, J=8.0 Hz), 7.39 (d, 1H, J=2.0 Hz), 7.32 (t, 1H, J=7.8 Hz), 7.26 (d, 1H, J=2.4 Hz), 7.25-7.21 (m, 1H), 7.11 (d, 1H, J=8.0 Hz), 7.01 (dd, 1H, J=8.8, 2.0 Hz), 6.97 (dd, 1H, J=8.0, 2.0 Hz), 4.60 (dt, 2H, J=47.6, 6.0 Hz), 4.13 (br s, 2H), 4.08 (t, 2H, J=6.4 Hz), 3.10 (br s, 4H), 2.11 (d quintuplets, 2H, J=26.0, 6.0 Hz); MS (ES+): m/e 361.3 (M+1); CHN (for $C_{20}H_{22}ClFN_2O.HCl$) calcd: C, 60.46; H, 5.83; N, 7.05. found: C, 60.48; H, 5.86; N, 7.16.

By the method of Example 483 the following compounds were prepared and isolated as the hydrochloride except where noted:

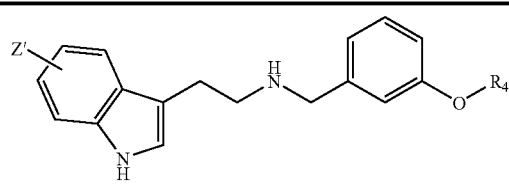

| No. | Z' | R$_4$ | Data |
|---|---|---|---|
| 484 | 6-fluoro | 3-fluoropropyl | mp: 174.8-176.0° C.; $^1$H NMR (400 MHz, dmso-$d_6$): 11.03 (br s, 1 H), 9.35 (br s, 2 H), 7.52 (dd, 1 H, J = 8.8, 5.2 Hz), 7.30 (t, 1 H, J = 7.8 Hz), 7.22-7.17 (m, 2 H), 7.13-7.06 (m, 2 H), 6.95 (dd, |

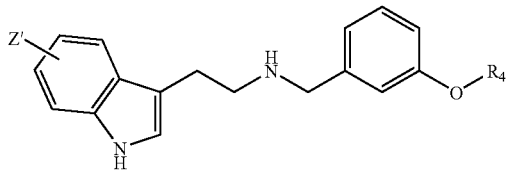

| No. | Z' | R$_4$ | Data |
|---|---|---|---|
| | | | 1 H, J = 7.8, 2.2 Hz), 6.83 (ddd, 1 H, J = 9.6, 8.8, 2.4 Hz), 4.58 (dt, 2 H, J = 47.2, 5.8 Hz), 4.11 (s, 2 H), 4.06 (t, 2 H, J = 6.2 Hz), 3.08 (br s, 4 H), 2.08 (d quintuplets, 2 H, J = 26.0, 6.0 Hz); MS (ES+); m/e 345.3 (M + 1); CHN (for C$_{20}$H$_{22}$F$_2$N$_2$O·HCl) calcd: C 63.07, H 6.09, N 7.36; found: C 62.82, H 6.13, N 7.57 |
| 485 | 6-fluoro | 2,2-difluoro ethyl | mp 165.0-166.5° C. $^1$H NMR (400 MHz, dmso-d$_6$): 11.08 (br s, 1 H), 7.56 (dd, 1 H, J = 8.7, 5.2 Hz), 7.39-7.31 (m, 2 H), 7.21 (d, 1 H, J = 2.0 Hz), 7.18 (d, 1 H, J = 6.9 Hz), 7.12 (dd, 1 H, J = 10.4, 1.7 Hz), 7.04 (dd, 1 H, J = 8.7, 1.7 Hz), 6.89-6.81 (m, 1 H), 6.42 (tt, 1 H, J = 53.9, 3.5 Hz), 4.32 (td, 2 H, J = 11.3, 3.2 Hz), 4.14 (s, 2 H), 3.20-3.00 (m, 4 H); MS: (ES+): m/e 349.0 (M + 1) |
| 486 | 6-chloro | 2,2-difluoro ethyl | mp 131.6-133° C.: $^1$H NMR (400 MHz, dmso-d$_6$): 11.15 (br s, 1 H), 9.50 (br s, 2 H), 7.57 (d, 1 H, J = 8.8 Hz), 7.39 (d, 1 H, J = 2.0 Hz), 7.36 (t, 1 H, J = 8.2 Hz), 7.32 (br s, 1 H), 7.26 (d, 1 H, J = 2.0 Hz), 7.17 (d, 1 H, J = 7.6 Hz), 7.04 (dd, 1 H, J = 7.8, 2.2 Hz), 7.01 (dd, 1 H, J = 8.4, 2.0 Hz), 6.41 (tt, 1 H, J = 54.4, 3.4 Hz), 4.32 (td, 2 H, J = 14.8, 3.6 Hz), 4.14 (br s, 2 H), 3.11 (br s, 4 H); MS (ES+): m/e 365.3 (M + 1); CHN (for C$_{19}$H$_{19}$F$_2$ClN$_2$O•HCl•0.3 H$_2$O) calcd: C 56.11; H 5.11; N 6.89; found: C 56.03; H 4.95; N 7.18 |
| 487 | 6-chloro | 2,2,3,3,3-pentafluoro propyl | mp 199.8-201.1° C.; $^1$H NMR (400 MHz, dmso-d$_6$): 11.15 (br s, 1 H), 9.35 (br s, 2 H), 7.57 (d, 1 H, J = 8.4 Hz), 7.44-7.32 (m, 3 H), 7.26 (d, 1 H, J = 2.0 Hz), 7.22 (d, 1 H, J = 8.0 Hz), 7.10 (dd, 1 H, J = 8.4, 2.0 Hz), 7.00 (dd, 1 H, J = 8.6, 1.8 Hz), 4.85 (t, 2 H, J = 13.2 Hz), 4.13 (s, 2 H), 3.10 (br s, 4 H); MS (ES+); m/e 433.0 (M + 1); CHN (for C$_{20}$H$_{18}$ClF$_5$N$_2$O•0.97HCl) calcd: C 51.31, H 4.08, N 5.98; found: C 51.61, H 4.07, N 6.00 |
| 488 | 5-isopropyl | 2,2,3,3,3-pentafluoro propyl | mp 168.5-171.0° C.; MS (ES+); m/e 441.1 (M + 1); CHN (for C$_{23}$H$_{25}$F$_5$N$_2$O•HCl•0.3H$_2$O) calcd: C 57.28, H 5.56, N 5.81; found: C 57.10, H 5.21, N 6.03 |
| 489 | 5-isopropyl | 2,2,3,3-tetrafluoro propyl | mp 167.0-168.2° C.; $^1$H NMR (400 MHz, dmso-d$_6$): 10.72 (br s, 1 H), 7.44 (t, 1 H, J = 7.8 Hz), 7.34 (br s, 1 H), 7.22-7.15 (m, 2 H), 7.14 (br s, 1 H Hz), 7.06 (d, 1 H, J = 7.6 Hz), 7.01 (dd, 1 H, J = 8.4, 1.6 Hz), 6.69 (tt, 1 H, J = 51.6, 5.6 Hz), 5.86 (s, 1 H), 4.70-4.50 (m, 2 H), 3.50-3.25 (m, 4 H, overlapping with H$_2$O), 3.17-3.05 (m, 1 H), 3.05-2.91 (m, 2 H), 1.24 (d, 6 H, J = 6.8 Hz); MS (ES+); m/e 422.1 (M + 1) |

Example 490

N-(2-(6-Chloro-1H-indol-3-yl)ethyl)-N-methyl-3-(2,2-difluoroethoxy)benzylamine

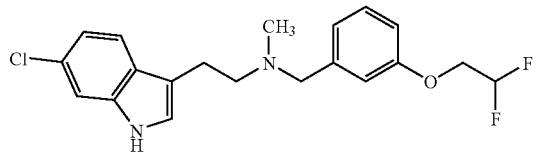

Combine N-(2-(6-chloro-1H-indol-3-yl)ethyl)-3-(2,2-difluoroethoxy)benzylamine (276 mg, 0.76 mmol) and formaldehyde (55.5 µL of a 38% aqueous solution, 0.76 mmol) in dichloroethane (15 mL) and stir at room temperature for 10 minutes; then add in two portions over 10 minutes sodium triacetoxyborohydride (321 mg, 1.51 mmol). Stir the reaction mixture at room temperature overnight and dilute with methanol (10 mL) and quench with one drop of glacial acetic acid. Remove the solvent in vacuo, to give a residue, redissolve the crude residue in methanol and directly load onto a 10 g SCX column. After washing the column thoroughly with methanol, elute with 2 N ammonia in methanol. Concentrate in vacuo to give the title compound as an oil. Dissolve the oil (239 mg, 0.64 mmol) in methanol (20 mL) and treat with a solution of ammonium chloride (36 mg, 0.67 mmol) in methanol (5 mL). Sonicate the mixture for 10 minutes before removal of the solvent in vacuo to give the title compound as the hydrochloride salt Dissolve the salt in 10 mL of 1:1 acetonitrile-water and lyophilize overnight, providing a fluffy white solid. Triturate the solid with diethyl ether (10 mL) and acetonitrile (2 drops), filter, and dry to give the title compound as the hydrochloride salt: mp: 63.8-65.8° C.; $^1$H NMR (400 MHz, dmso-$d_6$): 11.10 (br s, 1H), 7.52 (d, 1H, J=8.4 Hz) 7.36 (d, 1H, J=2.0 Hz), 7.40-7.26 (m, 2H), 7.22 (d, 1H, J=2.4 Hz), 7.20-7.11 (m, 1H), 7.04 (br d, 1H, J=7.6 Hz), 6.96 (dd, 1H, J=8.6, 1.4 Hz), 6.38 (tt, 1H, J=54.4, 3.6, Hz), 4.50-4.02 (br m, 2H), 4.30 (td, 2H, J=14.4, 3.2 Hz), 3.15 (br s, 4H), 2.68 (br s, 3H); MS (ES+): m/e 378.9 (M+1.

By the method of Example 490 the following compounds were prepared and isolated as the hydrochloride except where noted:

Example 495

N-(2-(6-Chloro-1H-indol-3-yl)ethyl)-N-isopropyl-3-(2,2,3,3,3-pentafluoropropoxy benzylamine

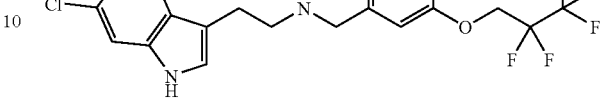

Combine N-(2-(6-Chloro-1H-indol-3-yl)ethyl)-3-(2,2,3,3,3-pentafluoropropoxy)benzylamine (254 mg, 0.59 mmol)

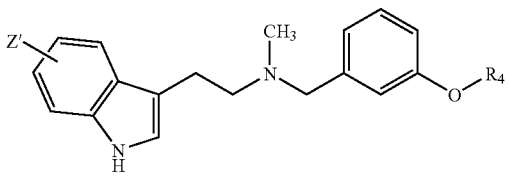

| No. | Z' | $R_4$ | Data |
|---|---|---|---|
| 491 | 6-fluoro | 2,2-difluoro ethyl | mp: 70.8-73.0° C.; $^1$H NMR (400 MHz, CDCl$_3$): 9.01 (br s, 1 H), 7.40-7.35 (m, 1 H), 7.35 (dd, 1 H, J = 8.8, 5.6 Hz), 7.31-7.25 (m, 1 H), 7.10-7.02 (m, 2 H), 6.97-6.91 (m, 2 H), 6.77 (td, 1 H, J = 9.2, 2.0 Hz), 6.05 (tt, 1 H, J = 54.8, 4.0 Hz), 4.21 (td, 2 H, J = 13.0, 4.0 Hz), 4.08 (br s, 2 H), 3.30-3.18 (m, 2 H), 3.18-3.05 (m, 2 H), 2.66 (s, 3 H); MS (APCI): m/e 363.1 (M + 1) |
| 492 | 6-fluoro | 3-fluoro propyl | mp: 66.4-69.3° C.; $^1$H NMR (300 MHz, dmso-$d_6$): 11.04 (s, 1 H), 11.20-10.70 (br s, 1 H), 7.52 (dd, 1 H, J = 8.8, 5.5 Hz), 7.34 (t, 1 H, J = 7.9 Hz), 7.30-7.20 (m, 1 H), 7.20 (d, 1 H, J = 2.2 Hz), 7.12 (AB$_q$, 2 H, J$_{AB}$ = 2.4 Hz, ΔJ$_{AB}$ = 9.8 Hz), 7.00 (br d, 1 H, J = 8.4 Hz), 6.84 (ddd, 1 H, J = 9.9, 8.8, 2.2 Hz), 4.61 (dt, 2 H, J = 47.2, 5.9 Hz), 4.44-4.03 (br m, 2 H), 4.08 (t, 2 H, J = 6.4 Hz), 3.17 (br s, 4 H), 2.68 (br s, 3 H), 2.11 (dquintuplets, 2 H, J = 25.6, 6.1 Hz); MS (ES+): m/e 358.9 (M + 1) |
| 493 | 6-chloro | 3-fluoro propyl | mp: 6.14-63.4° C.; $^1$H NMR (400 MHz, DMSO-$d_6$): 11.14 (s, 1 H), 7.54 (d, 1 H, J = 8.4 Hz), 7.40 (d, 1 H, J = 2.4 Hz), 7.35 (t, 1 H, J = 8.0 Hz), 7.32-7.23 (m, 2 H), 7.13 (br d, 1 H, J = 7.2 Hz), 7.07-7.00 (m, 1 H), 6.99 (dd, 1 H, J = 8.6, 1.8 Hz), 4.60 (dt, 2 H, J = 46.8, 5.8 Hz), 4.50-4.15 (br m, 2 H), 4.08 (t, 2 H, J = 6.4 Hz), 3.18 (br s, 4 H), 2.72 (br s, 3 H), 2.11 (dquintuplets, 2 H, J = 26.0, 6.4 Hz); MS (APCI): m/e 375.1 (M + 1) |
| 494 | 6-chloro | 2,2,3,3,3-pentafluoro propyl | mp 206.6-207.5° C.; $^1$H NMR (400 MHz, methanol-$d_4$): 7.97 (d, 1 H, J = 8.0 Hz 7.93-7.85 (m, 2 H), 7.75-7.68 (m, 2 H), 7.65 (br d, 1 H, J = 7.2 Hz), 7.58 (br d, 1 H, J = 8.0 Hz), 7.47 (br d, 1 H, J = 9.2 Hz), 5.21 (t, 2 H, J = 13.0 Hz), 4.60 (br s, 2 H), 3.61 (br s, 4 H), 3.14 (br s, 3 H); MS (ES+): m/e 447.1 (M + 1); CHN (for C$_{21}$H$_{20}$ClF$_5$N$_2$O•HCl calcd: C 52.19; H 4.38; N 5.80; found: C 52.16; H 4.29; N 5.82 | in 20 mL of 95:5 methanol-acetic acid, treat with acetone (441 µL, 5.9 mmol) followed by sodium cyanoborohydride in portions (148 mg, 2.3 mmol). Stir the reaction mixture at 50° C. overnight; then at room temperature for an additional 2 days. Remove the solvent in vacuo to give a residue. Chromatograph the residue on silica gel eluting with 4% methanol in dichloromethane to give the title compound as a colorless oil. Dissolve the oil (237 mg, 0.49 mmol) in methanol (15 mL) and treat with a solution of ammonium chloride (27 mg, 0.49 mmol) in methanol (5 mL). Sonicate the mixture for 10 minutes before concentrating it to a tacky white solid. Dissolve the tacky solid in 10 mL of 1:1 acetonitrile-water and lyophilize to give 241 mg (96%) of the title compound as the hydrochloride: mp: 77.0-80.2° C.; $^1$H NMR (400 MHz, methanol-$d_4$): 7.31 (br t, 1H, J=7.8 Hz), 7.26-7.21 (m, 1H), 7.16 (br d, 1H, J=8.4 Hz), 7.15-7.07 (m, 2H), 7.05-6.95 (m, 2H), 6.83 (dd, 1H, J=8.0, 2.0 Hz), 4.52 (t, 2H, J=12.8 Hz), 4.12 (br s, 2H), 3.53 (br s, 1H), 3.11 (br s, 2H), 2.89 (br s, 2H), 1.27 (br s, 6H); MS (APCI): m/e 475.1 (M+1).

By the method of Example 495 the following compounds were prepared and isolated as the maleate:

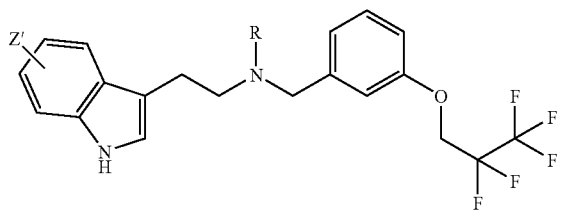

| No. | Z' | R | Data |
|---|---|---|---|
| 496 | 6-chloro | propyl | mp 92.4-94.6° C. Mass (ES+): m/z 475.0 (M + 1). Elemental Analysis Calculated for $C_{23}H_{24}ClF_5N_2O \cdot 1.0C_4H_4O_4 \cdot 0.5H_2O$: C, 53.30; H, 4.93; N, 4.57. Found: C, 53.00; H, 4.55; N, 4.86. |
| 497 | 6-chloro | ethyl | mp 101.0-1-104.0° C. Mass (ES+): m/z 461.0 (M + 1). |

Example 500

N-(2-(6-Chloro-5-methoxy-1H-indol-3-yl)ethyl)-3-(2,2,3,3-tetrafluoropropoxybenzylamine

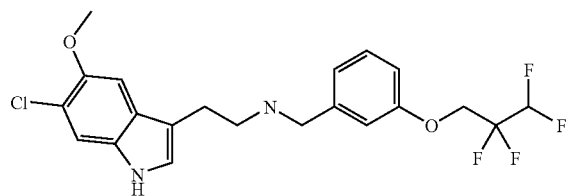

Combine 5-methoxy-6-chlorotryptamine (0.2 mmol) in dichloromethane (1 mL) and 3-(2,2,3,3-tetrapropylfluororpropoxy)benzaldehyde (0.32 mmol) in dichloromethane (1 mL) and rotate. After 2 h, add sodium borohydride (37.83 mg, 1.0 mmol) as a stock solution in dichloromethane (1 mL). After overnight rotation, dilute the reaction mixture with 1 mL of methanol, and apply the resulting solution directly to a 2 g SCX column. Thoroughly wash the column with methanol, elute with 2 M ammonia-methanol and concentrate to a residue. If a TLC of eluent indicates that the reaction was not complete. Dilute the residue with dichloromethane (1 mL) and add a second stock solution of sodium borohydride (37.83 mg, 1.0 mmol) in 1-methyl-2-pyrrolidinone (1 mL). After rotation for 2 h, dilute the reaction mixture with 1 mL of methanol, and directly apply the resulting solution to a 2 g SCX column. Thoroughly wash the column with methanol, elute with 2 M ammonia-methanol and concentrate to a residue. Further purification on a SI column. Elution with straight ethyl acetate. Compound was characterized using LC method 1 or 2. LCMS $R_f$ 2.749 min at 254 nm, 2.800 min at 220 nm; m/e 445 (M+1).

General LC Methods:
Method 1: (Shimadzu QP8000) 10-90 in 4.5 min. Solvent A: water 0.1% trifluoroacetic acids Solvent B: acetonitrile 0.1% trifluoroacetic acid. Column: C18 Metachem, monochrom 3 micron, 2.5×25.
Method 2: (Shimadzu) 10-80 in 9 min. Solvent A: water 0.1% trifluoroacetic acid, Solvent B: acetonitrile 0.08% trifluoroacetic acid. Column: C18 Metachem, monochrom 5 micron, 4.6×50.

The following compounds were prepared in a manner similar to Example 500 and isolate as the base unless otherwise indicated:

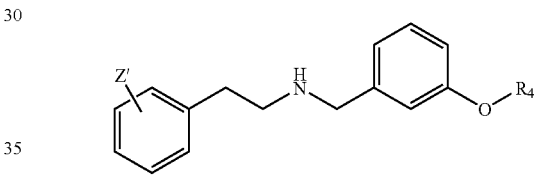

| No. | Z' | $R_4$ | Data |
|---|---|---|---|
| 501 | 3-$CF_3$ | 2,2,2-trifluoroethyl | Method 2: LC Rf 3.90 min at 220 nm, 3.908 min at 264 nm. |
| 502 | 3,5-dimethoxy | 2,2,2-trifluoroethyl | Method 2: LC Rf 3.620 min at 254 nm, 3.62 min at 220 nm, m/e 220 nm, m/e 367 (M + 1). |
| 503 | 3-chloro | 2,2,3,3-tetrafluoro propyl | Method 1: LCMS Rf 2.800 min at 220 nm, m/e 376 (M + 1). |
| 504 | 3-$CF_3$ | 2,2,3,3-tetrafluoro propyl | Method 1: LCMS Rf 2.885 min at 254 nm, m/e 410 (M + 1). |
| 506 | 3-chloro | 2-fluoroethyl | Method 2: LC Rf 3.420 min at 254 nm, 3.42 min at 220 nm. |
| 507 | 3-trifluoromethyl | 2-fluoroethyl | Method 2: LC Rf 3.580 min at 254 nm, 3.58 min at 220 nm. |
| 508 | 3,5-dimethoxy | 2-fluoroethyl | Method 2: LC Rf 3.212 min at 254 nm, 3.22 min at 220 nm. |
| 509 | 3-trifluoromethyl | propyl | Method 2: LC Rf 3.892 min at 254 nm, 3.89 min at 220 nm. |
| 510 | 2-chloro | phenyl | Method 1: LCMS Rf 2.479 min at 2854 nm, m/e 338 (M + 1). |
| 511 | 3-trifluoromethyl | phenyl | Method 1: LCMS Rf 2.969 min at 254 nm, m/e 372 (M + 1). |

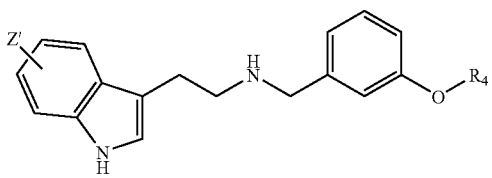

| No. | Z' | R$_4$ | Data |
|---|---|---|---|
| 512 | 5-methoxy 6-chloro | 2,2,2-trifluoroethyl | Method 1: LCMS Rf 2.651 min at 220 nm, m/e 413 (M + 1). |
| 513 | 6-fluoro | 2,2,2-trifluoroethyl | Method 1: LCMS Rf 2.618 min at 254 nm, 2.700 min at 220 nm, m/e 367 (M + 1). |
| 514 | 4-chloro 5-methoxy | 2,2,2-trifluoroethyl | Method 1: LCMS Rf 2.683 min at 254 nm, 2.661 min at 220 nm, m/e 399 (M + 1). |
| 515 | 5-methoxy 6-chloro | 2,2,3,3-tetrafluoropropyl | Method 1: LCMS Rt 2.749 min 254 nm, 2.800 min at 220 nm, m/e 445 (M + 1). |
| 516 | 6-fluoro | 2,2,3,3-tetrafluoropropyl | Method 1: LCMS Rf 2.683 min at 254 nm, 2.661 min at 220 nm, m/e 399 (M + 1). |
| 517 | 4-chloro 5-methoxy | 2,2,3,3-tetrafluoropropyl | Method 1: LCMS Rf 2.682 min at 254 nm, 2.663 min at 220 nm, m/e 445 (M + 1). |
| 522 | 5-methoxy | 2-fluoroethyl | Method 2: LC Rf 3.19 min at at 220 nm. |

Example 523

N-(2-(6-Trifluoromethyl-1H-indol-3-yl)ethyl)-3-phenoxybenzylamine

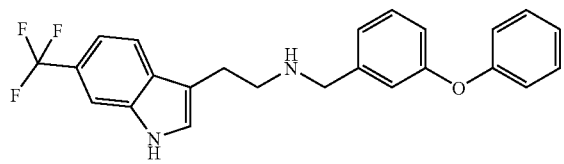

Combine 5-trifluoromethyltryptamine (0.1 mmol) in methanol (1 mL) and 3-phenoxybenzaldehyde (0.2 mmol) in methanol (1 mL) and rotate. After 3 h, add sodium borohydride (18 mg, 0.5 mmol) as a stock solution in 1-methyl-2-pyrrolidinone (0.5 mL). After overnight rotation, dilute the reaction mixture with 1 mL of methanol, directly apply the resulting solution to a 2 g SCX column. Wash thoroughly the column with methanol, and elute with 2 M ammonia-methanol and concentrate the eluent. Further purification on SI column eluting with ethyl acetate affords the desired compound. Characterization of the compound is achieve by using method 1. LCMS R$_f$ 2.954 min at 254 nm, 2.954 min at 220 nm, m/e 411 (M+1).

LC method:

Method 1: (Shimadzu QP8000) 10-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared following a similar procedure as in Example 523 and isolated as the base unless otherwise indicated:

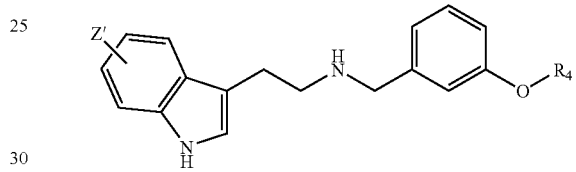

| No. | Z' | R$_4$ | Data |
|---|---|---|---|
| 524 | 6-trifluoromethyl | phenyl | Method 1: LCMS Rf 2.954 min at 2.54 nm, 2.954 min at 220 nm, m/e 411 (M + 1). |
| 525 | 6-fluoro | phenyl | Method 1: LCMS Rf 2.712 min at 254 nm, 2.712 min at 220 nm, m/e 361 (M + 1). |
| 526 | 5-methoxy 6-chloro | phenyl | Method 1: LCMS Rf 2.757 min at 254 nm, 2.757 min at 220 nm, m/e 407 (M + 1). |
| 527 | 4-chloro 5-methoxy | propyl | Method 1: LCMS Rf 2.578 min at 254 nm, 2.577 min at 220 nm, m/e 373 (M + 1). |
| 528 | 6-trifluoromethyl | propyl | Method 1: LCMS Rf 2.850 min at 254 nm, 2.849 min at 220 nm, m/e 377 (M + 1). |
| 529 | 6-fluoro | propyl | Method 1: LCMS Rf 2.576 min at 254 nm, 2.576 min at 220 nm, m/e 327 (M + 1). |
| 530 | 5-methoxy 6-chloro | propyl | Method 1: LCMS Rf 2.637 min at 220 nm, m/e 373 (M + 1). |

Example 531

N-(2-(4-Sulfonamidophenyl)ethyl)-3-(2,2,3,3,3-pentafluoropropoxybenzylamine

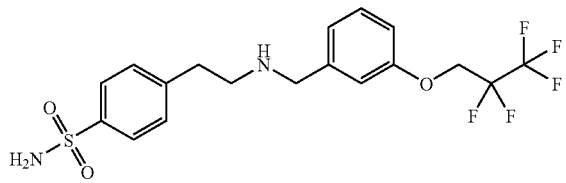

Combine 4-sulfonamidophenylethylamine (0.2 mmol) in methanol (1 mL) and 3-(2,2,3,3,3-pentapropylfluororpropoxy)benzaldehyde (0.32 mmol) in methanol (1 mL) and rotate. After 1 hour add sodium borohydride (18 mg, 1.0 mmol) as a stock solution in 1-methyl-2-pyrrolidinone (1 mL). After overnight rotation, dilute the reaction mixture with 1 mL of methanol, and directly apply the resulting solution to a 2 g SCX column. After thoroughly washing with methanol, elute the column with 2 M ammonia-methanol and concentrate the eluent to a residue. Further purification by Gilson UV prep system afforded the desired compound and the compound was characterized using method 1. LCMS $R_f$ 2.345 mm at 254 nm, 2.347 min at 220 nm, the 439 (M+1) 461 (M+22).

LC method:

Method 1: (Shimadzu QP8000) 10-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared using a similar procedure as in Example 531 and isolated as the base unless otherwise indicated:

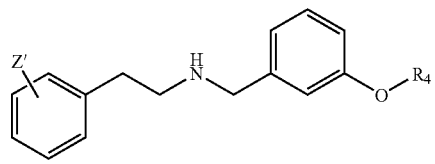

| No. | Z' | $R_4$ | Data |
|---|---|---|---|
| 532 | 2,5-dimethoxy | 2,2,3,3,3-pentafluoropropyl | Method 1: LCMS Rf 2.816 min at 254 nm, 2.815 min at 220 nm, m/e 420 (M + 1). |
| 533 | 3,4-dimethoxy | 2,2,3,3,3-pentafluoropropyl | Method 1: LCMS Rf 2.634 min at 254 nm, 2.637 min at 220 nm, m/e 420 (M + 1). |
| 534 | 4-sulfonamide | 2,2,3,3-tetrafluoropropyl | Method 1: LCMS Rf 2.155 min at 254 nm, 2.156 min at 220 nm, m/e 421 (M + 1). |
| 535 | 4-sulfonamide | 3-fluoropropyl | Method 1: LCMS Rf 1.816 min at 254 nm, 1.818 min at 220 nm, m/e 367 (M + 1), 389 (M + 22). |
| 537 | 4-sulfonamide | 2-fluoroethyl | Method 1: LCMS Rf 1.606 min at 254 nm, 1.606 min at 220 nm, m/e 375 (M + 22). |
| 538 | 3,4-dimethoxy | phenyl | Method 1: LCMS Rf 2.511 min at 254 nm, 2.511 min at 220 nm, m/e 364 (M + 1). |
| 539 | 4-sulfonamide | 2,2-difluoroethyl | Method 1: LCMS Rf 1.782 min at 254 nm, 1.782 min at 220 nm, m/e 371 (M + 1), 393 (M + 22). |
| 540 | 2,5-dimethoxy | 2,2-difluoroethyl | Method 1: LCMS Rf 2.359 min at 254 nm, m/e 352 (M + 1). |
| 541 | 3,4-dimethoxy | 2,2-difluoroethyl | Method 1: LCMS Rf 2.085 min at 254 nm, 2.070 min at 220 nm, m/e 335 (M + 1), 352 (M + 22). |
| 542 | 4-sulfonamide | 2,2-difluoroethyl | Method 1: LCMS Rf 1.816 min at 254 nm, 1.818 min at 220 nm, m/e 367 (M + 1), 389 (M + 22). |
| 543 | 2,5-dimethoxy | 3-fluoropropyl | Method 1: LCMS Rf 2.387 min at 254 nm, 2.381 min at 220 nm, m/e 348 (M + 1). |

Example 545

N-(2-(6-Methoxy-1H-indol-3-yl)ethyl)-3-(2,2,3,3,3-pentafluoropropoxy)benzylamine

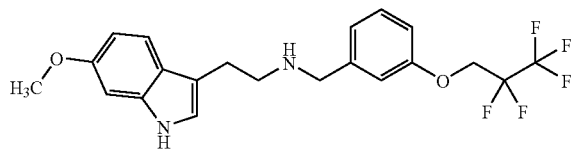

Combine amine (0.2 mmol) in 1-methyl-2-pyrrolidinone (1 mL) and aldehyde (0.32 mmol) in dichloromethane (1 mL) and rotate. After 1 h, add sodium borohydride (18 mg, 1.0 mmol) as a stock solution in 1-methyl-2-pyrrolidinone (1 mL). After rotation overnight, dilute the reaction mixture with 1 mL of 10% acetic acid/methanol, and directly apply the resulting solution to a 2 g SCX column. Thoroughly wash with methanol, elute the column with 2 M ammonia-methanol and concentrate the eluent to a residue, which was further purified by Gilson UV prep system. Characterize the compound using method 1. LCMS Rf 3.752 min at 254 nm, 3.753 min at 220 nm, in/c 429 (M+1).

LC method:

Method 1: (Shimadzu QP8000) 10-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared by following a similar procedure to Example 545:

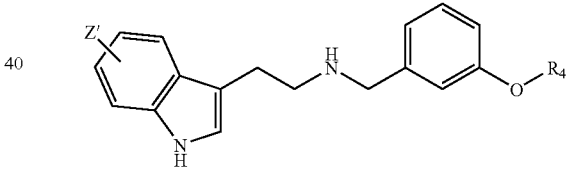

| No. | Z' | $R_4$ | Data |
|---|---|---|---|
| 546 | 4-chloro | 2,2,3,3,3-pentafluoropropyl | Method 1: LCMS Rf 3.873 min at 254 nm, 3.877 min at 220 nm, m/e 433 (M + 1). |
| 547 | 4-methoxy | 2,2,3,3,3-pentafluoropropyl | Method 1: LCMS Rf 3.828 min at 254 nm, 3.833 min at 220 nm, m/e 429 (M + 1). |
| 548 | 5-methoxy 2-methyl | 2,2,3,3,3-pentafluoropropyl | Method 1: LCMS Rf 3.802 min at 254 nm, 3.805 min at 220 nm, m/e 433 (M + 1). |
| 549 | 7-methoxy | 2,2,3,3,3-pentafluoropropyl | Method 1: LCMS Rf 3.800 min at 254 nm, 3.806 min at 220 nm, m/e 429 (M + 1). |
| 550 | 6-chloro | 2,2,3,3,3-pentafluoropropyl | Method 1: LCMS Rf 3.947 min at 254 nm, 3.952 min at 220 nm, m/e 433 (M + 1). |
| 551 | 4-methoxy | 2,2,3,3-tetrafluoropropyl | Method 1: LCMS Rf 3.695 min at 254 nm, 3.695 min at 220 nm, m/e 411 (M + 1). |
| 552 | 5-methoxy 2-methyl | 2,2,3,3-tetrafluoropropyl | Method 1: LCMS Rf 3.654 min at 254 nm, 3.654 min at 220 nm, m/e 425 (M + 1). |
| 553 | 7-methoxy | 2,2,3,3-tetrafluoropropyl | Method 1: LCMS Rf 3.659 min at 254 nm, 3.661 min at 220 nm, m/e 411 (M + 1). |
| 554 | 6-chloro | 2,2,3,3- | Method 1: LCMS Rf 3.821 min |

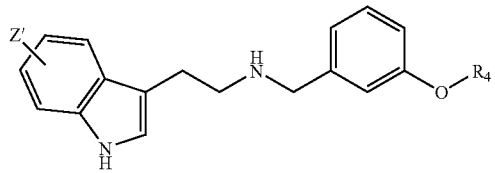
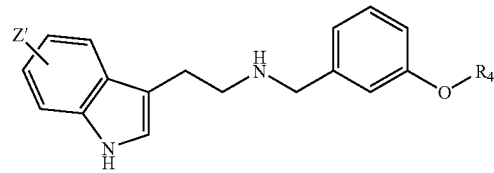

| No. | Z' | R4 | Data |
|---|---|---|---|
| | | tetrafluoro propyl | at 254 nm, 3.821 min at 220 nm, m/e 415 (M + 1). |
| 555 | 6-methoxy | 2-fluoroethyl | Method 1: LCMS Rf 3.169 min at 254 nm, 3.169 min at 220 nm, m/e 345 (M + 1). |
| 556 | 4-chloro | 2-fluoroethyl | Method 1: LCMS Rf 3.411 min at 254 nm, 3.412 min at 220 nm, m/e 347 (M + 1). |
| 557 | 4-methoxy | 2-fluoroethyl | Method 1: LCMS Rf 3.303 min at 254 nm, 3.304 min at 220 nm, m/e 343 (M + 1). |
| 558 | 5-methoxy 2-methyl | 2-fluoroethyl | Method 1: LCMS Rf 3.236 min at 254 nm, 3.236 min at 220 nm, m/e 357 (M + 1). |
| 559 | 7-methoxy | 2-fluoroethyl | Method 1: LCMS Rf 3.263 min at 254 nm, 3.264 min at 220 nm, m/e 343 (M + 1). |
| 560 | 6-chloro | 2-fluoroethyl | Method 1: LCMS Rf 3..465 min at 254 nm, 3.466 min at 220 nm, m/e 347 (M + 1). |
| 561 | 6-methoxy | 2,2-difluoroethyl | Method 1: LCMS Rf 3.190 min at 254 nm, 3.190 min at 220 nm. |
| 562 | 6-chloro | phenyl | Method 1: LCMS Rf 3.795 min at 254 nm, 3.795 min at 220 nm, m/e 377 (M + 1). |
| 563 | 6-fluoro | 2-fluoroethyl | Method 1: LCMS Rf 3.305 min at 254 nm, 3.306 min at 220 nm, m/e 331 (M + 1). |
| 571 | 4-chloro | propyl | Method 1: LCMS Rf 3.668 min at 254 nm, 3.668 min at 220 nm, m/e 343 (M + 1). |
| 572 | 4-methoxy | propyl | Method 1: LCMS Rf 3.581 min at 254 nm, 3.582 min at 220 nm, m/e 339 (M + 1). |
| 573 | 5-methoxy 2-methyl | propyl | Method 1: LCMS Rf 3.524 min at 254 nm, 3.524 min at 220 nm, m/e 353 (M + 1). |
| 574 | 7-methoxy | propyl | Method 1: LCMS Rf 3.553 min at 254 nm, 3.554 min at 220 nm, m/e 339 (M + 1). |
| 575 | 6-chloro | propyl | Method 1: LCMS Rf 3.736 min at 254 nm, 3.736 min at 220 nm, 343 (M + 1). |
| 576 | 4,6-difluoro 5-methoxy | phenyl | Method 1: LCMS Rf 3.830 min at 254 nm, 3.832 min at 220 nm, m/e 423 (M + 1). |
| 577 | 6-methoxy | phenyl | Method 1: LCMS Rf 3.527 min at 254 nm, 3.531 min at 220 nm, m/e 373 (M + 1). |
| 578 | 4-chloro | phenyl | Method 1: LCMS Rf 3.749 min at 254 nm, 3.749 min at 220 nm, m/e 377 (M + 1). |
| 579 | 4-methoxy | phenyl | Method 1: LCMS Rf 3.657 min at 254 nm, 3.658 min at 220 nm, m/e 373 (M + 1). |
| 580 | 5-methoxy-2-methyl | phenyl | Method 1: LCMS Rf 3.609 min at 254 nm, 3.609 min at 220 nm, m/e 3387 (M + 1). |
| 581 | 7-methoxy | phenyl | Method 1: LCMS Rf 3.622 min at 254 nm, 3.622 min at 220 nm, m/e 373 (M + 1). |
| 582 | 6-chloro | phenyl | Method 1: LCMS Rf 3.795 min at 254 nm, 3.795 min at 220 nm, m/e 377 (M + 1). |
| 583 | 4,6-difluoro 5-methoxy | 2,2-difluoroethyl | Method 1: LCMS Rf 3.514 min at 254 nm, 3.519 min at 220 nm, m/e 411 (M + 1). |
| 585 | 4-chloro | 2,2-difluoro ethyl | Method 1: LCMS Rf 3.418 min at 254 nm, 3.419 min at 220 nm, m/e 365 (M + 1). |
| 586 | 4-methoxy | 2,2-difluoroethyl | Method 1: LCMS Rf 3.301 min at 254 nm, 3.305 min at 220 nm, m/e 361 (M + 1). |
| 587 | 5-methoxy-2-methyl | 2,2-difluoroethyl | Method 1: LCMS Rf 3.269 min at 254 nm, 3.269 min at 220 nm, m/e 375 (M + 1). |
| 588 | 7-methoxy | 2,2-difluoroethyl | Method 1: LCMS Rf 3.265 min at 254 nm, 3.271 min at 220 nm, m/e 361 (M + 1). |
| 589 | 6-chloro | 2,2-difluoroethyl | Method 1: LCMS Rf 3.476 min at 254 nm, 3.476 min at 220 nm, m/e 365 (M + 1). |
| 590 | 6-fluoro | 2,2-difluoroethyl | Method 1: LCMS Rf 3.326 min at 254 nm, 3.326 min at 220 nm, m/e 349 (M + 1). |
| 592 | 6-methoxy | 3-fluoropropyl | Method 1: LCMS Rf 3.170 min at 254 nm, 3.176 min at 220 nm, m/e 357 (M + 1). |
| 593 | 4-chloro | 3-fluoropropyl | Method 1: LCMS Rf 3.400 min at 254 nm, 3.407 min at 220 nm, m/e 361 (M + 1). |
| 594 | 4-methoxy | 3-fluoropropyl | Method 1: LCMS Rf 3.326 min at 254 nm, 3.327 min at 220 nm, m/e 357 (M + 1). |
| 595 | 5-methoxy-2-methyl | 3-fluoropropyl | Method 1: LCMS Rf 3.277 min at 254 nm, 3.277 min at 220 nm, m/e 371 (M + 1). |
| 596 | 7-methoxy | 3-fluoropropyl | Method 1: LCMS Rf 3.290 min at 254 nm, 3.291 min at 220 nm, m/e 357 (M + 1). |
| 597 | 6-chloro | 3-fluoropropyl | Method 1: LCMS Rf 3.498 min at 254 nm, 3.499 min at 220 nm, m/e 361 (M + 1). |
| 598 | 6-fluoro | 3-fluoropropyl | Method 1: LCMS Rf 3.329 min at 254 nm, 3.330 min at 220 nm, m/e 345 (M + 1). |
| 600 | 6-methoxy | 2,2,2-trifluoroethyl | Method 1: LCMS Rf 3.288 min at 254 nm, 3.228 min at 220 nm, m/e 379 (M + 1). |
| 601 | 4-chloro | 2,2,2-trifluoroethyl | Method 1: LCMS Rf 3.518 min at 254 nm, 3.518 min at 220 nm, m/e 383 (M + 1). |
| 602 | 4-methoxy | 2,2,2-trifluoroethyl | Method 1: LCMS Rf 3.427 min at 254 nm, 3.428 min at 220 nm, m/e 379 (M + 1). |
| 603 | 5-methoxy-2-methyl | 2,2,2-trifluoroethyl | Method 1: LCMS Rf 3.378 min at 254 nm, 3.378 min at 220 nm, m/e 393 (M + 1). |
| 604 | 7-methoxy | 2,2,2-trifluoroethyl | Method 1: LCMS Rf 3.234 min at 254 nm, 3.255 min at 220 nm, m/e 379 (M + 1). |
| 605 | 6-chloro | 2,2,2-trifluoroethyl | Method 1: LCMS Rf 3.587 min at 254 nm, 3.587 min at 220 nm, m/e 383 (M + 1). |

The following compounds were prepared by following a similar procedure to Example 545:

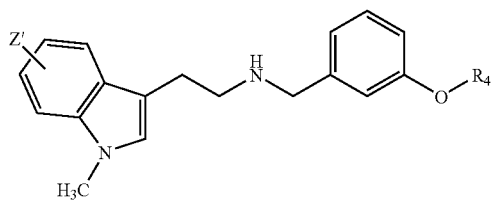

| No. | Z' | R₄ | Data |
|---|---|---|---|
| 606 | 6-methoxy | 2,2-difluoro-ethyl | Method 1: LCMS Rf 3.190 min at 254 nm, 3.190 min at 220 nm. |
| 607 | 4-fluoro 5-methoxy 6-fluoro | 3-fluoropropyl | Method 1: LCMS Rf 3.390 min at 254 nm, 3.395 min at 220 nm, m/e 401 (M + 1). |
| 608 | 4-fluoro 6-fluoro 5-methoxy | 2,2,2-trifluoroethyl | Method 1: LCMS Rf 3.442 min at 254 nm, 3.453 min at 220 nm, m/e 429 (M + 1). |

Example 620

N-(2-(5-Methoxy-1H-indol-3-yl)ethyl)-3-(2,2,3,3,3-pentafluoropropoxy)benzylamine

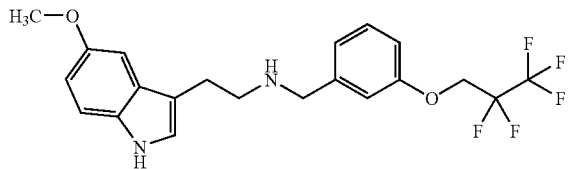

Combine amine (0.2 mmol) in dichloromethane (0.5 mL) and aldehyde (0.4 mmol) in dichloromethane (1 mL) and rotate. After 1 h, add sodium triacetoxyborohydride (82 mg, 0.8 mmol) as a stock solution in 1-methyl-2-pyrrolidinone (1 mL) and rotate. After overnight rotation, dilute the reaction mixture with 1 mL of methanol and directly apply to a 2 g SCX column. After thoroughly washing with methanol, elute the column with 2 M ammonia-methanol and concentrate the eluent to a residue, which was further purified by Gilson UV prep system. Compound was characterized using method 3. LCMS R$_f$ 4.823 min at 254 nm, 4.823 min at 220 nm, m/e 443 (M+1).

LC Method:

Method 3: (Shimadzu QP8000) 5-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared using a similar procedure as in Example 620:

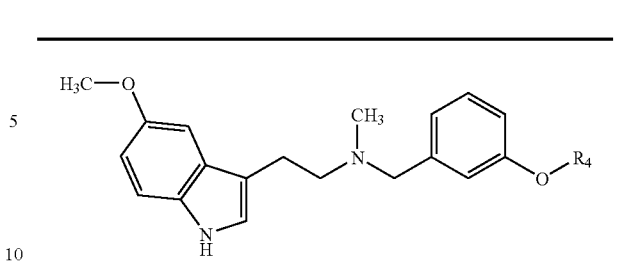

| No. | R⁴ | Data |
|---|---|---|
| 622 | 2,2,3,3-tetrafluoropropyl | Method 3: LCMS Rf 4.681 min at 254 nm, 4.692 min at 220 nm, m/e 425 (M + 1). |
| 623 | 2,2,2-trifluoroethyl | Method 3: LCMS Rf 4.639 min at 254 nm, 4.643 min at 220 nm, m/e 393 (M + 1). |

Example 624

N-(2-(6-Fluoro-1-methyl-1H-indol-3-yl)ethyl)-N-methyl-3-propoxybenzylamine

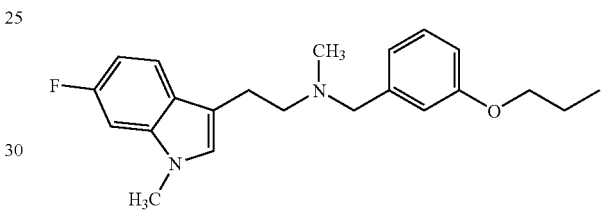

Combine N-methyl-N-(2-(6-fluoro-1-methyl-1H-indol-3-yl)ethylamine (0.2 mmol) in 1-methyl-2-pyrrolidinone (0.5 mL) and 3-propyloxybenzaldehyde (0.32 mmol) in dichloromethane (1 mL) and rotate. After overnight rotation, add sodium borohydride (1.0 mmol) as a stock solution in 1-methyl-2-pyrrolidinone (0.5 mL) and rotate. After rotation for 3 h, dilute the reaction mixture with 1 mL of 10% acetic acid/methanol, and directly apply the resulting solution to a 2 g SCX column. After thoroughly washing with methanol, elute the column with 2 M ammonia-methanol and concentrate the eluent to a residue, which was further purified by Gilson UV prep system.

LC method:

Method 1: (Shimadzu QP8000) 10-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared following a similar procedure as found in Example 624:

| | Z' | R₃ | R₄ | Data |
|---|---|---|---|---|
| 625 | 3-trifluoromethyl 4-fluoro | 4-CH₃ | propyl | Method 1: LCMS Rf 3.214 min at |

-continued

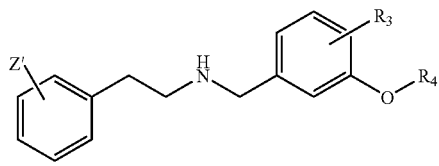

| No. | Z' | R₃ | R₄ | Data |
|---|---|---|---|---|
| | | | | 254 nm, 3.213 min at 220 nm, m/e 371 (M + 1). |
| 626 | 3-trifluoromethyl 4-fluoro | H | 3,3,3-tifluoropropyl | Method 1: LCMS Rf 3.042 min at 254 nm, 3.042 min at 220 nm, m/e 410 (M + 1). |
| 627 | 3-trifluoromethyl 4-fluoro | H | 2,2-difluoro ethyl | Method 1: LCMS Rf 2.828 min at 254 nm, 2.828 min at 220 nm, m/e 378 (M + 1). |
| 628 | 3-trifluoromethyl 4-fluoro | H | 2,2,3,3,3penta fluoro propyl | Method 1: LCMS Rf 3.196 min at 254 nm, 3.196 min at 220 nm, m/e 446 (M + 1). |
| 629 | 3-trifluoromethyl 4-fluoro | H | 2,2,2-trifluoroethyl | Method 1: LCMS Rf 2.984 min at 254 nm, 2.984 min at 220 nm, m/e 396 (M + 1). |
| 630 | 3-trifluoromethyl 4-fluoro | H | 3-fluoro propyl | Method 1: LCMS Rf 2.855 min at 254 nm, 2.855 min at 220 nm, m/e 374 (M + 1). |

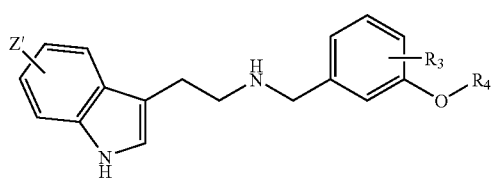

| No. | Z' | R₃ | R₄ | Data |
|---|---|---|---|---|
| 632 | 5-fluoro 6-chloro | 4-methyl | propyl | Method 1: LCMS Rf 3.141 min at 254 nm, 3.140 min at 220 nm, m/e 375 (M + 1). |
| 633 | 6-trifluoro methyl | H | 3,3,3-trifluoro propyl | Method 1: LCMS Rf 3.065 min at 254 nm, 3..066 min at 220 nm, m/e 431 (M + 1). |
| 634 | 5-fluoro 6-chloro | H | 3,3,3-trifluoro propyl | Method 1: LCMS Rf 2.977 min at 254 nm, 2.977 min at 220 nm, m/e 415 (M + 1). |
| 635 | 5,6-difluoro | H | 3,3,3-trifluoro propyl | Method 1: LCMS Rf 2.871 min at 254 nm, 2.872 min at 220 nm, m/e 399 (M + 1). |
| 636 | 6-trifluoro methyl | H | 3,3,3-trifluoro propyl | Method 1: LCMS Rf 3.065 min at 254 nm, 3..066 min at 220 nm, m/e 431 (M + 1). |
| 637 | 5-fluoro 6-chloro | H | 2,2-difluoro ethyl | Method 1: LCMS Rf 2.782 min at 254 nm, 2.782 min at 220 |

-continued

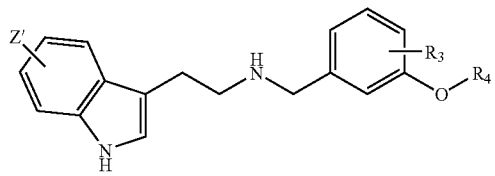

| No. | Z' | R₃ | R₄ | Data |
|---|---|---|---|---|
| | | | | nm, m/e 383 (M + 1). |
| 638 | 5,6-difluoro | H | 2,2-difluoro ethyl | Method 1: LCMS Rf 2.655 min at 254 nm, 2.655 min at 220 nm, m/e 367 (M + 1). |
| 639 | 6-trifluoro methyl | H | 2,2-difluoro ethyl | Method 1: LCMS Rf 2.876 min at 254 nm, 2.875 min at 220 nm, m/e 399 (M + 1). |
| 640 | 6-trifluoro methyl | H | 2,2,2 trifluoro ethyl | Method 1: LCMS Rf 3.009 min at 254 nm, 3.009 min at 220 nm, m/e 417 (M + 1). |
| 641 | 5-fluoro 6-chloro | H | 2,2,3,3,3-pentafluoro propyl | Method 1: LCMS Rf 3.135 min at 254 nm, 3.135 min at 220 nm, m/e 451 (M + 1). |
| 642 | 5,6-difluoro | H | 2,2,3,3,3-pentafluoro propyl | Method 1: LCMS Rf 3.027 min at 254 nm, 3.027 min at 220 nm, m/e 435 (M + 1). |
| 643 | 6-trifluoro methyl | H | 2,2,3,3,3-pentafluoro propyl | Method 1: LCMS Rf 3.202 min at 254 nm, 3.202 min at 220 nm, m/e 467 (M + 1). |
| 645 | 5,6-difluoro | H | 2,2,2-trifluoro ethyl | Method 1: LCMS Rf 2.982 min at 254 nm, 2.982 min at 220 nm, m/e 396 (M + 1). |
| 646 | 6-trifluoro methyl | H | 2,2,2-trifluoroethyl | Method 1: LCMS Rf 3.009 min at 254 nm, 3.009 min at 220 nm, m/e 417 (M + 1). |
| 647 | 5-fluoro 6-chloro | H | 3-fluoro propyl | Method 1: LCMS Rf 2.796 min at 254 nm, 2.796 min at 220 nm, m/e 379 (M + 1). |
| 648 | 5,6-difluoro | H | 3-fluoro propyl | Method 1: LCMS Rf 2.644 min at 254 nm, 2.646 min at 220 nm, m/e 363 (M + 1). |
| 649 A | 6-trifluoro methyl | H | 3-fluoro propyl | Method 1: LCMS Rf 2.900 min at 254 nm, 2.900 min at 220 nm, m/e 395 (M + 1). |

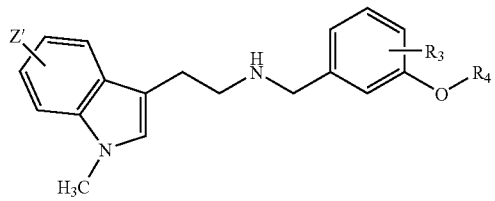

| No. | Z' | R₃ | R₄ | Data |
|---|---|---|---|---|
| 631 | 6-fluoro | 4-methyl | propyl | Method 1: LCMS Rf 3.152 min at 220 nm, m/e 355 (M + 1). |
| 633 | 6-fluoro | H | 3,3,3- | Method 1: LCMS Rf 2.949 |

-continued

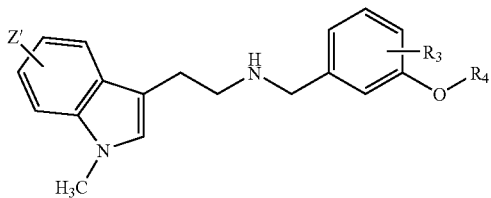

| No. | Z' | R₃ | R₄ | Data |
|-----|------|----|----|------|
| A   |      |    | trifluoro propyl | min at 254 nm, 2.953 min at 220 nm, m/e 395 (M + 1). |
| 640 A | 6-fluoro | H | 2,2,3,3,3-penta-fluoro propyl | Method 1: LCMS Rf 3.112 min at 254 nm, 3.117 min at 220 nm, m/e 431 (M + 1). |
| 649 | 6-fluoro | H | 2,2,2-trifluoro ethyl | Method 1: LCMS Rf 2.895 min at 254 nm, 2.898 min at 220 nm, m/e 381 (M + 1). |

Example 650

N-2-(3-chlorophenyl)ethyl-3-hydroxybenzylamine

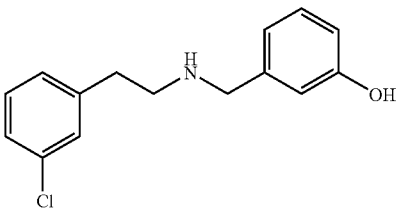

Combine 2-(3-chlorophenyl)ethylamine (1.866 gm; 15.28 mmol) and 3-hydroxybenzaldehyde (1.567 gm; 10.07 mmol) in 40 mL of methanol and stir at room temperature for 20 min and treat with sodium borohydride (0.950 gm; 25.1 mmol) in one portion. Stir the mixture at room temperature. After 15 h, add water (10 mL), and remove the methanol by rotary evaporation. Add to this slurry water (25 mL) and dichloromethane (50 mL), separate the layers and extract the aqueous layer with dichloromethane (50 mL). Wash the combined organic layers with saturated brine (3×), dry over MgSO₄, and concentrate to give the title compound.

Example 650A

N-t-Butoxycarbonyl-N-2-(3-chlorophenyl)ethyl-3-hydroxybenzylamine

Combine N-2-(3-chlorophenyl)ethyl-3-hydroxybenzylamine, dichloromethane (40 mL), and di-tert-butyl dicarbonate (1.556 gm; 7.131 mmol) and triethylamine (1.0 mL; 7.2 mmol). After 18 hours, pour into water (50 mL), separate the layers, and extract the aqueous layer with dichloromethane. Wash combined organic layers with water, dry over MgSO₄, and concentrate. Chromatograph on silica gel eluting with 5% ethyl acetate in hexanes to give the title compound.

Example 651

N-t-Butoxycarbonyl-N-2-(3-chlorophenyl)ethyl-3-propoxybenzylamine

Add a solution of 50% sodium hydroxide in water (0.8 mL) to a solution of N-t-butoxycarbonyl-N-2-(3-chlorophenyl) ethyl-3-hydroxybenzylamine (46.7 mg, 0.129 mmol), n-propyl iodide (0.17 gm. 1.00 mmol), and tetrabutylammonium bromide (18 mg, 0.057 mmol) in toluene (1 mL). Stir the mixture at 1200 rpm and heat at 50-54° C. After 64.5 hour pour the mixture into 5 mL of water, separate the phases and extract the aqueous phase twice with dichloromethane. Combine the organic phases and wash with saturated sodium bicarbonate solution, and then saturated brine, dry (MgSO₄), and concentrate to give a residue. Chromatograph the residue on silica gel to give the title compound: MS (ES+): m/e (M+1) 404. TLC (20% EtOAc in hexanes, $R_f$ 0.54).

Example 652

N-(2-3-Chlorophenyl)ethyl)-3-propoxybenzylamine

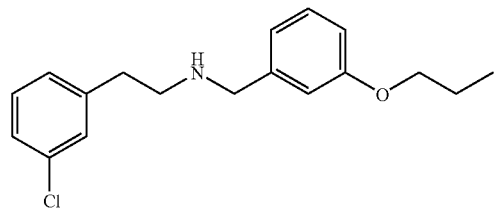

Add methanesulfonic acid (70 uL) to a solution of N-t-Butoxycarbonyl-N-2-(3-chlorophenyl)ethyl-3-propoxybenzylamine in dichloromethane (4 mL) and agitate the mixture for 3 hours at room temperature. Add 10% aqueous Na₂CO₃ (2 mL), separate the layers, and concentrate the organic layer in a nitrogen stream to give a residue. Dissolve the residue in 4 mL of 5% acetic acid in methanol and pass through a 1 gm SCX column, eluting with 1 M ammonia in methanol to give the title compound: MS (ES+): m/e (M+1). HPLC (10-90% water/acetonitrile over 7.5 min, Tr=4.490 min).

The following compounds were prepared by a similar procedure to Examples 651 and 652:

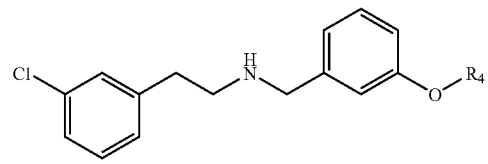

| No. | R₄ | Data |
|-----|-----|------|
| 654 | ethyl | Method 1: LCMS Rf 4.223 min at 254/220 nm; m/e 298.9 (M + 1) |
| 655 | butyl | Method 1: LCMS Rf 4.715 min at 254/220 nm; m/e 317.9 (M + 1) |
| 656 | hexyl | Method 1: LCMS Rf 5.137 min at 254/220 nm; m/e 354.9 (M + 1) |
| 658 | allyl | Method 1: LCMS Rf 4.373 min at 254/220 nm; m/e 301.9 (M + 1) |
| 660 | pyridin-2-ylmethyl | Method 1: LCMS Rf 3.547 min at 254/220 nm; m/e 352.9 (M + 1) |
| 661 | pyridin-3-ylmethyl | Method 1: LCMS Rf 3.487 min at 254/220 nm; m/e 352.9 (M + 1) |
| 662 | pyridin-4-ylmethyl | Method 1: LCMS Rf 3.455 min at 254/220 nm; m/e 352.9 (M + 1) |

Example 665

N-(2-(5-Methoxy-1-ethyl-1H-indol-3-yl ethyl)-N-ethyl-3-phenoxybenzylamine

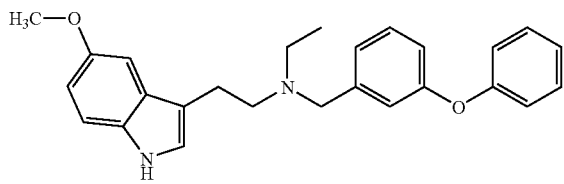

Add acetaldehyde (0.080 mL; 0.77 mmol) to a solution of N-(2-(5-methoxy-1H-indol-3-yl)ethyl)-3-phenoxybenzylamine (free base, 55.5 mg, 0.149 mmol) in dichloromethane (1 mL) followed by a suspension of sodium triacetoxyborohydride (64 mg; 0.30 mmol) in dichloromethane (1 mL). After 44 hours, quench by the addition of methanol (0.5 mL) and concentrate in a stream of nitrogen to give a residue. Dissolve the residue in 4 mL of 5% acetic acid in methanol and partially purify by passage through a 1 gm SCX column, eluting with 1 M ammonia in methanol to give a residue. Chromatograph the residue by preparative HPLC (C-18 column, flow rate of 20 ml/min, 5-90% water/acetonitrile over 12 min) to give the title compound: MS (ES+): m/e (M+1); HPLC: (10-90% water/acetonitrile-over 10 min, Tr=5.25 nm).

The following compounds were prepared following a similar procedure in Example 665:

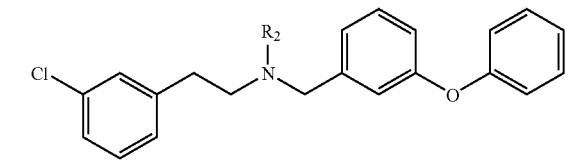

| No. | $R_2$ | Data |
|---|---|---|
| 666 | methyl | LC Method 2: Rf 5.12 min at 254/220 nm; m/e 351.9 (M + 1) |
| 667 | ethyl | LC Method 2: Rf 5.25 min at 254/220 nm; m/e 365.9 (M + 1) |

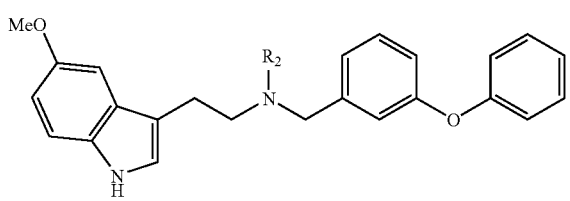

| No. | $R_2$ | Data |
|---|---|---|
| 668 | ethyl | LC Method 2: Rf 4.98 min at 254/220 nm; m/e 401.09 (M + 1) |

Example 670

3-Propoxybenzaldehyde

Combine 3-hydroxybenzaldehyde (7.50 gm; 61.4 mmol), n-propyl iodide (17.3 gm; 102 mmol), and potassium carbonate (16.90 gm; 122 mmol) in 2-butanone (100 mL) and reflux. After 17 h, allow the mixture to cool to room temperature, decant the solution and concentrate by rotary evaporation. Partition the residue between diethyl ether (150 mL) and water (150 mL), separate the layers and extract the aqueous layer with diethyl ether (2×100 mL). Combine organic layers and wash with water, 1 N NaOH, and then water, dry over $MgSO_4$, and concentrate to give a residue. Distill the residue to give the title compound: bp: 122-125° C. (15 mm); TLC (10% $Et_2O$/hexanes; $R_f$ 0.35).

Example 671

3-(3,3,3-Trifluoropropoxy)benzaldehyde

Cool a mixture of toluenesulfonyl chloride (7.43 gm; 39.0 mmol) and pyridine (50 mL) to 0° C., add 3,3,3-3,3,3-trifluoropropanol (2.23 gm; 19.5 mmol) and store the mixture at 3° C. After 48 hour, pour the reaction mixture into 350 mL of ice water and extract with diethyl ether (3×125 mL). Combine the organic layers and wash with 5 N HCl, water, saturated sodium bicarbonate solution, and brine, dry over $MgSO_4$, and concentrate to give 3,3,3-trifluoropropyl tosylate. The material was carried into the next step without purification.

Combine 3,3,3-trifluoropropyl tosylate (4.057 gm; 15.12 mmol), 3-hydroxybenzaldehyde (1.85 gm; 15.12 mmol), and $K_2CO_3$ (4.15 gm; 30.0 mmol) in DMF (80 mL) and heat at 100° C. After 18 hours, cool to room temperature, dilute with water (200 mL) and extract with dichloromethane (2×200 mL). Combine organic extracts and wash sequentially with water (100 mL), 0.1 M NaOH (2×100 mL), saturated sodium bicarbonate (100 mL) and saturated brine (100 mL), dry ($MgSO_4$), and concentrate. Chromatography on silica gel (0-20% ethyl acetate in hexane) to give the title product.

Example 672

3-(2-Fluoroethoxy)benzaldehyde

Combine 1-bromo-2-fluoroethane (4.575 g; 36.0 mmol), 3-hydroxybenzaldehyde (4.103 gm; 33.60 mmol), and $K_2CO_3$ (7.05 gm; 51.0 mmol) in 2-butanone (100 mL) and reflux. After 18 hour cool the mixture to ambient temperature, concentrate, and partition between 100 mL of water and 100 mL of dichloromethane. Separate the layers and extract the aqueous layer with dichloromethane (2×75 mL). Combine the organic layers and wash sequentially with brine (2×150 mL), 1 M NaOH (2×100 mL), $NaHCO_3$ (saturated, 100 mL), and brine (150

Example 673

N-(2-(5-Fluoro-1H-indol-3-yl)ethyl)-3-propoxybenzylamine

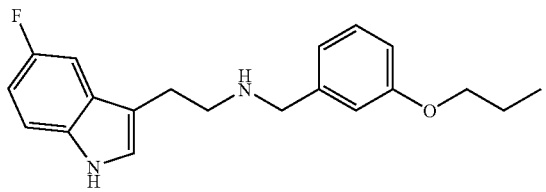

Combine 3-propoxybenzaldehyde (29.6 mg; 0.18 mmol) and 5-fluorotryptamine (14.2 mg; 0.080 mmol) in methanol (2 mL). Add a solution of sodium borohydride in diglyme (1 ml of a 0.5 M solution; 0.50 mmol) and agitate. After 63 h at room temperature concentrate in a stream of nitrogen. Dissolve the residue in methanol and add to a 1 gm SCX column previously rinsed pith 5% acetic acid in methanol. Elute the product from the SCX column with 1 M ammonia in methanol to give the title compound: MS (ES+): m/e (M+1); HPLC (10-90% water/acetonitrile over 10 min, Tr=4.08 min.

General LC Methods:

Method 1: (Shimadzu Class VP HPLC and Micromass Platform LC with HP1100 LC system) 10-90 in 7.5 min. Solvent A: water 0.1% trifluoroacetic acid, Solvent B: acetonitrile 0.1% trifluoroacetic acid. Column: C18 Metachem, monochrom 3 micron, 2.5×25.

Method 2: (Shimadzu Class VP HPLC and Micromass Platform LC with HP1100 LC system) 10-90 in 10 min. Solvent A: water 0.1% trifluoroacetic acid, Solvent B: acetonitrile 0.1% trifluoroacetic acid. Column: C18 Metachem, monochrom 3 micron, 2.5×25.

Method 3: (Waters Millennium HPLC and Micromass Platform LC with HP1100 LC system) 10-100 in 10 min. Solvent A: 0.1% trifluoroacetic acid, Solvent B: acetonitrile 0.08% trifluoroacetic acid. Column:YMC, 5 micron, 2.5×25.

Method 4: (Shimadzu QP8000) 10-90 in 4.5 min. Solvent A: water 0.1% trifluoroacetic acid, Solvent B: acetonitrile 0.1% trifluoroacetic acid. Column: C18 Metachem, monochrom 3 micron, 2.5×25.

The following compounds were prepared following a procedure following Example 673:

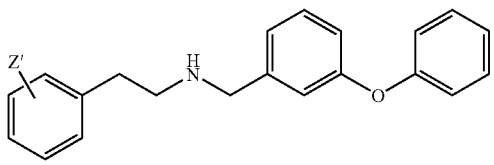

| No. | Z' | Data |
|---|---|---|
| 675 | 2-fluoro | LC Method 3: Rf 4.18 min at 254/220 nm; m/e 322.0 (M + 1) |
| 676 | 3-fluoro | LC Method 3: Rf 4.23 min at 254/220 nm; m/e 322.0 (M + 1) |
| 677 | 4-chloro | LC Method 3: Rf 4.48 min at 254/220 nm; m/e 337.9 (M + 1) |
| 678 | 4-hydroxy | LC Method 3: Rf 3.62 min at 254/220 nm; m/e 320.0 (M + 1) |
| 679 | 2-methoxy | LC Method 3: Rf 4.30 min at 254/220 nm; m/e 334.0 (M + 1) |
| 680 | 4-bromo 3-methoxy | LC Method 3: Rf 4.50 min at 254/220 nm; m/e 411.9 (M + 1) |
| 681 | 4-fluoro | LC Method 3: Rf 4.22 min at 254/220 nm; m/e 322.0 (M + 1) |
| 682 | 2-chloro | LC Method 3: Rf 4.36 min at 254/220 nm; m/e 338.0 (M + 1) |
| 683 | 4-bromo | LC Method 3: Rf 4.55 min at 254/220 nm; m/e 383.91 (M + 1) |
| 684 | 4-methyl | LC Method 3: Rf 4.42 min at 254/220 nm; m/e 318.0 (M + 1) |
| 685 | 3-methoxy | LC Method 3: Rf 4.19 min at 254/220 nm; m/e 334.0 (M + 1) |
| 686 | 4-methoxy | LC Method 3: Rf 4.15 min at 254/220 nm; m/e 334.0 (M + 1) |
| 687 | 2-ethoxy | LC Method 3: Rf 4.55 min at 254/220 nm; m/e 348.0 (M + 1) |
| 688 | 4-ethoxy | LC Method 3: Rf 4.43 min at 254/220 nm; m/e 348.0 (M + 1) |
| 689 | 4-phenoxy | LC Method 3: Rf 5.00 min at 254/220 nm; m/e 396.0 (M + 1) |
| 690 | 4-sulfonamide | LC Method 3: Rf 3.46 min at 254/220 nm; m/e 383.0 (M + 1) |
| 691 | 3,4-dichloro | LC Method 3: Rf 4.74 min at 254/220 nm; m/e 372.0 (M + 1) |
| 692 | 2,5-dichloro | LC Method 3: Rf 4.74 min at 254/220 nm; m/e 372.0 (M + 1) |
| 693 | 2,6-dichloro | LC Method 3: Rf 4.51 min at 254/220 nm; m/e 372.0 (M + 1) |
| 694 | 2,5-dimethoxy | LC Method 3: Rf 4.31 min at 254/220 nm; m/e 364.0 (M + 1) |
| 695 | 2,3-dimethoxy | LC Method 3: Rf 4.24 min at 254/220 nm; m/e 364.0 (M + 1) |
| 696 | 3,5-dimethoxy | LC Method 3: Rf 4.26 min at 254/220 nm; m/e 364.0 (M + 1) |
| 697 | 3-ethoxy-4-methoxy | LC Method 3: Rf 4.14 min at 254/220 nm; m/e 378.0 (M + 1) |

The following compounds were prepared following a procedure following Example 673:

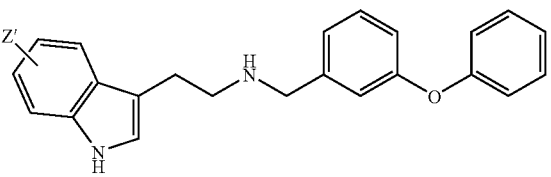

| No. | Z' | Data |
|---|---|---|
| 698 | 5-methyl | LC Method 4: Rf 2.852 min at 254/220 nm; m/e 357 (M + 1) |
| 699 | 5-chloro | LC Method 4: Rf 2.893 min at 254/220 nm; m/e 377 (M + 1) | mL), dried (MgSO$_4$), concentrate, and chromatograph on silica gel (0-25% diethyl ether in hexanes) to give the title compound.

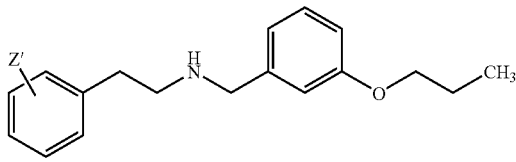

| No. | Z' | Data |
|---|---|---|
| 700 | 2-fluoro | LC Method 3: Rf 3.90 min at 254/220 nm; m/e 288.0 (M + 1) |
| 701 | 3-fluoro | LC Method 3: Rf 3.95 min at 254/220 nm; m/e 288.0 (M + 1) |
| 702 | 4-fluoro | LC Method 3: Rf 3.96 min at 254/220 nm; m/e 288.0 (M + 1) |
| 703 | 2-chloro | LC Method 3: Rf 4.23 min at 254/220 nm; m/e 303.9 (M + 1) |
| 704 | 4-chloro | LC Method 3: Rf 4.12 min at 254/220 nm; m/e 303.9 (M + 1) |
| 705 | 4-bromo | LC Method 3: Rf 4.33 min at 254/220 nm; m/e 347.9 (M + 1) |
| 706 | 4-methyl | LC Method 3: Rf 4.17 min at 254/220 nm; m/e 284.0 (M + 1) |
| 707 | 4-hydroxy | LC Method 3: Rf 3.26 min at 254/220 nm; m/e 286.0 (M + 1) |
| 708 | 2-methoxy | LC Method 3: Rf 4.03 min at 254/220 nm; m/e 300.0 (M + 1) |
| 709 | 3-methoxy | LC Method 3: Rf 3.91 min at 254/220 nm; m/e 300.0 (M + 1) |
| 710 | 4-methoxy | LC Method 3: Rf 3.91 min at 254/220 nm; m/e 300.0 (M + 1) |
| 711 | 3-ethoxy | LC Method 3: Rf 4.31 min at 254/220 nm; m/e 314.0 (M + 1) |
| 712 | 4-ethoxy | LC Method 3: Rf 4.14 min at 254/220 nm; m/e 314.0 (M + 1) |
| 713 | 4-phenoxy | LC Method 3: Rf 4.77 min at 254/220 nm; m/e 362.0 (M + 1) |
| 714 | 4-sulfonamide | LC Method 3: Rf 3.06 min at 254/220 nm; m/e 349.0 (M + 1) |
| 715 | 3,4-dichloro | LC Method 3: Rf 4.52 min at 254/220 nm; m/e 337.9 (M + 1) |
| 716 | 2,5-dichloro | LC Method 3: Rf 4.51 min at 254/220 nm; m/e 337.9 (M + 1) |
| 717 | 2,6-dichloro | LC Method 3: Rf 4.28 min at 254/220 nm; m/e 337.9 (M + 1) |
| 718 | 3,4-dimethoxy | LC Method 3: Rf 3.59 min at 254/220 nm; m/e 330.0 (M + 1) |
| 719 | 2,5-dimethoxy | LC Method 3: Rf 4.04 min at 254/220 nm; m/e 330.0 (M + 1) |
| 720 | 2,3-dimethoxy | LC Method 3: Rf 3.96 min at 254/220 nm; m/e 330.0 (M + 1) |
| 721 | 3,5-dimethoxy | LC Method 3: Rf 3.99 min at 254/220 nm; m/e 330.0 (M + 1) |
| 722 | 3-bromo 4-methoxy | LC Method 3: Rf 4.22 min at 254/220 nm; m/e 379.9 (M + 1) |
| 723 | 4-ethoxy-3-methoxy | LC Method 3: Rf 3.88 min at 254/220 nm; m/e 344.0 (M + 1) |
| 724 | 3-ethoxy-4-methoxy | LC Method 3: Rf 3.84 min at 254/220 nm; m/e 344.0 (M + 1) |

The following compounds were prepared following a procedure following Example 673:

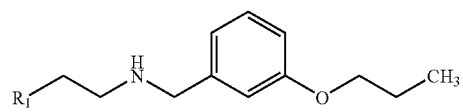

| No. | R₁ | Data |
|---|---|---|
| 725 | pyridine-2-yl | LC Method 3: Rf 2.38 min at 254/220 nm; m/e 271.0 (M + 1) |
| 726 | pyridin-3-yl | LC Method 3: Rf 2.25 min at 254/220 nm; m/e 271.0 (M + 1) |
| 727 | pyridin-4-yl | LC Method 3: Rf 2.21 min at 254/220 nm; m/e 271.0 (M + 1) |
| 729 | 7-methyl-1H-indol-3-yl | LC Method 3: Rf 4.19 min at 254/220 nm; m/e 323.0 (M + 1) |
| 730 | 6-methoxy-1H-indol-3-yl | LC Method 3: Rf 3.90 min at 254/220 nm; m/e 339.0 (M + 1) |
| 731 | thiophen-3-yl | LC Method 3: Rf 3.70 min at 254/220 nm; m/e 275.9 (M + 1) |
| 732 | 5-methyl-1H-indol-3-yl | LC Method 4: Rf 2.680 min at 254/220 nm; m/e 323 (M + 1) |
| 733 | 5-chloro-1H-indol-3-yl | LC Method 4: Rf 4.019 min at 254/220 nm; m/e 344 (M + 1) |

The following compounds were prepared following a procedure following Example 673:

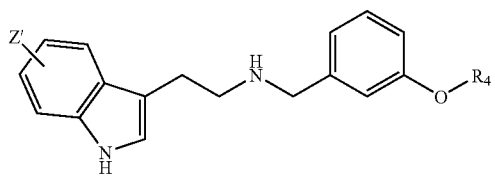

| No. | Z' | R4 | Data |
|---|---|---|---|
| 734 | 5-methyl | 2-fluoroethyl | LC Method 4: Rf 2.381 min at 254/220 nm; m/e 327 (M + 1) |
| 735 | 5-fluoro | 2-fluoroethyl | LC Method 4: Rf 2.300 min at 254/220 nm; m/e 331 (M + 1) |
| 736 | 5-methyl | 2,2-difluoroethyl | LC Method 4: Rf 2.520 min at 254/220 nm; m/e 345 (M + 1) |
| 737 | 5-fluoro | 2,2difluoroethyl | LC Method 4: Rf 2.445 min at 254/220 nm; m/e 349 (M + 1) |
| 738 | 5-chloro | 2,2-difluoroethyl | LC Method 4: Rf 2.598 min at 254/220 nm; m/e 365 (M + 1) |
| 739 | 5-fluoro | 4,4,4-trifluorobutyl | LC Method 4: Rf 3.017 min at 254/220 nm; m/e 395 (M + 1) |
| 740 | 5-fluoro | 2,2,2-trifluoroethyl | LC Method 4: Rf 2.7 87 min at 254/220 nm; m/e 367 (M + 1) |
| 741 | 5-methoxy | 2,2,2-triflurorethyl | LC Method 4: Rf 2.681 min at 254/220 nm; m/e 379 (M + 1) |
| 742 | 5-chloro | 4,4,4-trifluorobutyl | LC Method 4: Rf3.151 min at 254/220 nm; m/e 411 (M + 1) |
| 743 | 5-fluoro | 3-fluoropropyl | LC Method 4: Rf 2.475 min at 254/220 nm; m/e 345 (M + 1) |
| 744 | 5-methoxy | 3,3,3-trifluoropropyl | LC Method 4: Rf 2.889 min at 254/220 nm; m/e 393 (M + 1) |
| 745 | 5-chloro | 3-fluoropropyl | LC Method 4: Rf 2.628 min at 254/220 nm; m/e 361 (M + 1) |
| 746 | 5-fluoro | 2,2,3,3-tetrafluoropropyl | LC Method 4: Rf 2.680 min at 254/220 nm; m/e 399 (M + 1) |
| 747 | 5-methyl | 2,2,3,3-tetrafluoropropyl | LC Method 4: Rf 2.756 min at 254/220 nm; m/e 397 (M + 1) |
| 748 | 5-chloro | 2,2,3,3-tetrafluoropropyl | LC Method 4: Rf 2.820 min at 254/220 nm; m/e 417 (M + 1) |
| 750 | 5-fluoro | 2,2,3,3,3-pentafluoropropyl | LC Method 4: Rf 2.833 min at 254/220 nm; m/e 417 (M + 1) |
| 751 | 5-methyl | 2,2,3,3,3-pentafluoropropyl | LC Method 4: Rf 2.908 min at 254/220 nm; m/e 415 (M + 1) |
| 752 | 5-chloro | 2,2,3,3,3-pentafluoropropyl | LC Method 4: Rf 2.784 min at 254/220 nm; m/e 433 (M + 1) |
| 754 | 5-methyl | 3-fluoropropyl | LC Method 4: Rf 2.457 min at 254/220 nm; m/e 341 (M + 1) |
| 755 | 5-methoxy | 4,4,4-trifluorobutyl | EC Method 4: Rf 2.931 min at 254/220 nm; m/e 406 (M + 1) |
| 756 | 5-methoxy | 2,2,3,3-tetrafluoropropyl | LC Method 4: Rf 2.795 min at 254/220 nm; m/e 411 (M + 1) |
| 757 | 5-chloro | 2-fluoroethyl | LC Method 4: Rf 2.477 min at 254/220 nm; m/e 347 (M + 1) |

The following compounds were prepared following a procedure following Example 673:

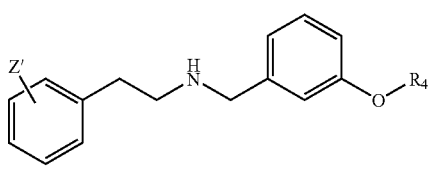

| No. | Z' | R4 | Data |
|---|---|---|---|
| 758 | 3-trifluoromethyl | 2,2,3,3-tetrafluoro propyl | LC Method 4: Rf 2.650 min at 254/220 nm; m/e 410 (M + 1) |
| 759 | 3-trifluoromethyl | 4,4,4-trifluoro butyl | LC Method 4: Rf 2.761 min at 254/220 nm; m/e 406 (M + 1) |

Example 760

3-Trifluoromethoxyphenethylamine

Combine nitromethane (1.8 g, 30 mmol), ethanol (4 mL) and 10 N NaOH (0.1 mL). Add 3-trifluoromethoxybenzaldehyde (5.0 g, 28.6 mmol) and stir. After 20 hours, pour into ethyl acetate, wash with water, dried over $Na_2SO_4$, filter, and concentrate to give a residue. Chromatograph the residue on silica gel to give 2-nitro-1-(3-trifluoroethoxyphenyl)ethanol: MS (M−1) 250; $^1$H NMR ($CDCl_3$) 7.45 (1 H, t, J=8.4 Hz), 7.36-7.30 (2 h, m), 7.24-7.20 (1 h, m), 5.51 (1 h, dt, J=8.8 and 4.0 Hz), 4.62-4.51 (2 H, m).

Combine 2-nitro-1-(3-trifluoroethoxyphenyl)ethanol (6.1 g, 24.2 mmol) and methanesulfonyl chloride (2.02 mL) in dichloromethane (50 mL) and cool in an ice-bath. Add dropwise, triethylamine (7.28 mL) while maintaining the temperature near 0° C. After 2 hours, pour into ethyl acetate, wash with water, dry with $Na_2SO_4$, filter, and then concentrate to residue. Chromatograph the residue on silica gel to give 3-(2- nitrovinyl)-1-trifluoroethoxybenzene: MS (MH+) 234; ¹H NMR (CDCl₃) 7.97 (1 H, d, J=13.6 Hz), 7.57 (1 H, d, J=13.6 Hz), 7.53-7.48 (2 H, m), 7.40-7.35 (2 H, m).

Combine 3-(2-nitrovinyl)-1-trifluoroethoxybenzene (3.0 g, 12.88 mmol) and methanol (50 mL) and concentrated HCl (5 mL) and hydrogenate at ambient temperature and 50 psi (340 kPa) in the presence of PtO₂ (0.6 g). After 5 hours, filter to the catalyst, dilute the filtrate with 1N HCl (50 mL) and wash with ethyl acetate. Separate the aqueous layer, neutralize with 2N NaOH (100 mL), extract with ether, dry with Na2SO4, filter and then concentrated to give the title compound which can be used without further purification. MS (MH+) 206; ¹H NMR (CDCl₃) 7.32 (1 H, t, J=7.6 Hz), 7.18-7.06 (3 H, m), 2.98 (2 H, t, J=7.2 Hz), 2.77 (2 H, t, J=7.2 Hz).

Example 761

N-(243-Trifluoromethoxyphenyl)ethyl-3-(2,2,2-trifluoroethyl)benzylamine

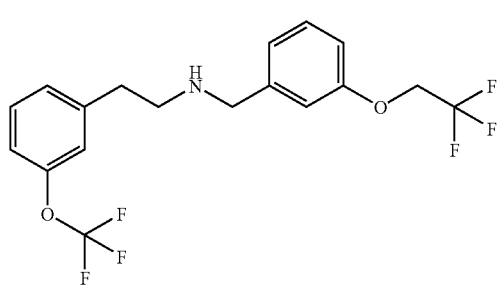

Combine trifluoromethoxyphenethylamine (400 mg, 1.95 mmol), and 3-(2-trifluoroethoxy)benzaldehyde (596 mg, 2.92 mmol), and 4 Å molecular sieve (4.0 g) in ethanol (30 mL) and reflux. after 4.5 hours, decant and treat of NaBH₄ (221 mg, 5.85 mmol). After 1 hour, evaporate and partition between 5N NaOH and dichloromethane. Separate the organic layer, dry over Na₂SO₄, filter, and concentrate to give a residue. Chromatograph the residue by HPLC to give the title compound. The HCl salt of the title compound gives a white solid: MS (MH+) 394; ¹H (DMSO-d6) 9.48 (2 H, br s), 7.48 (1H, t, J=7.6 Hz), 7.40 (1 H, t, J=8.0 Hz), 7.34 (1 H, s), 7.32-7.21 (4 H, m), 7.11 (1 H, dd, J=8.4 and 2.8 Hz), 4.79 (2 H, q, J=8.8 Hz), 4.15 (2 H, s), 3.22-3.12 (2 H, m), 3.11-3.04 (2 H, m).

Example 762

N-(2-(3-Trifluoromethoxyphenyl)ethyl)-3-(2,2,3,3-tetrafluoropropyl)benzylamine

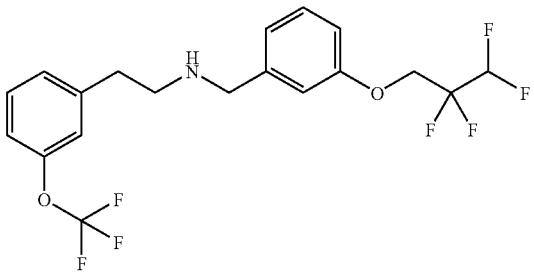

The method of Example 761 gives the title compound. The HCl salt of the title compound gives a white solid: MS (MH+) 426; ¹H (DMSO-d6) 9.42 (2 H, br s), 7.48 (1 H, t, J=7.6 Hz), 7.40 (1 H, t, J=7.6 Hz), 7.32-7.26 (3 H, m), 7.20 (1 H, d, J=7.2 Hz), 7.11 (1 H, dd, J=8.4 and 2.8 Hz), 6.70 (1 H, tt, J=52 and 5.2 Hz), 4.62 (2 H, t, J=13.6 Hz), 4.15 (2 H, s), 3.22-3.12 (2 H, m), 3.10-3.02 (2 H, M).

Example 763

N-(2(4,7-Difluoro-1H-indol-3-ylethyl)-3-(2,2,2-trifluoroethoxybenzylamine

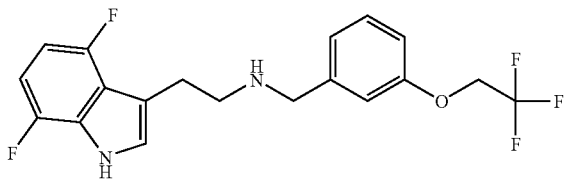

Combine 2-(4,7-difluoro-1H-indol-3-yl)ethylamine (483 mg, 2.46 mmol) and ethanol (45 mL) and stir. After 10 minutes treat with 3-(2,2,2-trifluoroethoxy)benzaldehyde (502 mg, 2.46 mmol) and anhydrous sodium sulfate (3.5 g) and stir under nitrogen and heat at 70° C. After 2 h., cool the reaction vacuum filter to remove the sodium sulfate and treat with sodium borohydride (279 mg, 7.38 mmol) in a 500 mL round bottom flask equipped with magnetic stirring. Allow the solution to stir for 2 hours at room temperature and then carefully treat with three drops of glacial acetic acid to quench the excess hydride. Remove the solvent in vacuo and re-dissolve the crude material in methanol. Purify by a 10 g SCX column by washing thoroughly with methanol, eluting with 2N ammonia in methanol, and concentrating in vacuo to give the title compound as a straw colored oil. Prepare the hydrochloride salt by dissolving the free base (800 mg, 2.08 mmol) in methanol (15 mL) and treating with a solution of ammonium chloride (111 mg, 2.08 mmol) in methanol (5 mL). Sonicate the mixture for 10 minutes before concentrating in vacuo to give a white solid. Recrystallize from ethyl acetate to obtain the hydrochloride salt of the title compound: mp 208.5-

210.0° C.; $^1$H NMR (400 MHz, dmso-d$_6$): 11.79 (br s, 1H), 9.21 (br s, 2H), 7.39 (t, 1H, J=7.8 Hz), 7.32 (d, 1H, J=2.0 Hz) 7.30 (s, 1H), 7.18 (d, 1H, J=8.0 Hz), 7.11 (dd, 1H, J=2.6, 8.2 Hz), 6.85-6.91 (m, 1H), 6.67-6.73 (m, 1H), 4.77 (q, 2H, J=8.8 Hz), 4.16 (s, 4H), 3.12-3.16 (m, 4H); MS (APCI): m/e 385.1 (M+1); CHN (for C$_{19}$H$_{17}$F$_5$N$_2$O.HCl) calcd: C, 54.23; H, 4.31; N, 6.66. found: C, 54.20; H, 4.30; N, 6.66.

Example 764

N-(2-(4,5,6,7-Tetrafluoro-1H-indol-3-yl)ethyl)-3-(2,2,2-trifluoroethoxy)benzylamine

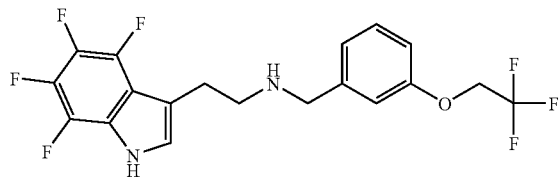

By a method similar to Example 763, using 2-(4,5,6,7-tetrafluoro-1H-indol-3-yl)ethylamine (484 mg, 2.08 mmol), ethanol (45 mL), 3-(2,2,2-trifluoroethoxy)benzaldehyde (425 mg, 2.08 mmol), anhydrous sodium sulfate (3.5 g) sodium borohydride (236 mg, 6.24 mmol) to give the free base of the title compound as a straw colored solid. Recrystallize from methylene chloride to obtain the title compound: mp 107.2-108.2° C. $^1$H NMR (400 MHz, dmso-d$_6$): 11.92 (br s, 1H), 7.32 (s, 2H), 6.95-6.99 (m, 2H), 6.87 (dd, 1H, J=2.4, 8.0 Hz) 4.68 (q, 2H, J=8.8 Hz), 3.70 (s, 2H), 2.88 (t, 2H, J=7.2 Hz) 2.75 (t, 2H, J=7.2 Hz). MS (ES+): m/e 421.1 (M+1). CHN (for C$_{19}$H$_{15}$F$_7$N$_2$O.1HCl.0.20H$_2$O) calcd: C, 53.83; H, 3.66; N, 6.61. found: C, 53.75; H, 3.33; N, 6.

Example 765

5-Trifluoromethyltryptamine

Combine 4-trifluoromethylaniline (32.2 g, 199.8 mmol) and dichloromethane (600 ml) in a 2 L round bottomed flask under nitrogen and cool to −70° C. Add tert-butylhypochlorite (protected from the light) (22.8 g, 210 mmol) in dichloromethane (150 ml) stir for a total of 45 nm in at about −65 to −70° C. At 35 min, add a solution of methylthioacetaldehyde dimethylacetal (30 g, 220.2 mmol) in dichloromethane (150 ml) is added. At 45 min at −70° C., add a solution of triethylamine (31.2 ml, 22.78 g, 225.1 mmol) in dichloromethane (80 ml). Bring the reaction mixture to room temperature. Wash with water and evaporate to dryness to give 72 g an oil.

Dissolve the oil in toluene (600 ml) and add triethylamine (60 ml). Heat to reflux. After 24 hours, evaporate the solvent and dry the residue under vacuum to yield 7a residue. Combine the residue, diethyl ether (600 ml), and 2N HCl (500 ml) and stir 24 hours at room temperature. Separate the aqueous layer and wash the organic layer successively with water and saturated NaHCO$_3$, dry over MgSO$_4$, filter, and evaporate to give a residue. Chromatograph on silica gel by eluting with cyclohexane-ethyl acetate (8/2, v/v), and pool the fractions containing the expected and evaporate to give 33.8 g of 2-methylthio-5-trifluoromethyl-1H-indole.

Combine moist Raney nickel (330 g), 2-methylthio-5-trifluoromethyl-1H-indole (33.8 g, 146.2 mmol) and absolute ethanol (850 ml) and stir. After 1.5 hours, filter the mixture through celite and wash the celite with ethanol (500 ml).

Evaporate the filtrate to dryness, add toluene (20 ml) and evaporate and dry to give 5-trifluoromethylindole: mp=55-60° C.

Dissolve 5-trifluoromethylindole (24 g, 130 mmol) in anhydrous diethyl ether (288 ml) and cool to 10° C. and add dropwise oxalyl chloride (12 ml) over 10 min. (exothermic reaction) and stir at room temperature for 4 h. Add and additional amount of oxalyl chloride (3 ml) and stir overnight at room temperature to give a solid. Collect the solid, wash with anhydrous diethyl ether (20 ml), and dry to give 2-(5-(trifluoromethyl-1H-indol-3-yl)-2-oxo-acetyl chloride.

Combine 2-(5-(trifluoromethyl-1H-indol-3-yl)-2-oxo-acetyl chloride an NH$_4$OH 1N (700 ml) and stir the suspension intensely. After 3 hours, collect the 2-(5-(trifluoromethyl)-1H-indol-3-yl)-2-oxo-acetamide.

Add LiAlH$_4$ (37.95 g, 1.00 mol) to THF (650 mL) under ice-bath cooling. Prepare a solution of AlCl$_3$ (50 g, 375 mmol) in THF (600 ml) and add dropwise to the LiAlH$_4$ solution over 45 min at 5-1° C. While maintaining the temperature at about 5° C., add a solution of 2-(5-(trifluoromethyl)-1H-indol-3-yl)-2-oxo-acetamide (21.4 g, 83.5 mmol) in THF (600 ml) and stir overnight with warning to ambient temperature. Cool the mixture with ice water and treat with 30% NaOH (100 ml) while maintaining the temperature at less than about 30° C. After stirring for about 30 minutes, filter, wash with THF (2 L), and evaporate the filtrate to give the title compound. Form of the HCl salt by dissolving the title compound in diethyl ether and adding of a solution of HCl in diethyl ether (until acidic). Collect the solid by filtration, wash with diethyl ether, and dry under reduced pressure to give the hydrochloride salt of the title compound.

The title compound can be further purified by basic extraction of the hydrochloride salt into ethyl acetate, drying over MgSO$_4$, filter, and evaporate to dryness followed by hydrochloride salt formation in diethyl ether.

Example 766

3-Propoxybenzaldehyde

Combine 3-hydroxybenzaldehyde (790 g), K$_2$CO$_3$, (1627 g) and DMF (8 L). Add 1-iodopropane (1000 g) and heat to 105° C. and stir for 4 h. Cool to about 50° C. and add water (15 L), continue cooling to about room temperature and add toluene (10 L). Separate the organic layer and extract the aqueous phase with toluene (2×10 L), combine organic phases and wash with NaOH 1N (2×5.8 L), concentrate the combined organic layers in vacuo to afford the title compound.

Example 777

N-(2-(5-Methoxy-1H-indol-3-yl)ethyl)-3-propoxybenzylamine

Combine 3-propoxybenzaldehyde (14.05 g, 0.0856 mole) and 5-methoxytryptamine (13.64 g, 0.0717 mole) in 390 mL absolute EtOH. Add molecular sieves (19.2 g) and heat the suspension to reflux. After 4 hours, cool to room temperature and add NaBH$_4$ (37.32 g, 0.2146 mole) in 3 portions. Stir the mixture for 1 hour at room temperature, filter, evaporate the filtrate to a mass of about 100 g, add water and dichloromethane. After separation, wash the aqueous phase with dichloromethane, combine the organic layers, dry over MgSO$_4$, filter, evaporate the solvent in vacuo to afford the title compound.

Combine the title compound and isopropanol (250 mL) and slowly add a solution of HCl in EtOH (33 ml, 2.5N). Heat to reflux and stir for 30 min. Cool to room temperature and stir for 2 h to give a solid. collect the solid by filtration, wash isopropanol, and dry to give the hydrochloride salt of the title compound.

Example 778

2,2,3,3,3-Pentafluoropropyl tosylate

Combine 2,2,3,3,3-pentafluoropropan-1-ol (9.7 ml) and pyridine. Cool to between 0° C. and 10° C. and add portionwise the p-toluenesulfonylchloride (6.2 g) and stir with warming to room temperature. After 3 hours at room temperature, pour the reaction mixture into ice water and stir for 30 min to give a solid. Filter the solid, wash with water, and dry to give of the title compound.

Example 779

3,3,3-Trifluoro-propyl tosylate

Add 3,3,3-trifluoropropan-1-ol (618 ml) and pyridine (224 ml). Cool to between 0° C. and 10° C. and add portion-wise p-toluenesulfonylchloride (147 g). Allow to warm to ambient temperature and stir overnight. Add HCl 0.5N (1.6 L), extract with ethyl acetate, combine the organic layers, dry over MgSO$_4$, filter, and evaporate to give the title compound.

Example 780

6-Fluorotryptamine

Add dropwise 422 mL of glacial acetic acid to 40% aqueous dimethylamine (408 mL) over 40 minutes while maintaining the temperature below about 15° C. Cool to 0° C. After stirring for 20 minutes at 0° C., slowly add 37% aqueous formaldehyde (289 mL, 1.3 eq.) over about 15 minutes. Add 6-fluoroindole (400 g, 2.96 mol, 1 eq.) in four portions over about 15 minutes. After 30 minutes, divide the reaction mixture into two portions. To one portion, slowly 1149 g (75% of total mass) over 30 minutes to 3 L of 10% NaOH and stir at room temperature. After 18 hours, collect the solid that forms, wash three times with 200 mL of water, dry by suction to give wet 3-(N,N-dimethylaminomethyl)-6-fluoroindole.

Dilute another portion of the reaction mixture (383 g, 25% of total mass) with aqueous NaOH till pH 12-13 to give a solid. After 30 minutes, collect the solid by filtration, wash with water, dry at 50° C. overnight to give 3-(N,N-dimethylaminomethyl)-6-fluoroindole.

Combine KCN (50.8 g, 0.78 mol), 3-(N,N-dimethylaminomethyl)-6-fluoroindole (100 g, 0.52 mol), DMF (400 mL) and water (200 mL). Heat to reflux. Evolution of gas begins at about 70° C. Maintain the reflux for 4 hours. Cool the reaction mixture to room temperature, dilute with water and toluene and stir for 10 minutes. Decant the organic layer and wash successively with of saturated aqueous sodium bicarbonate and of 2M aqueous hydrochloric acid. Concentrate to dryness the organic layer to give 2-(6-fluoro-1H-indol-3-yl)acetonitrile.

Combine 2-(6-fluoro-1H-indol-3-yl)acetonitrile (165 g, 0.925 mol) and THF (1.32 L). Slowly add 1M solution of BH$_3$ (2.042 L, 1,832 Kg, 0.131 mol) in THF over about 40 minutes. When the addition is complete, heat to reflux within 1 hour. After 1 hour at reflux, cool to room temperature and the reaction mixture, over about 25 minutes, to a well-stirred 15% aqueous solution of NaOH (1.9 L, 9.5 mol). After addition, slowly and gradually heat to 50° C. After 1 hour, heat 60° C. After 30 minutes, heat to reflux for 1 hour. Cool to room temperature and stir overnight, decant the alkaline aqueous layer and replace by water. Heat to 30° C. under a pressure of 200 mbars in order to distill the THF until about 2.5 kg of distilate is removed. Extract the mixture with dichloromethane. Slowly add to the combined organic layers over a 25 minutes a mixture of 37% aqueous HCl (143 g) and water (220 g) and stir to give a solid. After 1 hour, collect the solid by filtration, wash with of dichloromethane, aid dry overnight to afford of the hydrochloride salt of the title compound.

Combine 6-fluorotrytamine hydrochloride (100 g, 0.437 mol), 2% w/w NaOH (2.5 kg), and dichloromethane (1.5 L) and stir. After 15 minutes, decant the organic layer, extract the aqueous layer with dichloromethane, combine organic layers, and concentrate to give a residue. Combine the residue and isopropanol and evaporate in vacuo to give the title compound.

Example 782

N-(2-(6-Fluoro-1H-indol-3-yl)ethyl)-3-(2,2,3,3-tetrafluoropropyl)benzylamine

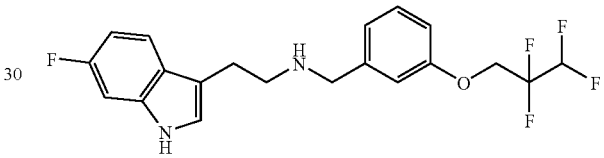

Combine isopropanol (500 g), 2,2,3,3-tetrafluoropropylbenzaldehyde (116.8 g), and 6-fluorotryptamine (1.15 equiv.). Heat to reflux over about 1.5 hour. After 30 minutes at the reflux, distill and over 30 minutes collect about 380 g of distillate. Cool the reaction mixture to 50° C. and add NaBH$_4$ (19.71 g) in one portion. After 1 hour at 50° C., slowly add water over 15 minutes and allow the resulting solution to cool to room temperature overnight. Distill the isopropanol under reduced pressure to give a residue and extract with dichloromethane, combine organic layers, and treat with 1N aqueous HCl (650 mL) to give a solid. Stir the heavy suspension for 2 hours at 20-25° C. Collect the solid by filtration, wash with dichloromethane and dry at 50° C. under vacuum overnight to afford title compound.

Example 783A 3-(2,2,2-Trifluoroethoxy)benzaldehyde

Combine 3-hydroxybenzaldehyde (134.3 g), potassium carbonate (304.0 g), 2,2,2-trifluoroethyl p-toluenesulfonate (293.6 g) and dimethylformamide (2 L). Heat the mixture at 90° C. After 15 hours, cool to room temperature, pour on ice-water, and extract with dichloromethane. Combine the organic layers, wash with 1N sodium hydroxide, and then with water. Dry the organic phase over magnesium sulfate, filter, and concentrate to a residue. Dissolve residue in toluene (200 ml), Chromatograph on silica gel eluting sequentially with toluene and then ethyl acetate to give a residue. Distill the reside under reduced pressure using a Claisen flask equipped with a Vigreux column gives title compound: bp 0.8 mm Hg, 84-85° C. Redistilling some fractions using a Claisen flask equipped with a Vigreux column and subsequently an adiabatic column filled with Rasching rings gives title compound: bp 0.9-1.0 mm Hg, 74-76° C.

Example 783B 3-(2,2,3,3-Tetrafluoropropoxy)benzaldehyde

Combine 3-(2,2,3,3-tetrafluoropropoxy)tosylate (200 g, 0.664 mol), 3-hydroxybenzaldehyde (101.7 g, 0.833 mol), dimethylformamide (1.5 L) and powdered potassium carbonate (192 g). Heat under stirring at 92° C. for about 22 h. Cool the reaction mixture to 40° C., pour over ice-water and extract with ethyl acetate. Combine organic phases, wash with 1 N sodium hydroxide (1 L and 0.5 L) and then a solution of saturated sodium hydrogen carbonate, dry over magnesium sulfate, filter, evaporate to dryness to provide a oily residue. Distill the oily residue under reduced pressure in a Claisen flask to give a first fraction of the title compound: bp 108-110° C. under 0.4-0.5 mmHg and a second fraction at 110-111° C. under 0.4-0.5 mmHg.

Example 784

3-(2,2,3,3-Tetrafluoropropoxy)benzaldehyde Combine 3-(2,2,3,3-tetrafluoropropoxy)tosylate (5.72 g, 17.2 mmol), 3-hydroxybenzaldehyde (2.44 g, 20.0 mmol), dimethylformamide (36 ml) and powdered potassium carbonate (3.03 g) and heat at 110° C. for 10 h. Cool to 20° C. Pass through a bed of aluminium-oxide-90 (57.2 g, 70-230 mesh, grade II-III, Brockmann: Merck # 1.01097) and elute with toluene (120 ml). Wash the eluted organic phase with 1N HCl (36 ml) and then water. Evaporate the organic layer under reduced pressure to give the title compound.

Example 785

2-(5-Chloro-1H-Indol-3-yl)-2-oxo-acetyl chloride

Combine 5-chloroindole (20 g, 0.13 mole) and dibutyl ether (230 mL) and cool to 5° C. and slowly add the oxalyl chloride (20.08 g, 0.16 mole) over 15 min while maintaining the temperature between 5° C. and 10° C. Warm to room temperature and stir for 1 hour to give a solid. Cool to 5° C. and stir for 15 minutes, collect the solid by filtration, wash with dibutyl ether, and dry under vacuum to give the title compound.

Example 786

(2-(5-Chloro-1H-Indol-3-yl)-2-oxoacetamide

Combine 2-(5-chloro-1H-indol-3-yl)-oxo-acetyl chloride (28.9 g, 0.12 mole) and NH$_4$OH 1N solution (720 ml) to give a suspension. After 18 hours, filter, wash with water, and dry under vacuum to give the title compound.

Example 787

5-Chlorotryptamine

Cool to 5° C., a suspension of LiAlH$_4$ (40.97 g) in THF (700 ml). Add a solution of AlCl$_3$ (53.9 g, 0.40 mole) to THF (645 ml) over about 30 minutes while maintaining the temperature at about 5° C. and 10° C. Add (2-(5-chloro-1H-Indol-3-yl)-2-oxo-acetamide (20 g, 0.09 mole) in THF (900 ml) while maintaining the temperature at between 5° C. and 7.5° C. When the addition is complete warm to room temperature. Stir overnight and then cool to 7° C. and slowly add a solution of NaOH 50% (342 g, 4.28 mol). After stirring for about 1 hour, add anhydrous Na$_2$SO$_4$ (30 g) and filter the suspension on a celite bed. Evaporate the filtrate to dryness to give an oil. Combine the and Et$_2$O (500 mL) and add a solution of Et$_2$O/HCl 4.5N (15 mL) at room temperature to give a solid. Stir the suspension at room temperature for 1 hour, filter, and wash with 50 mL Et$_2$O, dry under vacuum at 50° C. to give the hydrochloride of the title compound.

Add 5-chlorotryptamine hydrochloride (15 g, 0.06 mole) water (150 ml), NaOH 1N (75 ml), and dichloromethane (350 mL). Stir the mixture at room temperature for 30 minutes, and separate the phases. Wash the aqueous phase with dichloromethane, combine the organic phases, dry over MgSO$_4$, filter, and evaporate to dryness under vacuum to give the title compound.

Example 789

N-(5-Chloro-1H-indol-3-yl)ethyl)-3-(2,2,3,3-tetrafluoro-propoxy)benzylamine

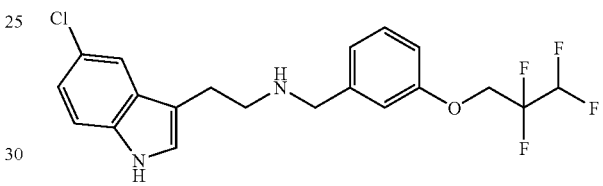

Combine 5-chlorotryptamine (12.1 g, 0.0621 mol) and 3-(2,2,3,3-tetrafluoropropoxybenzaldehyde (17.6 g, 0.0621 mole) in EtOH (340 mL). Add molecular sieves and heat to reflux and stir for 4 h. Cool the mixture to room temperature and add NaBH$_4$ (7 g, 0.1876 mol) in 3 portions. Stir the for 1 h at room temperature. Filter the solid and evaporate the filtrate to a weight of about 90 g, add water, and extract with dichloromethane. Dry the combined organic layers over MgSO$_4$, filter, and remove the solvent under reduced pressure to afford the title compound.

Combine the title compound (27.6 g) and isopropanol (300 mL). Add a solution of oxalic acid (6 g) in isopropanol (60 mL) to give a suspension. Heat the suspension to reflux and stir for 30 nm in and then cool to room temperature. Stir for 1 hour at room temperature. collect the solid by filtration, wash with isopropanol, and dry under vacuum to afford the oxalate of the title compound.

Example 790

N-2-(5-Chloro-1H-indol-3-yl)ethyl)-3-(2,2,3,3-tetrafluoro-propoxy)benzylamine L-tartaric salt Combine N-2-(5-chloro-1H-indol-3-yl)ethyl)-(3-(2,2,3,3-tetrafluoropropoxy)benzylamine oxalic acid salt and dichloromethane (700 mL) and add NaOH 1N (150 mL), water (450 mL) and MeOH (190 mL). Stir the mixture for 1 h at room temperature. Separate the layers. Add water (200 mL) to the aqueous phase and extract with dichloromethane, combine the organic layers, dry over MgSO$_4$, filter, and evaporate under vacuum to afford 19.4 g of N-2-(5-chloro-1H-indol-3-yl)ethyl)-3-(2,2,3,3-tetrafluoropropoxy)benzylamine.

Combine N-2-(5-chloro-1H-indol-3-yl)ethyl)-3-(2,2,3,3-tetrafluoropropoxy)benzylamine (19.4 g) in isopropanol (125 mL) and warm to dissolve. Add a solution of L-tartaric acid (7.02 g) in isopropanol (70 mL). Add seeding crystals and stir to give a solid. After 2.5 hours, collect the solid by filtration, wash with isopropanol, and dry under vacuum at 45° C. to afford the title compound.

By the method of Example 221 the following compounds were prepared, isolated as the maleate except where noted;

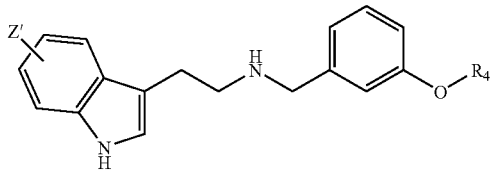

| No. | Z' | R$_4$ | Data |
|---|---|---|---|
| 791 | 6-bromo | 2,2,3,3-tetrafluoropropyl | mp 162-164° C. Analysis for $C_{24}H_{23}BrF_4N_2O_5$: Calcd: C, 50.10; H, 4.03; N, 4.87; found: C, 50.24; H, 4.02; N, 4.87. |
| 792 | 6-bromo | 2,2,2-trifluoroethyl | mp 168-171° C. Analysis for $C_{23H22}BrF_3N_2O_5$: Calcd: C, 50.84; H, 4.08; N, 5.16; found: C, 51.02; H, 4.13; N, 5.21. |
| 793 | 6-methanesulfonyl | 2,2,3,3-tetrafluoropropyl | mp 233-235° C. MS (ACPI): m/e 459.1 (M + 1). Analysis for $C_{21}H_{23}ClF_4N_2O_3S$: Calcd: C, 50.96; H, 4.68, N, 5.66; found: C, 50.87; H, 4.65; N, 5.64. (isolated as the hydrochloride) |
| 794 | 6-methanesulfonyl | 2,2,2-trifluoroethyl | mp 234-236° C. MS (ACPI): m/e 427.0 (M + 1). Analysis for $C_{20}H_{22}ClF_3N_2O_3S$: Calcd: C, 51.89; H, 4.79; N, 6.05; found: C, 51.84; H, 4.79; N, 6.10. (isolated as the hydrochloride) |
| 795 | 6-benzenesulfonyl | 2,2,3,3-tetrafluoropropyl | mp 213-215° C. MS (ACPI): m/e 521.0 (M + 1). Analysis for $C_{26}H_{25}ClF_4N_2O_3S$: Calcd: C, 56.07; H, 4.52; N, 5.03; found: C, 55.81; H, 4.66; N, 4.96. (isolated as the hydrochloride) |
| 796 | 6-benzenesulfonyl | 2,2,2-trifluoroethyl | mp 231-233.5° C. MS (ACPD: m/e 489.0 (M + 1). Analysis for $C_{25}H_{24}ClF_3N_2O_3S$: Calcd: C, 57.20; H, 4.61; N, 5.34; found: C, 56.98; H, 4.63; N, 5.21. (isolated as the hydrochloride) |

Example 799

6-Methanesulfonyl-1H-indole

Dissolve 6-Methanesulfonyl-indol-1-ol (5.0 g, 23.7 mmol) in triethyl phosphite (35 ml) and heat at 160° for 5 hours. Cool the solution to ambient temperature and dilute with diethyl ether. Wash the ether solution with brine and water followed by drying (sodium sulfate) and reducing to residue. Crystallize the residue from warm ethyl acetate to give the title compound as colorless cubes: mp 149-152° C. MS (ACPI): m/e 196.0 (M+1). Analysis for $C_9H_9NO_2S$: Calcd: C, 55.37; H, 4.65; N, 7.17. found: C, 55.14; H, 4.71; N, 7.20.

Example 800

6-Benzenesulfonyl-1H-indole

Dissolve 6-Bromoindole (6.0 g, 30.6 mmol) in THF (100 ml) and cool the mixture to −10°. Slowly add 60% NaH in mineral oil (3.67 g). After 1 hour, add triisopropylsilyltrifluoromethane sulfonate (9.9 ml, 36.7 mmol) slowly, remove the cooling bath, and stir for 24 hours. Quench excess NaH with ice and remove the THF under vacuum. Dilute the remaining residue with water and extract with dichloromethane. Combine, wash (brine), dry (sodium sulfate), and reduce the extracts to residue. Purify the residue on silica gel using 60% hexanes/dichloromethane to give a yellow oil.

Cool a solution of 6-bromo-1-triisopropylsilanyl-1H-indole (5.5 g, 15.7 mmol) in 100 mL anhydrous THF to −78° C. under nitrogen and treat with 1.7 M t-butyl lithium (20.5 mL, 34.5 mmol) while keeping the temperature at −78° C. After the addition, slowly add phenylsulfonyl fluoride (2.1 ml, 17.3 mmol) and stir for 30 minutes at −78° C. Warm the mixture to ambient temperature and stir for 1 hour. Quench excess t-butyl lithium with ice and dilute the mixture with water followed by extraction with ethyl acetate. Combine, wash (brine), dry (sodium sulfate), and reduce the extracts to residue. Purify the residue on silica gel using 50% hexanes/dichloromethane to give the product as a white solid.

Dissolve the resulting white solid in THF (50 ml) and treat the solution with 1 M tetrabutylammonium fluoride (18.1 mL) and 1 M boric acid (18.1 ml). After stirring for 1.5 hours at ambient temperature, dilute the mixture with water and extract with ethyl acetate. Combine, wash (brine), dry (sodium sulfate), and reduce the extracts to residue. Purify the residue on silica gel using 1% methanol/dichloromethane to give the title compound as a white solid: mp 141-144° C. MS (ACPI): m/e 258.0 (M+1). Analysis for $C_{14}H NO_2S$: Calcd: C, 65.35; H, 4.31; N, 5.44. found: C, 64.99; H, 4.31; N, 5.39.

By the method of Example 440 the following compounds were prepared and isolated as the hydrochloride except where noted:

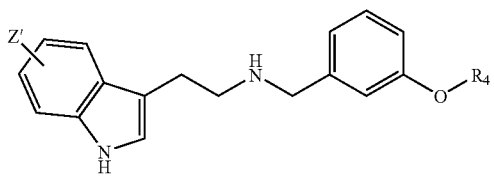

| No. | Z' | R4 | Data |
|-----|-----|-----|------|
| 802 | 7-Chloro | 2,2,3,3-tetrafluoropropyl | ISMS 415 (M + 1); $^1$H NMR (DMSO-$d_6$-HCl salt) 11.3 (bs, 1 H), 9.4 (bs, 2 H), 7.6-7.5 (m, 1 H), 7.45-7.3 (m, 3 H), 7.25-6.95 (m, 4 H), 6.9-6.5 (m, 1 H), 4.7-4.5 (m, 2 H), 4.2 (bs, 2 H), 3.25 (bs, 4 H) |
| 803 | 6-Methoxy | 2,2,3,3-tetrafluoropropyl | $^1$H NMR (CDCl$_3$-freebase) 7.99 (bs, 1 H), 7.47-7.44 (d, 1 H), 7.23-7.19 (m, 1 H), 6.94-6.92 (d, 1 H), 6.89-6.88 (m, 1 H), 6.83-6.82 (m, 2 H), 6.79-6.75 (m, 2 H), 6.19-5.90 (m, 1 H), 4.29-4.22 (m, 2 H), 3.82 (s, 3 H), 3.78 (m, 2 H), 2.95 (s, 4 H), no N—H observed |

By the method of Example 270 the following compounds were prepared, isolated as the maleate except where noted;

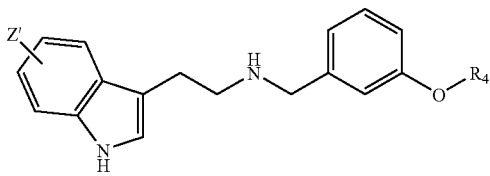

| No. | Z' | R4 | Data |
|-----|-----|-----|------|
| 809 | 5-(4-fluorophenyl) | phenyl | ISMS 437 (M + 1); $C_{29}H_{26}FClN_2O$~0.2 H2O: calcd: C, 73.08; H, 5.58; N, 5.88; found: C, 72.99; 11, 5.38; N, 5.83 |

Example 811

N-(2-(5-Methoxy-1H-indol-3-yl)-ethyl)-(3-(3,3,3-trifluoropropoxy)benzyl)amine

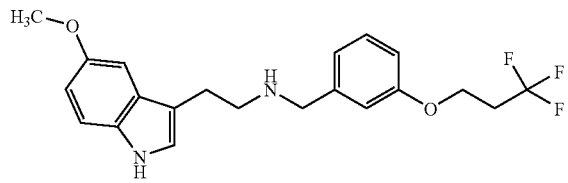

Combine 350 mg (1.8 mmol) 5-methoxytryptamine, 401 mg 3-trifluoropropoxybenzaldehyde (1.8 mmol) and 4 g 4A molecular sieves in 35 mL EtOH and reflux overnight. Decant the liquid into a separate flask and treat with 209 mg (5.5 mmol) NaBH$_4$. Stir the reaction at ambient temperature for 1 hour. Concentrate under vacuum, and partition between 50 mL 1 N NaOH and 25 mL dichloromethane. Extract the aqueous layer with 25 ml dichloromethane and combine the organic layers and concentrate to dryness. Purify the resulting oil by radial chromatography (SiO$_2$; 1% MeOH in CHCl$_3$ mixed with conc. NH$_4$OH) to afford 705 mg (1.8 mmol; 100%) of the desired compound as an oil. Conversion to it's HCl salt by stirring a solution of the compound in 50 mL 50/50 THF/EtOH with 1 g polyvinyl pyridine hydrochloride overnight, filtering and concentrating to a solid. Recrystallize the product from EtOAc: Analysis for $C_{21}H_{23}F_3N_2O_2$·HCl: calcd: C, 58.81; H, 5.64; N, 6.53. found: C, 58.42; H, 5.44; N, 6.51. ISMS 393 (M+1).

By the method of Example 811 the following compounds were prepared, isolated as the hydrochloride except where noted:

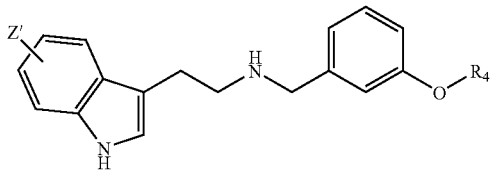

| No. | Z' | R₄ | Data |
|---|---|---|---|
| 812 | 5-fluoro | 3,3,3-trifluoro propyl | Analysis for $C_{20}H_{20}F_4N_2O \cdot HCl$: calcd: C, 57.63; H, 5.08; N, 6.72; found: C, 57.49; H, 5.04; N, 6.76; ISMS 381 (M + 1) |
| 814 | 5-bromo. | phenyl | Analysis for $C_{23}H_{21}BrN_2O \cdot HCl \cdot 0.5\ H_2O$: calcd: C, 59.18; H, 4.97; N, 6.00; found: C, 59.18; H, 4.80; N, 5.92 ISMS 422 (M + 1) |
| 815 | 5-bromo | 2,2,3,3-tetrafluoro propyl | Analysis for $C_{20}H_{19}BrF_4N_2O \cdot HCl$: calcd: C, 48.46; H, 4.07; N, 5.65; found: C, 48.39; H, 3.95; N, 5.55; ISMS 459 (M+) |
| 816 | 5-bromo | 2,2,3,3,3-pentafluoro propyl | Analysis for $C_{20}H_{18}BrF_5N_2O \cdot HCl$: calcd: C, 46.76; H, 3.73; N, 5.45; found: C, 46.47; H, 3.67; N, 5.46; ISMS 478 (M + 1) |
| 817 | 5-$SO_2CH_3$ | phenyl | Analysis for $C_{20}H_{18}BrF_5N_2O \cdot HCl \cdot 0.5$ HHD $2O \cdot 0.4\ C_7H_8$: calcd: C, 64.01; H, 5.85; N, 5.57; found: C, 64.09; H, 5.64; N, 5.48 ISMS 421 (M + 1) |
| 818 | 5-cyano | phenyl | Analysis for $C_{24}H_{21}N_3O \cdot HCl \cdot 0.3\ H_2O$: calcd: C, 70.42; H, 5.57; N, 10.27; found: C, 70.55; H, 5.41; N, 10.25 ISMS 368 (M + 1) |
| 819 | 5-carboxylic acid methyl ester | phenyl | Analysis for $C_{25}H_{24}N_2O_3 \cdot HCl \cdot 0.3\ H_2O$: calcd: C, 68.04; H, 5.62; N, 6.35; found: C, 68.06; H, 5.64; N, 6.43 ISMS 401 (M + 1) |
| 820 | 5-carboxylic acid methyl ester | 2,2,2-trifluoroethyl | Analysis for $C_{21}H_{21}F_3N_2O_3 \cdot HCl \cdot 0.1\ H_2O$: calcd: C, 56.72; H, 5.03; N, 6.30; found: C, 56.46; H, 4.77; N, 6.04 ISMS 407 (M + 1) |
| 821 | 5-carboxylic acid amide | phenyl | ISMS 385 (M+); Analysis for $C_{24}H_{23}N_3O_2 \cdot HCl \cdot 0.9\ H_2O \cdot 0.1\ C_7H_8$: calcd: C, 66.32; H, 5.99; N, 9.39; found: C, 66.07; H, 5.68; N, 9.01; $^1$H NMR (Free base $CDCl_3$) δ 8.56 (s, 1H), 8.13 (s, 1 H), 7.64-7.62 (m, 1 H), 7.33-7.22 (m, 4 H), 7.10-6.94 (m, 6 H), 6.87-6.84 (m, 1 H), 6.2 (bs, 1 H), 5.8 (bs, 12 H), 3.77 (s, 2 H), 2.99-2.94 (m, 4 H), 1.7 (bs, 1 H) |

Example 825

N-2-(5-Nitro 1H-indol-3-yl)-ethyl)-3-phenoxybenzylamine

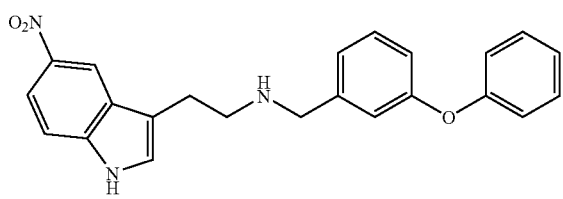

Combine 5-nitrotryptamine (500 mg, 2.4 mmol), 3-phenoxybenzaldehyde (480 mg, 2.4 mmol) and 4 g 4A molecular sieves in 30 mL EtOH and reflux overnight. Decant the liquid into a separate flask and treat with $NaBH_4$ (280 mg, 7.2 mmol) at ambient temperature. After 1 hour concentrate under vacuum and partition the residue between 25 mL 1 NaOH and 25 mL dichloromethane. Extract the aqueous layer with 25 ml dichloromethane and dry the combined organic layers over $MgSO_4$ and concentrate to dryness. Purify the resulting oil by radial chromatography ($SiO_2$; 2% MeOH in $CHCl_3$) to afford the desired compound as an oil. Convert to the HCl salt by treating a solution of the compound in 10 mL EtOH with 0.25 mL 5 N HCl and 40 mL toluene then concentrating to a solid. Analysis for $C_{23}H_{21}N_3O_3.HCl.0.2$ EtOH: calcd: C, 64.62; H, 5.17; N, 9.75. found: C, 64.89; H, 5.40; N, 9.75. ISMS 388 (M+1).

By the method of Example 825 the following compounds were prepared, isolated as the hydrochloride except where noted:

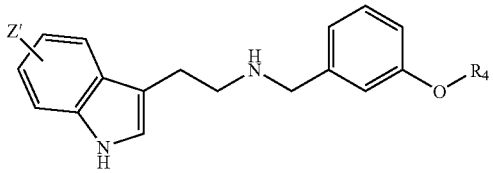

| No. | Z' | R4 | Data |
|---|---|---|---|
| 826 | 5-butoxy | phenyl | Analysis for $C_{27}H_{30}N_2O_2 \cdot HCl \cdot 0.4\ H_2O$: calcd: C, 70.77; H, 7.00; N, 6.11; found: C, 70.87; H, 6.84; N, 6.14; ISMS 415 (M + 1) |
| 827 | 5-benzamide | phenyl | Analysis for $C30H_{27}N_3O_2 \cdot HCl \cdot 0.2\ H_2O$: calcd: C, 71.83; H, 5.71; N, 8.38; found: C, 71.63; H, 5.35; N, 8.09; ISMS 462 (M + 1) |
| 828 | 5-benzamide | 2,2,2-trifluoro ethyl | Analysis for $C_{26}H_{24}F_3N_3O_2 \cdot HCl$: calcd: C, 61.97; H, 5.00; N, 8.33; found: C, 61.78; H, 5.16; N, 7.97; ISMS 468 (M + 1) |
| 829 | 5-benzamide | 2,2,3,3-tetrafluoro propyl | Analysis for $C_{27}H_{25}F_4N_3O_2 \cdot HCl$: calcd: C, 60.51; H, 4.89; N, 7.84; found: C, 60.47; H, 4.95; N, 7.49; ISMS 500 (M + 1) |
| 830 | 5-methane sulfonamide | phenyl | Analysis for $C_{24}H_{25}N_3O_3S \cdot HCl \cdot 0.5\ H_2O \cdot 0.5\ C_7H_8$: calcd: C, 63.53; H, 5.86; N, 8.08; found: C, 63.57; H, 5.77; N, 7.81; ISMS 436 (M + 1) |
| 831 | 5-methane sulfonamide | 2,2,2-trifluoro ethyl | Analysis for $C_{20}H_{22}F_3N_3O_3S \cdot HCl \cdot 0.1\ H_2O \cdot 0.5\ C_7H_8$: calcd: C, 53.68; H, 5.21; N, 7.99; found: C, 53.48; H, 5.19; N, 7.72; ISMS 442 (M + 1) |
| 832 | 5-methane sulfonamide | 2,2,3,3-tetrafluoro propyl | Analysis for $C_{21}H_{23}F_4N_3O_3S \cdot HCl \cdot 0.1\ EtOH \cdot 0.8\ C_7H_8$: calcd: C, 54.72; H, 5.31; N, 7.14; found: C, 54.63; H, 5.25; N, 6.99; ISMS 474 (M + 1) |
| 833 | 5-isopropoxy | phenyl | Analysis for $C_{26}H_{28}N_2O_2 \cdot 1.1\ HCl \cdot 0.1\ H_2O$: calcd: C, 70.58; H, 6.68; N, 6.33; found: C, 70.37; H, 6.31; N, 6.35; ISMS 401 (M + 1) |
| 834 | 5-isopropoxy | 2,2,2-trifluoro ethyl | Analysis for $C_{22}H_{25}F_3N_2O_2 \cdot HCl \cdot 0.3\ H_2O$: calcd: C, 58.94; H, 5.98; N, 6.25; found: C, 59.08; H, 5.78; N, 6.25; ISMS 407 (M + 1) |
| 835 | 5-isopropoxy | 2,2,3,3-tetrafluoro propyl | Analysis for $C_{23}H_{26}F_4N_2O_2 \cdot HCl \cdot 0.3\ H_2O$: calcd: C, 57.51; H, 5.79; N, 5.83; found: C, 57.66; H, 5.55; N, 5.80; ISMS 439 (M + 1) |
| 836 | 5-ethoxy | phenyl | Analysis for $C_{25}H_{26}N_2O_2 \cdot HCl \cdot 0.2\ H_2O$: calcd: C, 70.39; H, 6.47; N, 6.57; found: C, 70.40; H, 6.32; N, 6.68; ISMS 387 (M + 1) |
| 837 | 5-ethoxy | 2,2,2-tri fluoroethyl | Analysis for $C_{21}H_{23}F_3N_2O_2 \cdot HCl$: calcd: C, 58.81; H, 5.64; N, 6.53; found: C, 58.61; H, 5.61; N, 6.52; ISMS 393 (M + 1) |
| 838 | 5-ethoxy | 2,2,3,3-tetra fluoropropyl | Analysis for $C_{22}H_{24}F_4N_2O_2 \cdot HCl$: calcd: C, 57.33; H, 5.47; N, 6.08; found: C, 57.01; H, 5.35; N, 6.03; ISMS 425 (M + 1) |
| 839 | 2,2,2-trifluoro-ethoxy | phenyl | Analysis for $C_{25}H_{23}F_3N_2O_2 \cdot HCl$: calcd: C, 62.96; H, 5.07; N, 5.87; found: C, 62.76; H, 4.93; N, 5.88; ISMS 441 (M + 1) |
| 840 | 2,2,2-trifluoro-ethoxy | 2,2,2-trifluoro ethyl | Analysis for $C_{21}H_{20}F_6N_2O_2 \cdot HCl$: calcd: C, 52.24; H, 4.38; N, 5.80; found: C, 52.21; H, 4.28; N, 6.18; ISMS 447 (M + 1) |
| 841 | 2,2,2-trifluoro-ethoxy | 2,2,3,3-tetra fluoropropyl | Analysis for $C_{22}H_{21}F_7N_2O_2 \cdot HCl \cdot 0.2\ H_2O \cdot 0.2\ C_7H_8$: calcd: C, 52.35; H, 4.51; N, 5.22; found: C, 52.15; H, 4.30; N, 5.58; ISMS 479 (M + 1) |
| 842 | 5-butyloxy | pyridin-2-yl | Analysis for $C_{26}H_{29}N_3O_2 \cdot 2\ HCl \cdot 0.5\ EtOH \cdot 0.3\ C_7H_8$: calcd: C, 64.83; H, 6.81; N, 7.79; found: C, 64.99; H, 6.48; N, |

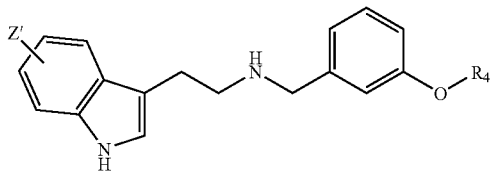

| No. | Z' | R4 | Data |
|---|---|---|---|
| | | | 7.47; ISMS 416 (M + 1) |
| 843 | 5-isopropyl | 2,2,2-tri fluoroethyl | Analysis for $C_{22}H_{25}F_3N_2O \cdot HCl$: calcd: C, 61.90; H, 6.14; N, 6.56; found: C, 61.72; H, 6.14; N, 6.42; ISMS 391 (M + 1) |
| 844 | 5-isopropyl | phenyl | Analysis for $C_{26}H_{28}N_2O \cdot HCl$: calcd: C, 74.18; H, 6.94; N, 6.65; found: C, 73.82; H, 6.79; N, 6.65; ISMS 385 (M + 1) |
| 845 | 5-benzene sulfonyl | phenyl | Analysis for $C_{29}H_{26}N_2O_3S \cdot 2\ HCl$: calcd: C, 67.11; H, 5.24; N, 5.40; found: C, 67.46; H, 5.37; N, 5.09; ISMS 483 (M + 1) |
| 846 | 5-benzene sulfonyl | 2,2,3,3-tetra fluoropropyl | Analysis for $C_{26}H_{24}F_4N_2O_3S \cdot HCl \cdot 0.3$ EtOH $\cdot 0.2\ C_7H_8$: calcd: C, 57.07; H, 4.86; N, 4.75; found: C, 56.95; H, 4.68; N, 4.77 ISMS 521 (M + 1) |
| 847 | 5-benzene sulfonyl | 2,2,2-tri fluoroethyl | Analysis for $C_{26}H_{29}N_3O_2 \cdot HCl \cdot 0.6$ $H_2O$: calcd: C, 56.04; H, 4.74; N, 5.23; found: C, 56.05; H, 4.71; N, 5.12; ISMS 489 (M + 1) |
| 848 | 5-carboxylic acid ethyl ester | 2,2,2-tri fluoroethyl | Analysis for $C_{22}H_{23}F_3N_2O_3 \cdot HCl$: calcd: C, 57.84; H, 5.30; N, 6.13; found: C, 57.85; H, 5.17; N, 6.09; ISMS 421 (M + 1) |
| 849 | 5-carboxylic acid propylamide | 2,2,3,3-tetra fluoropropyl | Analysis for $C_{23}H_{26}F_3N_3O_2 \cdot HCl \cdot 0.6$ $H_2O \cdot 0.1\ C_7H_8$: calcd: C, 56.84; H, 5.79; N, 8.05; found: C, 56.65; H, 5.63; N, 7.71; ISMS 466 (M + 1) |
| 850 | 5-carboxylic acid propylamide | phenyl | Analysis for $C_{27}H_{29}N_3O_2 \cdot HCl \cdot 0.4$ $H_2O \cdot 0.2\ C_7H_8$: calcd: C, 69.66; H, 6.61; N, R.58; found: C, 69.75; H, 6.57; N, 8.38; ISMS 428 (M + 1) |
| 851 | 5-carboxylic acid propylamide | 2,2,2-tri fluoroethyl | Analysis for $C_{23}H_{26}F_3N_3O_2 \cdot HCl \cdot 0.8$ $H_2O \cdot 0.1\ C_7H_8$: calcd: C, 57.67; H, 6.00; N, 8.51; found: C, 57.55; H, 5.77; N, 8.43; ISMS 434 (M + 1) |
| 852 | 5-carboxylic acid butylamide | phenyl | Analysis for $C_{28}H_{31}N_3O_2 \cdot HCl \cdot 0.7$ $H_2O$: calcd: C, 68.54; H, 6.86; N, 8.56; found: C, 68.41; H, 6.60; N, 8.37; ISMS 442 (M + 1) |
| 853 | 5-carboxylic acid butylamide | 2,2,3,3-tetra fluoropropyl | Analysis for $C_{25}H_{29}F_4N_3O_2 \cdot HCl \cdot H_2O$: calcd: C, 56.23; H, 6.04; N, 7.87; found: C, 56.23; H, 5.79; N, 7.84; ISMS 480 (M + 1) |
| 854 | H | 2,2,3,3-tetra fluoro propyl | Analysis for $C_{20}H_{20}F_4N_2O \cdot HCl \cdot 0.5\ H_2O$: calcd: C, 56.41; H, 5.21; N, 6.58; found: C, 56.98; H, 4.93; N, 6.53; ISMS 381 (M + 1) |
| 855 | 5-benzyloxy | 2,2,2-tri fluoroethyl | Analysis for $C_{26}H_{25}F_3N_2O \cdot HCl$: calcd: C, 63.61; H, 5.34; N, 5.71; found: C, 63.46; H, 5.53; N, 5.72; ISMS 455 (M + 1) |
| 856 | 5-benzyloxy | 2,2,3,3 tetra fluoropropyl | Analysis for $C_{27}H_{26}F_4N_2O_2 \cdot HCl$: calcd: C, 62.01; H, 5.20; N, 5.36; found: C, 62.04; H, 5.16; N, 5.36; ISMS 487 (M + 1) |
| 857 | 6-phenoxy | phenoxy | ISMS 435 (M + 1); $C_{29}H_{27}ClN_2O_2$~0.1 $H_2O$: calcd: C, 73.67; H, 5.80; N, 5.93; found: C, 73.49; H, 5.49; N, 5.82 |
| 858 | 6-Phenoxy | 2,2,3,3-tetra fluoropropyl | ISMS 473 (M + 1); $C_{26}H_{25}F_4ClN_2O_2$: calcd: C, 61.36; H, 4.95; N, 5.50; found: C, 61.02; H, 4.67; N, 5.42 |
| 859 | 6-Phenoxy | 2,2,2-tri fluoroethyl | ISMS 441 (M + 1); $C_{26}H_{25}F_4ClN_2O_2$~0.2 $H_2O$: calcd: C, 62.49; H, 5.12; N, 5.83; found: C, 62,27; H, 4.78; N, 5.74 |
| 860 | 5(3- | 2,2,3,3-tetra | ISMS 474 (M + 1); $C_{25}H_{25}F_4Cl_2N_3O_2$~0.5 $H_2O$: |

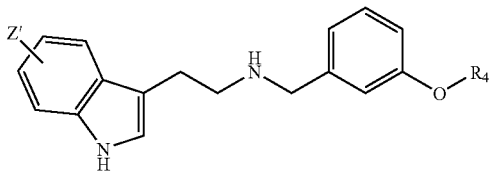

| No. | Z' | R4 | Data |
|---|---|---|---|
|  | pyridyloxy) | fluoropropyl | calcd: C, 54.06; H, 4.72; N, 7.57; found: C, 53.97; H, 4.76; N, 7.29 |
| 861 | 5-(Pyridinyl-3-oxy) | 2,2,2-tri fluoroethyl | ISMS 442 (M + 1); $^1$H NMR (CDCl$_3$) 8.37-8.36 (m, 1 H), 8.27-8.26 (m, 1 H), 8.01 (bs, 1 H), 7.35-7.32 (m, 1 H), 7.26-7.24 (m, 3 H), 7.22-7.18 (m, 2 H), 7.08-7.07 (m, 1 H), 6.93-6.91 (m, 2 H), 6.9-6.86 (m, 1 H), 6.79-6.76 (m, 1 H), 4.31-4.25 (m, 2 H), 3.77 (s, 2 H), 3.77 (s, 4 H). Isolated as dihydrochloride salt |

Example 863

6-Phenoxytryptamine

By using a method similar to Example 422, the title compound was prepared: ISMS 253 (M+1); $^1$H NMR (CDCl$_3$) 8.1 (bs, 1H), 7.56-7.54 (m, 1H), 7.32-7.28 (m, 3H), 7.07-6.98 (m, 4H), 6.89-6.86 (m, 1H), 3.06-3.02 (m, 2H), 2.92-2.88 (m, 2H), 1.68 (bs, 2H).

Example 864

2-(5-(Pyridin-3-yloxy)-1H-indol-3-yl)-ethylamine

By using a method similar to Example 422, the title compound was prepared: ISMS 254 (M+1); C$_{15}$H$_{15}$N$_3$O.1.1 C$_2$H$_2$O$_4$.0.2H$_2$O: calcd: C, 58.04; H, 4.98; N, 11.81. found: C, 58.17; H, 4.62; N, 11.45.

Example 865

6-Phenoxy-1H-indole-3-carbaldehyde

By using a method similar to Example 414, the title compound was prepared: ISMS 238 (M+1); $^1$H NMR (CDCl$_3$) 10.78 (bs, 1H), 9.95 (s, 1H), 8.20-8.18 (m, 1H), 7.76-7.75 (m, 1H), 7.30-7.26 (m, 2H), 7.06-7.02 (m, 2H), 7.00-6.95 (m, 3H).

Example 866

5-(Pyridin-3-yloxy)-1H-indole-3-carbaldehyde

By using a method similar to Example 414, the title compound was prepared: ISMS 239 (M+1); C$_{14}$H$_{10}$N$_2$O$_2$.0.3H$_2$O: calcd: C, 69.01; H, 4.39; N, 11.50. found: C, 68.91; H, 4.16; N, 11.39.

Example 867

3-(3-Methyl-4-nitrophenoxy)pyridine

Rinse 35% oil dispersion of KH (12 g, 11 mmol) with 100 mL hexanes twice and dry under vacuum before cooling in an ice bath. Add 100 mL dry DMF then a solution of 3-hydroxypyridine (10 g, 105 mmol) in 100 mL DMF dropwise. Treat with a solution of 5-fluoro-2-nitrotoluene (16.3 g, 105 mmol) in 50 mL DMF to obtain a dark solution. Stir at ambient temperature for 1 hour, pour the mixture into 1 liter of brine and extract twice with 200 mL of EtOAc. Combine the extracts and wash twice with 500 mL brine, dry over MgSO$_4$ and concentrate to 24 g of a dark oil. Purification by chromatography 20% EtOAc in hexanes give the title compound as an oil: ISMS 231 (M+1); C$_{12}$H$_{10}$N$_2$O$_3$: calcd: C, 62.61; H, 4.38; N, 12.17. found: C, 62.63; H, 4.58; N, 12.06.

Example 869

3-Ethoxybenzaldehyde

Combine 5.6 g of 3-hydroxybenzaldehyde (46 mmol) and 10.7 g of 1-iodoethane (69 mmol) in DMSO (25 mL) and warm to 8° C. and treat with 22.4 g of cesium carbonate (69 mmol) portionwise and stir. After 1 hour, pour into 200 mL brine and extract twice with 150 mL diethyl ether. Combine the extracts and wash twice with 200 mL brine, dry over MgSO$_4$ and concentrate under vacuum to give an oil. Purification by chromatography (SiO$_2$; 2.5% EtOAc in Hexanes) affords 5.73 g (38 mmol; 83%) of the desired compound as an oil: $^1$H NMR (CDCl$_3$) 9.94 (s, 1H), 7.42-7.41 (m, 2H), 7.36-7.35 (m, 1H), 7.16-7.13 (m, 1H), 4.10-4.04 (q, 2H), 1.64-1.40 (t, 3H).

Example 870

3-Propoxybenzaldehyde

By using a method similar to Example 869, the title compound was prepared: $^1$H NMR (CDCl$_3$) 9.95 (s, 1H), 7.43-7.41 (m, 2H), 7.37-7.36 (m, 1H), 7.17-7.14 (m, 1H), 9.98-3.95 (t, 2H), 1.84-1.79 (m, 2H), 1.05-1.02 (t, 3H).

Example 872

4-Phenoxy-1-methyl-2-nitrobenzene

Combine phenyl boronic acid (7.32 g, 60 mmol), 4-methyl-3-nitrophenol (4.5 g, 30 mmol), and Cu (oAC)$_2$-H$_2$O (6 g, 30 mmol) in 30 mL CH$_2$Cl$_2$ and treat with 6 g 4A molecular sieves powder. Add Et$_3$N (15.18 g, 150 mmol) dropwise, and stir the reaction at ambient temperature for 8 days. Dilute with 100 mL CH$_2$Cl$_2$ and filter through celite and concentrate to dryness. Purification by chromatography using 2% EtOAc in hexanes gave the desired product as a yellow oil.

Example 873

6-Phenoxy-1H-indole

Combine 4-phenoxy-1-methyl-2-nitro-benzene (6 g, 26.2 mmol) and DMF dimethylacetal (15.6 g, 131 mmol) in 60 mL dry DMF and heat at 170° C. for 16 hours. Cool to room temperature and concentrate to dryness. Dissolve residue in 50 mL EtOAc and hydrogenate with 2 g 5% Pd/C and hydrogen for 3 hours at atmospheric pressure. Filter through celite and concentrate to an oil. Purify by chromatography using Hex/EtOAC to obtain a tan solid: ISMS 210 (M+1)
$^1$H NMR (CDCl$_3$) 8.08 (bs, 1H), 7.61-7.59 (m, 1H), 7.34-7.29 (m, 2H), 7.18-7.17 (m, 1H), 7.18-7.0 (m, 4H), 6.92-6.89 (m, 1H), 6.56-6.54 (m, 1H).

Example 874

5-Pyridin-3-yl-1-methyl-2-nitro-benzene

By a method similar to Example 872, the title compound was prepared.

Example 875

5-(Pyridin-3-yloxy)-1H-indole

By a method similar to Example 873, the title compound was prepared: ISMS 211 (M+1); C$_{13}$H$_{10}$N$_2$O.0.1 H$_2$O: calcd: C, 73.64; H, 4.85; N, 13.21. found: C, 73.76; H, 4.80; N, 13.09.

Example 877

N-2-(5-Phenoxy-1H-indol-3-1-ethyl)-3-phenoxybenzylamine

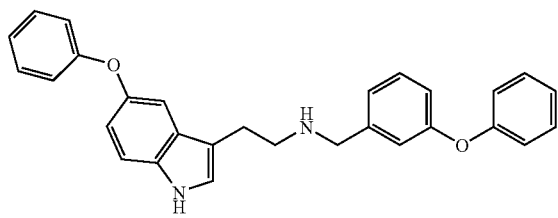

Combine 2-(5-phenoxy-1H-indol-3-yl)ethylamine (0.400 g, 1.59 mmol), 3-phenoxybenzaldehyde (0.377 g, 1.90 mmol) and molecular sieves 4A (0.40 g) and stir in methanol (15 mL) After 4 h, filter the molecular sieves and wash several times with MeOH. To this MeOH solution, add portionwise NaBH$_4$ (61.5 mg, 1.59 mmol), stir the resulting mixture at room temperature for 1 h. Remove MeOH under vacuum, dilute the residue with CH$_2$Cl$_2$/water, extract with Cl$_2$C$_{12}$, the combine the organic layers and dry over Na$_2$SO$_4$. Concentrate in vacuo the solvent, purification on silica gel (CH$_2$Cl$_2$ 1 MeOH) to give the free base of the title compound React free base with oxalic acid to form the salt: m.p. 196-198° C.; $^1$H NMR (300 MHz, DMSO-d6) 2.95-3.15 (m, 4H), 4.15 (s, 2H), 6.85-7.46 (m, 18H), 11.06 (br, 1H); MS (ELECTROSPRAY) m/e: 435.3 (M+1); HRMS (ES+) calcd for C$_{29}$H$_{27}$N$_2$O$_2$ (M+H) 435.2084 found 435.2073.

Example 878

(3-Phenoxybenzyl)-(2-henoxy-1H-indol-3-yl)-ethyl)-carbamic acid tert butyl ester Combine (3-phenoxy-benzyl)-(2-(5-phenoxy-1H-indol-3-yl)ethyl)-amine (0.96 g, 2.2 mmol) and NaOH (87.7 mg, 2.2 mmol) and dissolve in THF (10 mL), stir at room temperature for 15 min. Add di-tert-butyl dicarbonate (0.58 g, 2.64 mmol) in THF (10 mL) and stir. After 2 h, dilute the reaction with water, extract with EtOAc (3×15 mL), dry over Na$_2$SO$_4$. Concentrate the organic solvent on vacuum to give the title compound as an oil: $^1$H NMR (300 MHz, CDCl$_3$) 1.36 (s, 9H), 2.85-2.91 (m, 2H), 3.89-3.65 (m, 2H), 4.26 (s, 1H), 4.39 (s, 1H) 6.83-7.13 (m, 10H), 7.21-7.33 (m, 7H), 8.00 (s, 1H); MS (ELECTROSPRAY) m/e 534.9 (M+1).

Example 879

N-Methyl-N-2-(5-Phenoxy-1H-indol-3-yl)ethyl)-3-phenoxybenzylamine

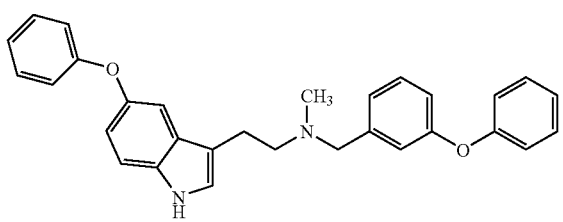

Add slowly 1.0 M solution of LiAlH$_4$-THF (5.5 mL, 5.5 mmol) to a solution of (3-phenoxy-benzyl)-(2-(5-phenoxy-1H-indol-3-yl)-ethyl)-carbamic acid tert butyl ester (0.60 g, 1.12 mmol) in 10 mL dry THF. After addition, heat to reflux the reaction mixture. After 2 h, cool to room temperature, quench the reaction by adding water 1.5 mL cautiously, followed by 2N NaOH (1.0 mL). Filter the suspension and wash repeatedly with ether, dry the organic solution over Na$_2$SO$_4$ and concentrate in vacuo. Purification on silica gel using CH$_2$Cl$_2$/MeOH as eluent gives the free base of the title compound and further reaction with oxalic acid to form the salt: m.p. 174-175° C.; $^1$H NMR (250 MHz, DMSO-d6) 2.51 (s, 3H), 3.00-3.13 (m, 4H), 4.15 (s, 2H), 6.81-7.03 (m, 7H), 7.11-7.42 (m, 11H), 11.05 (br, 1H); MS (ELECTROSPRAY) m/e: 449.1 (M+1–C$_2$H$_2$O$_4$).

Example 880

N-(2-(6-Chloro-1H-indol-3-yl)ethyl)-(3-(2,2-difluoro ethoxy)benzyl)amine

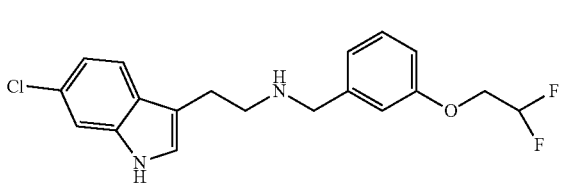

Combine 2-(6-chloro-1H-indol-3-yl)ethylamine hydrochloride (1.0 g, 4.3 mmol) and ethyldiisopropylamine (900 μL, 5.2 mmol) in ethanol (150 mL) and stir at room temperature and treat with 3-(2,2-difluoroethoxy)benzaldehyde (856 mg, 4.6 mmol) and anhydrous sodium sulfate (12 g) and heat at 78° C. overnight. Cool to room temperature and filter. Treat the resulting filtrate with sodium borohydride (488 mg, 12.9 mmol) and stir the milky-white mixture at room temperature overnight. Remove in vacuo the solvent, and purification of the crude on silica gel eluting with 10% methanol in dichloromethane gives the free base of the title compound as a light yellow oil. Dissolve a portion of the oil (651 mg, 1.78 mmol) in methanol (15 mL) and treat with a homogenous solution of ammonium chloride (95 mg, 1.78 mmol) in methanol (3 mL). Sonicate the resulting solution for 10 minutes before removal of the solvent in vacuo to provide an off-white solid. Triturate with diethyl ether containing a few drops of acetonitrile. Filtration and drying of the precipitate afforded the title hydrochloride as a white solid: mp 131.6-133° C.; $^1$H NMR (400 MHz, dmso-$d_6$): 11.15 (br s, 1H), 9.50 (br s, 2H), 7.57 (d, 1H, J=8.8 Hz), 7.39 (d, 1H, J=2.0 Hz), 7.36 (t, 1H, J=8.2 Hz), 7.32 (br s, 1H), 7.26 (d, 1H, J=2.0 Hz), 7.17 (d, 1H, J=7.6 Hz), 7.04 (dd, 1H, J=7.8, 2.2 Hz), 7.01 (dd, 1H, J=8.4, 2.0 Hz), 6.41 (tt, 1H, J=54.4, 3.4 Hz), 4.32 (td, 2H, J=14.8, 3.6 Hz), 4.14 (br s, 2H), 3.11 (br s, 4H); MS (ES+): m/e 365.3 (M+1); CHN (for $C_{19}H_{19}F_2ClN_2 \cdot O \cdot HCl \cdot 0.3H_2O$) calcd: C, 56.11; H, 5.11; N, 6.89. found: C, 56.03; H, 4.95; N, 7.18.

Example 881

N-Methyl-N-(2-(6-Chloro-1H-indol-3-yl)ethyl)-3-(2,2-difluoroethoxy)benzylamine

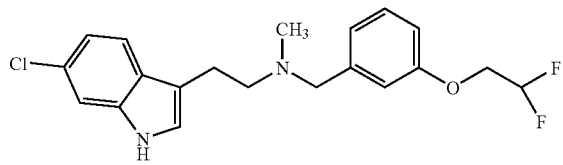

Combine (2-(6-chloro-1H-indol-3-yl)ethyl)-(3-(2,2-difluoroethoxy)benzyl)amine (276 mg, 0.76 mmol) and formaldehyde (55.5 µL of a 38% aqueous solution, 0.76 mmol) in dichloroethane (15 mL) and stir at room temperature for 10 minutes; add in two portions sodium triacetoxyborohydride (321 mg, 1.51 mmol) over 10 minutes and stir at room temperature overnight before diluting with methanol (10 mL) and quenching with one drop of glacial acetic acid. Remove in vacuo the solvent, and redissolve the crude residue in methanol and directly load onto a 10 g SCX column. After washing thoroughly with methanol, elute the column with 2 N ammonia in methanol. Concentrate in vacuo the eluant to give the free base of the title compound as a straw-colored oil. Dissolve the free base (239 mg, 0.64 mmol) in methanol (20 mL) and treat with a solution of ammonium chloride (36 mg, 0.67 mmol) in methanol (5 mL). Sonicate the mixture for 10 minutes before removal of the solvent in vacuo to give the hydrochloride salt as a tacky yellow oil. Dissolve the oil in 10 mL of 1:1 acetonitrile-water and lyophilize overnight, providing a fluffy white solid and triturate with diethyl ether (10 mL) and acetonitrile (2 drops). Filtration and drying of the resulting precipitate afforded the desired hydrochloride as a white amorphous solid: mp: 63.8-65.8° C.; $^1$H NMR (400 MHz, dmso-$d_6$): 11.10 (br s, 1H), 7.52 (d, 1H) J=8.4 Hz) 7.36 (d, 1H, J=2.0 Hz), 7.40-7.26 (m, 2H), 7.22 (d, 1H, J=2.4 Hz), 7.20-7.11 (m, 1H), 7.04 (br d, 1H, J=7.6 Hz), 6.96 (dd, 1H, J=8.6, 1.4 Hz), 6.38 (tt, 1H, J=54.4, 3.6, Hz), 4.50-4.02 (br m, 2H), 4.30 (td, 2H, J=14.4, 3.2 Hz), 3.15 (br s, 4H), 2.68 (br s, 3H); MS (ES+): n/e 378.9 (M+1); CHN (for $C_{20}H_{21}ClF_2N_2 \cdot O \cdot HCl \cdot 0.7H_2O$) calcd: C, 56.14; H, 5.51; N, 6.55. found: C, 55.72; H, 5.32; N, 7.07.

By the method of Example 319 the following compounds were prepared, isolated as the oxalate except where noted:

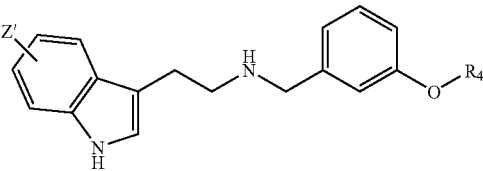

| No. | Z' | $R_4$ | Data |
|---|---|---|---|
| 883 | 4,7-difluoro | 2,2,2-trifluoroethyl | mp 208.5-210.0° C.; $^1$H NMR (400 MHz, dmso-$d_6$): 11.79 (br s, 1 H), 9.21 (br s, 2 H), 7.39 (t, 1 H, J = 7.8 Hz), 7.32 (d, 1 H, J = 2.0 Hz) 7.30 (s, 1 H), 7.18 (d, 1 H, J = 8.0 Hz), 7.11 (dd, 1 H, J = 2.6, 8.2 Hz), 6.85-6.91 (m, 1 H), 6.67-6.73 (m, 1 H), 4.77 (q, 2 H, J = 8.8 Hz), 4.16 (s, 4 H), 3.12-3.16 (m, 4 H). MS (APCI): m/e 385.1 (M + 1). CHN (for $C_{19}H_{17}F_5N_2O \cdot HCl$) calcd: C 54.23, H 4.31, N 6.66; found: C 54.20, H 4.30, N 6.66. |
| 884 | 4,5,6,7-tetrafluoro | 2,2,2-trifluoroethyl | mp 107.2-108.2° C.; $^1$H NMR (400 MHz, dmso-$d_6$): 11.92 (br s, 1 H), 7.32 (s, 2 H), 6.95-6.99 (m, 2 H), 6.87 (dd, 1 H, J = 2.4, 8.0 Hz) 4.68 (q, 2 H, J = 8.8 Hz), 3.70 (s, 2 H), 2.88 (t, 2 H, J = 7.2 Hz) 2.75 (t, 2 H, J = 7.2 Hz). MS (ES+): m/e 421.1 (M + 1). CHN (for $C_{19}H_{15}F_7N_2O \cdot 1$ HCl$\cdot 0.20$ $H_2O$) calcd: C 53.83, H 3.66, N 6.61; found: C 53.75, H 3.33, N 6.54. |

-continued

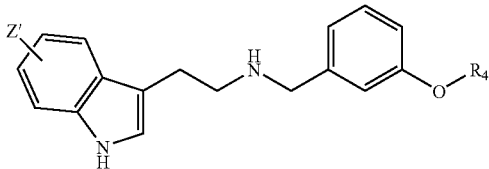

| No. | Z' | R₄ | Data |
|---|---|---|---|
| 885 | 4,7-difluoro | 2,2,3,3 tetrafluoro propyl | mp 171.8-173.0° C.; $^1$H NMR (400 MHz, dmso-$d_6$): 11.80 (br s, 1 H), 9.21 (s, 2 H), 7.39 (t, 1 H, J = 8.0 Hz), 7.30-7.33 (m, 2 H), 7.18 (d, 1 H, J = 7.6 Hz), 7.10 (dd, 1 H, J = 2.4, 8.0 Hz), 6.85-6.91 (m, 1 H), 6.54-6.83 (m, 2 H), 4.60 (t, 2 H, J = 13.6 Hz), 4.16 (s, 2 H), 3.16 (s, 4 H). MS (APCI): m/e 417.1 (M + 1). CHN (for $C_{20}H_{11}F_6N_2O$•1 HCl•0.25 $H_2O$) calcd: C 52.53, H 4.30, N 6.13; found: C 52.75,114.24, N 5.76. |
| 886 | 4,5,6,7-tetrafluoro | 2,2,3,3-tetra fluoropropyl | mp 262.5-263.8° C.; $^1$H NMR (400 MHz, dmso-$d_6$): 12.16 (br s, 1 H), 9.43 (s, 2 H), 7.44 (d, 1 H, J = 2.0 Hz), 7.34-7.40 (m, 2 H) 7.19-7.21 (d, 1 H, J = 3.6 Hz) ,7.08-7.10 (dd, 1 H, J = 2.0, 8.0 Hz), 6.69 (tt, 1 H, J = 5.2, 52.0 Hz) 4.59 (t, 2 H, J = 13.4 Hz), 4.15 (s, 2 H), 3.16 (s, 4 H). MS (APCI): m/e 453.1 (M + 1). CHN (for $C_{20}H_{16}F_8N_2O$•1 HCl•0.10 $H_2O$) calcd: C 48.96, H 3.53, N 5.71; found: C 48.74, H 3.33, N 5.61. |
| 887 | 7-trifluoro methyl | 2,2,2-trifluoroethyl | mp 173.8-175.6° C. $^1$H NMR (400 MHz, dmso-$d_6$): 11.36 (br s, 1 H), 9.07 (br s, 1 H), 7.87 (d, 1 H, J = 7.6 Hz), 7.45 (d, 1 H, J = 7.6 Hz) 7.38-7.42 (m, 1 H), 7.36 (d, 1 H, J = 2.4 Hz), 7.28-7.29 (m, 2 H), 7.16-7.29 (m, 2 H) 7.11 (dd, 1 H, J = 2.0, 8.0 Hz), 4.77 (q, 2 H, J = 8.8 Hz), 4.15 (s, 2 H), 3.12-3.16 (m, 4 H). MS (APCI): m/e 417.1 (M + 1). CHN (for $C_{20}H_{18}F_6N_2O$•1 HCl•0.20 $H_2O$) calcd: C 52.63, H 4.28, N 6.14; found: C 52.56, H 4.05, N 5.79. |
| 888 | 7-trifluoro methyl | 2,2,3,3-tetra fluoropropyl | mp 154.0-155.8° C.; $^1$H NMR (400 MHz, dmso-$d_6$): 11.35 (br s, 1 H), 9.51 (br s, 2 H), 7.91 (d, 1 H, J = 8.0 Hz), 7.36-7.45 (m, 4 H) 7.22 (d, 1 H, J = 8.0 Hz) 7.17 (t, 1 H, J = 7.6 Hz), 7.09 (dd, 1 H, J = 2,2, 8.0 Hz), 6.69 (tt, 1 H, J = 5.2, 52.0 Hz), 4.60 (1, 2 H, J = 13.6 Hz), 4.15 (s, 2 H), 3.13-3.20 (m, 4 H). MS (ES+): m/e 449.0 (M + 1). CHN (for $C_{21}H_{19}F_7N_2O$ •1 HCl•0.10 $H_2O$) calcd: C 51.83, H 4.18, N 5.76; found: C 51.54, H 3.97, N 5.68. |
| 889 | 7-nitro | 2,2,2-trifluoroethyl | mp 133.0-134.8° C.; $^1$H NMR (400 MHz, dmso-$d_6$): 11.81 (s, 1 H), 9.46 (br s, 2 H) 8.14 (d, 1 H, J = 8.0 Hz), 8.11 (d, 1 H, J = 8.0 Hz) 7.45 (d, 1 H, J = 2.0 Hz) 7.39 (t, 1 H, J = 8.0 Hz), 7.36-7.37 (m, 1 H), 7.25 (1, 1 H, J = 8.0 Hz), 7.21 (d, 1 H, J = 8.0 Hz), ) 7.10 (dd, 1 H, J = 2.0, 8.0 Hz), 4.78 (q, 2 H, J = 8.8 Hz), 4.15 (s, 2 H), 3.12-3.24 (m, 4 H). MS (APCI): m/e 394.1 (M + 1). CHN (for $C_{19}H_{18}F_3N_3O_3$•HCl•0.80 $H_2O$) calcd: C 51.37, H 4.67, N 9.46; found: C 51.02, H 4.43, N 10.19. |
| 890 | 7-nitro | 2,2,3,3-tetra fluoropropyl | mp 175.0-176.8° C.; H NMR (400 MHz, dmso-$d_6$): 11.81 (br s, 1 H), 9.32 (br s, 2 H), 8.13 (d, 1 H, J = 8.0 Hz), 8.11 (d, 1 H, J = 8.0 Hz) 7.45 (d, 1 H, J = 2.0 Hz) 7.39 (t, 1 H, J = 8.0 Hz), 7.31-7.32 (m, 1 H), 7.25 (t, 1 H, J = 8.0 Hz), 7.20 (d, 1 H, J = 7.6 Hz), ) 7.10 (dd, 1 H, J = 2.4, 8.4 Hz), 6.69 (tt, 1 H, J = 5.2, 52.0 Hz), 4.60 (t, 2 H, J = 13.2 Hz), 4.16 (s, 2 H), 3.18 (s, 4 H). MS (APCI): m/e 426.1 (M + 1). CHN (for $C_{20}H_{19}F_4N_3O_3$•1 HCl•0.90 $H_2O$) calcd: C 50.25, H 4.60, N 8.79; found: C 49.98, H 4.38, N 9.47. |

Example 892

2-(7-Trifluoromethyl-1H-indol-3-yl)-ethylamine

Combine in a 500 mL round bottom flask equipped with magnetic stirring, (2-trifluoromethyl-phenyl)-hydrazine (5.0 g, 28.4 mmol) and 4-aminobutyraldehyde dimethyl acetal (4.54 g, 34.1 mmol) and stir. After 5 minutes, slowly add 1N HCl (200 mL) and heat the reaction to 85° C. for 2 hours forming an orange-red colored solution. Increase the temperature to 100° C. for 10 minutes and cool to room temperature. Pour the reaction mixture over ice and stir for 10 minutes followed by adjustment to pH ~10 with ammonium hydroxide. Extract the mixture with methylene chloride, pool the organic phases, dry over sodium sulfate, and concentrate in vacuo to give a dark orange-brown oil. Purification on a pre-packed, HMDS treated silica column using a step gradient of 9% to 17% methanol in methylene chloride gives the pure title compound as an orange oil: $^1$H NMR (400 MHz, dmso-$d_6$): 11.18 (br s, 1H), 7.82 (d, 1H, J=7.6 Hz), 7.40 (d, 1H, J=7.2 Hz), 7.24 (d, 1H, J=2.0 Hz), 7.13 (t, 1H, J=7.6 Hz) 2.76-2.83 (m, 4H). MS (APCI): m/e 229.0 (M+1), 212.0 (M−NH$_2$).

Example 893

(7-Nitro-1H-indol-3-yl)-acetonitrile

Dissolve in a 500 mL round bottom flask equipped with magnetic stirring, 7-nitro indole (4.55 g, 28.1 mmol) in 130 mL of glacial acetic acid and heat to 70° C. Add di-methyl-methylene ammonium iodide (Eschenmoser's salt) and stir the mixture at 70° C. After 45 minutes, cool the reaction mixture and remove the solvent in vacuo to give a crude yellow solid. Treat the crude material with 200 mL ammonium hydroxide and extract with ethyl acetate. Pool the organic phases and dry over magnesium sulphate and concentrate in vacuo to give the amine intermediate as a yellow crystalline solid. Immediately dissolve the intermediate in 200 mL of dimethyl sulphoxide, treat with methyl iodide (4.55 mL, 56.2 mmole), and stir overnight at room temperature. Add potassium cyanide (18.30 g, 281 mmol), and 18-crown-6 (226 mg) and stir the mixture at 50° C. for 25 minutes. Pour the resulting brown-yellow suspension over ice, stir for 10 minutes, saturate with sodium chloride, and extracted with ethyl acetate. Wash the pooled extracts once with water, twice with brine, dry over sodium sulfate, and concentrate in vacuo to give the title compound as a yellow-brown solid. No further purification was necessary. $^1$H NMR (400 MHz, dmso-$d_6$): 11.92 (br s, 1H) 8.14 (d, 1H, J=8.0 Hz), 8.12 (d, 1H, J=8.0 Hz) 7.53 (d, 1H, J=2.0 Hz) 7.31 (t, 1H, J=8.0 Hz), 4.16 (s, 2H), MS (ES−): m/e 200.0 (M−1).

Example 894

2-(7-Nitro-1H-indol-3-yl)ethylamine

Dissolve in a 500 mL round bottom flask equipped with magnetic stirring, and a nitrogen inlet, (7-nitro-1H-indol-3-yl)-acetonitrile (5.27 g, 26 mmol) in dry tetrahydrofuran (150 mL). Treat the solution with 1M BH$_3$:THF (55 mL, 55 mmol) and stir at room temperature. After 20 hours, quench the reaction by the cautious dropwise addition of water (9 mL) and stir until foaming and gas evolution has stopped. Concentrate the mixture to dryness in vacuo, redissolve in 1 N HCl (300 ml) and extracte with ethyl acetate. Basify the aqueous phase 5 N NaOH and extract with ethyl acetate. Pool the ethyl acetate extracts and dry over sodium sulfate and concentrate in vacuo to give the title compound as an orange-brown solid: $^1$H NMR (400 MHz, dmso-$d_6$): 11.66 (br s, 1H) 8.07 (t, 2H, J=7.6 Hz), 7.32 (s, 1H), 7.20 (t, 1H, J=8.0 Hz) 2.79-2.83 (m, 4H), MS (APCI): m/e 189.0 (M−NH$_2$).

Example 895

N-(2-(6-Fluoro-1H-indol-3-yl)ethyl)-4-fluoro-3-phenoxy-benzylamine

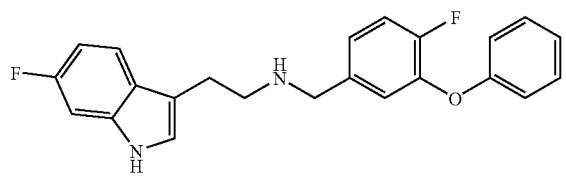

The method of Example 340 gives the hydrochloride of the title compound: mp 173-175° C.; MS (m/e): 379 (M+1), 377 (M−1); Calculated for $C_{23}H_{20}F_2N_2O\cdot HCl$: Calcd: C, 66.59; H, 5.10; N, 6.75. Found: C, 66.39; H, 5.05; N, 6.57.

Example 896

N-(2-(6-Fluoro-1H-indol-3-yl)ethyl)-3-phenoxybenzylamine

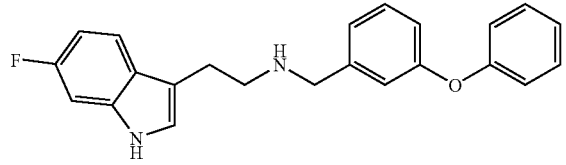

The method of Example 340 gives the hydrochloride of the title compound: mp 196-199° C.; MS (m/e): 361 (M+1), 359 (M−1); Calculated for $C_{23}H_{21}FN_2O\cdot HCl$: Calcd: C, 69.60; H, 5.59; N, 7.06. Found: C, 69.23; 14, 5.58; N, 7.00.

Example 897

4-Fluoro-1-methyl-3-phenoxybenzene

Add triethylamine (28.6 mL, 205 mmol) dropwise to a mixture of 2-fluoro-5-methylphenol (5.18 g, 41.1 mmol), copper(II) acetate (7.46 g, 41.1 mmol), phenylboronic acid (10.0 g, 82.1 mmol), powdered 4 Å sieves (7 g), and methylene chloride (400 mL). Stir at ambient temperature. After 22 h, filter and concentrate the filtrate. Pirify the residue by silica gel chromatography (50% methylene chloride/hexanes), concentrate and purify again by silica gel chromatography (100% hexanes) to give 2.4 g (29%) of the title compound: MS (m/e): 202 (M$^+$).

Example 898

4-Fluoro-3-phenoxybenzaldehyde

Combine 4-fluoro-1-methyl-3-phenoxybenzene (2.43 g, 12.0 mmol), N-bromosuccinimide (4.92 g, 27.6 mmol), benzoyl peroxide (408 mg, 1.68 mmol), and carbon tetrachloride (55 mL). Heat the mixture at reflux temperature for 6.5 h and cool to 0° C. for 64 h. Filter the solids and concentrate the filtrate. Dissolve the residue in chloroform and wash with ice cold sodium carbonate solution. Dry the chloroform solution over sodium sulfate, filter and concentrate under reduced pressure. Dissolve the residue in acetonitrile (50 mL) and add 4-methylmorpholine-4-oxide (4.6 g, 39.1 mmol) and powdered 4 Å sieves (200 mg). Stir at ambient temperature for 20 h, filter and concentrate. Purify by silica gel chromatography (5%, 30% ethyl acetate/hexanes) to give 220 mg (8%) of the title compound: MS (m/e): 216 (M+).

Example 899

7-Fluorotryptamine

Combine lithium aluminum hydride (12.8 g; 336.1 mmol) and 0° C. anhydrous tetrahydrofuran (160 mL). Cool resulting exotherm to 0° C. Add 7-fluoro-3-(2-nitrovinyl)-1H-indole (11.55 g, 56.0 mmol) in anhydrous THF (200 mL) dropwise. After 30 min, warm to ambient temperature. After 4 hours, cool to 0° C. and add saturated sodium sulfate solution (35 mL) dropwise. Filter the solids and wash with THF and ethyl acetate. Concentrate the filtrate and dissolve the residue in methylene chloride. Filter the precipitate to give 1.26 g of product as brown crystals. Concentrate the filtrate and chromatograph on silica gel eluting with 5%, 7%, 10% 2N ammonia in methanol/methylene chloride to give product: MS (m/e): 179 (M+1), 177 (M−1); Calculated for $C_{10}H_{11}FN_2$: Calcd: C, 67.40; H, 6.22; N, 15.72. Found: C, 67.06; H, 6.11; N, 15.48.

Example 900

3-(2-Nitrovinyl)-6-methanesulfonyl-1H-indole

Combine 1-dimethylamino-2-nitroethylene (892.1 mg, 7.68 mmol) and TFA (9.0 ml) and stir until dissolved. Add 6-methanesulfonyl-1H-indole (1.5 g, 7.68 mmol) and stir at ambient temperature. After 24 hours, pour the reaction mixture into ice/water, extract with ethyl acetate, then wash ethyl acetate with brine and saturated sodium bicarbonate. Filter, wash, and dry the precipitate to give the title compound as a yellow powder: mp>250° C. MS (ACPI): m/e 267.0 (M+1). Analysis for $C_{11}H_{10}N_2O_4S$: Calcd: C, 49.62; H, 3.79; N, 10.52. found: C, 49.86; H, 3.97; N, 10.25.

Example 901

3-(2-Nitrovinyl)-6-benzenesulfonyl-1H-indole

Combine 1-dimethylamino-2-nitroethylene (676.9 mg, 5.83 mmol) and TFA (9.0 ml) and stir until dissolved. Add 6-benzenesulfonyl-1H-indole (1.5 g, 5.83 mmol) and stir at ambient temperature. After 24 hours, pour the reaction mixture into ice/water and adjust to pH 8. After stirring, filter the precipitate, wash with water, and dry to give the title compound as a yellow powder: mp 110° C., dec. MS (ACPI): m/e 329.0 (M+1). Analysis for $C_{16}H_{12}N_2O_4S$: Calcd: C, 58.53; H, 3.68; N, 8.53. found: C, 58.54; H, 3.83; N, 7.85.

Example 902

(3-Phenoxybenzyl)-(2-pyridin-2-yl-ethyl)amine oxalic acid salt

Combine 2-pyridin-2-yl-ethylamine (Aldrich, 0.36 mL, 3.0 mmol), 3-phenoxybenzaldehyde (Aldrich, 0.58 mL, 3.66 mmol), 3 A molecular sieves (0.5 g), and methanol (30 mL) and heat to reflux for 4 hours. Remove the molecular sieves by filtration. Add sodium borohydride (0.35 g, 9.0 mmol) slowly and stir the reaction at room temperature. After 1 hour, concentrate the reaction and dissolve the residue in a mixture of 1N NaOH solution and methylene chloride and extract the mixture with methylene chloride. Wash the organic extract with water, dry ($Na_2SO_4$) and concentrated to give a pale yellow oil. Form the salt with oxalic acid and crystallize from ethyl acetate to give a white solid: mp=183-185° C.; ms: ion at 305.2.

Example 903

(3-[1,3]Dioxolan-2-yl-phenyl)-pyridin-2-ylamine

Combine 2-aminopyridine (8.25 g, 95 mmol), 2-(3-bromophenyl)-[1,3]dioxolane (13.8 mL, 90 mmol), sodium t-butoxide (12.2 g, 126 mmol), BINAP (210 mg, 0.62 mmol), Pd2(dbu)3 (630 mg, 0.21 mmol) and toluene (100 mL) and heat to reflux for 48 hours. Cool the reaction to room temperature, dissolve in ether and filter and concentrate the resulting solution. Purification by flash chromatography (hexanes/EtOAc (8.5:1.5) and then hexanes/EtOAc (7:3)) provides the title compound as a yellow oil.

Example 904

3-(Pyridin-2-ylamino)benzaldehyde

Dissolve (3-[1,3]dioxolan-2-yl-phenyl)-pyridin-2-ylamine (10.32 g, 42.6 mmol) in THF (150 mL). Add concentrated HCl solution (37.5 mL) and stir the solution at room temperature overnight. Concentrate the reaction, treat with water, and extract with $CH_2Cl_2$. Wash the organic extract with water, dry ($Na_2SO_4$) and concentrate to give the crude product. Purification by flash chromatography (hexanes/EtOAc (7:3)) provides the title compound as a yellow solid.

Example 905

N-(3-(2-(6-Chloro-1H-indol-3-yl)ethyl)-3-(pyrid-2-ylamino)benzylamine

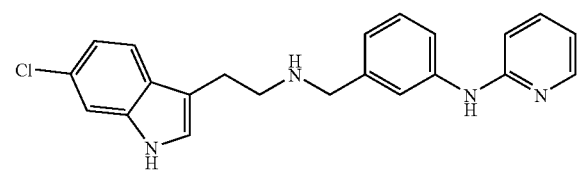

Combine 6-chlorotryptamine (0.22 g, 1.1 mmol), 3-(pyridin-2-ylamino)benzaldehyde (0.22 g, 1.1 mmol), 3 A molecular sieves (0.5 g), and methanol (25 mL) are and heat to reflux for 4 hours. Remove the molecular sieves by filtration. Add sodium borohydride (0.16 g, 3.3 mmol) slowly and stir the reaction at room temperature. After 1 hour, concentrate the reaction and dissolve the residue in a mixture of 1N NaOH solution and methylene chloride and extract the mixture with methylene chloride. Wash the organic extract with water, dry ($Na_2SO_4$) and concentrate to give the crude product. Purification by flash chromatography (EtOAc/MeOH (9:1) with 2% concentrated $NH_4OH$ solution) provides the desired product as a colorless oil. Form the dihydrochloride salt and crystallize from EtOAc to give the desired product: mp=164-166° C.; ms: ion at 377.1.

The following compounds were prepared following a procedure following Example 673:

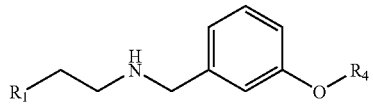

| No: | R₁ | R₄ | Data |
|---|---|---|---|
| 906 | pyrid-2-yl | phenyl | LC Method 3: Rf 2.83 min at 54/220 nm; m/e 305.0 (M + 1) |
| 907 | thien-2-yl | phenyl | LC Method 3: Rf 4.00 min at 254/220 nm; m/e 3309.9 (M + 1) |

The following compounds were prepared following a procedure following Example 673:

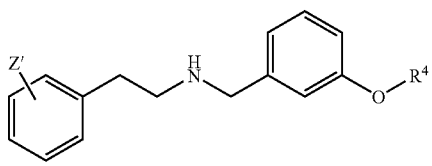

| No.: | Z' | R₄ | Data |
|---|---|---|---|
| 908 | 3-Br | propyl | LC Method 3: Rf 4.48 min at 254/220 nm; m/e 349.9 (M + 1) |
| 908a | 3-COOCH₃ | phenyl | MS = 362 (m + 1), IR; 1718.51, 1584.26, 1489.84, 1445.78, 1285.67, 1253.07, 1199.51 cm⁻¹ |

The following compounds were prepared following a similar procedure in Example 665:

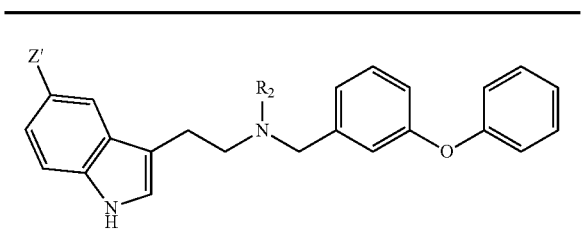

| No.: | Z' | R₂ | Data |
|---|---|---|---|
| 909 | H | isopropyl | LC Method 3: Rf 5.43 min at 254/220 nm; m/e 385.0 (M + 1) |

-continued

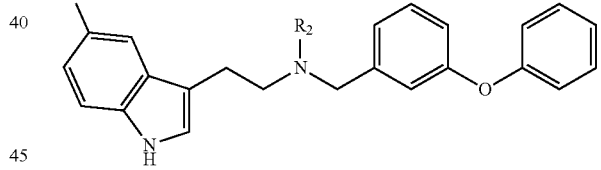

| No.: | Z' | R₂ | Data |
|---|---|---|---|
| 910 | methoxy | methyl | LC Method 2: Rf 4.86 min at 254/220 nm; m/e 385.0 (M + 1) |

By the method of Example 221 the following compounds were prepared, isolated as the maleate except where noted:

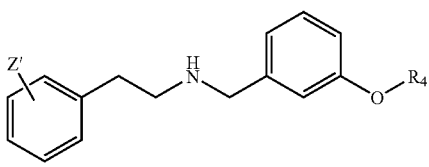

| No. | Z'' | R₄ | Data |
|---|---|---|---|
| 911 | 3-chloro | 2-fluoro- | LC Method 3: Rf 4.61 min at 254/220 nm; m/e |

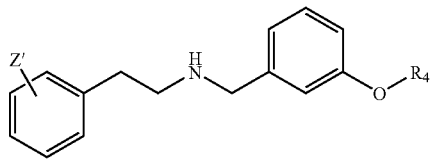

| No. | Z" | R$_4$ | Data |
|---|---|---|---|
| 912 | 3-chloro | benzyl 4-fluoro-benzyl | 369.9 (M + 1) LC Method 3: Rf 4.62 min at 254/220 nm; m/e 369.9(M + 1) |
| 913 | 3-chloro | 2,3-difluoro-benzyl | LC Method 3: Rf 4.76 min at 254/220 nm; m/e |

Example 914

3-Propoxybenzonitrile

Combine 3-hydroxybenzonitrile (11.052 gm; 92.8 mmol), n-propyl bromide (24.4 gm; 198 mmol), and potassium carbonate (38.65 gm; 280 mmol) in 2-butanone (175 mL) and heat and reflux. After 17 h., cool the mixture to room temperature, and decant the solution and concentrate by rotary evaporation. Partition the residue between diethyl ether (150 mL) and water (150 mL), separate the layers and extract the aqueous layer with diethyl ether (2×100 mL). Combine the organic layers and wash with water, 1 N NaOH, and water, dry over MgSO$_4$, and concentrate. Distill the residue to give the title compound.

Example 915

3-Propoxybenzylamine hydrochloride

Combine 100 mL of lithium aluminum hydride (1 M in THF) and 50 mL of THF and add sulfuric acid (100%) dropwise at 10° C. Allow the mixture to warm to room temperature and stir. After a 1 h period, remove the solids by filtration through diatomaceous earth using nitrogen pressure, and to the clear solution add dropwise a solution of nitrile in 50 mL of THF at 0° C. Allow the reaction to stir. After 1 h at 0° C., allow to warm to ambient temperature and stir over a 2.5 h period. Cool the reaction to 0° C. and add dropwise 16 mL of a 1:1 solution of water/THF, and add dropwise addition of 2 M NaOH (60 mL). Filter the resulting mixture, wash the solids with THF (2×100 mL), combine the organic layers dry over sodium sulfate and concentrate. Dissolve the residue in dry ether (250 mL) and acidify with HCl/dioxane solution (20 mL of 4 M solution). Wash the resulting solid with ether to yield the title compound as a white solid.

Example 916

2-(3-Bromophenyl)N-(3-propoxybenzyl)acetamide

Combine 3-propoxy-benzylamine in 50 mL of dichloromethane and add dropwise to a mixture of 3-bromophenylacetyl chloride (4.90 gm; 21.0 mmol) and triethylamine (3.60 gm; 35.9 mmol) in 250 mL of dichloromethane at 0° C. Allow the reaction to warm to room temperature and stir for 18 h. Pour the reaction into 100 mL of saturated brine, separate the layers and extract the aqueous layer with 100 ml of dichloromethane. Combine organic layers, wash with brine, dry (MgSO$_4$), and concentrate. Purification by chromatography on silica gel with 40% EtOAc in hexanes gives the title compound.

Example 917

2-(4'-Fluorobiphenyl-3-yl)-N-(3-propoxybenzyl) acetamide

Combine bromoamide (0.365 gm; 1.008 mmol), 4-fluorophenylboronic acid (0.175 gm; 1.25 mmol), cesium fluoride (0.360 gm; 2.37 mmol), and dichloro(bistriphenylphosphine)palladium(11) (0.062 gm; 0.088 mmol) in NMP (3 mL) and heat at 104° C. After 13.3 h. cool to ambient temperature and dilute with 40 mL each of dichloromethane and water. Separate the layers and extract the aqueous layer with dichloromethane (2×20 mL). Combine the organic layers, wash four times with 10 mL portions of saturated brine, dry (MgSO$_4$) and concentrate. Purification by chromatography on silica gel with 40% EtOAc in hexanes gives the title compound.

Example 918

N-(2-(3-(4-Fluorophenyl)phenyl)ethyl)-3-propoxy-benzylamine

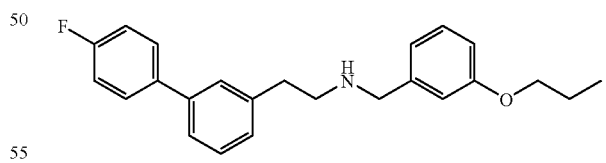

Combine 2-(4'-fluorobiphenyl-3-yl)-N-(3-propoxybenzylacetamide in 15 mL of THF and add a solution of BH$_3$—SMe$_2$ (2 M in THF) dropwise at 0° C. Allow the reaction to warm to ambient temperature and stir. After 5 h. Cautiously add ethanol (1 mL), and concentrate the mixture. Dissolve the residue in ethanol (2 mL), heat to reflux for 2 h, and concentrate. Purification using gives the title compound as a tan solid. Dissolve the amine in 10 mL of 1:1 dichloromethane/methanol and add 600 mg of polyvinylpyridine hydrochloride. Shake the mixture for 4 h, removed by filtration the polymer and concentrate the residue and wash with ether to give the title compound as the hydrochloride: MS (ES+): m/e 364 (M+1).

Example 919

N-(2-(5-Benzyloxy-1H-indol-3-yl)-ethyl)-3-phenoxybenzylamine

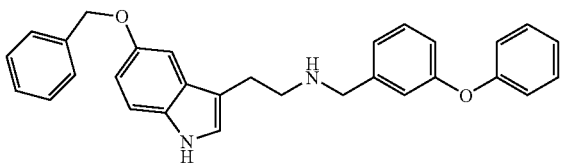

Combine 5-benzyloxy tryptamine (1.23 g, 4.6 mmol), 3-phenoxybenzaldehyde (97%, 1.09 g, 5.53 mmol) and molecular sieves 4A (1.0 g) and stir in methanol (15 mL) for 4 h. Filter the molecular sieves and wash several times with MeOH. To this MeOH solution, add portionwise NaBH$_4$ (174 mg, 4.60 mmol), stir the resulting mixture at room temperature for 1 h. Remove MeOH under vacuum, dilute the residue with CH$_2$CL$_2$/water, extract with CH$_2$Cl$_2$, combine organic layers, dry over Na$_2$SO$_4$ and concentrate the solvent in vacuo. Purification by silica gel chromatography (CH$_2$Cl$_2$/MeOH) to give the free base. Combine the free base with oxalic acid to form the salt: (300 MHz, DMSO-d$_6$) 2.95-3.15 (m, 4H), 3.93 (s, 2H), 4.10 (br, 1H), 5.05 (s, 2H), 6.85-7.46 (m, 18H), 10.67 (br, 1H); ms (ELECTROSPRAY) m/e: 449.2 (M+1).

Example 921

N-(2-(5-Benzyloxy-1H-indol-3-yl)ethyl)-N-methyl-3-phenoxy-benzylamine

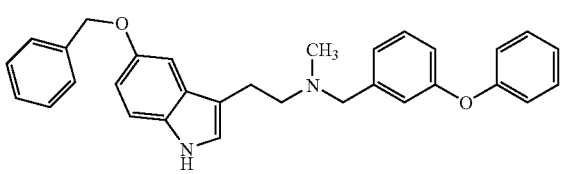

Combine N-(2-(5-benzyloxy-1H-indol-3-yl)ethyl)-3-phenoxy-benzylamine (1.61 g, 3.59 mmol) and NaOH (143.6 mg, 3.59-1.75 mmol) and dissolve in THF (25 mL) and stir at room temperature. After 15 min., add di-tert-butyl dicarbonate (1.57 g, 7.18 mmol) in THF (20 mL) and heat to reflux for 4 h. Remove the solvent, dilute with water, extract with CH$_2$Cl$_2$, (3×15 mL), dry over Na$_2$SO$_4$ and concentrate in vacuo to give a brown oil. The crude product was used directly in the next step without purification.

Combine 1.0 M solution of LiAlH$_4$-THF (13.4 ml, 13.4 mmol) and (3-phenoxy-benzyl)-(2-(5-benzyloxy-1H-indol-3-yl)-ethyl)-carbamic acid tert-butyl ester (1.83 g, 3.34 mmol) and slowly add 15 mL dry THF. After addition, heat the reaction mixture to reflux. After 4.5 h, cool down to room temperature. Quench the reaction by adding water (1.5 mL) cautiously, followed by 10% NaOH. Filter off the suspension and wash repeatedly with ether. Dry the organic solution over Na$_2$SO$_4$ and concentrate the solvent in vacuo. Purification by silica gel chromatography using CH$_2$Cl$_2$/MeOH as eluent to give the free base: $^1$H NMR (300 MHz, CDCl$_3$) 2.35 (s, 3H), 2.69-2.74 (m, 2H), 2.91-2.96 9 m, 2H), 3.65 (s, 2H), 5.07 (s, 2H), 6.90-7.53 (m, 18H), 7.80 (s, 1H). This compound reacted further with oxalic acid to form the salt.

Example 922

N-(2-(6,7-Difluoro-1H-indol-3-yl)-ethyl)-3-(pyridin-4-yloxy)benzylamine

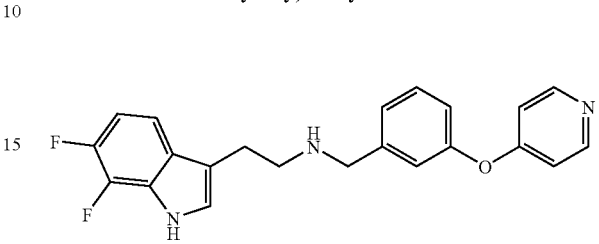

Combine 6,7-difluoro tryptamine (0.285 g, 1.450 mmol), 3-pyridin-4-yloxybenzaldehyde (0.303 g, 1.52 mmol, 1.05 eq.) and molecular sieves 4A (0.30 g) and stir in methanol (12 mL). After 4 h. filter the molecular sieves and wash several times with MeOH. To this MeOH solution, add portionwise NaH$_4$ (55.0 mg, 1.45 mmol), and stir at room temperature for 1 h. Remove MeOH in vacuo, dilute the residue with CH$_2$Cl$_2$/water, extract with CH$_2$Cl$_2$, combine organic layers, dry over Na$_2$SO$_4$ and concentrate in vacuo. Purification by flash chromatography on silica gel (CH$_2$Cl$_2$/MeOH) to give the free base which is converted to the hydrochloride salt: $^1$H NMR (300 MHz, DMSO-d$_6$) 3.13 (s, 4H), 4.20 (s, 2H), 6.85-7.55 (m, 10H), 8.47-8.50 (m, 1H), 9.58 (br, 1H), 11.57 (br, 1H): MS (electrospray) m/e: 380.2 (M+1–HCl), 378.3 (M–1–HCl).

The present invention also provides novel intermediates of the compounds of formula I. The present invention provides intermediates of formula III:

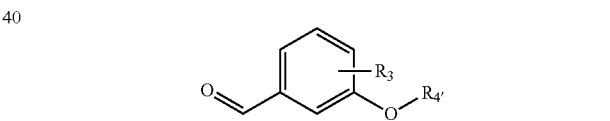

wherein
R$_3$ is selected from the group consisting of hydrogen, fluoro, and methyl;
R$_4$' is fluorinated C$_2$-C$_4$ alkyl.

The present invention also provides novel crystalline forms of the compounds of formula I. Thus, for example, N-(2-(6-fluoro-1H-indol-3-ylethyl)-3-(2,2,3,3-tetrafluoropropoxy) benzylamine hydrochloride may be prepared by crystallization under controlled conditions to give novel crystalline forms. Crystallization from a solution and slurrying techniques are contemplated to be within the scope of the present process. In practice, a number of factors can influence the form of (N-(2-(6-fluoro-1H-indol-3-yl)ethyl)-3-(2,2,3,3-tetrafluoropropoxy)benzylamine hydrochloride obtained, including temperature and solvent composition. While the precise conditions under which crystalline (N-2-(6-fluoro-1H-indol-3-yl)ethyl)-3-(2,2,3,3-tetrafluoropropoxy)benzylamine hydrochloride is formed may be empirically determined it is only possible to give a number of methods which have been found to be suitable in practice. A preferred polymorphic form of N-(2-6-fluoro-1H-indol-3-yl)ethyl)-3-(2,2,3,3-tetrafluoropropoxy)benzylamine hydrochloride can be prepared by crystallization or slurry from diethyl ether. Another preferred polymorphic form of N-(2-(6-fluoro-1H-indol-3-yl)ethyl)-3-(2,2,3,3-tetrafluoropropoxy)benzylamine hydrochloride can be prepared by crystallization from aqueous dichloromethane, aqueous acetone, ethyl acetate, ethyl acetate/cyclohexane, ethyl acetate/hexane, ethyl acetate/heptane, acetone/cyclohexane, isopropanol/hexanes, acetonitrile, acetonitrile/toluene, n-propanol/isoamylacetate/hexane, isopropyl acetate/diethyl ether, methyl t-butyl ether/acetone, water, water/acetone, water/diethyl ether.

Crystalline (N-(2-(6-fluoro-1H-indol-3-yl)ethyl)-3-(2,2,3,3-tetrafluoropropoxy)benzylamine may be prepared by direct crystallization under controlled conditions. The novel crystalline forms of the present invention may also be prepared by dissolving (N-(2-(6-fluoro-1H-indol-3-yl)ethyl)-3-(2,2,3,3-tetrafluoropropoxy)benzylamine in a solvent and then forming the hydrochloride salt by the addition of a solution containing hydrochloric acid and then allowing crystallization while controlling the temperature.

A number of methods are available to characterize crystalline forms of organic compounds. For example methods include differential scanning calorimetry, solid state NMR spectrometry, infra-red spectroscopy, and X-ray powder diffraction. Among these X-ray powder diffraction and solid state NMR spectroscopy are very useful for identifying and distinguishing between crystalline forms.

X-ray powder diffraction analysis are performed by a variety of methods known to the skilled person. These methods can be varied to increase sensitivity by sample preparation techniques and by using more intense radiation, smaller scan steps, and slower scan rates. One method is as follows. Either with or without lightly grinding the sample with an agate mortar and pestle, the sample is loaded into a sample holder for the X-ray powder diffraction measurement. The X-ray powder diffraction patterns are measured using a Siemens D5000 X-ray powder diffractometer equipped with a $CuK_\alpha$ source ($\lambda \approx 1.54056$ Å) operated at 50 kV and 40 mA using divergence slit size of 1 mm, receiving slit of 1 mm, and detector slit of 0.1 mm. Samples can be scanned between 4° and 35° (2θ) with a step size of 0.02° and a maximum scan rate of 3 sec/step. Data is collected using a Kevex solid-state silicon lithium detector. Optimally, a silicon standard is run routinely to check the instrument alignment.

It is well known in the crystallography art that, for any given crystal form, the relative intensities and peak widths of the diffraction peaks may vary due to a number of factors, including the effects of preferred orientation and/or particle size. Where the effects of preferred orientation and/or particle size are present, peak intensities may be altered, but the characteristic peak positions of the polymorph are unchanged. See, e.g., The United States Pharmacopoeia #24, National Formulary #19, pages 1843-1844, 2000.

Grinding may be used to minimize peak intensity. However, if grinding significantly alters the diffractogram or alters the crystalline state of the sample, then the diffractogram of the unground sample should be used. Grinding is done in a small agate mortar and pestle. The mortar is held during the grinding and light pressure was applied to the pestle.

Thus, a properly prepared sample crystalline compound of formula I may be characterized by one or more 2θ values in an X-ray diffraction pattern obtained as described above.

Crystalline compounds of formula I may also be characterized by solid state NMR spectroscopy. Solid state $^{13}C$ chemical shifts reflect not only the molecular structure of but also the electronic environment of the molecule in the crystal.

Solid state NMR ($^{13}C$) analysis can be carried out using $^{13}C$ Cross polarization/magic angle spinning (CP/MAS) NMR (solid-state NMR or SSNMR) spectra are obtained using a Varian Unity 400 MHz spectrometer operating at a carbon frequency of 100.580 MHz, equipped with a complete solids accessory and Varian 7 mm VT CP/MAS probe. Acquisition parameters are readily determined and typically are 90° proton r.f. pulse width 4.0 µs, contact time 1.0 ms, pulse repetition time 5 s, MAS frequency 7.0 kHz, spectral width 50 kHz, and acquisition time 50 ms. Chemical shifts are generally reported by referenced to the methyl group of external hexamethylbenzene, that is, by sample replacement with hexamethylbenzene.

Thus, crystalline compounds of formula I may be characterized one or more resonances in the solid state $^{13}C$ nuclear magnetic spectra obtained as described above.

The compounds of the present invention can be administered alone or in the form of a pharmaceutical composition, that is, combined with pharmaceutically acceptable carriers or excipients. The compounds of the present invention, while effective themselves, may be formulated and administered in the form of their pharmaceutically acceptable salts, for purposes of stability, convenience, solubility, and the like. In practice, the compounds of formula I and II are usually administered in the form of pharmaceutical compositions, that is, in admixture with pharmaceutically acceptable carriers or diluents.

Thus, the present invention provides pharmaceutical compositions comprising a compound of the formula I or II and a pharmaceutically acceptable diluent.

The compounds of formula I and II can be administered by a variety of routes. In effecting treatment of a patient afflicted with disorders described herein, a compound of formula I and II can be administered in any form or mode which makes the compound bioavailable in an effective amount, including oral and parenteral routes. For example, compounds of formula I and II can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the ant of preparing formulations can readily select the proper form and mode of administration depending upon the particular characteristics of the compound selected, the disorder or condition to be treated, the stage of the disorder or condition, the solubility and chemical properties of the compound selected, the chosen route of administration, and other relevant circumstances considered in standard pharmaceutical practice. (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I and II present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I and II or its pharmaceutical salt from about 0.1 to about 10% w/v (weight per unit volume).

The compounds of formula I and II are antagonists of 5-$HT_6$ receptors. Such antagonism can be identified by the methods below.

Example A

Assay for 5$HT_6$ Binding

The assay buffer used is 50 mM Tris-HCl pH 7.4, 120 mM NaCl, 5 mM KCl, 5 mM $MgCl_2$, 1 mM EDTA. The radioligand used is $^3$H-LSD from New England Nuclear Cat. # NET 638-75.9 Ci/mmol. The membranes used are from Receptor Biology, Cat. No. RB-HS6. These are membranes from HEK-293 cells expressing the Human 5$HT_6$ receptor.

Test compounds are obtained as 10 mM stocks in 100% DMSO. They are diluted to 1 mM in 100% DMSO by adding 180 µl DMSO to 20 µl of stock in 96 well plates using a multidrop. The 1 mM stocks are then diluted to make an 11 point concentration range from 125 µM down to 1.25 nM in half log increments using 10% DMSO as diluent. This is done using a TECAN robot. The final DMSO at this stage is 21.25%.

Radioligand is diluted in assay buffer to make a 125 nM solution and each vial of membranes is diluted up to 92 mL in assay buffer. The final assay volume is 250 µl consisting of 210 µl of diluted membranes, 20 µl of compound or 21.25% DMSO for total binding, and 20 µl of diluted radioligand. The compounds are transferred from drug dilution plates into corning 96 well assay plates using a 96 well Multimek pipettor. Radioligand and membranes are added to assay plates using multidrop pipettors. Non-specific binding is determined in wells containing a final serotonin concentration of 10 µM. In the final assay volume the radioligand is 10 nM and the membrane protein is approximately 25 µg/well. The final drug concentration range in half logs is from 10 µM down to 0.1 nM. The final DMSO in the assay is 1.7%.

After addition of drug, membrane, and ligand, the plates are incubated for one hour at room temperature. During this time 96 well Millipore filter plates (MAFBNOB50) are soaked for a least 30 minutes with 200 µl per well of 0.5% polyethyleneimine.

The 0.5% PEI is removed from filterplate wells using a TiterTek MAP aspirator and 200 µl of the incubation mixture is transferred from the incubation plate to the filterplate after mixing. This transfer is done using the 96 tip Mutimek pipettor. After transfer to the filterplate filterplates are extracted and washed twice with 220 µl per well of cold buffer on the MAP aspirator. The peel away bottoms are removed from the filterplates and 100 µl per well of microscint 20 scintillation fluid is added per well using a multidrop. Plates are placed into suitable holders and are left at room temperature for three hours and are counted for $^3$H in either a Wallac Microbeta counter or on a Packard Topcount.

In one embodiment, the present invention provides methods of treating disorders associated with the 5-$HT_6$ receptor, comprising: administering to a patient in need thereof an effective amount of a compound of formula I. Thus, the present invention contemplates the various disorders described to be treated herein and others which can be treated by such antagonists as are appreciated by those skilled in the art.

In particular, because of their ability to antagonize the 5-$HT_6$ receptor, it is recognized that the compounds of the present invention are useful for treating cognitive disorders, that is, disorders involving cognitive deficits. A number of the disorders which can be treated by 5-$HT_6$ antagonists are known according to established and accepted classifications, while others are not.

Some of the disorders to be treated according to the present invention are not well categorized and classified because cognition is a complicated and sometimes poorly defined phenomenon. It is, however, widely recognized that cognition includes various "domains." These domains include short term memory, long term memory, working memory, executive function, and attention.

While many of the disorders which can be treated according to the present invention are not uniformly described and classified in the art, it is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined, but includes decline in the cognitive domains, particularly the memory and attention domains, which accompany aging. Another is mild cognitive impairment. Again, this disorder is not well defined in the art, but involves decline in the cognitive domains, and is believed to represent a group of patients the majority of which have incipient Alzheimer's disease. Also, a wide variety of insults, including stroke, ischemia, hypoxia, inflammation, and infectious processes can result in cognitive deficits as a sequella which can be treated according to the present invention.

Where the disorders which can be, treated by $5\text{-}HT_6$ antagonists are, at present, known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision, (ICD-10) provides classifications for many of the disorders described herein. The skilled artisan will recognize that there are alternative nomenclatures, nosologies, and classification systems for disorders described herein, including those not well characterized by the art and those described in the DMS-IV and ICD-10, and that terminology and classification systems evolve with medical scientific progress.

In one embodiment, the present invention provides methods of treating disorders selected from the group consisting of: age-related cognitive disorder, mild cognitive impairment, mood disorders (including depression, mania, bipolar disorders), psychosis (in particular schizophrenia), anxiety (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/ hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, amylotrophic lateral sclerosis, and multiple sclerosis, comprising: administering to a patient in need thereof an effective amount of a compound of formula I or II. That is, the present invention provides for the use of a compound of formula I and II or pharmaceutical composition thereof for the treatment disorders associated with the $5\text{-}HT_6$ receptor.

It is recognized that the terms "treatment" and "treating" are intended to include improvement of the cognitive deficit associated with each of the disorders associated with the $5\text{-}HT_6$ receptor described herein. Also, it is also recognized that one skilled in the art may affect the disorders by treating a patient presently afflicted with the disorders or by prophylactically treating a patient believed to be susceptible to such disorders with an effective amount of the compound of formula I. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders. For example, the present invention specifically encompasses the treatment of the cognitive deficits associated with schizophrenia, stroke, Alzheimer's disease, and the other disorders described herein. Thus, it is understood that the present invention includes adjunctive treatment of the disorders described herein. More specifically, the compounds of formula I and II are useful to treat cognition disorders in combination with a wide variety of therapeutic agents, in particular, in combination with AMPA potentiators; with typical and atypical antipsychotics, including olanzapine; with a variety of agents such as mGluR agonists, with NMDA antagonists, with IL 1-6 inhibitors, and the like; with cholinergics, including cholinesterase inhibitors, such as tacrine and donepezil, and compounds that inhibit amyloid protein processing, including inhibitors of amyloid precursor protein processing and antibodies directed against amyloid proteins; with antidepressants, including SSRIs; and with anxiolytic agents; etc. It is believed that the combinations above are synergistically beneficial providing efficacy at doses that are a small fraction of those required to produce the same effect with the individual components.

As used herein, the term "patient" refers to a warm blooded animal such as a mammal which is afflicted with one or more disorders associated with the $5\text{-}HT_6$ receptor. It is understood that guinea pigs, dogs, cats, rats, mice, horses, cattle, sheep, pigs, and humans are examples of animals within the scope of the meaning of the term.

As used herein, the term "effective amount" of a compound of formula I or II refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of formula I, a number of factors are considered by the attending diagnostician, including, but not limited to the compound of formula I or II to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I and II is expected to vary from about 0.1 milligram per kilogram of body weight per day (mg/kg/day) to about 100 mg/kg/day. Preferred amounts are able to be determined by one skilled in the art.

Of the disorders to be treated according to the present invention a number are particularly preferred.

In a preferred embodiment the present invention provides a method of treating cognitive disorders, comprising: administering to a patient in need thereof an effective amount of a compound of claim 1.

In another preferred embodiment the present invention provides a method for treating Alzheimer's disease, comprising: administering to a patient in need thereof an effective amount of a compound of formula I.

In a preferred embodiment the present invention provides a method for treating schizophrenia, comprising: administering to a patient in need thereof an effective amount of a compound of formula I.

The fourth edition of the Diagnostic and Statistical Manual of Mental Disorders (DSM-IV™) (1994, American Psychiatric Association, Washington, D.C.), provides a diagnostic tool including schizophrenia and related disorders, all of which are understood to be specifically included in the scope of this invention.

In a preferred embodiment the present invention provides a method for treating migraine, comprising: administering to a patient in need thereof an effective amount of a compound of formula I or II or a pharmaceutical composition thereof.

In one of the available sources of diagnostic tools, *Dorland's Medical Dictionary* (23$^{rd}$ Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes to these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In a preferred embodiment the present invention provides a method for treating anxiety disorders, including generalized anxiety disorder, panic disorder, and obsessive compulsive disorder, comprising: administering to a patient in need thereof an effective amount of a compound of formula I.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorders as specifically described in the DSM-IV and the term "anxiety" is intended to include like disorders that are described in other diagnostic sources.

A number of preclinical laboratory animal models have been described for the disorders described herein.

Example B

Fear Potentiated Startle Paradigm

Male Sprague-Dawley rats weighing 325-400 g were purchased from Harlan Sprague-Dawley, Inc. (Cumberland, Ind.) and given a one week acclimation period before testing. Rats were individually housed with food and water ad libitum in an animal room on a 12-hour light/dark cycle with lights on between 6:00 A.M. and 6:00 P.M. The compound of Example 16 was prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl) propionic acid was prepared in sterile water. Control rats were given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes were analyzed by Jmp statistical software using a One-way Anova (analysis of variance, t-test). Group differences were considered to be significant at $p<0.05$.

The radial arm maze model can be used as a model of cognition and can be used to evaluate the present compounds.

Example C

Radial Arm Maze

The delayed non-match to sample task has been used to study the effect of drugs on memory retention (Pussinen, R. and Sirvio, J. *J of Psychopharm* 13: 171-179 (1999); Staubli, U., et al. *Proc Natl Acad Sci* 91: 777-781 (1994)) in the eight arm radial maze.

Well-trained rats were allowed to retrieve food rewards from four randomly selected arms of the maze (sampling phase). Some time later, the rats were exposed to eight open arms and were tested for their ability to remember and avoid the arms they had previously entered to obtain food. Re-entry into an arm that was baited during the sampling session was counted as a reference error, whereas entry into the same arm more than once during the retention session was counted as working error. The total (reference+working) number of errors made during the retention test increases with increasing delay periods. For example, young male rats made 0.66 (+0.4) errors at a 1 minute delay, 2 (+0.5) errors at a one hour delay, and 3.95 (+0.2) errors at a seven hour delay (observations of this lab).

Male Sprague-Dawley rats were individually housed and maintained on a 121, light-dark cycle (lights on at 6 am). The rats were given free access to water and maintained at 85% of their free-feeding weight by supplemental feedings of Purina Lab Chow.

The rats were initially trained to search for food at the end of each of the eight arms. Once the rats had reached the criteria of no more than two errors (i.e. entering the same arm more than once during a session) on three consecutive days, a delay of one minute was imposed between the fourth and the fifth arm choices. This training ensured that the rats were thoroughly familiar with the procedural aspects of the task before any drugs were administered. Once stable performance had been obtained on the delay task (i.e. no more than one error was made on three consecutive days), drug and vehicle tests commenced using a seven hour delay period. A novel set of arms was baited each day for each rat and the maze was thoroughly cleaned during the delay period.

During the sampling session, each rat was placed on the center platform with access to all eight arms of the maze blocked. Four of the eight arms were randomly selected and baited with food. The gates of the baited arms were raised and the rat was allowed five minutes to obtain the food at the end of each of the four arms. As soon as the rat had obtained the food, it was removed, administered vehicle or various doses of compounds, and placed back in its home cage. Seven hours later (retention session), the rat was placed back onto the center platform with access to all eight arms blocked. The four arms that were previously baited during the sampling session, were baited and the gates to all eight arms were raised. The rat was allowed five minutes to obtain the remaining four pieces of food. An entry into a non-baited arm or a re-entry into a previously visited arm was counted as an error. Significance (p<0.05) was determined using a repeated measure ANOVA followed by a Dunnett's test for comparison with control.

In order to compare test compounds with standards, scopolamine and tacrine were administered s.c. immediately after the sampling phase. The effects of scopolamine, a known amnesic, were tested after a three-hour delay, whereas the effect of tacrine, a cholinesterase inhibitor used in the treatment of Alzheimer's disease was tested after a six-hour delay. Scopolamine disrupted retention after a three-hour delay in a dose-related fashion. Tacrine significantly improved retention after a six-hour delay at 10, but not at 3 mg/kg.

Example D

Acquisition in the Radial Maze 8-arm Radial Maze Acquisition

A prominent early feature of Alzheimer's disease (AD) symptomology is a pronounced deficit in declarative memory (R. W. Parks, R. F. Zec & R. S. Wilson (Eds.), *Neuropsychology of Alzheimer's disease and other dementias*. NY: Oxford University Press pp. 3-80 (1993).

As the disease progresses, other domains of cognition become severely affected as well. Among the brain regions affected early in the progression of AD is the hippocampus, which is a critical neural substrate for declarative memory (West M. J., Coleman P. D., Flood D. G. & Troncoso J. C. Differences in the pattern of hippocampal neuronal loss in normal aging and Alzheimer's disease. *Lancet*, 344: 769-772 (1994). One behavioral test that is often used to assess hippocampal function in animal models is the 8-arm radial maze (Olton D. S. The radial arm maze as a tool in behavioral pharmacology. Physiology & Behavior, 40: 793-797 (1986)).

Lesions or pharmacological blockade of the hippocampus disrupt performance of this task. Moreover, aged animals generally show deficits in this task (Porsolt R. D., Roux S. & Wettstein J. G. Animal models of dementia. Drug Development Research, 35: 214-229 (1995)).

In this test of spatial learning and memory, a hungry rat is placed in the center of the maze and allowed to traverse the maze in search of food located at the end of each ninway amt. In this version of the maze, the rat learns a win-shift strategy in which a visited arm is not replaced. Therefore, the most efficient foraging strategy is to visit each arm once. The version of the maze also taps into general learning processes as the rat is naïve to the maze on day one of the four day experiment.

Upon arrival, male Sprague Dawley®, rats were individually housed in a regular light-cycle colony room and allowed to acclimate for at least 4 days prior to testing. Each rat was reduced to and maintained at 85% of their target body weight throughout the experiment. Proper body weight was maintained by adjusting the allotment of lab chow based on a combination of age and the rat's daily bodyweight reading.

A session began with an individual rat being placed into the hub of the maze and then all guillotine doors were raised, allowing free access to all areas of the maze. A food hopper was located at the end of each of the 8 runway arms and a single food pellet was placed in each food hopper. Each daily session terminated when either all 8 food-hoppers had been visited or when the rat timed out (15 min on Day 1: 5 min on Days 2-4). The number of aim entries was recorded. Errors were counted as repeat arm entries or failures to visit an arm in the session period. An animal was excluded from the study if it failed to visit at least one arm on Day 1, 2 arms on Day 2, and at least 4 arms on Days 3 & 4.

Each rat was pseudo-randomly assigned to either a vehicle or drug group and received the same treatment throughout the experimental period. Vehicle consisted of 5% acacia within sterile water. Injections were administered subcutaneously 20-30 minutes prior to each daily session.

In this acquisition task, vehicle-treated animals do not consistently show significant acquisition of maze learning as compared to the number of errors committed on Day 1. We have found that in compounds that facilitate acquisition of maze learning, the effects are often not observed until the fourth day of training. Therefore, results consisted of total Day 4 errors across treatment groups.

We claim:

1. A method of treating Alzheimer's disease comprising administering to a patient in need thereof an effective amount of a combination of a 5-$HT_6$ receptor antagonist and a cholinesterase inhibitor, or pharmaceutically acceptable salts thereof, wherin the 5-$HT_6$ receptor antagonist is of structural formula I:

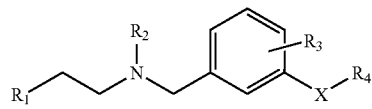

formula I wherein X is selected from the group consisting of —O—, —NH—, —S—, —$SO_2$—, —$CH_2$—, —CH(F)—, —CH(OH)—, and —C(O)—;

$R_1$ is selected from the group consisting of optionally substituted phenyl, optionally substituted naphthyl, optionally substituted 5 to 6 membered monocyclic aromatic heterocycle having one heteroatom selected from the group consisting of nitrogen, oxygen, and sulfur and which 5 to 6 membered monocyclic aromatic heterocycle is optionally benzofused;

$R_2$ is selected from the group consisting of hydrogen and $C_1$-$C_3$ alkyl;

$R_3$ is selected from the group consisting of hydrogen, fluoro, and methyl; and $R_4$ is selected from the group consisting of hydrogen, allyl, $C_2$-$C_4$ alkyl, fluorinated $C_2$-$C_4$ alkyl, optionally substituted phenyl, optionally substituted phenylsulfonyl, optionally substituted benzyl, and optionally substituted 5 to 6 membered monocyclic aromatic heterocycle having one or two heteroatoms selected from the group consisting of nitrogen, oxygen, and sulfur, provided that $R_4$ is not optionally substituted phenylsulfonyl when X is —$SO_2$—, —$CH_2$—, —CH(F)—, —CH(OH)—, or —C(O)—.

2. The method of claim 1, wherein X is —O—; or a pharmaceutically acceptable salt thereof.

3. The method of claim 2, wherein $R_3$ is hydrogen; or a pharmaceutically acceptable salt thereof.

4. The method of claim 3, wherein $R_4$ is selected from the group consisting of $C_2$-$C_4$ fluorinated alkyl and optionally substituted phenyl; or a pharmaceutically acceptable salt thereof.

5. The method of claim 4, wherein $R_1$ is optionally substituted 5 to 6 membered monocyclic aromatic heterocycle having one heteroatom selected from the group consisting of nitrogen, oxygen, and sulfur and which 5 to 6 membered monocyclic aromatic heterocycle is benzofused; or a pharmaceutically acceptable salt thereof.

6. The method of claim 5, wherein $R_4$ is fluorinated $C_2$-$C_4$ alkyl; or a pharmaceutically acceptable salt thereof.

7. The method of claim 6, wherein the 5-$HT_6$ receptor antagonist is N-(2-(6-fluoro-1H-indol-3-yl)ethyl)-3-(2,2,3,3-tetrafluoropropoxy)benzylamine, or a pharmaceutically acceptable salt thereof.

8. The method of claim 6, wherein the 5-$HT_6$ receptor antagonist is N-(2-(6-fluoro-1H-indol-3-yl)ethyl)-3-(2,2,3,3-tetrafluoropropoxy)benzylamine hydrochloride.

9. The method of claim 8, wherein the cholinesterase inhibitor is tacrine.

10. The method of claim 8, wherein the cholinesterase inhibitor is donepezil.

* * * * *